United States Patent
Arya et al.

(10) Patent No.: US 10,203,334 B2
(45) Date of Patent: *Feb. 12, 2019

(54) METHODS AND COMPOSITIONS RELATED TO NUCLEIC ACID BINDING ASSAYS

(71) Applicant: Nubad, LLC, Greenville, SC (US)

(72) Inventors: Dev P. Arya, Greenville, SC (US); Frank Anderson Norris, Anderson, SC (US); Jason Derrick Watkins, Greenville, SC (US)

(73) Assignee: Nubad, LLC, Greenville, SC (US)

( * ) Notice: Subject to any disclaimer, the term of this patent is extended or adjusted under 35 U.S.C. 154(b) by 142 days.

This patent is subject to a terminal disclaimer.

(21) Appl. No.: 15/086,935

(22) Filed: Mar. 31, 2016

(65) Prior Publication Data

US 2016/0282357 A1    Sep. 29, 2016

Related U.S. Application Data

(63) Continuation of application No. 13/939,950, filed on Jul. 11, 2013, now Pat. No. 9,410,186.

(60) Provisional application No. 61/670,141, filed on Jul. 11, 2012.

(51) Int. Cl.
    *C12Q 1/68*      (2018.01)
    *C07H 21/00*     (2006.01)
    *G01N 21/64*     (2006.01)
    *G01N 33/58*     (2006.01)
    *C12Q 1/6816*    (2018.01)

(52) U.S. Cl.
    CPC ......... *G01N 33/582* (2013.01); *C12Q 1/6816* (2013.01); *G01N 21/6428* (2013.01); *G01N 21/6486* (2013.01); *G01N 2021/6439* (2013.01)

(58) Field of Classification Search
    CPC .................................. C12Q 1/68; G01N 21/64
    See application file for complete search history.

(56) References Cited

U.S. PATENT DOCUMENTS

| | | | |
|---|---|---|---|
| 3,329,566 A | 7/1967 | Pines et al. | |
| 5,593,835 A | 1/1997 | Rando et al. | |
| 9,017,943 B2* | 4/2015 | Arya | G01N 21/6486 435/6.1 |
| 9,410,186 B2* | 8/2016 | Arya | G01N 21/6486 |
| 2002/0155432 A1* | 10/2002 | Schwartz | A61K 48/0058 435/5 |
| 2005/0049305 A1* | 3/2005 | Kalinec | A61K 31/205 514/546 |
| 2005/0085413 A1 | 4/2005 | Jin et al. | |
| 2007/0049741 A1* | 3/2007 | Rege | B01D 15/362 530/412 |
| 2011/0046982 A1 | 2/2011 | Arya et al. | |

FOREIGN PATENT DOCUMENTS

| | | |
|---|---|---|
| WO | 2007/016455 | 2/2007 |
| WO | 2013/016321 | 1/2013 |

OTHER PUBLICATIONS

Escude et al., PNAS 95 : 3591 (1998). (Year: 1998).*
Kohler et al.,Forced Intercalation Probes (FIT Probes) : Thiazole Orange as a Fluorescent Base in Peptide Nucleic Acids for Homogeneous Single Nucleotide—Polymorphism Detection. ChemBioChem 6 :69 (2005). (Year: 2005).*
Nunez et al., Long-Range Guanine Oxidation in DNA Restriction Fragments by a Triplex-Directed Naphthalene Diimide Intercalator. Biochemistry 39 : 6190 (2000). (Year: 2000).*
Watkins et al., An assay for human telomeric G-quadruplex DNA binding drugs. Bioorganic & Medicinal Chemistry Letters 23 : 6695 (Year: 2013).*
Andersen, E.S., et al., "Role of the trans-activation response element in dimerization of HIV-1 RNA," J. Biol. Chem., vol. 279, No. 21, 2004, pp. 22243-22249.
Arbuzova et al.,Fluorescently labeled neomycin as a probe of phosphatidylinositol-4,5-bisphosphate in membranes. Biochimica et Biophysica Acta 1464 :35-48 (2000).
Arya, D.P., et al., "Aminoglycoside (neomycin) preference is for A-form nucleic acids, not just RNA: results from a competition dialysis study," J. Am. Chem. Soc., vol. 125, vol. 34, 2003, pp. 10148-10149.
Arya, D.P., et al. Aminoglycoside-Nucleic Acid Interactions: Remarkable Stabilization of DNA and RNA Triple Helices by Neomycin, J. Am. Chem. Soc., vol. 123, No. 23, 2001, pp. 5385-5395.
Arya, D.P., "Aminoglycoside-Nucleic Acid Interactions: The case for Neomycin," Topics in Current Chem.: DNA Binders, J.B. Chaires and M.J. Waring, Heidelburg, Springer Verlage, vol. 253, 2005, pp. 149-178.
Arya, D.P., et al., "Combining the Best in Triplex Recognition: Synthesis and Nucleic Acid Binding of a BQQ-Neomycin Conjugate," J. Am. Chem. Soc., vol. 125, No. 27, 2003, pp. 8070-8071.

(Continued)

*Primary Examiner* — Ethan C Whisenant
(74) *Attorney, Agent, or Firm* — Meunier Carlin & Curfman LLC

(57) ABSTRACT

Small molecule fluorescent probes for established drug targets such as nucleic acids including DNA and RNA has been developed and disclosed herein. These nucleic acid probes bind to multiple DNA and RNA structures, and to sites crucial for nucleic acid function, such as DNA and RNA major grooves. Displacement of the probes by other binders such as small molecule compounds and/or proteins illicits a fluorescence change in the probe that once detected and analyzed provide binding information of these other binders of interest. Similarly, changes in fluorescence upon binding of the probes to nucleic acid have been applied to screen nucleic acid of different sequence and conformation. The nucleic acid probes and method of uses disclosed herein are advantageously suitable for high-through put screening of libraries of small molecule compounds, proteins, and nucleic acids.

20 Claims, 14 Drawing Sheets

Specification includes a Sequence Listing.

(56) References Cited

OTHER PUBLICATIONS

Arya, D.P., et al., "DNA Triple Helix Stabilization by Aminoglycoside Antibiotics," Bioorg. & Med. Chem. Lett., vol. 10, No. 17, 2000, pp. 1897-1899.
Arya, D.P., et al., "From triplex to B-form duplex stabilization: reversal of target selectivity by aminoglycoside dimers," Bioorg. & Med. Chem. Lett., vol. 14, No. 18, 2004, pp. 4643-4646.
Arya, D.P., et al., "Neomycin Binding to DNA Triplex Watson-Hoogsteen (W-H) Groove: A Model," J. Am. Chem. Soc., vol. 125, 2003, pp. 3733-3744.
Arya, D.P., et al., "Neomycin Induced Hybrid Triplex Formation," J. Am. Chem. Soc., vol. 123, No. 44, 2001, pp. 11093-11094.
Arya, D.P., "New Approaches Toward Recognition of Nucleic Acid Triple Helices," Accounts of Chemical Research, vol. 44, No. 2, 2011, pp. 134-146.
Arya, D.P., et al., "Reaching into the Major Groove of B-DNA; Synthesis and Nucleic Acid Binding of a Neomycin—Hoechst 33258 Conjugate," J. Am. Chem. Soc., vol. 125, No. 41, 2003, pp. 12398-12399.
Bailly, C. et al., "Drug-DNA Sequence-Dependent Interactions Analysed by Electric Linear . Dichroism, J. Mol. Recognition," vol. 5, No. 4, 1992, pp. 155-171.
Bailly, C. et al., "The binding mode of drugs to the TAR RNA of HIV-1 studied by electric linear dichroism," Nucleic Acids Research, vol. 24, No. 8, 1996, pp. 1460-1464.
Bailly, C. et al., "The different binding modes of Hoechst 33258 to DNA studied by electric linear dichroism," Nucleic Acids Research, vol. 21, No. 16, 1993, pp. 3705-3709.
Bannwarth, S., et al., "HIV-1 TAR RNA: The Target of Molecular Interactions Between the Virus and its Host," Current HIV Research, vol. 3, No. 1, 2005, pp. 61-71.
Barbieri, C.M., et al., "Complete Thermodynamic Characterization of the Multiple Protonation Equilibria of the Aminoglycoside Antibiotic Paromomycin: A Calorimetric and Natural Abundance $^{15}$N NMR Study," Biophysical J., vol. 90, 2006, pp. 1338-1349.
Bengtsson, M., et al., "A new minor groove binding asymmetric cyanine reporter dye for real-time PCR," Nucleic Acids Research, vol. 31, No. 8, five pages.
Berkhout, B., "Structural features in TAR RNA of human and simian immunodeficiency viruses: a phylogenetic analysis," Nucleic Acids Research, vol. 20, No. 1, 1992, pp. 27-31.
Blanchard, S.C., et al., "rRNA Chemical Groups Required for Aminoglycoside Binding," Biochemistry, vol. 37, 1998, pp. 7716-7724.
Charles, I., et al., "Synthesis of Aminoglycoside-DNA Conjugates," Bioorg. & Med. Chem. Lett., vol. 12, No. 9, 2002, pp. 1259-1262.
Cho, J., et al., "Specific binding of Hoechst 33258 to site 1 thymidylate synthase mRNA," Nucleic Acids Research, vol. 28, No. 10, 2000, pp. 2158-2163.
Chow, C.S., et al., "A Structural Basis for RNA-Ligand Interactions," Chemical Reviews, vol. 97, Nos. 4-6, 1997, pp. 1489-1514.
Cordingley, M.G., et al., "Sequence-specific interaction of Tat protein and Tat peptides with the transactivation-responsive sequence element of human immunodeficiency virus type 1 in vitro," Proc Natl Acad Sci USA, vol. 87, No. 22, 1990, pp. 8985-8989.
Dassonneville, L., et al., "Binding of Hoechst 33258 to the TAR RNA of HIV-1. Recognition of a pyrimidine bulge-dependent structure," Nucleic Acids Research, vol. 25, No. 22, 1997, pp. 4487-4492.
Dingwall, C., et al., "HIV-1 tat protein stimulates transcription by binding to a U-rich bulge in the stem of the TAR RNA Structure," The EMBO J., vol. 9, No. 12, 1990, pp. 4145-4153.
Eftink, M.R., "Fluorescence methods for studying equilibrium macromolecule-ligand interactions," Methods Enzymol, vol. 278, 1997, pp. 221-257.
Faber, C., et al., "Structural Rearrangements of HIV-1 Tat-responsive RNA upon Binding of Neomycin B," J. Biological Chem., vol. 275, No. 27, 2000, pp. 20660-20666.

Ford et al., Further Characterization of Neomycin B and Neomycin C. JACS 77, 1955, (20): 5311.
Forge, A., et al., "Aminoglycoside Antibiotics," Audio Neurootol., vol. 5, 2000, pp. 3-22.
François, B., et al., "Crystal structures of complexes between aminoglycosides and decoding A site oligonucleotides: role of the number of rings and positive charges in the specific binding leading to miscoding," Nucleic Acids Research, vol. 33, No. 17, 2005, pp. 5677-5690.
Frankel, A.D., "Activation of HIV transcription by Tat," Current Opinion in Genetics and Development, vol. 2, No. 2, 1992, pp. 293-298.
Friedrich, K., et al., "Electrostatic Potential of Macromolecules Measured by pKa Shift of a Fluorophore 1. the 3' Terminus of 16S RNA," Eur. J. Biochem, vol. 173, 1988, pp. 227-231.
Froeyen, M., et al., "RNA as a Target for Drug Design, the Example of Tat-TAR Interaction," Current Topics in Med. Chem., vol. 2, No. 10, 2002, pp. 1123-1145.
Gerding, D.N., "Antimicrobial Cycling: Lessons Learned From the Aminoglycoside Experience," Infection Control and Hospital Epidemiology, vol. 21, 2000, pp. S12-S17.
Grzesiek, S., et al., "Measurement of amide proton exchange rates and NOEs with water in $^{13}C/^{15}N$-enriched calcineurin B," J. Biomolecular NMR, vol. 3, No. 6, 1993, pp. 627-638.
Hamasaki, K., et al., "A High-Throughput Fluorescence Screen to Monitor the Specific Binding of Antagonists to RNA Targets," Anal. Biochemistry, vol. 261, No. 2, 1998, pp. 183-190.
Hamma, T., et al., "Interactions of Hairpin Oligo-2'-O-Methylribonucleotides Containing Methylphosphonate Linkages with HIV TAR RNA," Antisense and Nucleic Acid Drug Development, vol. 13, No. 1, 2003, pp. 19-30.
Hamma, T., A., et al., "Inhibition of HIV Tat-TAR Interactions by an Antisense Oligo-2'-O-methylribonucleoside Methylphosphonate," Bioorg. & Med. Chem. Lett., vol. 13, No. 11, 2003, pp. 1845-1848.
Haq, I., et al., "Specific Binding of Hoechst 33258 to the d(CGCAAATTTGCG)2 Duplex: Calorimetric and Spectroscopic Studies," J. Mol. Biol., vol. 27, No. 2, 1997, pp. 244-257.
Herbert, A., et al., "Double-stranded RNA adenosine deaminase binds Z-DNA in vitro," Nucleic Acids Symposium Series No. 33, 1995, pp. 16-19.
Hermann, T., et al., "Aminoglycoside binding to the hammerhead ribozyme: a general model for the interaction of cationic antibiotics with RNA," J. Mol. Biol. 276, 1998, pp. 903-912.
Hermann, T., et al., "RNA as a drug target: chemical, modelling, and evolutionary tools," Current Opinion in Biotechnology, vol. 9, No. 1, 1998, pp. 66-73.
Hermann, T., et al., "RNA bulges as architectural and recognition motifs," Structure, vol. 8, No. 3, 2000, pp. R47-R54.
Hermann, T., "Strategies for the Design of Drugs Targeting RNA and RNA-Protein Complexes," Angew Chem Int Ed Engl, vol. 39, No. 11, 2000, pp. 1890-1904.
Jin, E., et al., "Aminoglycoside Binding in the Major Groove of Duplex RNA: The Thermodynamic and Electrostatic Forces that Govern Recognition," J. Mol. Biol., vol. 298, No. 1, 2000, pp. 95-110.
Karlsson, HJ, et al., "Groove-binding unsymmetrical cyanine dyes for staining of DNA: syntheses and characterization of the DNA-binding," Nucleic Acids Research., vol. 31, No. 21, Nov. 1, 2003, pp. 6227-6234.
Kaul, M., et al., "Coupling of Drug Protonation to the Specific Binding of Aminoglycosides to the A Site of 16 S rRNA: Elucidation of the Number of Drug Amino Groups Involved and their Identities," J. Mol. Biol., vol. 326, 2003, pp. 1373-1387.
Kaul, M., et al., "Thermodynamics of Aminoglycoside-rRNA Recognition: The Binding of Neomycin-Class Aminoglycosides to the A Site of 16S rRNA," Biochemistry, vol. 41, No. 24, 2002, pp. 7695-7706.
Kirk et al., Neomycin-Acridine Conjugate: A Potent Inhibitor of Rev-RRE Binding. JACS 122: 980 (2000).
Kolb, H. C., et al., "Click Chemistry: Diverse Chemical Function from a Few Good Reactions," Angew. Chem. Int. Ed., vol. 40, No. 11, 2001, pp. 2004-2021.

(56) References Cited

OTHER PUBLICATIONS

Kopka, M.L. et al. "The molecular origin of DNA-drug specificity in netrospin and distamycin," Proc. Nat. Acad. Sci. USA, vol. 82, 1985, pp. 1376-1380.

Krebs, A., et al., "Targeting the HIV Trans-Activation Responsive Region—Approaches towards RNA-Binding Drugs," Chembiochem, vol. 4, No. 10, 2003, pp. 972-978.

Kubista, M., et al., "Determination of Equilibrium Constants by Chemometric Analysis of Spectroscopic Data," Anal. Chem., vol. 65, No. 8, 1993, pp. 994-998.

Kubista, M., et al., "Quantitative spectral analysis of multicomponent equilibria," Anaytica Chimica Acta., vol. 302, 1995, pp. 121-125.

Kumar, S., "Targeting DNA and RNA using Dimeric Aminoglycosides," A Dissertation Presented to the Graduate School of Clemson University, Clemson, South Carolina, 2011, 590 pages.

Kumar, S., et al., "Click Dimers to Target HIV TAR RNA Conformation," Biochemistry, vol. 51, 2012, pp. 2331-2347.

Lapidot, A., et al., "Structure-activity relationships of aminoglycoside-arginine conjugates that bind HIV-1 RNAs as determined by fluorescence and NMR spectroscopy," FEBS Lett., vol. 577, No. 3, 2004, pp. 415-421.

Leng, F. et al., "Ultratight DNA Binding of a New Bisintercalating Anthracycline Antibiotic," Biochemistry, vol. 37, No. 7, 1998, pp. 1743-1753.

Loontiens, F.G., et al., "Binding of Hoechst 33258 and 4',6'-Diamidino-2-phenylindole to Self-Complementary Decadeoxynucleotides with Modified Exocyclic Base Substituents," Biochemistry, vol. 30, No. 1, 1991, pp. 182-189.

Loontiens, F.G., et al., "Binding Characteristics of Hoechst 33258 with Calf Thymus DNA, Poly[d(A-T)], and d(CCGGAATTCCGg): Multiple Stoichiometries and Determination of Tight Binding with a Wide Spectrum of Site Affinities," Biochemistry, vol. 29, No. 38, 1990, pp. 9029-9039.

Loret, E. P., et al., "Circular dichroism and molecular modeling yield a structure for the complex of human immunodeficiency virus type 1 trans-activation response Rna and the binding region of Tat, the trans-acting transcriptional activator," Proc. Natl. Acad. Sci. USA, vol. 89, No. 20, 1992, pp. 9734-9738.

Luedtke, N. W., et al., "Fluorescence-Based Methods for Evaluating the RNA Affinity and Specificity of HIV-1 Rev-RRE Inhibitors," Biopolymers, vol. 70, No. 1, 2003, pp. 103-119.

Lynch, S. R. et al. "Structural Origins of Aminoglycoside Specificity for Prokaryotic Ribosomes," J. Mol. Biol., vol. 306, 2001, pp. 1037-1058.

Lynch, S. R., et al., "Structure of a Eukaryotic Decoding Region A-site RNA" J. Mol. Biol., vol. 306, 2001, pp. 1023-1035.

Marciniak, R. A., et al., "HIV-1 Tat Protein Trans-Activates Transcription In Vitro," Cell, vol. 63, No. 4, 1990, pp. 791-802.

Matsumoto, C., et al., "A High-Throughput Screening Utilizing Intramolecular Fluorescence Resonance Energy Transfer for the Discovery of the Molecules that Bind HIV-1 TAR RNA Specifically," Bioorg. & Med. Chem. Lett., vol. 10, No. 16, 2000, pp. 1857-1861.

Mei, H-Y, et al., "Inhibition of an HIV-1 Tat-Derived Peptide Binding to TAR RNA by Aminoglycoside Antibiotics," Bioorg. & Med. Chem. Lett., vol. 5, No. 22, 1995, pp. 2755-2760.

Miyaguchi, H., et al., "An antibiotic-binding motif of an RNA fragment derived from the A-site-related region of Escherichia coli 16S rRNA," Nucleic Acids Research, vol. 24, No. 19, 1996, pp. 3700-3706.

Moazed, D., et al., "Interaction of antibiotics with functional sites in 16S ribosomal RNA," Nature, vol. 327, No. 6121, 1987, pp. 389-394.

Murakami, A., et al., "Fluorescent-labelled oligonucleotide probes: detection of hybrid formation in solution by fluorescence polarization spectroscopy," Nucleic Acids Research, vol. 19, No. 15, 1991, pp. 4097-4102.

Nygren et al., The Interactions Between the Fluorescent Dye Thiazole Orange and DNA. Biopolymers 46 : 39 (1998).

Phanstiel, IV, O., et al., "The Effect of Polyamine Homologation on the Transport and Cytotoxicity Properties of Polyamin—(DNA-Intercalator) Conjugates," J. Org. Chem., vol. 65, Nos. 17-19, 2000, pp. 5590-5599.

Pilch, D.S., et al., "Berenil Binding to Higher Ordered Nucleic Acid Structures: Complexation with a DNA and RNA Triple Helix," Biochemistry, vol. 34, No. 49, 1995, pp. 16107-16124.

Pilch, D.S., et al., "Berenil [1,3-Bis(4'-amidinophenyl)triazene] Binding to DNA Duplexes and to a RNA Duplex: Evidence for Both Intercalative and Minor Groove Binding Properties," Biochemistry, vol. 34, No. 31, 1995, pp. 9962-9976.

Piotto, M., et al., "Gradient-tailored excitation for single-quantum NMR spectroscopy of aqueous solutions," J. Biomolecular NMR, vol. 2, No. 6, 1992, pp. 661-665.

Purohit, P., et al., "Interactions of a small RNA with antibiotic and RNA ligands of the 30S subunit," Nature, vol. 370, 1994, pp. 659-662.

Rajur, S.B., et al., "Hoechst 33258 Tethered by a Hexa(ethylene glycol) Linker to the 5'-Termini of Oligodeoxynucleotide 15-Mers: Duplex Stabilization and Fluorescence Properties," J. Org. Chem., vol. 62, Nos. 1-4, 1997, pp. 523-529.

Recht, M.I., et al., "RNA Sequence Determinants for Aminoglycoside Binding to an A-site rRNA Model Oligonucleotide," J. Mol. Biol., vol. 262, 1996, pp. 421-436.

Ren, J., et al., "Preferential Binding of 3,3'-Diethyloxadicarbocyanine to Triplex DNA," J. Am. Chem. Soc., vol. 122, No. 2, 2000, pp. 424-425.

Ren, J., et al., "Rapid Screening of Structurally Selective Ligand Binding to Nucleic Acids," Methods in Enzymology, vol. 340, 2001, pp. 99-108.

Rich, A., "DNA comes in many forms," Gene, vol. 135, Nos. 1-2, 1993, pp. 99-109.

Riguet, E., et al., "A route for preparing new neamine derivatives targeting HIV-1 TAR RNA," Tetrahedron, vol. 60, 2004, pp. 8053-8064.

Riguet, E., et al., "Neamine dimers targeting the HIV-1 TAR RNA," Bioorg. & Med. Chem. Lett., vol. 15, No. 21, 2005, pp. 4651-4655.

Riguet, E., et al., "A Peptide Nucleic Acid—Neamine Conjugate That Targets and Cleaves HIV-1 TAR RNA Inhibits Viral Replication," J. Med. Chem., vol. 47, No. 20, 2004, pp. 4806-4809.

Rostovtsev, V.V., et al., "A Stepwise Huisgen Cycloaddition Process: Copper(I)-Catalyzed Regioselective "Ligation" of Azides and Terminal Alkynes," Angew. Chem. Int. Ed., vol. 41, No. 14, 2002, pp. 2596-2599.

Roy, S., et al., "A bulge structure in HIV-1 TAR RNA is required for Tat binding and Tat-mediated trans-activation," Genes & Development, vol. 4, No. 8, 1990, pp. 1365-1373.

Santucci, R.A., et al., "Gentamicin for the Practicing Urologist: Review of Efficacy, Once-Daily Dosing and "Switch" Therapy," J. Urology, vol. 163, 2000, pp. 1076-1084.

Sehlstedt, U., et al., "Interactions of the Antiviral Quinoxaline Derivative 9-OH-B220 {2,3-dimethyl-6-(dimethylaminoethyl)-9-hydroxy-6H-indolo-[2,3-b]quinoxaline} with Duplex and Triplex Forms of Synthetic DNA and RNA," J. Mol. Biol., vol. 278, No. 1, 1998, pp. 31-56.

Sigma-Aldrich Product Information for Neomycin trisulfate salt hydrate. Downloaded (Aug. 25, 2014).

Sjöback, R., et al., "Characterization of Fluorescein-Oligonucleotide Conjugates and Measurement of Local Electrostatic Potential," Biopolymers, vol. 46, 1998, pp. 445-453.

Tok et al., Aminoglycoside Antibiotics are Able to Specifically Bind the 5-Untranslated Region of Thymidylate Synthase Messenger RNA. Biochemistry 38: 199 (1999).

Vicens, Q. et al., "Crystal Structure of Paromomycin Docked into the Eubacterial Ribosomal Decoding A Site," Structure, vol. 9, 2001, pp. 647-658.

Vicens, Q., et al., "RNA as a Drug Target: The Case of Aminoglycosides," Chembiochem, vol. 4, No. 10, 2003, pp. 1018-1023.

Wang, S., et al., "Binding of Neomycin to the TAR Element of HIV-1 RNA Induces Dissociation of Tat Protein by an Allosteric Mechanism," Biochemistry, vol. 37, No. 16, 1998, pp. 5549-5557.

(56) References Cited

OTHER PUBLICATIONS

Wang, Y., et al., "Specificity of Aminoglycoside Binding to RNA Constructs Derived from the 16S rRNA Decoding Region and the HIV-RRE Activator Region," Biochemistry, vol. 36, No. 4, 1997, pp. 768-779.

Wang, H., "Design, Synthesis and RNA Binding of Aminoglycoside Antibiotics," (Ph.D ed.), A Dissertation submitted to the University of California, San Diego, California, 1998, 164 pages.

Wang et al., RNA Molecules That Specifically and Stoichiometrically Bind Aminoglycoside Antibiotics with High Affinites. Biochemistry 38: 199 (1999).

Warshel, A., "Electrostatic Basis of Structure-Function Correlation in Proteins," Acc. Chem. Res., vol. 14, 1981, pp. 284-290.

Watkins, D. et al. "A fluorescence-based screen for ribosome binding antibiotics," Anal. Biochemistry, vol. 434, 2013, pp. 300-307.

Wei, A-P, et al., "Antibody-Mediated Fluorescence Enhancement Based on Shifting the Intramolecular Dimer <-> Monomer Equilibrium of Fluorescent Dyes," Anal. Chem., vol. 66, No. 9, 1994, pp. 1500-1506.

Weiner, P. K., et al., "Electrostatic potential molecular surfaces," Proc. Natl. Acad. Sci. USA, vol. 79, 1982, pp. 3754-3758.

Weinstein, H., et al., "A Theoretical and Experimental Study of the Semirigid Cholinergic Agonist 3-Acetoxyquinuclidine," Mol. Pharmacol., vol. 11, 1975, pp. 671-689.

Willis, A., III, et al., An Expanding View of Aminoglycoside-Nucleic Acid Recognition, Advances in Carbohydrate Chemistry and Biochemistry, vol. 60, 2006, pp. 251-302.

Willis, A., III, et al., "Major Groove Recognition of DNA by Carbohydrates," Current Org. Chem., vol. 10, No. 6, 2006, pp. 663-673.

Willis, B., et al., "Recognition of B-DNA by Neomycin—Hoechst 33258 Conjugates," Biochemistry, vol. 45, No. 34, 2006, pp. 10217-10232.

Willis et al., Triple Recognition of B-DNA by a Neomycin-Hoechst 33258-Pyrene Conjugate. Biochemistry 49 : 452 (2010-ePub = Dec. 9, 2009).

Xavier, K.A., et al., "RNA as a drug target: methods for biophysical characterization and screening," Trends Biotechnol, vol. 18, No. 8, 2000, pp. 349-356.

Xi H. et al. "Calorimetric and spectroscopic studies of aminoglycoside binding to AT-rich DNA triple helices," Biochimie, vol. 92, 2010, pp. 514-529.

Xi, H. et al., "Thermodynamics of Nucleic Acid "Shape Readout" by an Aminosugar," Biochemistry, vol. 50, 2011, pp. 9088-9113.

Xu, Y., et al., "A Novel 5'-Iodonucleoside Allows Efficient Nonenzymatic Ligation of Single-stranded and Duplex DNAs," Tetrahedron Lett., vol. 38, No. 32, 1997, pp. 5595-5598.

Xu, Z., et al., "Modulation of Nucleic Acid Structure by Ligand Binding: Induction of a DNA•RNA•DNA Hybrid Triplex by DAPI Intercalation," Bioorg. & Med. Chem., vol. 5, No. 6, 1997, pp. 1137-1147.

Yajima, S., et al., "Neamine derivatives having a nucleobase with a lysine or an arginine as a linker, their synthesis and evaluation as potential inhibitors for HIV TAR-Tat," Bioorg. & Med. Chem., vol. 14, No. 8, 2006, pp. 2799-2809.

Yang, P., et al., "Engineering Bisquinolinium/Thiazole Orange Conjugates for Fluorescent Sensing of G-Quadruplex DNA," Angew. Chem., Int. Ed., vol. 48, 2009, pp. 2188-2191.

Zaman, G. J. et al., "Targeting RNA: new opportunities to address drugless targets," Drug Discovery Today, vol. 8, No. 7, 2003, pp. 297-306.

Zimmer, C., et al., "Nonintercalating DNA-Binding Ligands: Specificity of the Interaction and Their Use as Tools in Biophysical, Biochemical and Biological Investigations of the Genetic Material," Prog. Biophysics & Mol. Biol., vol. 47, Issue 1, 1986, pp. 31-112.

* cited by examiner

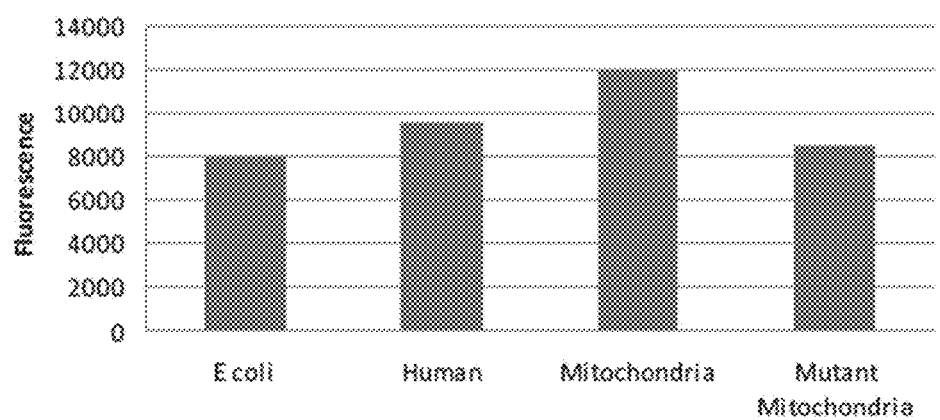

METHODS AND COMPOSITIONS RELATED TO NUCLEIC ACID BINDING ASSAYS

CROSS-REFERENCE TO RELATED APPLICATIONS

This application is a continuation of U.S. patent application Ser. No. 13/939,950, filed Jul. 11, 2013, which claims the benefit of priority to U.S. Provisional Application No. 61/670,141, filed on Jul. 11, 2012, both of which are incorporated herein by reference in their entirety.

STATEMENT REGARDING FEDERALLY SPONSORED RESEARCH

This invention was made with Government Support under Grant 1R15CA125724 and R41GM097917 awarded by the National Institutes of Health. The government has certain rights in the invention.

SEQUENCE LISTING/TABLE/COMPUTER PROGRAM LISTING

The present disclosure includes a sequence listing either submitted herewith or transferred herewith from a parent application in computer readable form. This sequence listing is hereby incorporated by reference.

TECHNICAL FIELD

The subject matter disclosed herein generally relates to nucleic acid probes and the methods of use. The subject matter disclosed herein further relates to the method of making the nucleic acid probes and use in high through put screening.

BACKGROUND

Fluorescently-tagged aminoglycosides have been synthesized by randomly coupling amine-reactive fluorescent dyes to amino groups of these antibiotics [Hamasaki & Rando, 1998; Tok, Cho, & Rando, 1999]. However, they are unsatisfactory for use in high-throughput screens because 1) amino groups critical for high affinity binding of the ribosomal RNA A-site have been modified and 2) the ribosomal RNA A-site binding does not change their fluorescence intensity and binding constants can only be extracted by monitoring changes in fluorescence anisotropy.

It is desirable to have nucleic acid probes which bind all type of nucleic acid, such as double stranded DNA, RNA, four stranded DNA/RNA or major groove interactors. The disclosed compositions and methods provide solutions to these problems in the art. The disclosed compositions and methods provide nucleic acid probes that will bind all forms of nucleic acid, and which will bind in such a way that the functional groups involved in DNA interactions are not used to attach the fluorescent tags.

SUMMARY

In accordance with the purposes of the disclosed materials, compounds, compositions, articles, devices, and methods, as embodied and broadly described herein, the disclosed subject matter, in one aspect, relates to nucleic acid probes and methods for preparing the probes and using them. Further, the subject matter disclosed herein relates to assay methods, including high through-put screening methods using the nucleic acid probes disclosed herein.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

FIG. 12 shows the binding of F-neo (42a) to *E. coli*, Human, Mitochondria, and Mutant Mitochondria A-site oligonucleotide.

Like reference numbers and designations in the various drawings indicate like elements.

DETAILED DESCRIPTION

Figure 1:
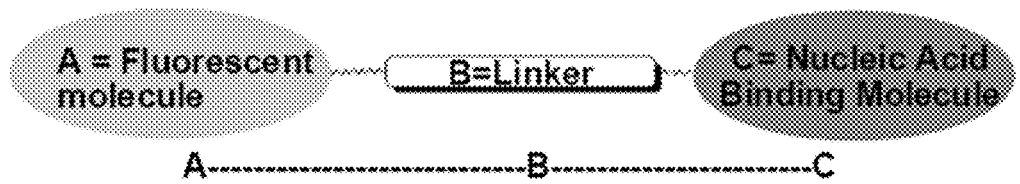
FIG. 1 is a schematic diagram showing a design of disclosed probes for nucleic acid targeted screening.

The present disclosure now will be described more fully hereinafter with reference to specific exemplary embodiments. Indeed, the present disclosure can be embodied in many different forms and should not be construed as limited to the embodiments set forth herein.

Nucleic acids are well known drug targets. (Dervan, 2001) (Autexier, 1999; Ecker & Griffey, 1999; Hurley et al., 2000; Mergny & Helene, 1998b; Oganesian & Bryan, 2007; Vicens & Westhof, 2003; Winters, 2000; Zaman, Michiels, & van Boeckel, 2003). Numerous antibacterial and anticancer drugs target nucleic acids such as DNA and RNA. (De et al., 2008; Mergny & Helene, 1998a; Shaw & Arya, 2008; Tor, 2003; Vicens & Westhof, 2003) A rapid way to facilitate nucleic acid target drug discovery is the development of methods and probes for high throughput screening for small molecules that bind nucleic acids such as DNA and RNA. While there are a number of planar molecules that intercalate between DNA and RNA base pairs, drugs that bind to the grooves of DNA and RNA structures are expected to be more selective due to the differences in groove sizes and widths of different nucleic acids. (Xi, Davis, Ranjan, Xue, Hyde-Volpe, & Arya, 2011a) (Hamilton & Arya, 2012) Therefore it is essential to have such groove binders as lead molecules for development of probes that can facilitate the discovery of more selective and higher affinity molecules.

Aminoglycosides are well known ribosome binding antibacterial drugs. (Arya, 2005; Arya, 2007; Willis & Arya, 2006b) However recent work by Arya has shown that a number of aminoglycosides bind nucleic acid grooves that include a variety of nucleic acid structures such as DNA duplex, (Hamilton & Arya, 2012; Kumar, Xue, & Arya, 2011; Willis & Arya, 2010) triplex, (Arya, 2011; Xi, Kumar, Dosen-Micovic, & Arya, 2010; Xue et al., 2010) quadruplex, (Ranjan, Andreasen, Kumar, Hyde-Volpe, & Arya, 2010; Xue, Ranjan, & Arya, 2011) DNA. RNA hybrid duplex and triplex, (Arya, Jr., & Charles, 2001; Shaw & Arya, 2008; Shaw, Xi, & Arya, 2008) poly A (Xi, Gray, Kumar, & Arya, 2009) in addition to RNA targets such as rRNA, HIV TAR RNA, etc. (Arya, Shaw, & Xi, 2007; Charles, Xi, & Arya, 2007)

Herein, nucleic acid probes, such as aminoglycoside based fluorescent probes (Scheme 1), are disclosed.

Scheme 1. Structure of fluorecein-neomycin (F-neo) probe 42a

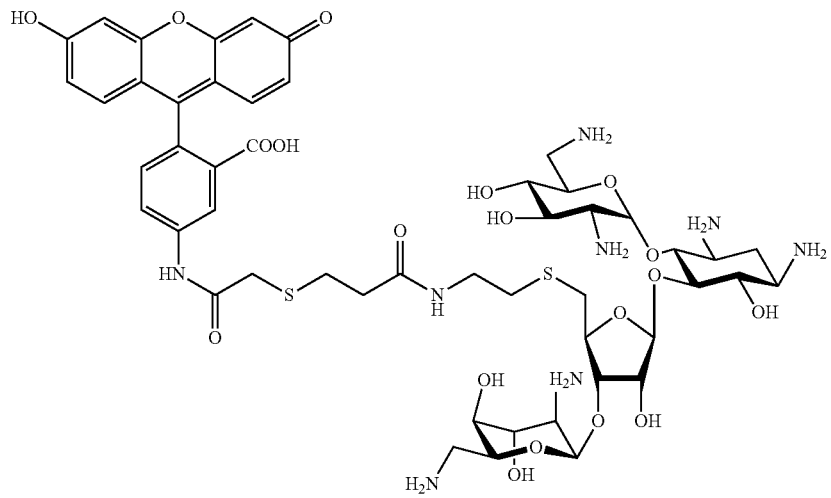

These disclosed probes can be used for discovery of numerous nucleic acid binding drugs. Nucleic acid targeted screening has mostly relied on the labeling of the nucleic acid target by a fluorophore. (Karn & Prescott, 2003; Knowles, Karn, Murchie, & Lentzen, 2001) This labeling can affect the conformation/structure of the target nucleic acid. Attempts to develop small molecule (e.g. aminoglycoside) based probes have shown some ability to allow screening against a few nucleic acid targets such as RNA and the ribosome. (Hamasaki & Rando, 1998; Tok, Cho, & Rando, 1999)(Ma et al., 2005; Rando & Wang, 1996) However, even in these limited applications, the chemistry employed in these applications to conjugate the fluorescent probe required the use of amino groups on the aminoglycosides. This poses significant problems because these amino groups are inherently required for binding to nucleic acid targets. (Tok, Cho, & Rando, 1999). (Ma et al., 2005; Rando & Wang, 1996).

Amino groups are critical in aminoglycoside binding to nucleic acids. Structural (NMR and X-ray) data has clearly shown the critical role protonated amino groups play in aminoglycoside binding (Lynch and Puglisi 2001b; Lynch and Puglisi 2001a; Blanchard, et al. 1998)(Vicens and Westhof 2001; Hermann and Westhof 1998; François, et al). Evidence for the role of amino groups in binding to negatively charged nucleic acids also comes from the fact that substitution of an amino group (neomycin vs. paromomycin) leads to order(s) of magnitude differences in affinity (Arya 2011; Xi, et al. 2010; Arya, et al. 2003; Arya, et al. 2001). ITC and NMR studies have clearly shown that protonation of aminoglycoside amino groups is critical upon binding to negatively charged RNA and DNA structures (Xi, et al. 2010; Barbieri and Pilch 2006; Kaul, et al. 2003; Kaul and Pilch 2002).

Additionally, the lack of selectivity of reacting different amines to fluorophore nucleophiles in these embodiments has produced low yields. Attempts were made to better control the selectivity of functionalization of the aminoglycosides by using a metal based approach. (Ghoshal M. & Salamone, 2010). This embodiment however also used the amino groups on aminoglycosides required for binding to nucleic acid targets.

Disclosed herein are nucleic acid probes, such as fluorescent aminoglycoside molecules, where fluorescent molecules (e.g. fluorescein, pyrene, methidium, thiazole orange etc) are covalently attached to monomeric aminoglycosides or dimeric aminoglycosides via selective conversion of OH groups on aminoglycosides to reactive groups such as amine, carboxylic acid, isothiocyanate, azide, or alkyne. These fluorescent probes bind to a number of nucleic acids such as DNA and RNA and can be displaced by small molecules. The probes are shown here to function in a high throughput format for a number of nucleic acid targets with a Z'>0.5.

The identification of drugs that bind specifically in the major groove is an important aspect of drug development. The major groove of nucleic acids contains more information for sequence recognition than that of the minor groove due to the greater variability of facial functional groups available in the grooves. In order to increase the specificity of nucleic acid binding molecules, it is important to identify lead compounds that bind to the major groove. The ability of the neomycin based fluorescent probes to discriminate between molecules that interact in the major minor groove demonstrates that the probes will be useful in the screening for drugs that bind specifically to the major groove.

In addition to the screening of small molecules that bind to the major groove, a logical extension of the use of these fluorescent probes is in the investigation of nucleic acid binding proteins or other macromolecules. Similar to the competitive binding assays for the small molecules, the displacement of the probes by transcription factors, ribosomal proteins, or other nucleic acid binding proteins would identify proteins that bind within the major groove of nucleic acids. Incubation of a nucleic acid binding protein with the nucleic acid probe would result in a change in the fluorescent signal, compared to the nucleic acid probe alone, only if the nucleic acid probe was displaced through interactions within the major groove.

Additionally, provided is the combining of a probe based competition assay with mutated or truncated proteins to identify the domains and residues that interact with major groove of the nucleic acids. The interactions of residues of a protein with the major groove are typically key elements of a protein's recognition and affinity with nucleic acids. Current methods of measuring the effect of mutations to a protein's binding affinity, such as filter binding and mobility shift assays, are slow, requiring multiple steps, and in many cases require radio-labeled nucleic acid, and only give information on the effects of the mutation on binding affinity. Random or directed mutations of suspected interacting residues could be quickly screened for their interactions within the major groove by comparing the change in the fluorescent signal (i.e., the displacement of the probe described herein) as a function of the mutation introduced. The probe-based assay is fast, uses a single step following the purification of the protein in a standard lab environment, and is capable of screening the effects of multiple mutations in a high throughput format.

The disclosed assays can be performed in a variety of ways, with a variety of steps. For example, some of the steps that can be present in the assays for inhibitors, such as inhibitors of DNA-protein interactions using, for example, a neomycin-thiazole orange (TO-neo) conjugate can include: Setting the fluorescence value of the nucleic acid probe, such as TO-neo alone to zero and setting the value of the nucleic acid probe, such as TO-neo, bound to the nucleic acid target to one.

The assays can be performed at different stoichiometric ratios of nucleic acid and nucleic acid probe, such as a 1:1, 1:2, 1:5, 5:1, or 2:1 ratio of the nucleic acid to nucleic acid probe.

Often there is some type of displacement step, where the nucleic acid bound nucleic acid probe (such as TO-neo, or any fluorescent probe as disclosed herein) is displaced from the nucleic acid, by the normal nucleic acid binding partner, such as a known drug or a known nucleic acid binding protein, such as a DNA binding protein, or even an unknown DNA binding molecule, such as a protein. These displacement steps can be performed at a variety of molar stoichiometries, of known nucleic acid binding molecule to the nucleic acid probe:nucleic acid complex, such as a 1:1, 1:2, 1:5, 5:1, or 2:1 ratio. This step can be performed by incubating the nucleic acid probe:nucleic acid complex with the known DNA binding protein or ligand/drug for example.

As discussed herein, the fluorescent emission of the nucleic acid probes will change based on binding or non-binding to DNA, and so binding of the nucleic acid probe to the nucleic acid, or displacement of the nucleic acid probe from the nucleic acid, or new binding of the nucleic acid probe to the nucleic acid can be done using standard fluorescent measurement devices and techniques. For example, fluorescent measurements can and have been taken using a plate reader in a 96 well Greiner black plate.

The emission of fluorescence can be measured at appropriate wavelength for the given nucleic acid probe. For example, for TO-neo, the emission is measured at wavelength 535 nm, using an excitation wavelength of 485 nm, averaging the results from multiple measurements.

As there are a number of binding steps in the disclosed assays, such as nucleic acid probe binding nucleic acid, displacement binding steps, and so forth, a variety of buffer conditions can be used for these binding steps. For example, most nucleic acid binding proteins bind under similar buffer conditions as those shown here for TO-neo binding (10 mM hepes (7.0), 50 mM NaCl, and 0.4 mM EDTA) and would be adaptable to specific assay conditions.

As the displacement step displaces the nucleic acid probe, there is a change in fluorescence emission. For example, when displacement of the TO-neo by the nucleic acid binding protein or ligand/drug occurs, this results in a decrease in fluorescence, if the protein or ligand/drug binding occurs in the major groove, as a function of affinity of the protein or ligand/drug compared to TO-neo affinity. A detailed discussed is disclosed by Watkins et al. in Ananlytical Biochemistry 434 (2013) 300-307 entitled "A fluorescence-based screen for ribosome binding antibiotics", which is incorporated herein by reference in its entirety.

An additional aspect to the disclosed assays can be to look at unknown ligands for DNA binding, i.e. molecules which may or may not have affinity for the major groove or DNA, or some other form of nucleic acid, such as A-form. These unknown ligands can be used in a displacement step, and their relative abilities to displace the nucleic acid probe, such as TO-neo, can be determined. For example, when performed on major groove nucleic acid, ligands that displace TO-neo from the DNA would be expected to compete with the major groove binding protein and lead to identification of inhibitors of DNA-protein interactions.

As discussed herein, the ability to bind a major groove, or a minor groove of DNA or RNA or the A-form or B form helix, or even quaternary complexes, depends on the aminoglycoside, whether the aminoglycoside is a homodimerized to another aminoglycoside or even another type of molecule, such as planar molecules, for example Hoechst 33258. The disclosed compounds and compositions, along with the disclosed chemistries are able to make any combination of a fluorescent molecule, a linker, and an aminoglycoside, in either monomeric, homo or hetero dimeric form, or derivatized form, with a non-aminoglycoside molecule, such as Hoechst 33258.

Compositions

The disclosed compositions provide nucleic acid probes which comprise a fluorophore moiety, a linker moiety, and a Nucleic acid binding moiety illustrated in FIG. 1. In certain embodiments, the fluorophore molecule is attached to the Nucleic acid binding moiety through the linker such that the primary amine groups of the Nucleic acid binding moiety remain free. In certain embodiments, the primary amine groups of the Nucleic acid binding moiety remain free because the linker is attached to the Nucleic acid binding moiety via, for example, the hydroxyl groups functionalized to yield ester, amide, and triazole linkages. The linkage can be any functional group that that would not use the amino groups of the aminoglycoside for linkage. Disclosed are linkages with an aminoglycoside where the linkage occurs through the hydroxyl group of an aminoglycoside. Thus, after attachment of the linker to the Nucleic acid binding moiety, the primary, secondary, or guanidino amino groups of the Nucleic acid binding moiety remain as primary, secondary, or guanidino amino groups. The nucleic acid binding moieties can include the molecules disclosed herein, including aminoglycosides, homo and heterodimer of aminoglycosides, as well as other nucleic acid binding molecules, such as bisbenzamide dyes.

Nucleic Acid Binding Moieties

The nucleic acid binding moieties as disclosed herein, contain at least one aminosugar, aminoglycoside, or aminoalcohol moiety. An aminosugar is any molecule that has a sugar that has an amino group in it. An aminoglycoside is any molecule having aminosugars in glycosidic linkage. An aminoalcohol is any molecule that has an amino and a hydroxyl. The disclosed nucleic acid binding molecules can be aminoglycosides conjugated to another aminoglycoside, either the same or different, or aminoglycosides conjugated to other molecules having affinity for nucleic acid, such as planar molecules, for example Hoechst 33258. Examples of nucleic binding moieties can be found in Scheme 2.

Scheme 2. Structures of aminosugars and dimeric aminosugars with possible sites of attachment.

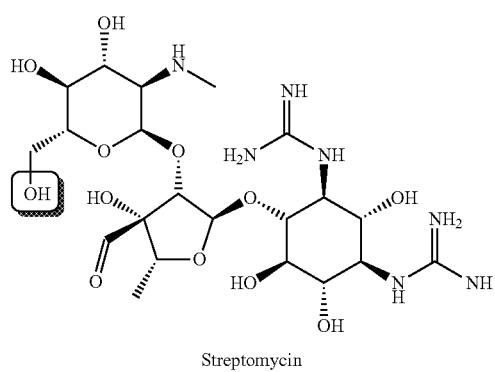

Streptomycin

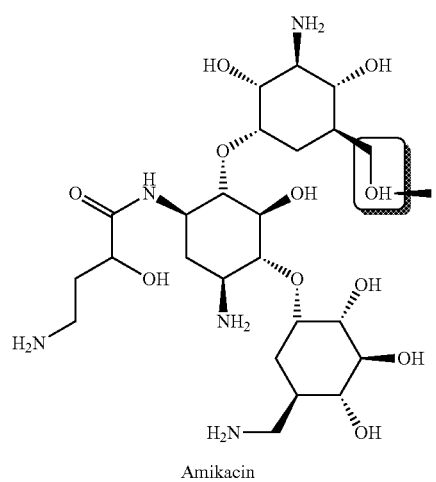

Amikacin

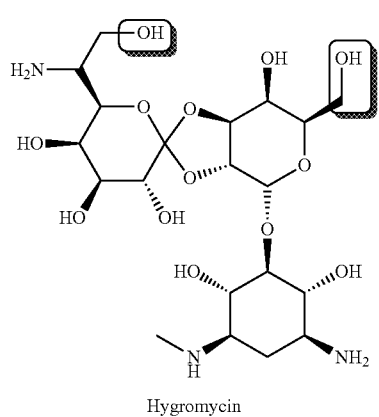
Hygromycin
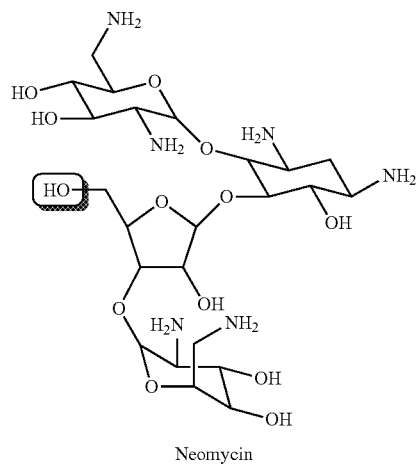
Neomycin
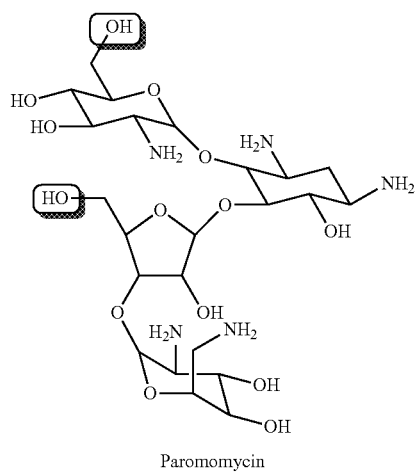
Paromomycin
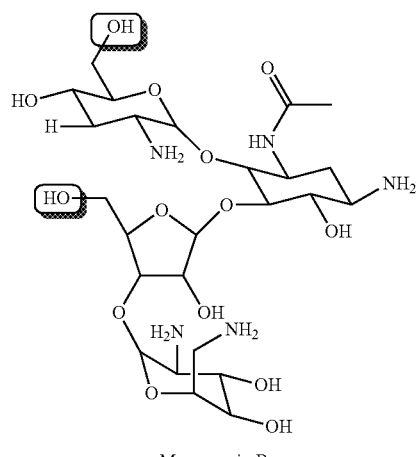
Monomycin B
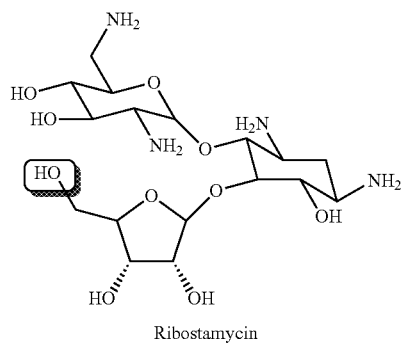
Ribostamycin
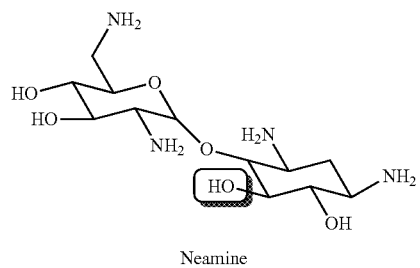
Neamine 11
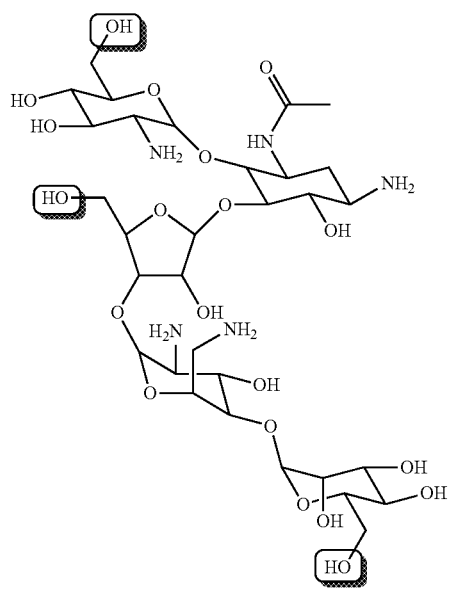
Lividomycin A
12
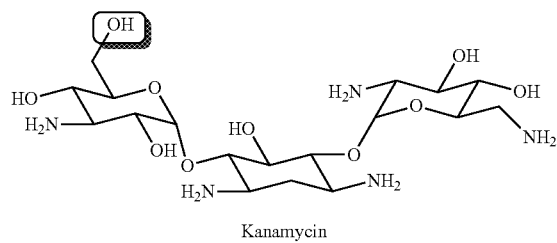
Kanamycin
53
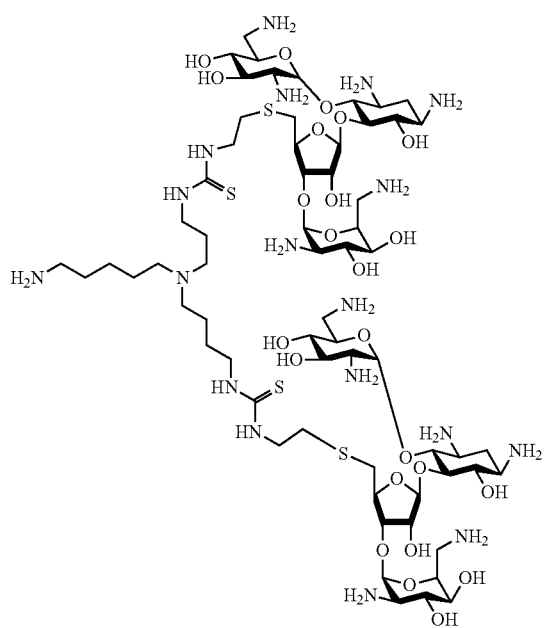
54
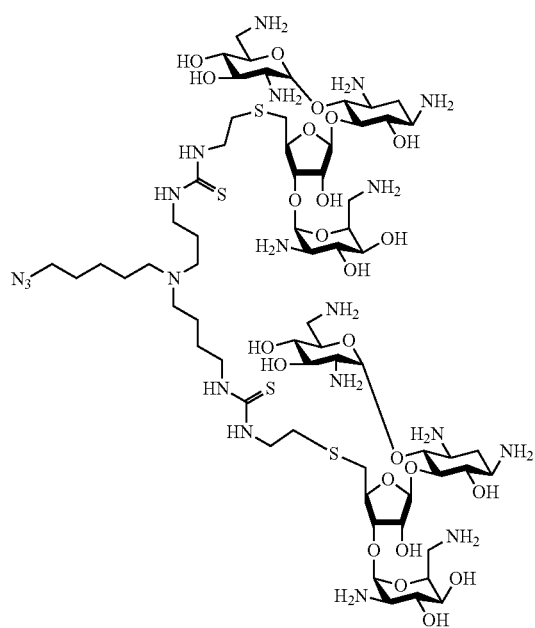

-continued

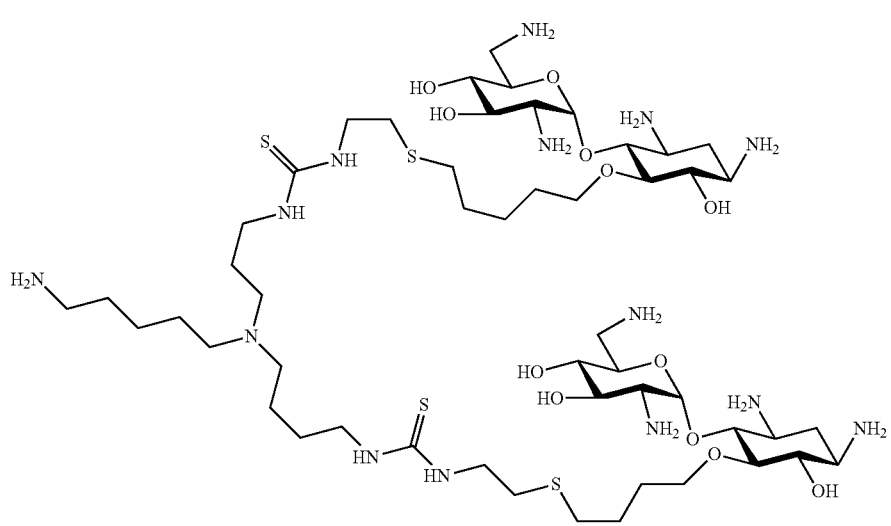

55

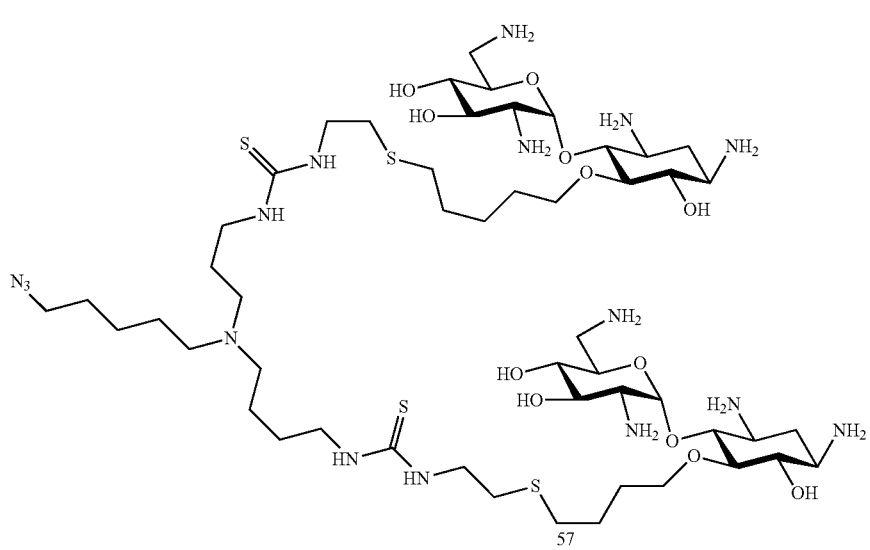

56

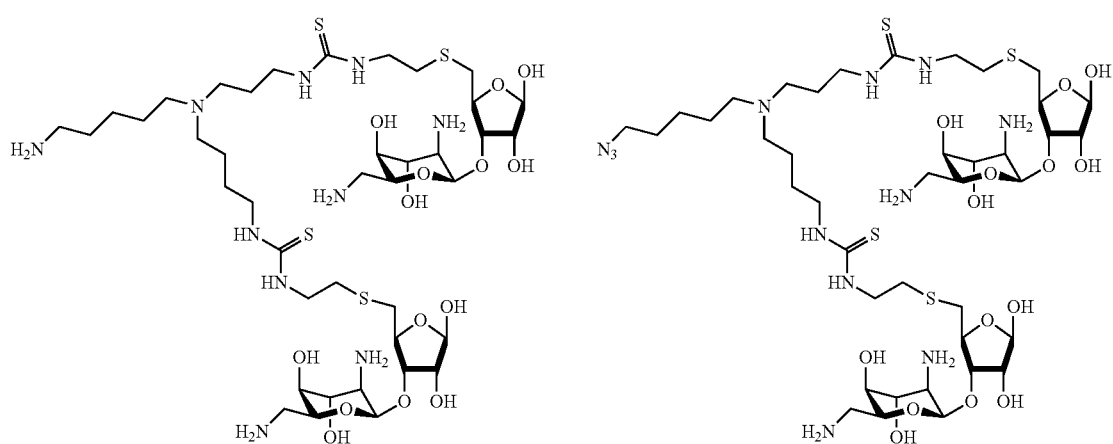

Aminoglycosides

PCT/US2006/029675 by Dev P. Arya filed on Jul. 31, 2006 is herein incorporated by reference in its entirety, but at least for material related to aminoglycosides, nucleic acids, and conjugates of these, as well as structural information of nucleic acids.

Aminoglycoside antibiotics are bactericidal drugs that have been at the forefront of antimicrobial therapy for almost five decades. The past decade (1990-2000) saw a resurgence in aminoglycoside-based drug development as their chemistry/mechanism of action became better understood. This work, however, had almost exclusively focused on targeting RNA.

Aminoglycosides are a group of antibiotics that are effective against certain types of bacteria. Those which are derived from *Streptomyces* species are named with the suffix-mycin, while those which are derived from *micromonospora* are named with the suffix-micin. The aminoglycosides are polar-cations which consist of two or more amino sugars joined in a glycosidic linkage to a hexose nucleus, which is usually in a central position. (Chow C S, et al (1997) Chem Rev 97:1489). Though they exhibit a narrow toxic/therapeutic ratio, their broad antimicrobial spectrum, rapid bactericidal action, and ability to act synergistically with other drags makes them highly effective in the treatment of nosocomial (hospital acquired) infections (Kotra L P, et al (2000) J Urol 163:1076). They are clinically useful in the treatment of urinary tract infections (Santucci R, et al (2000) J Urol 163:1076), lower respiratory infections, bacteremias, and other superinfections by resistant organisms (Forge A, et al (2000) Audio Neurootol 5:3). Their greatest potential has been in combination drug regimens for the treatment of infections that are difficult to cure with single agents and for use in patients who are allergic to other classes of drugs (Gerding D (2000) Infect Control Hosp Epidemiol 21: S12). Aminoglycosides contain a unique polyamine/carbohydrate structure, and have attracted considerable attention because of their specific interactions with RNA (Kaul M, et al (2003) J Mol Biol 326:1373). The bactericidal action of aminoglycosides is attributed to the irreversible inhibition of protein synthesis following their binding to the 30S subunit of the bacterial ribosome and thus interfering with the mRNA translation process. The miscoding causes membrane damage, which eventually disrupts the cell integrity, leading to bacterial cell death (Moazed D, et al (1987) Nature 327:389; Purohit P, et al (1994) Nature 370:659; Recht M I, et al D (1996) J Mol Biol 262:421; Miyaguchi H, et al (1996) Nucleic Acids Res 24:3700).

Aminoglycosides include: amikacin, apramycin, arbekacin, bambermycins, butirosin, dibekacin, dibekacin, dihydrostreptomycin, fortimicin, geneticin, gentamicins (e.g., gentamicin A, Cl, CIa, C2 and D), isepamicin, kanamycins (e.g. kanamycin A, B, and C), lividomycin, micronomicin, neamine, neomycins (e.g. neomycin B and C), netilmicin, paromomycin, ribostamycin, sisomicin, spectinomycin, streptomycin, streptonicozid, tobramycin, trospectomycin, and viomycin, analogs and derivatives thereof. The free bases, as well as pharmaceutically acceptable acid addition salts of these aminoglycoside antibiotics, can be employed.

Neomycin

In 1995, Mei and co-workers discovered that aminoglycoside antibiotics were able to inhibit Tat peptide binding to the TAR RNA (Mei 1995). They discovered the $IC_{50}$ values for neomycin, streptomycin, and gentamicin to be 0.92±0.09 µM, 9.5±0.8 µM, and 45±4 µM, respectively. Their study also determined that the aminoglycosides were bound to the duplex region of the RNA, directly below the bulge used for identification by Tat, and that neomycin B was able to form higher order complexes with the TAR. Further studies on the interactions of neomycin with TAR have since been completed, with up to three binding sites identified (Krebs, Ludwig et al. 2003), suggesting that dimeric and trimeric aminoglycosides could provide better specificity to TAR. From further studies (CD spectroscopy), it appears that the binding by neomycin induces a conformational change in the RNA, which is different from the usual architecture that Tat recognizes, acting as a noncompetitive inhibitor of the Tat-TAR interaction and increasing the rate constant ($k_{off}$) for the dissociation of the peptide (Wang, Huber et al. 1998). Wang et al. also determined that the aminoglycoside binds TAR in the minor groove, opposite to the major groove binding normally seen. Recently NMR was used to examine the structural changes that neomycin induces in the TAR RNA; it was found that the neamine core is covered with the bulge, thereby reducing the volume of the major groove in which Tat is normally bound (Faber, Sticht et al. 2000).

The conjugation of fluorescein with neomycin (F-neo, 42a, Scheme 1) allows the molecule to detect the specific binding of the probe to the RNA grooves, DNA major grooves, quadruplex and triplex grooves. The binding affinity of the F-neo (42a) also varies slightly with the sequence of the nucleic acid strands and small differences in sequences can be determined by differences in the fluorescent signal.

The conjugated molecule of fluorescein with the neomycin dimer (79) allows the probe to be directed toward long sequences of DNA (10-14 base pairs). As with the monomer form, F-neodimer 79 allows the detection of DNA sequences by the change in fluorescence by binding in the major groove of DNA.

Major Groove Binders

A major groove binder is a composition or compound which can bind the major groove of duplex nucleic acid. It is understood that there are B-major groove binders which bind B-form duplex and A-major groove binders which bind A-form duplex. It is understood that the disclosed probe can be either B-major groove binders, A-major groove binders or major groove binders for DNA conformations between A and B. The major groove binders disclosed are exemplary only.

Minor Groove Binders

A minor groove binder is a composition or compound which can bind the minor groove of duplex DNA. It is understood that there are B-minor groove binders which bind the minor groove of B-form duplex and A-minor groove binders which bind the minor groove of A-form duplex. It is understood that the disclosed probe can have either be A-minor groove binders or B-minor groove binders conjugated to it. The minor groove binders disclosed below are exemplary only.

Minor groove recognition relies on van der Waals' contacts, hydrogen bonds, Coulombic attraction and intrinsic properties of the DNA such as flexibility, hydration and electrostatic potential. Successful minor groove binding ligands typically consist of heterocyclic units such as pyrrole or imidazole groups linked by amides. The flexibility of the single bonds between the heterocyclic groups and the amide linkages is crucial to successful minor groove recognition since the ligand is able to adopt a twist that matches the helical winding of the DNA, thereby permitting the ligand to maintain contact with the DNA over the foil length of its recognition site. Two thoroughly studied minor groove binders (MGBs) are Hoechst 33258 (Hoechst) and DAPI, which bind preferentially at AT-rich regions of B-DNA. Also disclosed are minor groove binders, such as polyamides, that preferentially bind GC-rich regions.

Aminoglycoside Homo and Hetero Dimers

A variety of dimers of aminoglycosides can be conjugated together within the disclosed compounds and compositions. For example, certain types of dimers with certain types of linkages are disclosed in US Patent Application Publication No. 2011/0046982A1 (herein disclosed and incorporated by reference in its entirety, and at least for dimers and conjugates of aminoglycosides and their synthesis). Other dimers and conjugate of aminoglycosides can be found in WO/2007/016455 (herein disclosed and incorporated by reference in its entirety, and at least for dimers and conjugates of aminoglycosides and their synthesis).

Molecules Having an Affinity for Nucleic Acid

A variety of molecules having an affinity for nucleic acid can be conjugated to one or more aminoglycosides. The bisbenzimide dyes—Hoechst 33258, Hoechst 33342 and Hoechst 34580 are cell membrane-permeate, minor groove-binding DNA stains that fluoresce bright blue upon binding to DNA. Hoechst 33342 has slightly higher membrane permeability than Hoechst 33258, but both dyes are quite soluble in water (up to 2% solutions can be prepared) and relatively nontoxic. Hoechst 34580 has somewhat longer-wavelength spectra than the other Hoechst dyes when bound to nucleic acids. These Hoechst dyes, which can be excited with the UV spectral lines of the argon-ion laser and by most conventional fluorescence excitation sources, exhibit relatively large Stokes shifts (spectra) (excitation/emission maxima–350/460 nm), making them suitable for multicolor labeling experiments. The Hoechst 33258 and Hoechst 33342 dyes have complex, pH-dependent spectra when not bound to nucleic acids, with a much higher fluorescence quantum yield at pH 5 than at pH 8. Their fluorescence is also enhanced by surfactants such as sodium dodecyl sulfate (SDS). These dyes appear to show a wide spectrum of sequence-dependent DNA affinities and bind with sufficient strength to poly(d(A-T)) sequences that they can displace several known DNA intercalators. They also exhibit multiple binding modes and distinct fluorescence emission spectra that are dependent on dye:base pair ratios. Hoechst dyes are used in many cellular applications, including cell-cycle and apoptosis studies and they are common nuclear counter stains. Hoechst 33258, which is selectively toxic to malaria parasites, is also useful for flow-cytometric screening of blood samples for malaria parasites and for assessing their susceptibility to drugs; however, some of the SYTO dyes (cyanine derivatives) disclosed herein are likely to provide superior performance in these assays.

The Hoechst 33258 and Hoechst 33342 dyes are available as solids (H1398, H1399), as guaranteed high-purity solids (FluoroPure Grade; H21491, H21492) and, for ease of handling, as 10 mg/mL aqueous solutions (H3569, H3570). The Hoechst 34580 dye is available as a solid (H21486).

Others

It has been previously shown that distamycin A binds to the minor groove of B-form dsDNA (Zimmer C. and Wahnert, U. (1986) Prog. Biophys. Mol. Biol., 47, 31-112). Distamycin A has been shown to preferably bind to DNA duplex tracts containing a 5 bp A-T tract (Kopka M. L., Yoon, C., Goodsell, D., Pjura, P. and Dickerson, R. E. (1985) Proc. Nat. Acad. Sci. USA, 82, 1376-1380). Netropsin, on the other hand, preferentially binds to a DNA duplex tract containing a 4 bp A-T tract (Kopka M. L., Yoon, C., Goodsell, D., Pjura, P. and Dickerson, R. E. (1985) Proc. Nat. Acad. Sci. USA, 82, 1376-1380).

Among minor groove binders, the N-methylpyrrole carboxamide-containing antibiotics netropsin and distamycin bound to DNA with very pronounced AT specificity, as expected. More interestingly the dye Hoechst 33258, berenil and a thiazole-containing lexitropsin elicited negative reduced dichroism in the presence of GC-rich DNA which is totally inconsistent with a groove binding process. These three drugs share with DAPI the property of intercalating at GC-rich sites and binding to the minor groove of DNA at other sites. (Bailly, C, et al. 1992. Drug-DNA sequence-dependent interactions analysed by electric linear dichroism. Journal of Molecular Recognition. 5:4 (155-171).

4-[(3-Methyl-6-(benzothiazol-2-yl)-2,3-dihydro-(benzo-1,3-thiazole)-2-methylidene)]-1-methyl-pyridinium iodide (BEBO) is an asymmetric monovalent cyanine dye that binds in the minor groove of double-stranded (ds)DNA. (Bengtsson, M, et al. A new minor groove binding asymmetric cyanine reporter dye for real-time PCR. Nucleic Acids Res. 2003 Apr. 15; 31(8): e45). Similarly to that of DAPI and Hoechst, the binding of BEBO to poly(dG-dC)$_2$ is dominated by intercalation, and BEBO has a distinct preference for poly(dA-dT)$_2$ compared to poly(dG-dC)$_2$.

As judged from the linear and circular dichroism studies, the benzoxazole derivative BOXTO (4-[6-(benzoxazole-2-yl-(3-methyl-)-2,3-dihydro-(benzo-1,3-thiazole)-2-methylidene)]-1-methyl-quinolinium chloride) exhibited straightforward minor groove binding both to poly(dA-dT)$_2$ and calf thymus DNA (ctDNA), whereas the benzothiazole derivative BEBO showed a more heterogenous binding to the latter DNA, also with a greater tendency for aggregation. (Karlsson, H J, et al. Groove-binding unsymmetrical cyanine dyes for staining of DNA: syntheses and characterization of the DNA-binding. Nucleic Acids Res. 2003 Nov. 1; 31(21): 6227-6234).

Linker Moieties

The linker can comprise a backbone of less than 50 atoms, 40 atoms, 30 atoms, 20 atoms, and/or alone or in any combination with any other limitation or characteristic disclosed herein. Exemplary linkers are shown in Scheme 3.

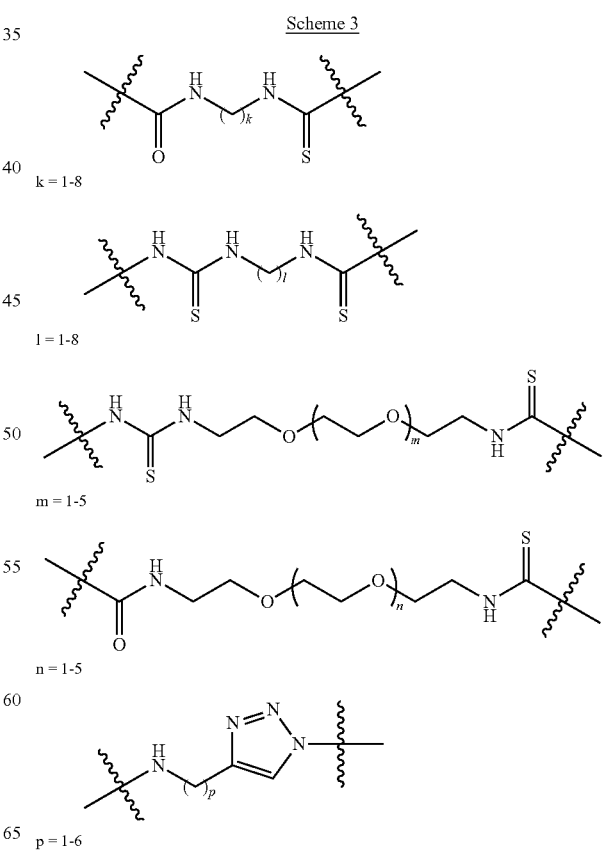

Scheme 3 k = 1-8 l = 1-8 m = 1-5 n = 1-5 p = 1-6

-continued

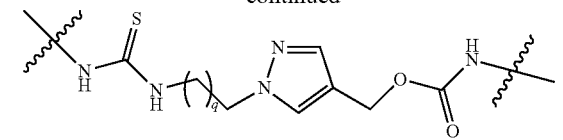

q = 1-9

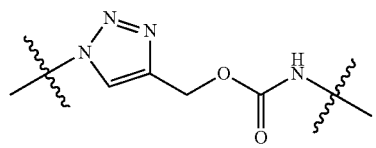

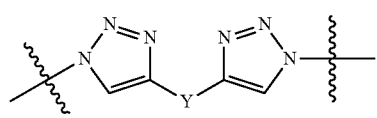

r = 1-9

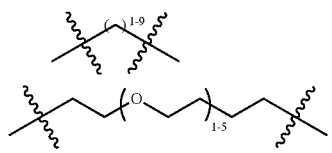

Y =

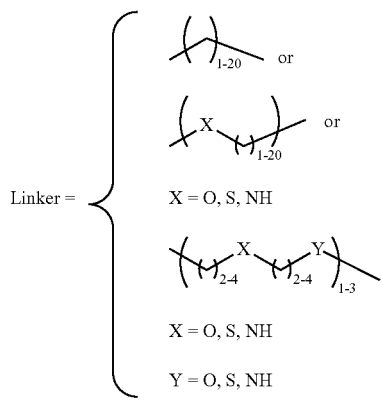

In certain embodiments the linker can be

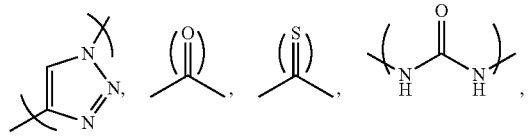

In certain embodiments the linker can be -(L$_1$)$_n$-(L$_2$)$_m$-(L$_3$)$_o$-(L$_4$)$_p$-(L$_5$)$_q$-(L$_6$)$_r$-(L$_7$)$_s$-(L$_8$)$_t$-(L$_9$)$_u$-, wherein n, m, o, p, q, r, s, t, u are independently 0 or 1, wherein (L$_1$), (L$_2$), (L$_3$), (L$_4$), (L$_5$), (L$_6$), (L$_7$), (L$_8$), and (L$_9$) are independently O, N, S, C$_1$-C$_8$ alkyl, C$_2$-C$_8$ alkenyl, C$_2$-C$_8$ alkoxy, aryl, heteroaryl, heterocyclyl,

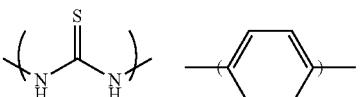

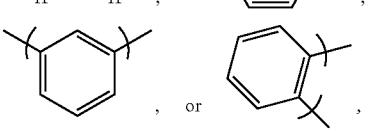

and/or alone or in any combination with any other limitation or characteristic disclosed herein.

In certain embodiments the linker can be -(L$_1$)$_v$-, wherein v is independently 1-20, wherein each (L$_1$) is independently O, N, S, C$_1$-C$_8$ alkyl, C$_2$-C$_8$ alkenyl, C$_2$-C$_8$ alkoxy, aryl, heteroaryl, heterocyclyl,

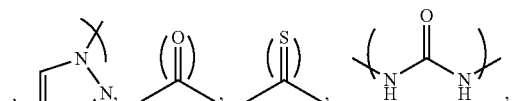

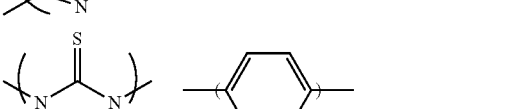

wherein each (L$_1$) can be the same or different, and/or alone or in any combination with any other limitation or characteristic disclosed herein, and/or alone or in any combination with any other limitation or characteristic disclosed herein In certain embodiments the linker can also be O, N, S, C$_1$-C$_8$ alkyl, C$_2$-C$_8$ alkenyl, C$_2$-C$_8$ alkoxy,

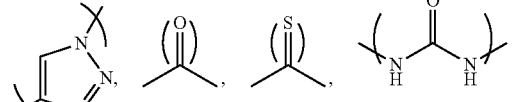

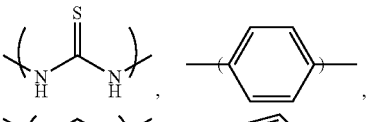

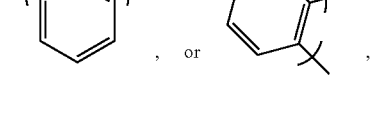

and/or alone or in any combination with any other limitation or characteristic disclosed herein.

Fluorescence and Fluorescent Moieties

Disclosed are fluorescent moieties which can be attached to the disclosed compounds. Examples of fluorescent moieties can be found in Scheme 4.

Scheme 4. Structures of fluorescent moieties for conjugation to nucleic acid binders.
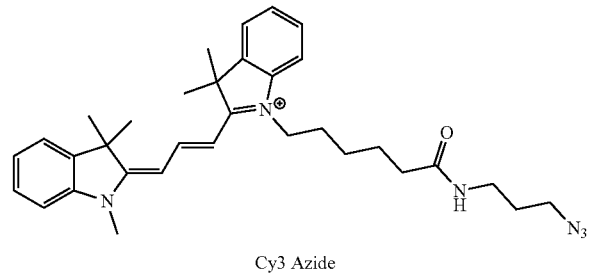
Cy3 Azide
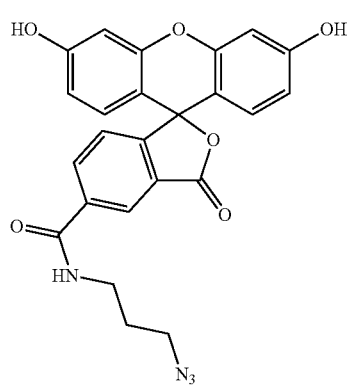
Fluorescein Azide
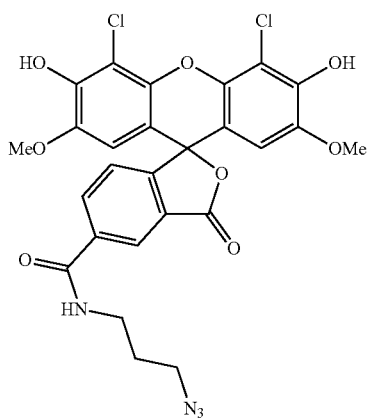
JOE azide 5-isomer
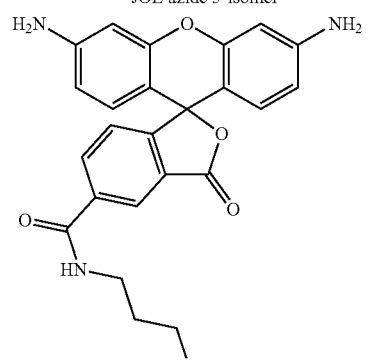
R110 azide 5-isomer
-continued
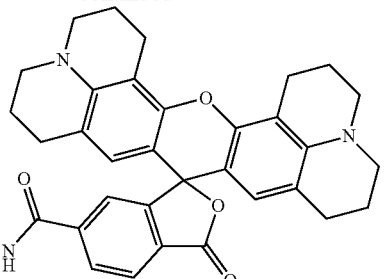
ROX azide 6-isomer
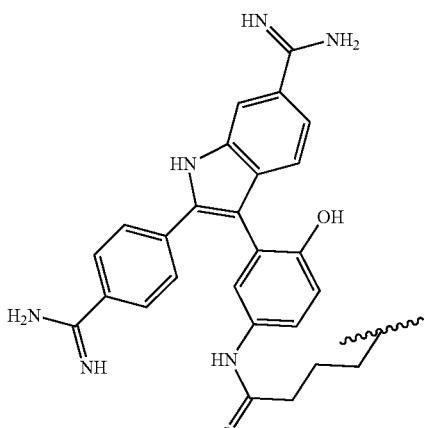
DAPI
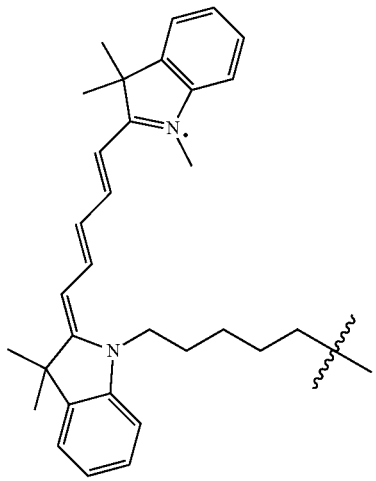
Cy 5
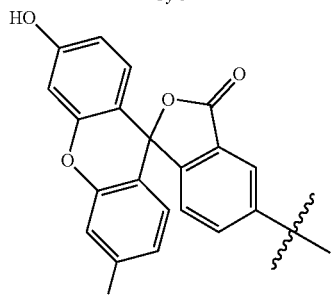
Fluorescein -continued
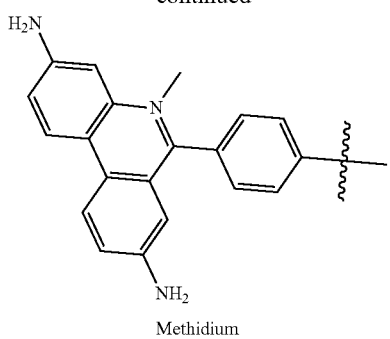
Methidium
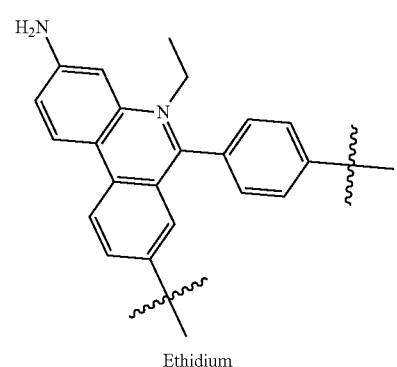
Ethidium
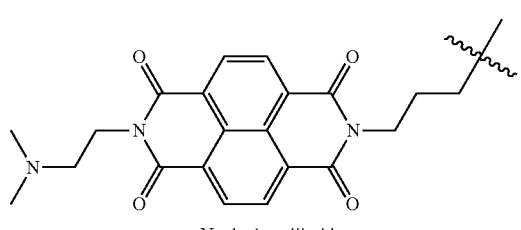
Naphtalenediimide
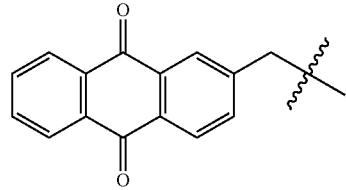
Anthraquinone
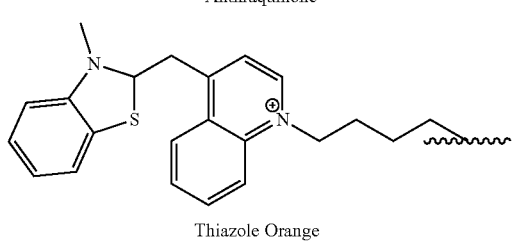
Thiazole Orange
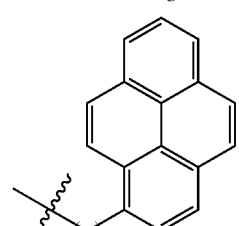
Pyrene
-continued
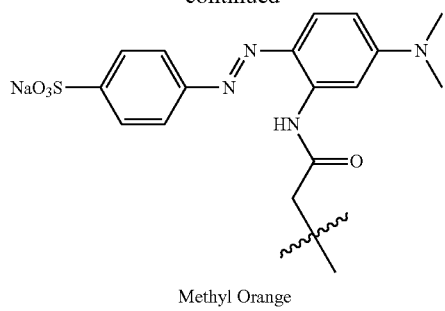
Methyl Orange
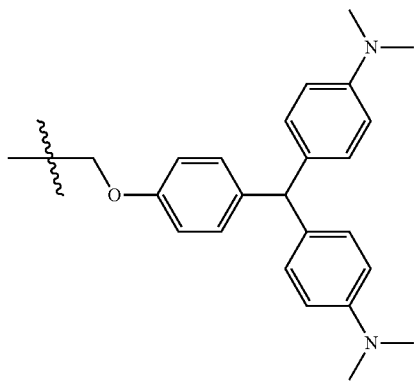
Leucomalachite green amine
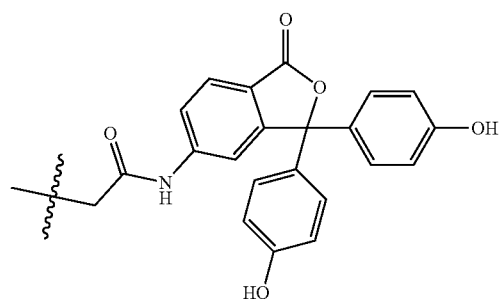
Phenolphthalein
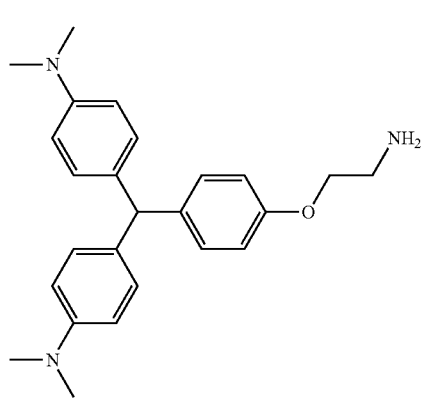
Leucomalachite green amine -continued
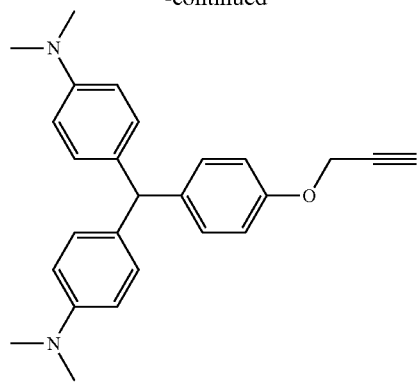
Leucomalachite green alkyne
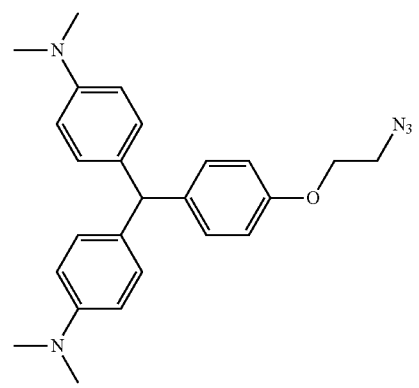
Leucomalachite green azide
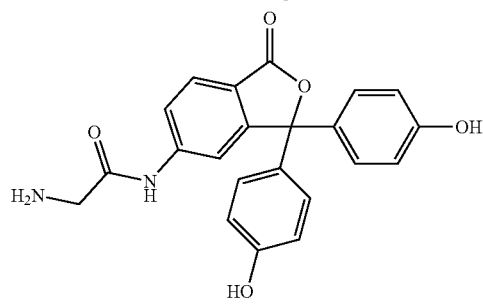
Phenolphthalein amine
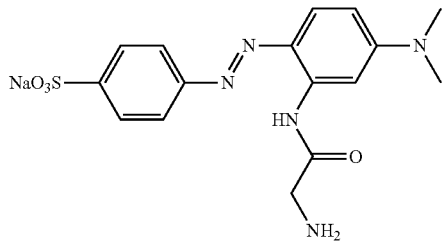
Methyl Orange amine
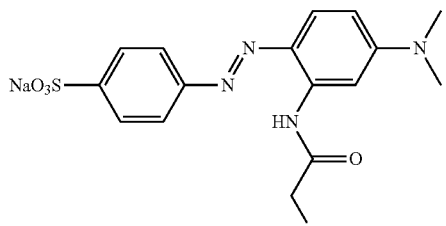
Methyl Orange azide
-continued
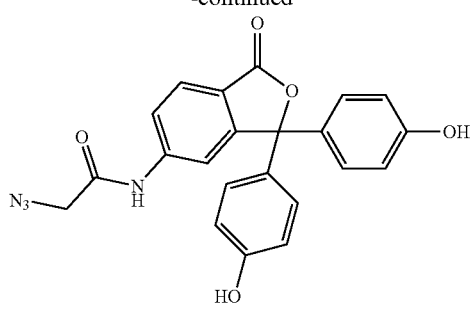
Phenolphthalein azide
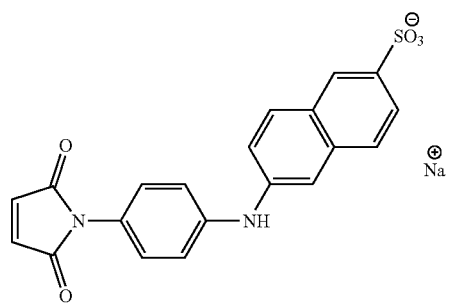
2-(4'-maleimidylanilino)naphthalene-
6-sulfonic acid, sodium salt
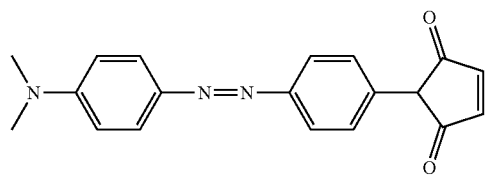
4-dimethylaminophenylazo-
phenyl-4'-maleimide
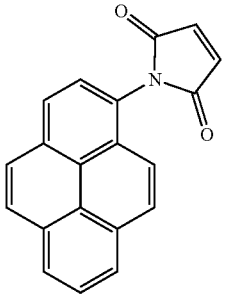
N-(1-pyrene)maleimide
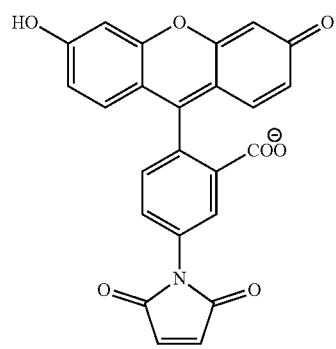
Fluorescein-5-maleimide -continued

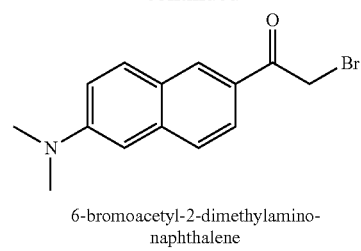

6-bromoacetyl-2-dimethylamino-
naphthalene

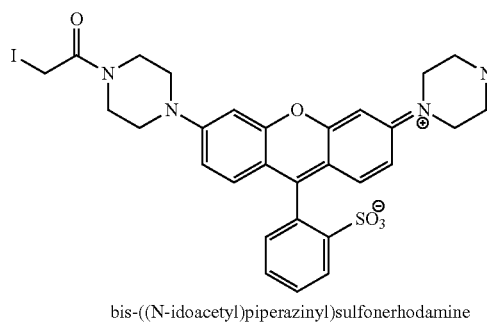

bis-((N-idoacetyl)piperazinyl)sulfonerhodamine

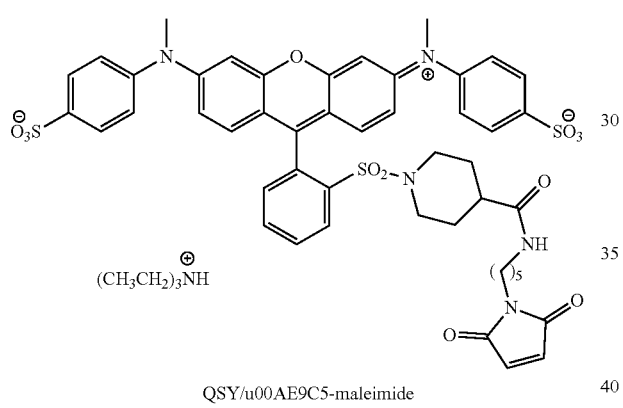

$(CH_3CH_2)_3NH^{\oplus}$

QSY\u00AE9C5-maleimide

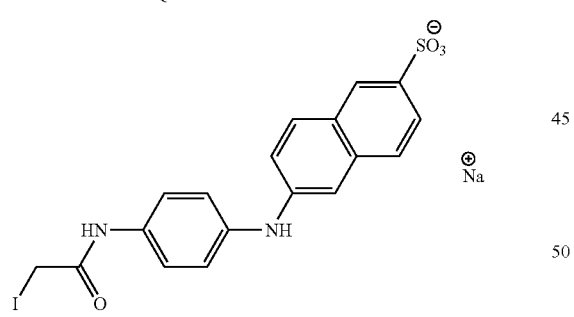

2-(4'-(iodoacetamido)anilino)napth-
thalene-6-sulfonic acid, sodium salt

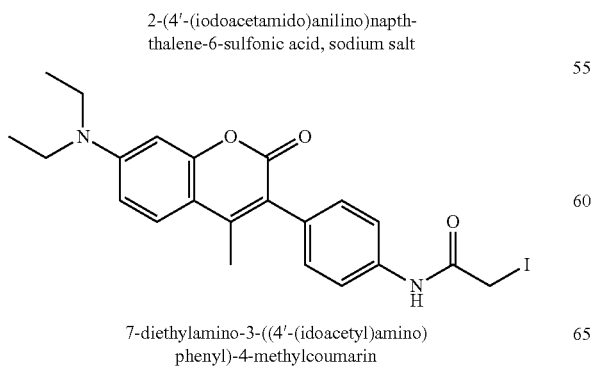

7-diethylamino-3-((4'-(idoacetyl)amino)
phenyl)-4-methylcoumarin

-continued

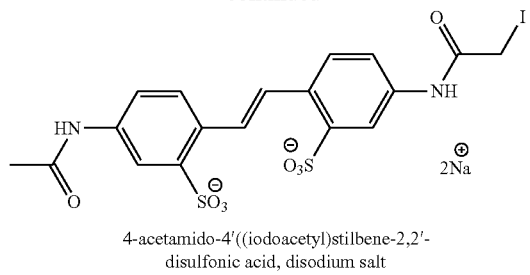

4-acetamido-4'((iodoacetyl)stilbene-2,2'-
disulfonic acid, disodium salt

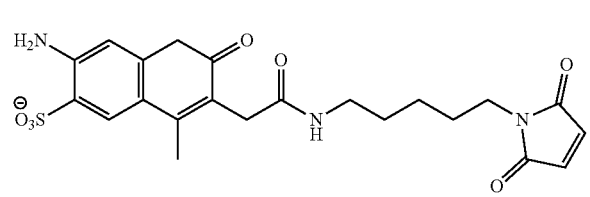

QSY\u00AE9 C5-maleimide

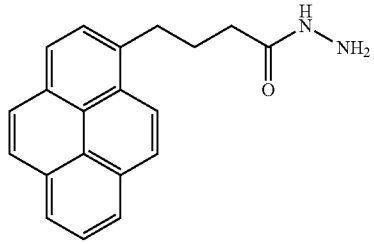

1-Pyrenebutanoic acid hydrazide

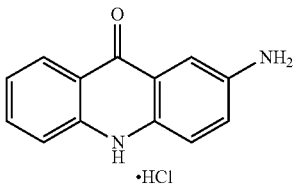

2-aminoacidone hydrochloride

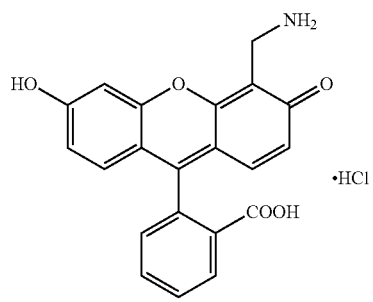

4-(aminomethyl) fluorescein hydrochloride

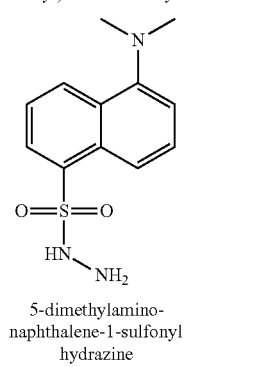

5-dimethylamino-
naphthalene-1-sulfonyl
hydrazine

29
-continued

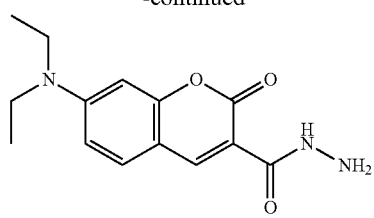

7-diethylamino-
coumarin-3-carboxylic acid,
hydrazide

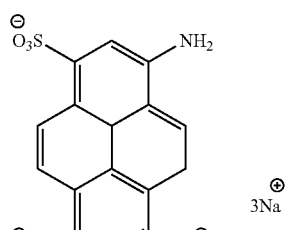

8-aminopyrene-1,3,6-
trisulfonic acid,
trisodium salt

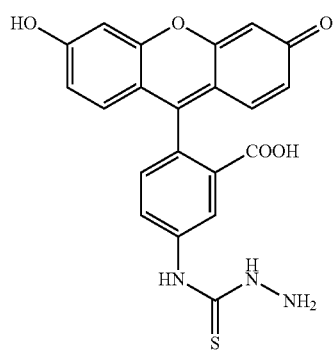

Fluorescein-5-thiosemicarbazide

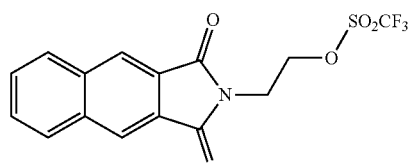

2-(2,3-napthalimino)ethyl
trifluoromethanesulfonate

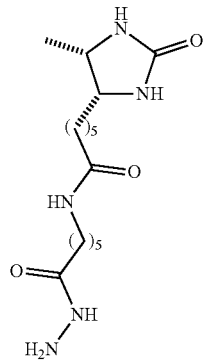

DSB-X/u2122 biotin hydrazide

30
-continued

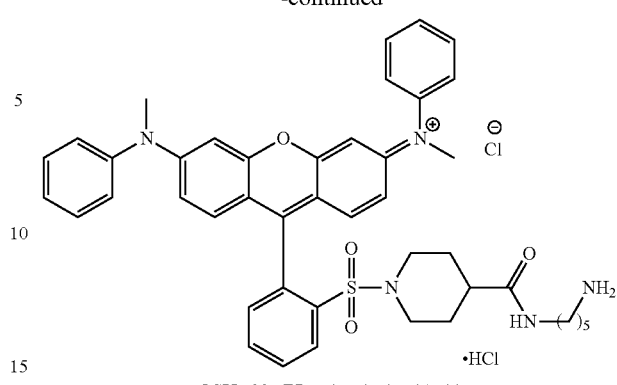

QSY\u00AE7 amine, hydrochloride

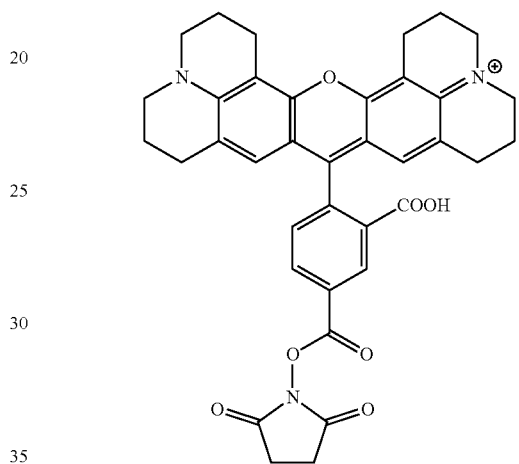

5-carboxy-X-rhodamine succninimidyl ester

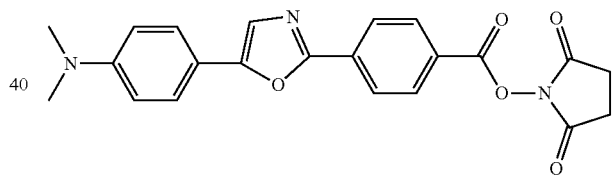

Dapoxyl\u00AE carboxylic acid succinimidyl ester

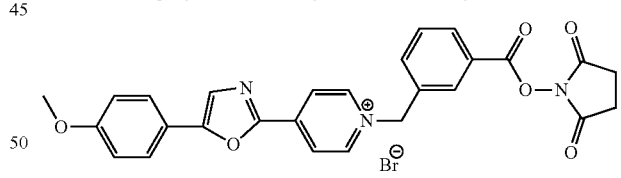

1-(3-((2,5-dioxopyrrolidin-1-yloxy)carbonyl)
benzyl)-4-(5-(4-methoxyphenyl)oxazol-2-yl)
pyridinium bromide

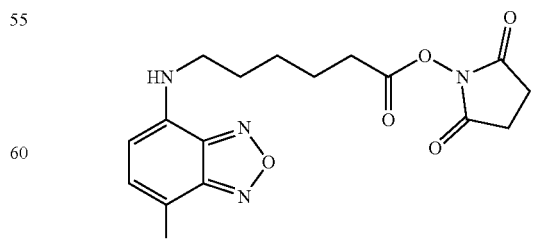

Succinimidyl 6-(N-(7-nitrobenz-2-oxa-1,3-
diazol-4-yl)amino)hexanoate

-continued
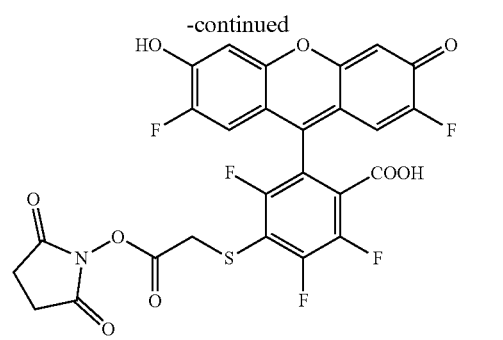
Oregon Green® 514 carboxylic acid, succinimidyl ester
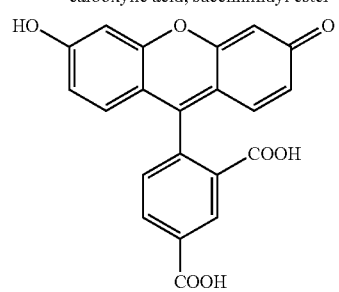
5-carboxyfluorescein
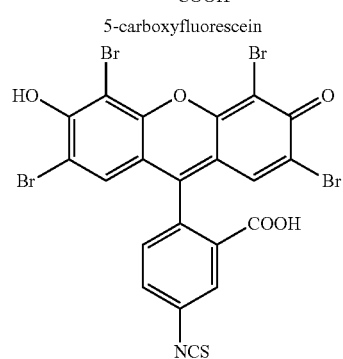
Eosin-5-isothiocyante
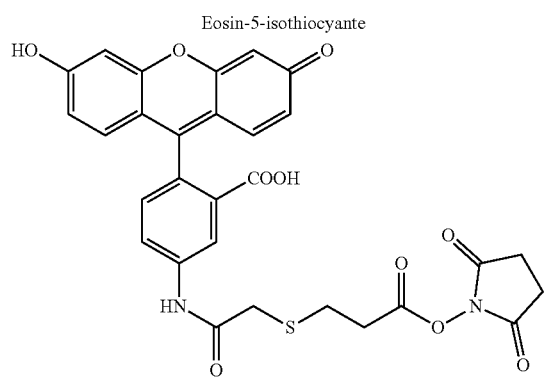
Fluorescein-5-EX, succinimidyl ester
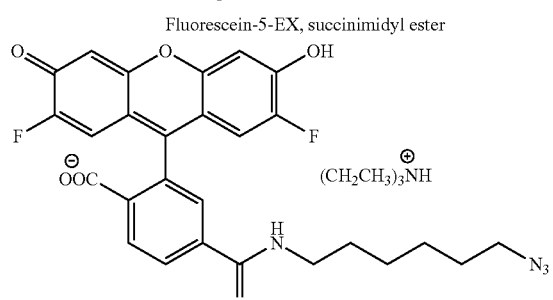
Oregon Green® 488 Azide
-continued
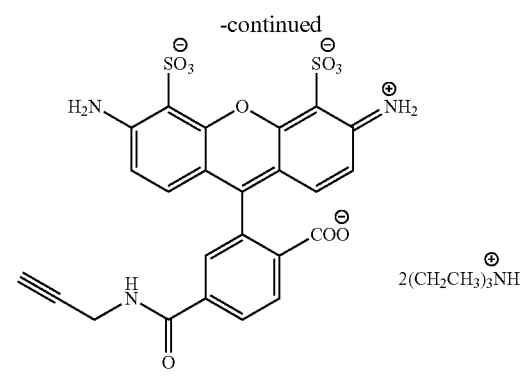
Alexa Fluor® 488 alkyne
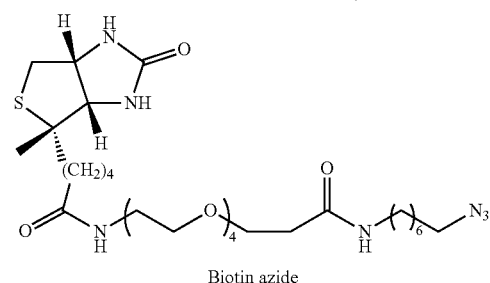
Biotin azide
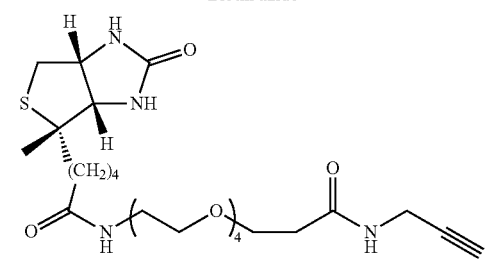
Biotin alkyne
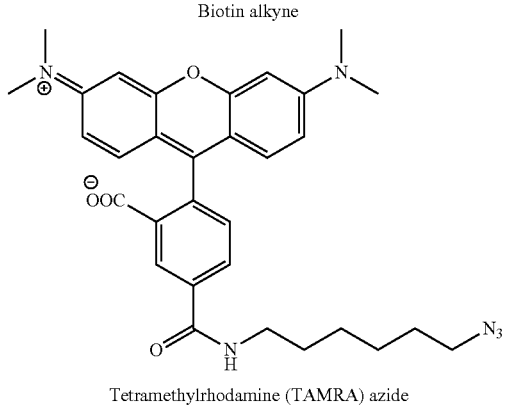
Tetramethylrhodamine (TAMRA) azide
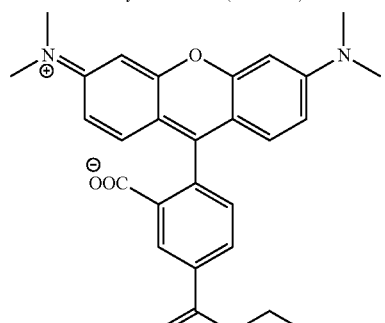
Tetramethylrhodamine (TAMRA) alkyne

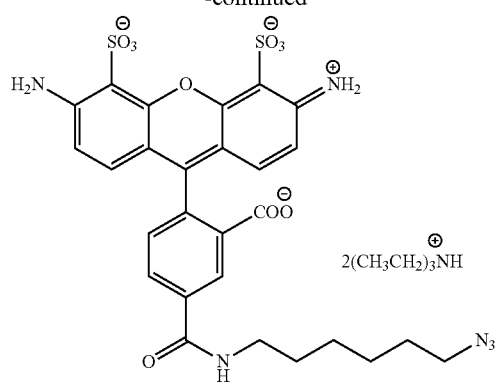
Alexa Fluor® 488 azide
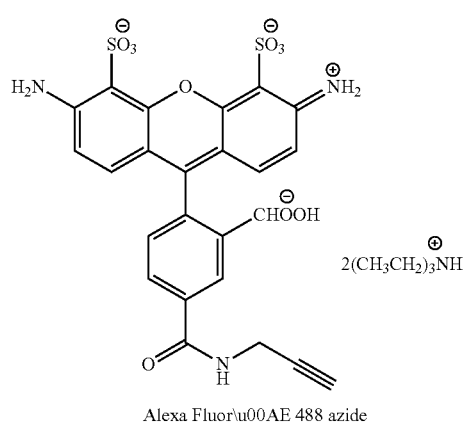
Alexa Fluor® 488 azide
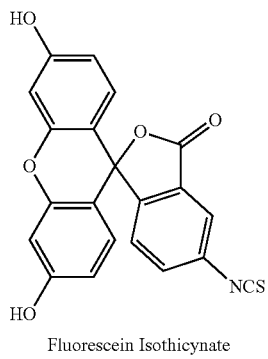
Fluorescein Isothicynate
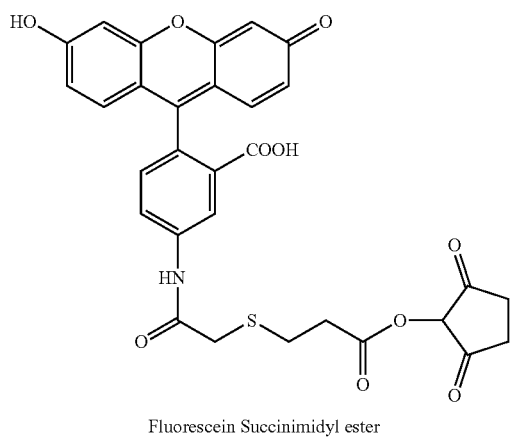
Fluorescein Succinimidyl ester
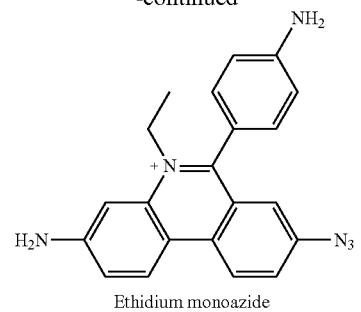
Ethidium monoazide
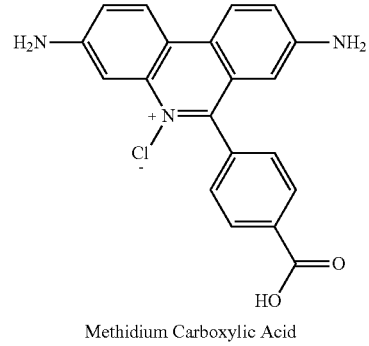
Methidium Carboxylic Acid
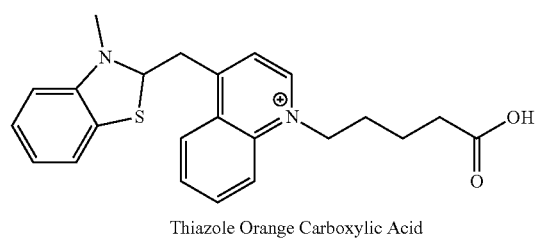
Thiazole Orange Carboxylic Acid
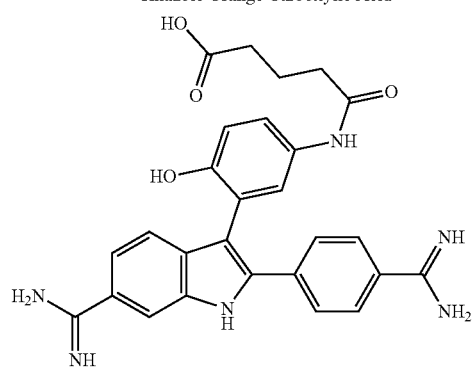
DAPI derivative
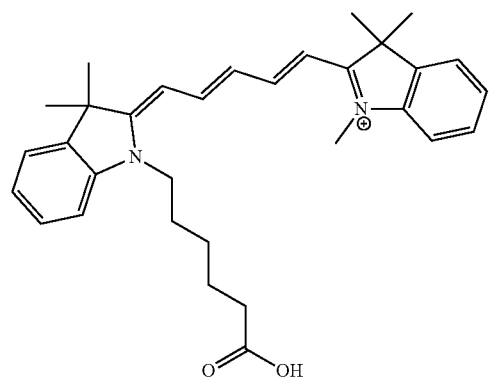
Cy5 Carboxylic acid derivative The term fluorescent as used herein is defined as a molecule having luminescence that is caused by the absorption of radiation at one wavelength followed by nearly immediate reradiation usually at a different wavelength and that ceases almost at once when the incident radiation stops, as understood in the art. The term fluorescent labeled molecule as used herein is defined as a fluorescent labeled molecule or a molecule containing a fluorophore moiety. The term fluorophore moiety as used herein refers to a moiety that has fluorescent properties. Illustrative fluorophore moieties for the present invention include dansyl, 4-(Diethylamino)azobenzene-4'-sulfonyl, fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as Quantum Dye™, fluorescent energy transfer dyes, such as thiazole orange-ethidium heterodimer, and the cyanine dyes Cy3, Cy3.5, Cy5, Cy5.5 and Cy7; as well as additional examples such as 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF (2',7'-bis-(2-carboxyethyl)-5-(and-6)-carboxyfluorescein), Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH$_3$, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Probe Equilibrium

The following equilibrium is used to help explain the probe function:

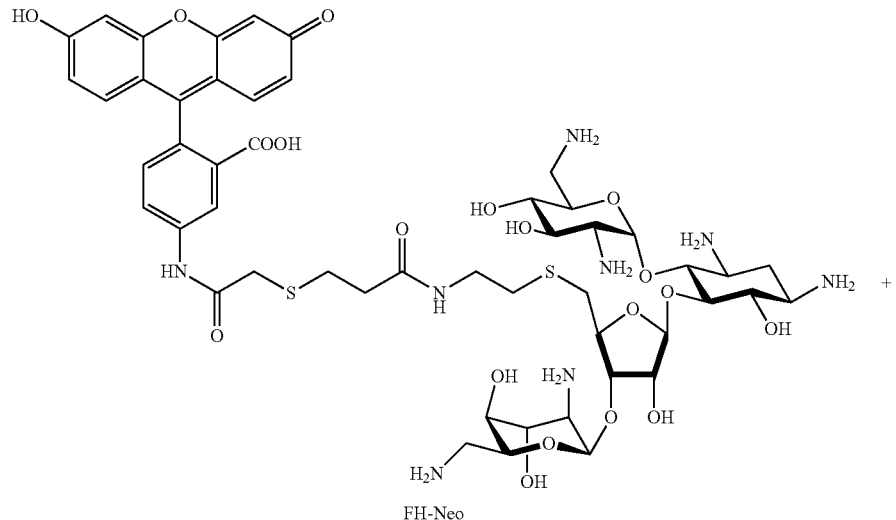

FH-Neo

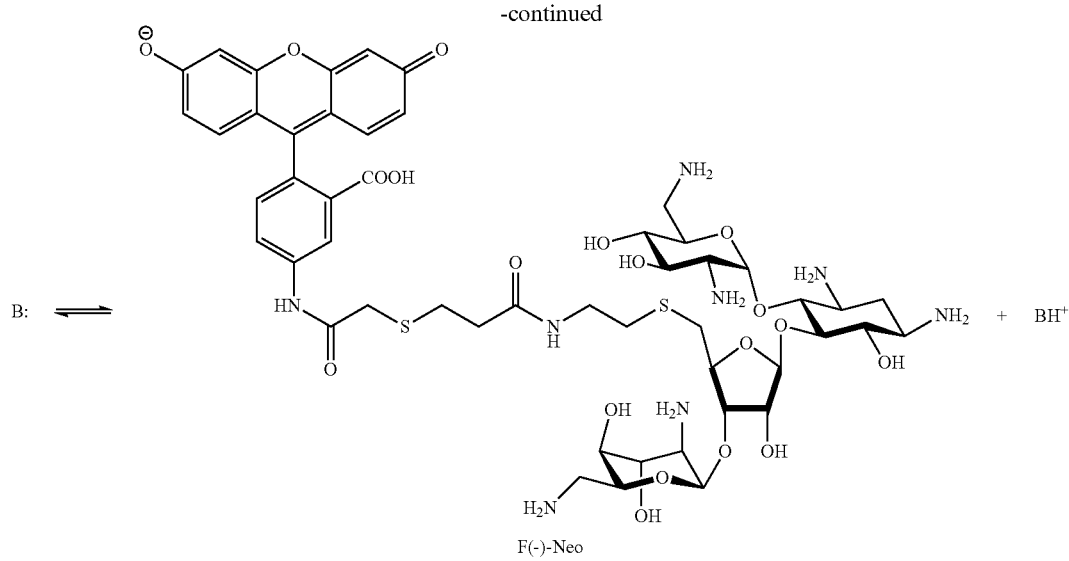

FHNeo + Base = F(-)Neo + BH⁺ where FHNeo represents the protonated form of F-neo. F(−)Neo, upon binding to nucleic acids such as DNA or RNA, is destabilized by the nucleic acid backbone negative potential, shifting the equilibrium towards FH, making F-neo a weaker acid, raising the pKa, which is what we observe upon binding to the A-site. For the A-site targeted assay, we calculated the Z' factor (Z=1-3(2.7+2.8)/(414-267)=0.89. A value of Z'=1 is ideal, Z' between 0.5 and 1 is considered excellent.

Synthesis of Disclosed Compounds and Compositions

The compounds and compositions disclosed herein and the compounds and compositions necessary to perform the disclosed methods can be made using any method known to those of skill in the art for that particular reagent or compound unless otherwise specifically noted. It is understood that the disclosed reactions are representative, and can be used to make the disclosed compounds and compositions, but various appropriate substitutions can be made and are understood.

Functionalization of Neomycin

Neomycin, like other aminoglycosides, such as neamine and kanamycin, can be functionalized in several ways to afford functional groups that serve as the centers of electrophilic/nucleophilic reactivity as shown in Scheme 5.

Scheme 5. Possible linkage functional groups for neamine, neomycin and kanamycin.

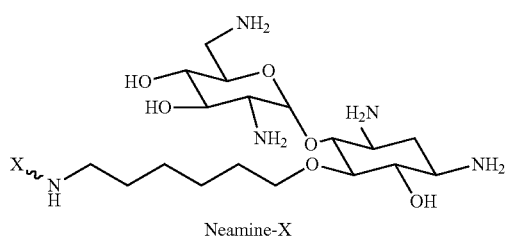

Neamine-X

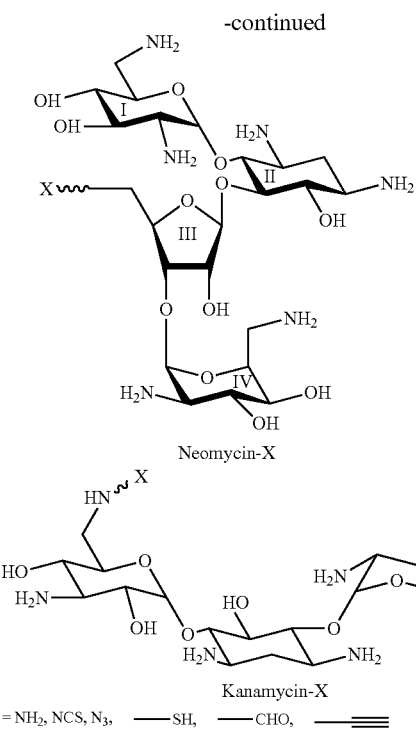

Neomycin-X

Kanamycin-X

X = NH₂, NCS, N₃, ⎯SH, ⎯CHO, ⎯≡

In addition to this, they can also be useful towards copper catalyzed click chemistry reactions. From commercially available neomycin B Sulfate, the first step of reaction is protection of all (such as six) amino groups (scheme 6a) using tertiary butyl carbonyl (Boc) groups, which lead to the formation of Boc protected neomycin 1. The protection of amino groups by Boc renders the solubility properties of neomycin from being water soluble to complete insolubility in water. This also allows much easier purification of the desired product from byproducts formed in the reaction. Neomycin has four rings, three of them (rings I, II and IV) contain amino groups on them while ring III contains a lone primary hydroxyl present in the molecule at the 5-position, in addition to a secondary hydroxyl group at 3-position in the ring (scheme 6a). The primary hydroxyl can then be selectively reacted with a bulky leaving group such as triisopropyl benzene sulfonyl chloride (TPS-Cl) which leads to the formation of compound 2. Conversion of the primary hydroxyl group on ring III to a good leaving group TPS facilitates smooth nucleophilic reactions at this position. The TPS functional group can be displaced in two ways. First, 2-aminoethanethiol can be deprotonated in the presence of base to displace the TPS group present in 2, thereby giving an amine terminated Boc protected neomycin 3 which can be conjugated directly. The TPS group can also be displaced by reaction of sodium azide in the presence of a polar protic solvent to afford an azide terminated Boc protected neomycin 5 which can be used straight for click chemistry. Compound 5 can be reduced in the presence of a heterogeneous catalyst to its corresponding amine 6 in quantitative yields. Thus, neomycin can be derivatized into amine functionalities in two ways which give us differing atom spacing at the 5"-end on ring III. The two —NH$_2$ terminated neomycin derivatives (3 or 6) can be converted to their corresponding isothiocyanates in a single step by reaction with TCDP (Charles, Xue, & Arya, 2002). The isothiocyanate functionality now serves as an electrophilic center for reactions with nucleophilic ligands. Neomycin amine 6 can then also be used to prepare a carboxyl terminated neomycin derivative 8 by reaction with succinic anhydride in the presence of DMF. Neomycin amine 6 can also be reacted with propargyl chloroformate in the presence of base to give a short alkyne terminated neomycin derivative 7 (Kumar, 2011) that reacts with azide partners in a facile way using copper catalyzed click chemistry. (Kolb, Finn, & Sharpless, 2001; Rostovtsev, Green, Fokin, & Sharpless, 2002) Compound 2 can also be reacted with 2-mercaptoethyl ether to give thiol ended neomycin derivative 10 which can be used in thiol maleimide coupling reactions. The primary hydroxyl group in 1 can be reacted under Mitsunobu conditions to form an aldehyde ended neomycin derivative 9 that can be used for condensation with amines. Alkyne terminated neomycin derivatives (with a triazole ring on its linker) can also be prepared by reaction with excess bisalkynes to give alkyne terminated neomycin derivatives with varying atoms spacing. A generalized scheme of the reaction is outlined in scheme 6b.

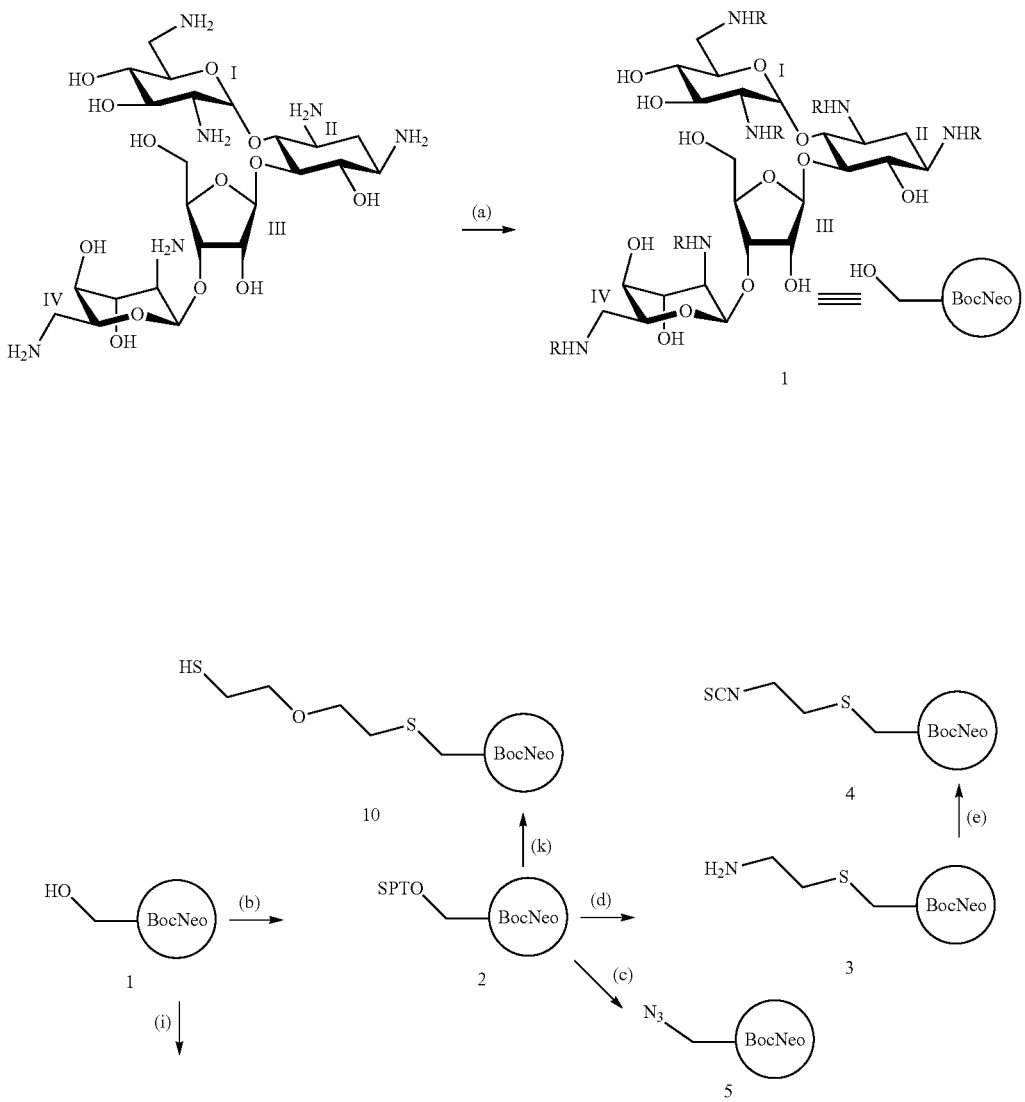

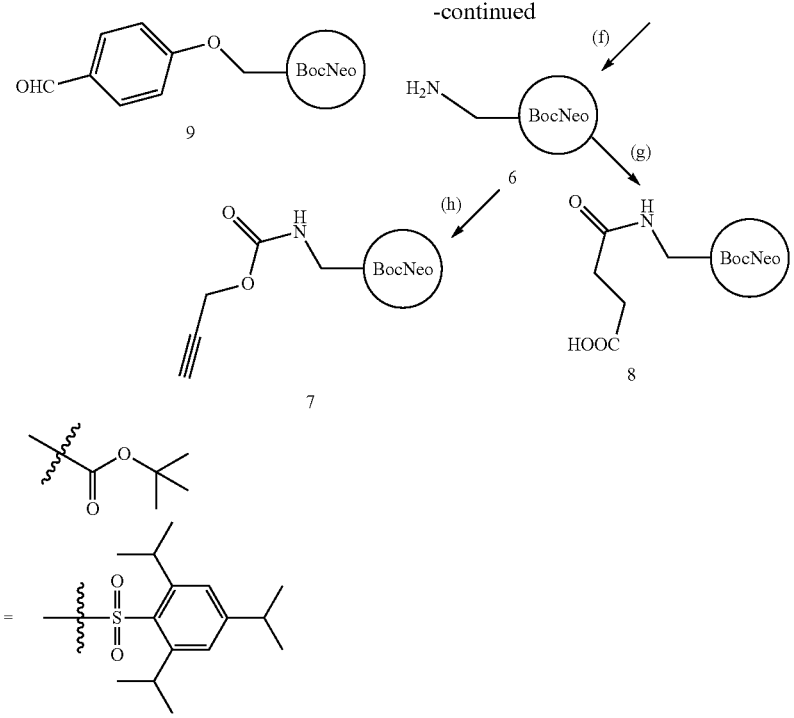

Scheme 6a. Scheme showing the modification of neomycin to acid, alkyne, amine, thiol, aldehyde or isothiocyanate functionalized aminosugar. Reagents and Conditions: (a) $(Boc)_2O$, $Et_3N$, $H_2O$, 75° C., 18 h, 75% (b) TPS-Cl, pyridine, rt, 3 days, 61% (c) $NaN_3$, $DMF:H_2O$ (10:1), 80° C., 12 h, 90% (d) Na(metal), ethanol(dry), $HSCH_2CH_2NH_2 \cdot HCl$, rt, 10 h, 70% (e) TCDP, DCM, rt, 24 h, 50% (f) Pd—C, $H_2$, rt, 12 h, qaunt. (g) Succinic anhydride, rt, overnight, DMF (h) Propargyl chloroformate, pyridine, rt, overnight, 60% (i) 4-hydroxy benzaldehyde, TPP, DIAD, Toluene (k) 2-mercaptoethyl ether, $Cs_2CO_3$, rt, 12 h, 92%.

Scheme 6b. Preparation of alkyne terminated neomycin derivatives with variable atom spacing

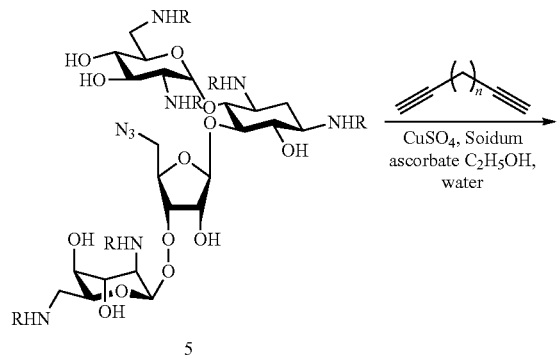

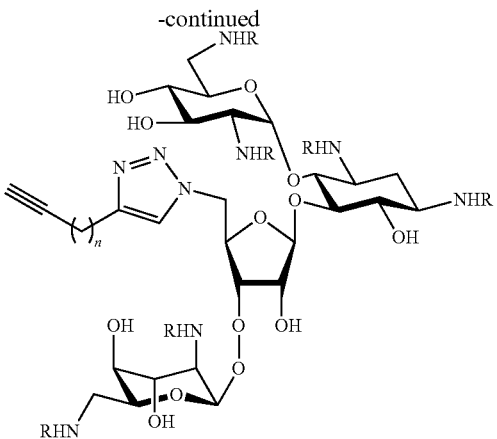

Functionalization of Neamine (Riguet et al., 2005; Riguet, Désiré, Bailly, & Décout, 2004)

Functionalization of Neamine requires protection of both amino and hydroxyl groups as shown in scheme 7. In the first step, neamine is reacted with trityl chloride in the presence of base to afford trityl protected amines 12. Reaction of the tetratritylated derivative of neamine with three equivalents of 4-methoxy benzyl chloride leads to both bis and tri benzylated products which can be purified using column chromatography to give 13. The 5-hydroxyl group can then be deprotonated in the presence of sodium hydride and then be reacted with excess alkyl bis bromides to give a bromo ended derivative 14a. The bromo group can be converted to azido functionality 14 by reaction with sodium azide in DMF. The azide functionality in 14 can be reduced to its corresponding amine 15 by reaction with $PPh_3$ in THF. The amine functionality in 15 can then be converted to various other functional groups. The amine can be reacted with TCDP to give its corresponding isothiocyanate 17. The amine can also be reacted with succinic anhydride in the presence of DMF to give carboxyl terminated neamine derivative 16. It can also be reacted with propargyl chloroformate in the presence of base to give alkyne terminated neamine derivative 18. The hydroxyl group in 13 can be reacted under Mitsunobu conditions to form an aldehyde ended neamine derivative 19 that can be used for condensation with amines. Compound 14a can also be reacted with 2-mercaptoethyl ether to give thiol ended neamine derivative 20 which can be used in thiol maleimide coupling reactions.

Scheme 7. Scheme showing the modification of neamine to acid, alkyne, amine, thiol, aldehyde or isothiocynate functionalized aminosugar.

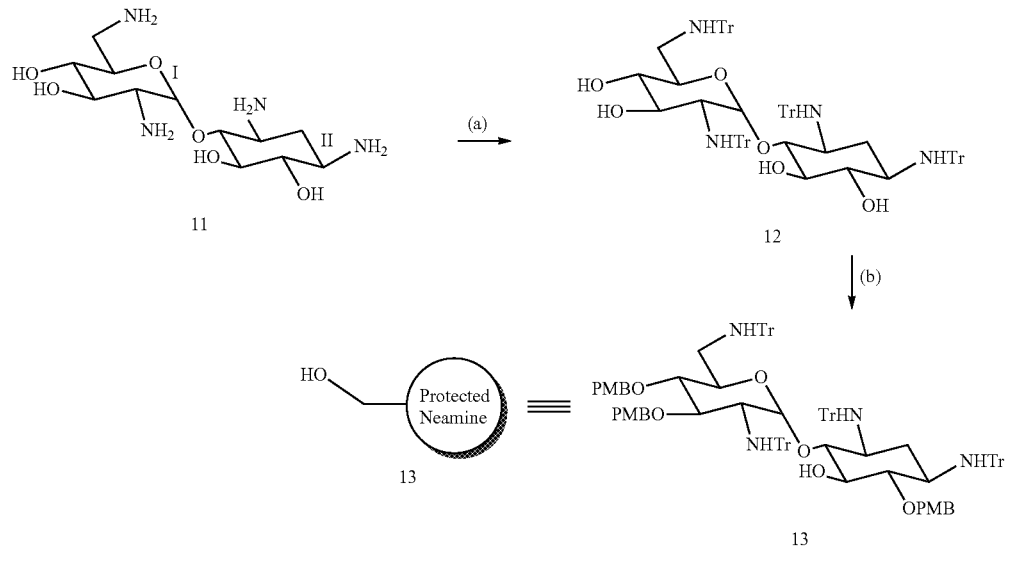

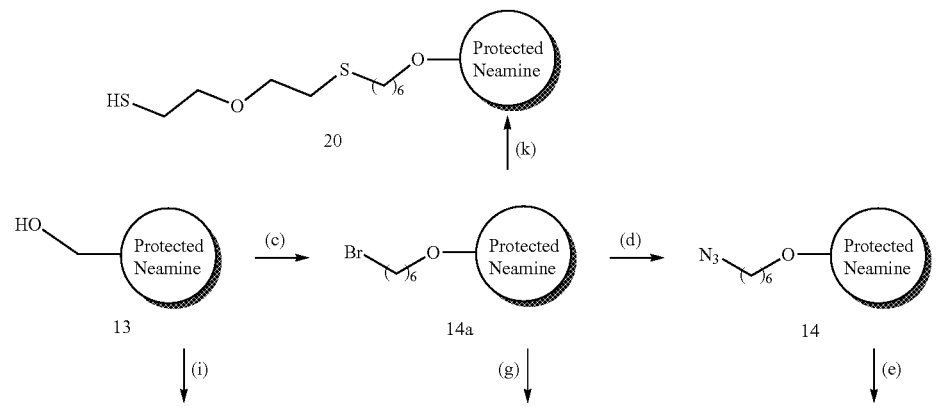

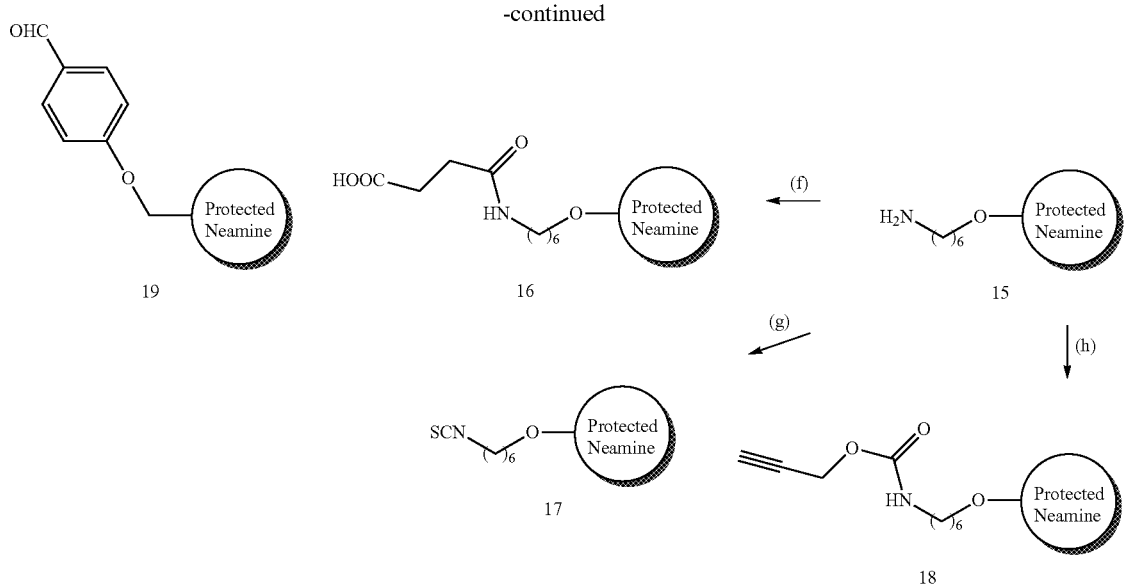

Reagent and conditions. (a) TrCl, Et₃N, DMF (b) PMB-Cl, NaH, TBAI, THF or THF/DMF 90:10 (c) 1,6-dibromohexane (5 equiv), NaH, DMF (d) NaN₃, DMF (e) Triphenylphosphine, H₂O, THF (f) Succinic anhydride, rt, DMF (g) TCDP, DCM, rt (h) Propargyl chloroformate, pyridine, rt (i) 4-hydroxy benzaldehyde, TPP, DIAD, Toluene (k) 2-mercaptoethyl ether, Cs₂CO₃, rt.

Functionalization of Kanamycin (Wang, 1998)(Charles, Xue, & Arya, 2002)

Functionalization of Kanamycin 21 starts with the Cbz protection of the five amino groups in the presence of a base (scheme 8). In the next step, the lone primary hydroxyl group present on the molecule is converted to a good leaving group in the form of triisopropyl benzene sulfonyl (TPS) derivative 22. In the next step, the Cbz groups can be removed by hydrogenolysis and the amino groups can be Boc protected in a one pot reaction. The TPS group can then be displaced by 2-amino ethane thiolate to give an amine terminated Kanamycin 23, which can be used for coupling reactions with isothiocyanates or ligands with free carboxylic acid groups. The amine 23 can also be converted to its corresponding isothiocyanate 24 by reaction with TCDP.

Compound 22 can also be converted to an azido derivative 25 by a combination of hydrogenolysis and Boc protection of amino groups followed by the displacement of the—TPS group by sodium azide in DMF. The azide 25 can be reduced to a shorter amine 26 by palladium catalyzed hydrogenation, which can then be used to make either a carboxyl terminated derivative 27 by reaction with succinic anhydride or an alkyne terminated derivative by reaction with propargyl chloroformate 28. The amine group in 26 can be reacted with 4-(2-isothiocyanatoethoxy)benzaldehyde to form an aldehyde ended kanamycin derivative 29 that can be used for condensation with amines. The TPS leaving group in 22 can also be reacted with 2-mercaptoethyl ether to give thiol ended kanamycin derivative 30 which can be used in thiol maleimide coupling reactions. The complete route to the syntheses to these derivatives is outlined in scheme 8.

Scheme 8. Scheme showing the modification of kanamycin to acid, alkyne, amine, thiol, aldehyde or isothiocyanate functionalized aminosugar.

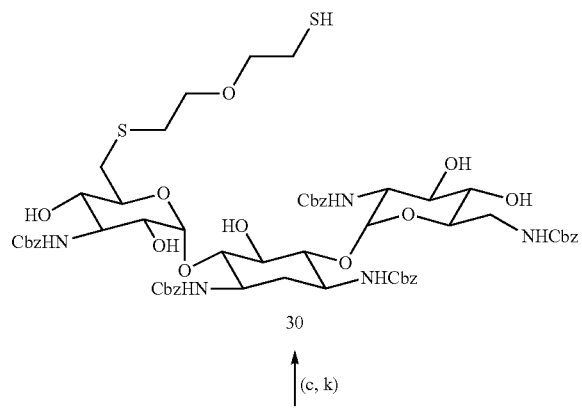

47 48
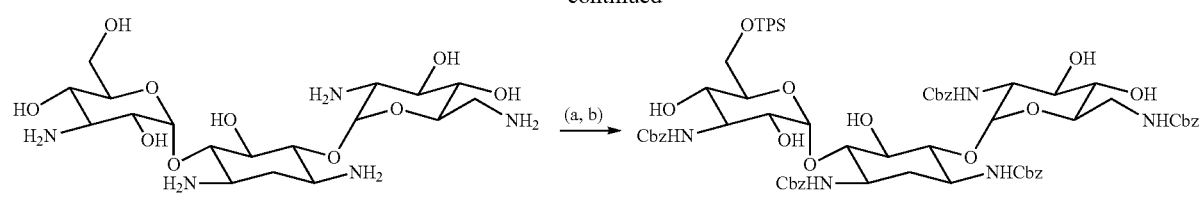
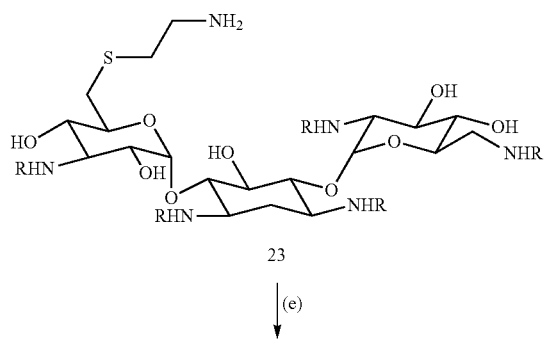
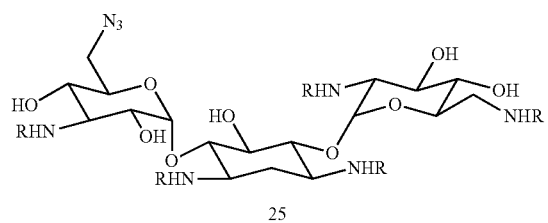
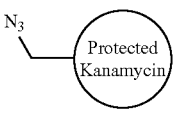
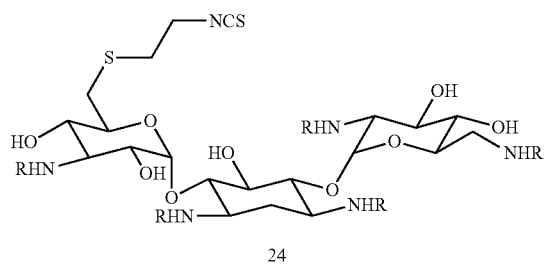
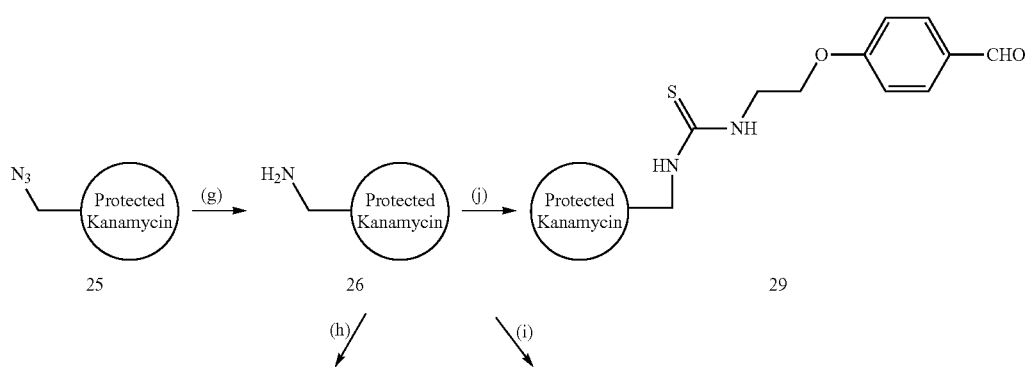

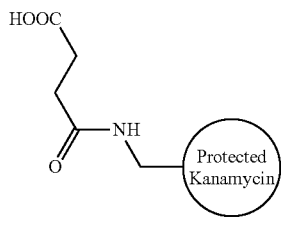 27

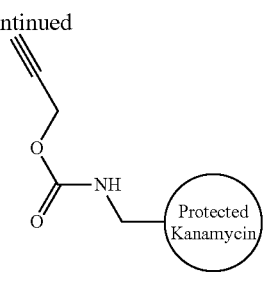 28

Reagent and conditions. (a) CbzCl, H₂O, Na₂CO₃, 98% (b) TPS-Cl, pyridine, 56% (c) (Boc)₂O, H₂, Pd/C and MeOH, 76% (d) HCl—NH₂CH₂CH₂SH, NaOEt, EtOH, 58% (e) 1,10-thiocarbonyldi-2(1H)pyridone, DMAP and CH₂Cl₂, 55% (f) NaN₃, DMF, 80% (g) Pd-C, H₂, rt, (h) Succinic anhydride, rt, DMF (i) Propargyl chloroformate, pyridine, rt (j) 4-(2-isothiocyanatoethoxy)benzaldehyde, pyridine, DMAP, rt (k) 2-mercaptoethyl ether, Cs₂CO₃, rt.

Cbz = Benzyloxycarbonyl

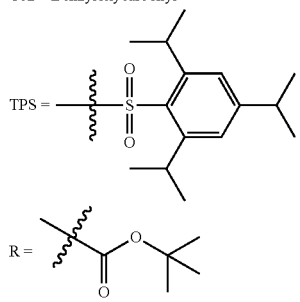

Compositions and Methods

Disclosed are nucleic acid probes comprising a fluorescent moiety, a linker moiety, and a nucleic acid binding moiety, wherein the fluorescent molecule is covalently attached to the linker moiety and the linker moiety is covalently attached to the nucleic acid binding moiety through a carbon or oxygen or sulfur atom of the nucleic acid binding moiety, examples show in Scheme 9. The linker is not bound to the nucleic acid binding moiety through an amino group of the nucleic acid binding moiety.

Scheme 9

Disclosed are nucleic acid probes, wherein the fluorescent moiety is fluorophore, for example shown in Scheme 4. The linker moiety comprises a backbone of less than 50 atoms, wherein the linker moiety comprises a backbone of less than 40 atoms, wherein the linker moiety comprises a backbone of less than 30 atoms, wherein the linker moiety comprises a backbone of less than 20 atoms, wherein the linker moiety comprises a linker shown in Scheme 3, wherein the nucleic acid binding moiety comprises a compound shown in scheme 2, alone and/or in any combination with the compounds, compositions, and methods disclosed herein.

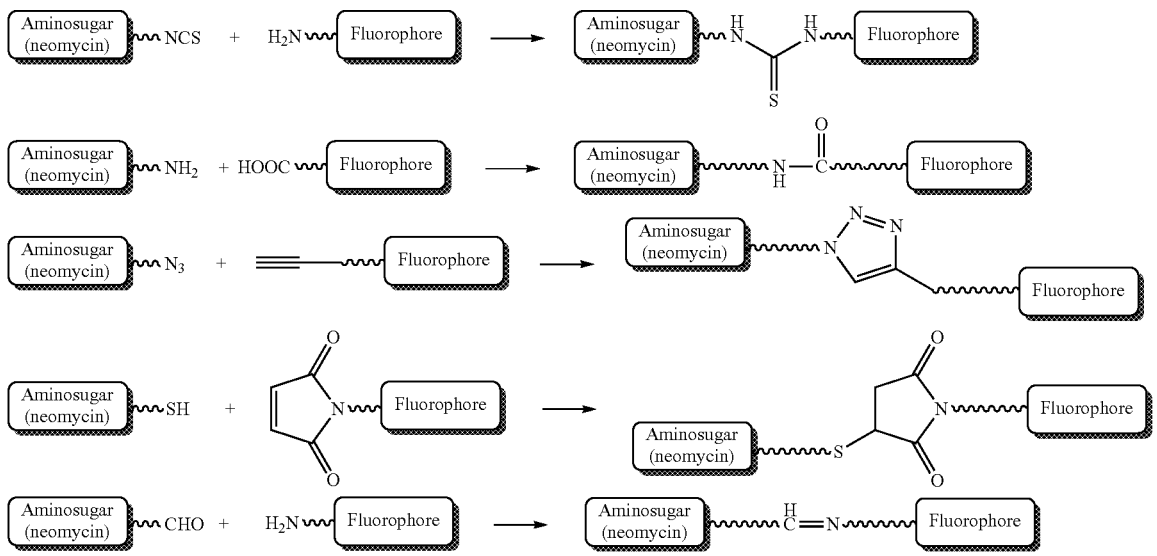

Disclosed are kits comprising a nucleic acid probe disclosed herein.

Disclosed are methods comprising incubating a nucleic acid with a nucleic acid probe disclosed herein, wherein the probe comprises a fluorophore, wherein fluoresence intensity of the fluorophore changes in a manner proportional to how tightly the probe is binding the nucleic acid.

In some embodiments, the fluorophore is fluorescein, which upon binding causes its fluorescence to decrease. In some embodiments, the fluorophore is thiozaole-orange, which upon binding causes the fluorescence to increase, alone and/or in any combination with the compounds, compositions, and methods disclosed herein.

Disclosed are methods comprising 1) incubating an oligonucleotide with a nucleic acid probe disclosed herein under conditions where the probe disclosed herein can bind the oligonucleotide to form a complex, 2) measuring a fluorescence emission intensity of the complex, 3) incubating a compound with the complex to form a incubation mixture, 4) measuring a fluorescence emission intensity on the incubation mixture, 5) comparing the fluorescence emission intensity of the complex and the incubation mixture to determine the binding affinity of the compound relative to the probe.

Disclosed are methods comprising, incubating a substrate with a nucleic acid probe disclosed herein, wherein the nucleic acid probe comprises a fluorophore, the fluoresence intensity of which changes in a manner proportional to how tightly the probe is binding the substrate, wherein the substrate is RNA, single stranded DNA, A-dsDNA, B-dsDNA, or four stranded DNA.

Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended.

Compositions with Similar Functions

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

Process Claims for Making the Compositions

Disclosed are processes for making the compositions as well as making, the intermediates leading to the compositions. There are a variety of methods that can be used for making these compositions, such as synthetic chemical methods and standard molecular biology methods. It is understood that the methods of making these and the other disclosed compositions are specifically disclosed.

Methods of Using the Compositions as Research Tools

The disclosed compositions can be used in a variety of ways as research tools. For example, the disclosed compositions, can be used to study the interactions between aminoglycosides and nucleic acids, by for example, identifying new molecules that bind the nucleic acids.

The compositions can be used for example as tools within combinatorial chemistry protocols or other screening protocols to isolate molecules that possess desired functional properties related to their nucleic acid binding.

The disclosed compositions can be used as discussed herein as, either reagents in micro arrays or as reagents to probe or analyze existing microarrays. The compositions can also be used in any known method of screening assays, related to chip/micro arrays.

Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like. As used herein, the term "activity" refers to a biological activity. The term "cell" as used herein also refers to individual cells, cell lines, or cultures derived from such cells. A "culture" refers to a composition comprising isolated cells of the same or a different type. The term co-culture is used to designate when more than one type of cell are cultured together in the same dish with either full or partial contact with each other. Compounds and compositions have their standard meaning in the art. It is understood that wherever, a particular designation, such as a molecule, substance, marker, cell, or reagent compositions comprising, consisting of, and consisting essentially of these designations are disclosed. Thus, where the particular designation marker is used, it is understood that also disclosed would be compositions comprising that marker, consisting of that marker, or consisting essentially of that marker. Where appropriate wherever a particular designation is made, it is understood that the compound of that designation is also disclosed. For example, if particular biological material, such as aminoglycoside, is disclosed aminoglycoside in its compound form is also disclosed. Disclosed are materials, compounds, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if an inhibitor is disclosed and discussed and a number of modifications that can be made to a number of R groups are discussed, each and every combination and permutation of the inhibitor and the modifications to its R group that are possible are specifically contemplated unless specifically indicated to the contrary. Thus, if a class of substituents A, B, and C are disclosed as well as a class of substituents D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Throughout the description and claims of this specification, the word "comprise" and variations of the word, such as "comprising" and "comprises," means "including but not limited to," and is not intended to exclude, for example, other additives, components, integers or steps.

The term "aldehyde" as used herein is represented by the formula —C(O)H.

The term "alkyl" as used herein is a branched or unbranched saturated hydrocarbon moiety. "Unbranched" or "Branched" alkyls comprise a non-cyclic, saturated, straight or branched chain hydrocarbon moiety having from 1 to 24 carbons, 1 to 12, carbons, 1 to 6 carbons, or 1 to 4 carbon atoms. Examples of such alkyl radicals include methyl, ethyl, propyl, butyl, pentyl, hexyl, heptyl, octyl, n-propyl, iso-propyl, butyl, n-butyl, sec-butyl, t-butyl, amyl, t-amyl, n-pentyl and the like. Lower alkyls comprise a noncyclic, saturated, straight or branched chain hydrocarbon residue having from 1 to 4 carbon atoms, i.e., C1-C4 alkyl. Moreover, the term "alkyl" as used throughout the specification and claims is intended to include both "unsubstituted alkyls" and "substituted alkyls", the later denotes an alkyl radical analogous to the above definition that is further substituted with one, two, or more additional organic or inorganic substituent groups. Suitable substituent groups include but are not limited to hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido, acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkoxy, heteroaryl, substituted heteroaryl, aryl or substituted aryl. It will be understood by those skilled in the art that an "alkoxy" can be a substituted of a carbonyl substituted "alkyl" forming an ester. When more than one substituent group is present then they can be the same or different. The organic substituent moieties can comprise from 1 to 12 carbon atoms or from 1 to 6 carbon atoms, or from 1 to 4 carbon atoms. It will be understood by those skilled in the art that the moieties substituted on the "alkyl" chain can themselves be substituted, as described above, if appropriate.

The term "alkenyl" as used herein is an alkyl residue as defined above that also comprises at least one carbon-carbon double bond in the backbone of the hydrocarbon chain. Examples include but are not limited to vinyl, allyl, 2-butenyl, 3-butenyl, 2-pentenyl, 3-pentenyl, 2-hexenyl, 3-hexenyl, 4-hexenyl, 5-hexanyl, 2-heptenyl, 3-heptenyl, 4-heptenyl, 5-heptenyl, 6-heptenyl and the like. The term "alkenyl" includes dienes and trienes of straight and branch chains.

The term "alkynyl" as used herein is an alkyl residue as defined above that comprises at least one carbon-carbon triple bond in the backbone of the hydrocarbon chain. Examples include but are not limited ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

The term "alkoxy" as used herein is an alkyl residue, as defined above, bonded directly to an oxygen atom, which is then bonded to another moiety. Examples include methoxy, ethoxy, n-propoxy, iso-propoxy, n-butoxy, t-butoxy, iso-butoxy and the like The term "aryl" as used herein is a ring radical containing 6 to 18 carbons, or preferably 6 to 12 carbons, comprising at least one aromatic residue therein. Examples of such aryl radicals include phenyl, naphthyl, and ischroman radicals. Moreover, the term "aryl" as used throughout the specification and claims is intended to include both "unsubstituted alkyls" and "substituted alkyls", the later denotes an aryl ring radical as defined above that is substituted with one or more, preferably 1, 2, or 3 organic or inorganic substituent groups, which include but are not limited to a halogen, alkyl, alkenyl, alkynyl, hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy or haloalkoxy, aryl, substituted aryl, heteroaryl, heterocyclic ring, ring wherein the terms are defined herein. The organic substituent groups can comprise from 1 to 12 carbon atoms, or from 1 to 6 carbon atoms, or from 1 to 4 carbon atoms. It will be understood by those skilled in the art that the moieties substituted on the "aryl" can themselves be substituted, as described above, if appropriate.

The term "acyl" as used herein is a R—C(O)— residue having an R group containing 1 to 8 carbons. Examples include but are not limited to formyl, acetyl, propionyl, butanoyl, iso-butanoyl, pentanoyl, hexanoyl, heptanoyl, benzoyl and the like, and natural or un-natural amino acids.

As used herein, the term "azide", "azido" and their variants refer to any moiety or compound comprising the monovalent group —$N_3$ or the monovalent ion —$N_3$.

The term "acyloxy" as used herein is an acyl radical as defined above directly attached to an oxygen to form an R—C(O)O— residue. Examples include but are not limited to acetyloxy, propionyloxy, butanoyloxy, iso-butanoyloxy, benzoyloxy and the like.

The term backbone atom when used herein with respect to a linker refers to an atom in the shortest direct path of covalent bonding between the two chief moieties that are linked by the linker.

The term "carbonate group" as used herein is represented by the formula —OC(O)OR, where R can be hydrogen, an alkyl, alkenyl, alkynyl, aryl, aralkyl, cycloalkyl, halogenated alkyl, or heterocycloalkyl group described above.

The term "carboxylic acid" as used herein is represented by the formula —C(O)OH.

The term "carbonyl group" as used herein is represented by the formula C=O.

The term "cycloalkyl" as used herein is a saturated hydrocarbon structure wherein the structure is closed to form at least one ring. Cycloalkyls typically comprise a cyclic radical containing 3 to 8 ring carbons, such as cyclopropyl, cyclobutyl, cyclopentyl, cyclopenyl, cyclohexyl, cycloheptyl and the like. Cycloalkyl radicals can be multicyclic and can contain a total of 3 to 18 carbons, or preferably 4 to 12 carbons, or 5 to 8 carbons. Examples of multicyclic cycloalkyls include decahydronapthyl, adamantyl, and like radicals.

Moreover, the term "cycloalkyl" as used throughout the specification and claims is intended to include both "unsubstituted cycloalkyls" and "substituted cycloalkyls", the later denotes an cycloalkyl radical analogous to the above definition that is further substituted with one, two, or more additional organic or inorganic substituent groups that can include but are not limited to hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido, acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkoxy, heteroaryl, substituted heteroaryl, aryl or substituted aryl. When the cycloalkyl is substituted with more than one substituent group, they can be the same or different. The organic substituent groups can comprise from 1 to 12 carbon atoms, or from 1 to 6 carbon atoms, or from 1 to 4 carbon atoms.

The term "cycloalkenyl" as used herein is a cycloalkyl radical as defined above that comprises at least one carbon-carbon double bond. Examples include but are not limited to cyclopropenyl, 1-cyclobutenyl, 2-cyclobutenyl, 1-cyclopentenyl, 2-cyclopentenyl, 3-cyclopentenyl, 1-cyclohexyl, 2-cyclohexyl, 3-cyclohexyl and the like.

The term "di-substituted amino" as used herein is a moiety comprising a nitrogen atom substituted with two organic radicals that can be the same or different, which can be selected from but are not limited to aryl, substituted aryl, alkyl, substituted alkyl or arylalkyl, wherein the terms have the same definitions found throughout. Some examples include dimethylamino, methylethylamino, diethylamino and the like.

The term "ether" as used herein is represented by the formula $AOA^1$, where A and $A^1$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ester" as used herein is represented by the formula —C(O)OA, where A can be an alkyl, halogenated alkyl, alkenyl, alkynyl, aryl, heteroaryl, cycloalkyl, cycloalkenyl, heterocycloalkyl, or heterocycloalkenyl group described above.

The term "haloalkyl" as used herein is an alkyl residue as defined above, substituted with one or more halogens, preferably fluorine, such as a trifluoromethyl, pentafluoroethyl and the like.

The term "haloalkoxy" as used herein a haloalkyl residue as defined above that is directly attached to an oxygen to form trifluoromethoxy, pentafluoroethoxy and the like.

The term "halo" or "halogen" refers to a fluoro, chloro, bromo or iodo group.

The term "heteroaryl" as used herein is an aryl ring radical as defined above, wherein at least one of the ring carbons, or preferably 1, 2, or 3 carbons of the aryl aromatic ring has been replaced with a heteroatom, which include but are not limited to nitrogen, oxygen, and sulfur atoms. Examples of heteroaryl residues include pyridyl, bipyridyl, furanyl, and thiofuranyl residues. Substituted "heteroaryl" residues can have one or more organic or inorganic substituent groups, or preferably 1, 2, or 3 such groups, as referred to herein-above for aryl groups, bound to the carbon atoms of the heteroaromatic rings. The organic substituent groups can comprise from 1 to 12 carbon atoms, or from 1 to 6 carbon atoms, or from 1 to 4 carbon atoms.

The term "heterocyclyl" or "heterocyclic group" as used herein is a non-aromatic mono- or multi ring radical structure having 3 to 16 members, preferably 4 to 10 members, in which at least one ring structure include 1 to 4 heteroatoms (e.g. O, N, S, P, and the like). Heterocyclyl groups include, for example, pyrrolidine, oxolane, thiolane, imidazole, oxazole, piperidine, piperizine, morpholine, lactones, lactams, such as azetidiones, and pyrrolidiones, sultams, sultones, and the like. Moreover, the term "heterocyclyl" as used throughout the specification and claims is intended to include both "unsubstituted alkyls" and "substituted alkyls", the later denotes an aryl ring radical as defined above that is substituted with one or more, preferably 1, 2, or 3 organic or inorganic substituent groups, which include but are not limited to a halogen, alkyl, alkenyl, alkynyl, hydroxyl, cycloalkyl, amino, mono-substituted amino, di-substituted amino, unsubstituted or substituted amido, carbonyl, halogen, sulfhydryl, sulfonyl, sulfonato, sulfamoyl, sulfonamide, azido acyloxy, nitro, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy or haloalkoxy, aryl, substituted aryl, heteroaryl, heterocyclic ring, ring wherein the terms are defined herein. The organic substituent groups can comprise from 1 to 12 carbon atoms or from 1 to 6 carbon atoms, or from 1 to 4 carbon atoms. It will be understood by those skilled in the art that the moieties substituted on the "heterocyclyl" can themselves be substituted, as described above, if appropriate.

The term "keto group" as used herein is represented by the formula —C(O)R, where R is an alkyl, alkenyl, alkynyl, aryl, aralkyl, cycloalkyl, halogenated alkyl, or heterocycloalkyl group described above.

As used herein, the terms "linked", "operably linked" and "operably bound" and variants thereof mean, for purposes of the specification and claims, to refer to fusion, bond, adherence or association of sufficient stability to withstand conditions encountered in single molecule applications and/or the methods and systems disclosed herein, between a combination of different molecules such as, but not limited to: between a detectable label and nucleotide, between a detectable label and a linker, between a nucleotide and a linker, between a protein and a functionalized nanocrystal; between a linker and a protein; and the like. For example, in a labeled polymerase, the label is operably linked to the polymerase in such a way that the resultant labeled polymerase can readily participate in a polymerization reaction. See, for example, Hermanson, G., 2008, Bioconjugate Techniques, Second Edition. Such operable linkage or binding may comprise any sort of fusion, bond, adherence or association, including, but not limited to, covalent, ionic, hydrogen, hydrophilic, hydrophobic or affinity bonding, affinity bonding, van der Waals forces, mechanical bonding, etc.

The term "linker" and its variants, as used herein, include any compound or moiety that can act as a molecular bridge that operably links two different molecules. There are many different linkers and types disclosed herein, such as those designated with a —B—.

The term "metabolite" refers to active derivatives produced upon introduction of a compound into a biological milieu, such as a patient.

The term "urethane" as used herein is represented by the formula —OC(O)NRR', where R and R' can be, independently, hydrogen, an alkyl, alkenyl, alkynyl, aryl, aralkyl, cycloalkyl, halogenated alkyl, or heterocycloalkyl group described above.

The term "mono-substituted amino" as used herein is a moiety comprising an NH radical substituted with one organic substituent group, which include but are not limited to alkyls, substituted alkyls, cycloalkyls, aryls, or arylalkyls. Examples of mono-substituted amino groups include methylamino (—NH—$CH_3$); ethylamino (—$NHCH_2CH_3$), hydroxyethylamino (—NH—$CH_2CH_2OH$), and the like.

A "moiety" is part of a molecule (or compound, or analog, etc). A "functional group" is a specific group of atoms in a molecule. A moiety can be a functional group or can include one or functional groups.

The term "silyl group" as used herein is represented by the formula —SiRR'R", where R, R', and R" can be, independently, hydrogen, an alkyl, alkenyl, alkynyl, aryl, aralkyl, cycloalkyl, halogenated alkyl, alkoxy, or heterocycloalkyl group described above.

When used with respect to pharmaceutical compositions, the term "stable" is generally understood in the art as meaning less than a certain amount, usually 10%, loss of the active ingredient under specified storage conditions for a stated period of time. The time required for a composition to be considered stable is relative to the use of each product and is dictated by the commercial practicalities of producing the product, holding it for quality control and inspection, shipping it to a wholesaler or direct to a customer where it is held again in storage before its eventual use. Including a safety factor of a few months time, the minimum product life for pharmaceuticals is usually one year and preferably more than 18 months. As used herein, the term "stable" references these market realities and the ability to store and transport the product at readily attainable environmental conditions such as refrigerated conditions, 2° C. to 8° C.

The term "sulfo-oxo group" as used herein is represented by the formulas —$S(O)_2R$, —$OS(O)_2R$, or, —$OS(O)_2OR$, where R can be hydrogen, an alkyl, alkenyl, alkynyl, aryl, aralkyl, cycloalkyl, halogenated alkyl, or heterocycloalkyl group described above.

A "detection agent" or like terms refers to any molecule or moiety which can be detected by, such as flourescence, radioactivity, phosphorescence, or the like.

The terms "higher," "increases," "elevates," or "elevation" or variants of these terms, refer to increases above basal levels, e.g., as compared to a control. The terms "low," "lower," "reduces," or "reduction" or variation of these terms, refer to decreases below basal levels, e.g., as compared to a control. For example, basal levels are normal in vivo levels prior to, or in the absence of, or addition of an agent such as an agonist or antagonist to activity.

By "inhibit" or other forms of inhibit means to hinder or restrain a particular characteristic. It is understood that this is typically in relation to some standard or expected value, in other words it is relative, but that it is not always necessary for the standard or relative value to be referred to. For example, "inhibits phosphorylation" means hindering or restraining the amount of phosphorylation that takes place relative to a standard or a control.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

A "labeled RNA binder" or like terms refers to a molecule comprising a detection agent.

"Optional" or "optionally" means that the subsequently described event or circumstance may or may not occur, and that the description includes instances where said event or circumstance occurs and instances where it does not.

As used herein, the term "pharmacological activity" refers to the inherent physical properties of a peptide or polypeptide. These properties include but are not limited to half-life, solubility, and stability and other pharmacokinetic properties.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

By "prevent" or other forms of prevent means to stop a particular characteristic or condition. Prevent does not require comparison to a control as it is typically more absolute than, for example, reduce or inhibit. As used herein, something could be reduced but not inhibited or prevented, but something that is reduced could also be inhibited or prevented. It is understood that where reduce, inhibit or prevent are used, unless specifically indicated otherwise, the use of the other two words is also expressly disclosed. Thus, if inhibits phosphorylation is disclosed, then reduces and prevents phosphorylation are also disclosed.

The term "pro-drug or prodrug" is intended to encompass compounds which, under physiologic conditions, are converted into therapeutically active agents. A common method for making a prodrug is to include selected moieties which are hydrolyzed under physiologic conditions to reveal the desired molecule. In other embodiments, the prodrug is converted by an enzymatic activity of the host animal.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself.

For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data are provided in a number of different formats, and that this data, represents endpoints and starting points, and ranges for any combination of the data points. For example, if a particular datum point "10" and a particular datum point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

By "reduce" or other forms of reduce means lowering of an event or characteristic. It is understood that this is typically in relation to some standard or expected value, in other words it is relative, but that it is not always necessary for the standard or relative value to be referred to. For example, "reduces phosphorylation" means lowering the amount of phosphorylation that takes place relative to a standard or a control.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

As used throughout, by a "subject" is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human.

"Treating" or "treatment" does not mean a complete cure. It means that the symptoms of the underlying disease are reduced, and/or that one or more of the underlying cellular, physiological, or biochemical causes or mechanisms causing the symptoms are reduced. It is understood that reduced, as used in this context, means relative to the state of the disease, including the molecular state of the disease, not just the physiological state of the disease.

The term "therapeutically effective" means that the amount of the composition used is of sufficient quantity to ameliorate one or more causes or symptoms of a disease or disorder. Such amelioration only requires a reduction or alteration, not necessarily elimination. The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1 Development of a Fluorescence-Based Assay for Aminoglycoside Binding to Target RNA A survey of a library of fluorescently-labeled neomycin derivatives was performed, and a compound exhibiting decrease in fluorescence intensity upon binding to the bacterial rRNA A-site oligonucleotide was identified. This compound F-neo or 42a is a fluorescein conjugate coupled through the 5" OH position of the ribose ring of neomycin B (H. Xi, E. Davis, N. Ranjan, L. Xue, D. Hyde-Volpe, D. P. Arya, Thermodynamics of nucleic Acid "shape readout" by an aminosugar, Biochemistry. 50 (2011) 9088-9113). *E. coli* rRNA Asite oligonucleotide (SEQ ID NO. 1, GGCGU-CACACCUUCGGGUGAAGUCGCC) is a synthetic RNA sequence 27 bases long designed to mimic the ribosomal A-site. The A-site oligonucleotide (SEQ ID NO. 1) is titrated into F-neo (42a) to give a concentration dependent loss of fluorescence of F-neo (42a). The titration of Scatchard analysis indicates one binding site of F-neo (42a) per oligonucleotide and a dissociation constant of $2.3 \times 10^7$. Molecular modeling of the interaction of F-neo (42a) with A-site oligonucleotide suggests that the fluorescein moiety localizes in the groove in a manner that places the phenol group adjacent to the phosphate backbone.

Figure 2A:
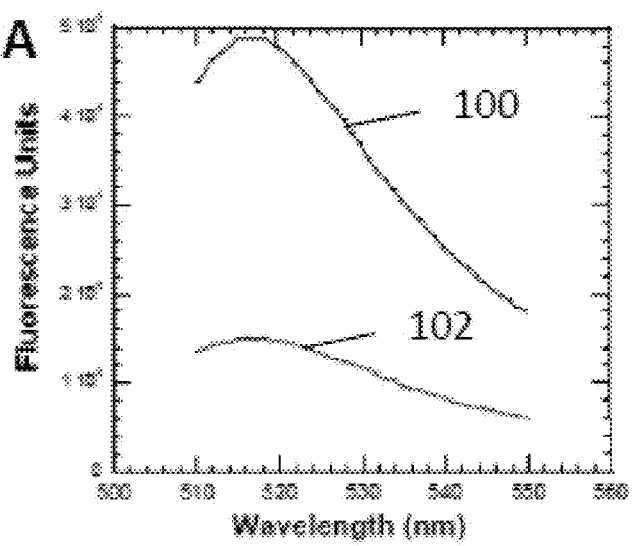
FIG. 2A shows the effect of bacterial A-site oligonucleotide (SEQ ID No. 1) on the fluorescence emission intensity of a fluorescein-neomycin conjugate (F-neo or 42a) disclosed herein.
Figure 2B:
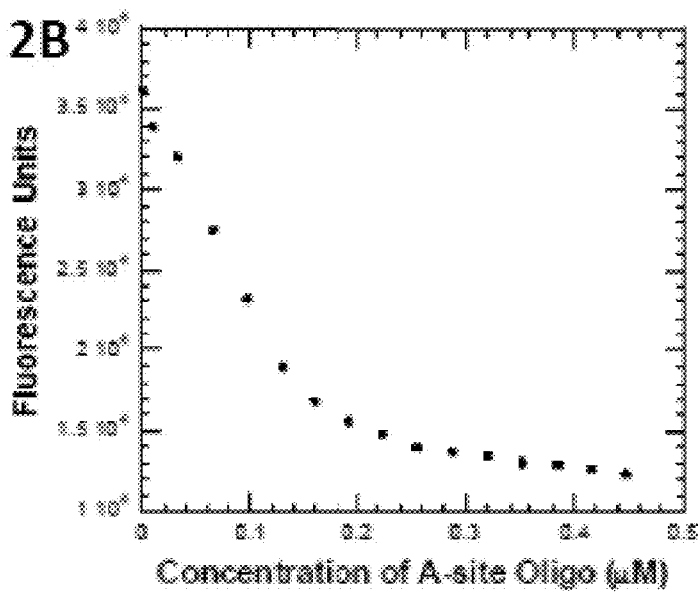
FIG. 2B shows the decrease of fluorescence emission intensity of F-neo with increased concentration of bacterial A-site oligonucleotide (SEQ ID NO. 1).

The effect of bacterial A-site oligonucleotide (SEQ ID No. 1) on the fluorescence emission intensity of a fluorescein-neomycin conjugate (F-neo or 42a) is recorded in FIG. 2. FIG. 2A shows that the emission spectra of 0.25 mM F-neo excited at 490 nm is line 100 and with the addition of 0.3 mM bacterial rRNA A-site oligonucleotide (SEQ ID No. 1) it lowered to line 102. FIG. 2B shows the effect of titration of fluorescence emission (517 nm) of 0.3 mM F-neo with increasing concentrations of A-site oligonucleotide (SEQ ID No. 1). Experiments were performed in 10 mM MOPSO, 0.4 mM EDTA, and 50 mM NaCl at pH 7.0. As shown in FIG. 2, the addition of a 1:1 stoichiometric ratio of conjugate (F-neo) and A-site oligonucleotide resulted in a 3-fold reduction in fluorescence emission intensity.

Figure 3:
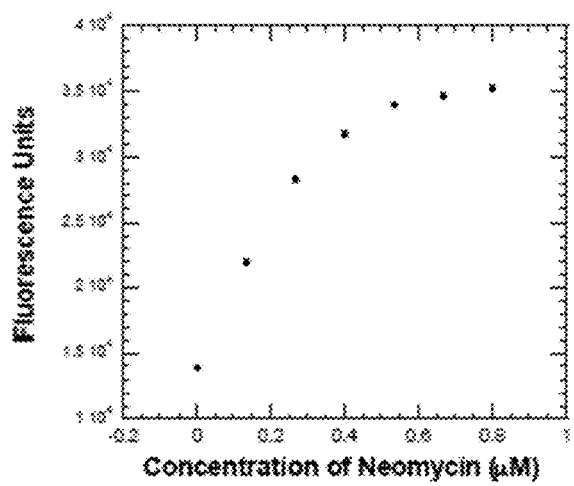
FIG. 3 shows the titration of bacterial A-site oligonucleotide (SEQ ID NO. 1)/fluorescein-neomycin conjugate (F-neo) complex with neomycin.

The F-neo (42a) can be competitively displaced from the A-site RNA oligonucleotide (SEQ ID No. 1) by the addition of non-fluorescent RNA binding drugs. Titrating neomycin into the F-neo (42a):A-site complex increases the fluorescence in a dose dependent manner that saturates at a 1:1 stoichiometric ratio of drug-to-complex. Additionally, a strong signal window, measured as an increase in fluorescence is present at a 3:1 molar ratio, and a maximum change in fluorescence at approximately 10:1 molar ratio. Titrating in neomycin reverses this effect in a dose dependent manner that saturated at a 1:1 stoichiometric ratio of drug-to-complex was shown in FIG. 3. Fluorescence emission intensity (517 nm) of 0.3 mM A-site oligocletide/F-neo complex solution increased with increasing concentration of neomycin. Experiments were performed in 10 mM MOPSO, 0.4 mM EDTA, and 50 mM NaCl at pH 7.0. This provides an example of how the assay system can function as a powerful assay for assessing the binding affinity of aminoglycosides and their derivatives towards RNA targets.

Example 2 Development of a High-Throughput Screening Assay (HTS)

Provided is a detailed example for the development of a HTS by the displacement of a fluorescene-neomycin (F-neo (42a)) from rRNA A-site oligonucleotide (SEQ ID No. 1) using a 96 well plate format and a fluorescent plate reader.

The high throughput screening (HTS) determines the binding of drugs to the ribosomal A-site. This HTS involves the displacement of a fluorescene-neomycin (F-neo (42a)) by potential RNA binding molecules in a 96 well plate format using a fluorescent plate reader. Initial studies of this system have demonstrated that the binding of F-neo (42a) to A-site RNA results in the quenching of the fluorophore, and the displacement of F-neo (42a) by a competitive binding molecule is measured by an increase in fluorescence.

Figure 4A:
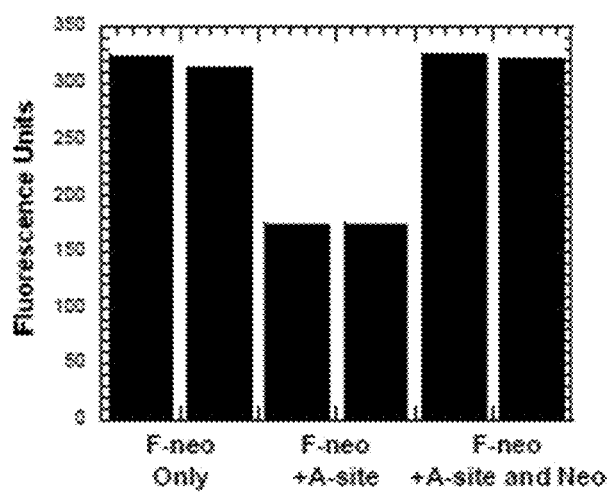
FIGS. 4A-C show results from a F-neo based RNA binding assay using a 96-well format.
Figure 4B:
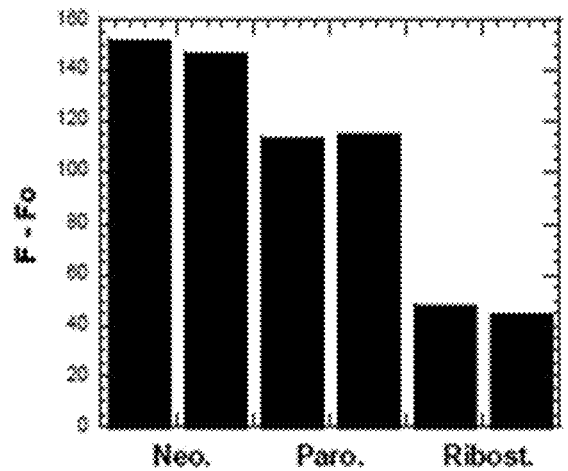
Figure 4C:
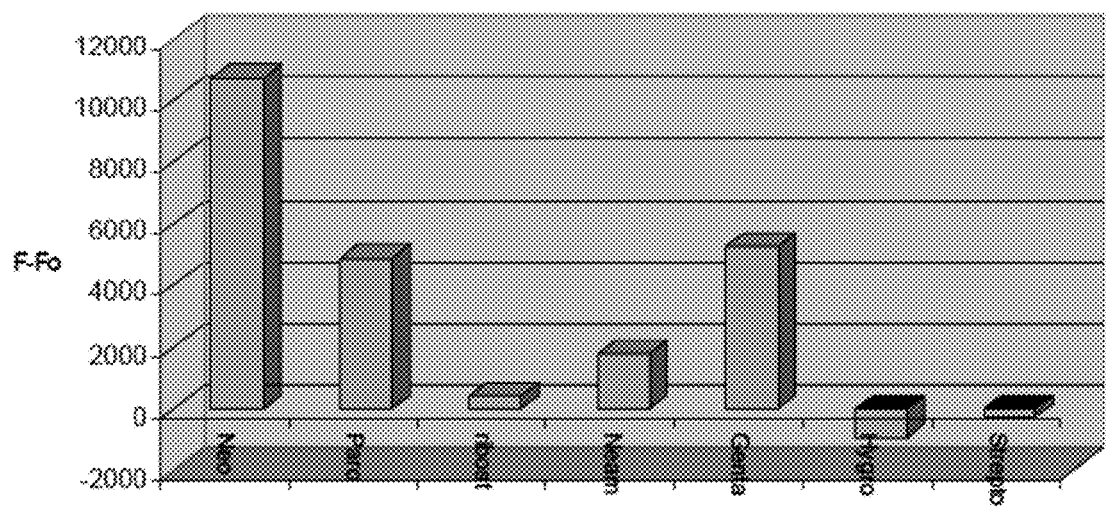

F-neo based RNA binding assays have been performed using a fluorescence spectrophotometer with a 96-well plate reader and results recorded in FIG. 4. FIG. 4A shows the duplicate measurements of the fluorescence emission intensity (517 nm) of 0.3 mM F-neo alone; 0.30 mM F-neo and 0.3 mM A-site oligonucleotide; and 0.30 mM F-neo, 0.3 mM A-site oligonucleotide and 1.0 mM neomycin. Duplicate F-neo samples in the left panel show low variation in fluorescence and responded to the addition of A-site with 2-fold reduction in fluorescence intensity. Moreover, the addition of neomycin to samples of F-neo/A-site oligonucleotide complex restored the intensity to F-neo only levels. FIG. 4B shows duplicate measurements of samples with 0.30 mM F-neo, 0.3 mM A-site oligonucleotide and 1.0 mM of one of neomycin, paromomycin, or ribostamycin. Sample volume was 200 mL and solutions contained 10 mM MOPSO, 0.4 mM EDTA, and 50 mM NaCl at pH 7.0. Fo is defined as the baseline fluorescence intensity of the RNA/F-neo complex and F is the intensity with added drug. The difference between the fluorescence intensity baseline of F-neo/A-site complex and complex with added drug (F-Fo) indicates the extent of the competition of drug for the binding site, this allows the relative binding affinities of aminoglycosides to be established. It has been reported that the relative binding affinities for neomycin, paromomycin, and ribostamycin with bacterial A-site oligos is neomycin>paromomycin>ribostamycin (Kaul, 2002). As seen in FIG. 4 right panel, the 96-well format of this competition assay was effective at assessing the relative binding affinity of these aminoglycosides. FIG. 4C shows the screening of aminoglycoside library with 10 Scans per Well. Aminoglycosides 0.3 µM neomycin, paromomycin, ribostamycin, neamine, gentamycin, hygromycin, and streptomycin were added to 0.1 M E. coli A-site/F-neo (42a) complex. Each result was taken from the average of ten experiments ran on a 96 well Greiner black plate. The emission was measured at wavelength 535 nm, using an excitation wavelength of 485 nm using a Tecan Genios Pro plate reader. All experiments were performed in 10 mM hepes (7.0), 50 mM NaCl, and 0.4 mM EDTA. F-Fo is calculated by subtracting the fluorescence of the experiment with the aminoglycoside present from the fluorescence of the A-site/F-neo (42a) complex in the absence of the aminoglycoside. Using the difference between the fluorescence intensity baseline of F-neo (42a)/A-site complex and complex with added drug (F-Fo) indicates the extent of the competition of drug for the binding site. This analysis allows the relative binding affinities of aminoglycosides to be established. These results further show that a F-neo (42a) based assay can be used for efficient high throughput screening of small molecule libraries such as aminoglycoside libraries for drug candidates.

The quality of the assay was determined by the calculation of a Z'-factor using equation 1 for the displacement of F-neo (42a) from the E. coli A-site by neomycin.

$$Z\text{-factor}=1-3\times(\sigma_p+\sigma_n)/|\mu_p-\mu_n| \qquad \text{Eq. (1)}$$

Figure 5:
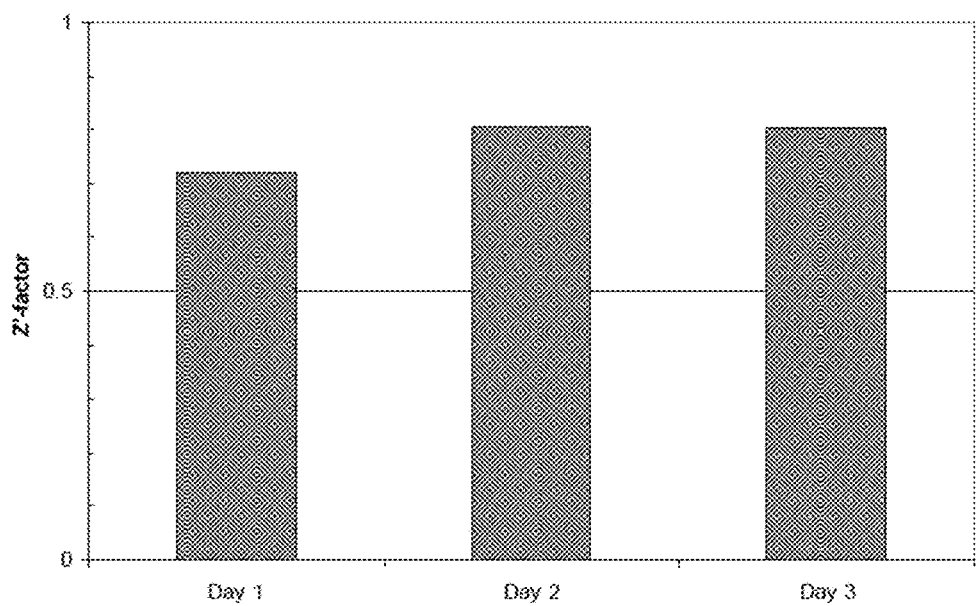
FIG. 5 shows the Z' factor of the displacement of F-neo (42a) from A-site oligonucleotide (SEQ ID No. 1) by neomycin in 96 well format.

The final assay results were obtained using the average (n) and standard deviation (σn) from 48 wells of 0.1 µM F-neo (42a)/E. coli ribosomal A-site as the negative control and from the average (µp) and standard deviation (σp) 48 wells of 0.1 µM F-neo (42a)/E. coli ribosomal A-site mixed with 0.3 µM neomycin as the positive control. The Z'-factor was calculated from the HTS with 0.3 µM neomycin to 0.1 µM E coli A-site/F-neo (42a) complex using 100 reads/well using a Tecan Genios Pro plate reader. Each bar represents an independent experiment ran on the designated day. Each Z' was calculated using the average and standard deviation of 48 wells on a 96 well black plate. The emission was measured at wavelength 535 nm, using an excitation wavelength of 485 nm. All experiments were performed in 10 mM hepes (7.0), 50 mM NaCl, and 0.4 mM EDTA. Three independent experiments performed on three consecutive days resulted in Z'-factor of 0.81, 0.80, and 0.87, indicated the high degree of reproducibility of the assay. FIG. 5 shows the results of these experiments. The accepted scale of the Z'-factor is >0.5 is excellent, 0<Z'<0.5 is marginal, and Z'<0 is unacceptable. Our results indicate that the assay is suitable for the detection drugs that bind to the ribosomal A-site of E. coli by the displacement of the F-neo (42a) probe in a high throughput format.

Figure 6A:
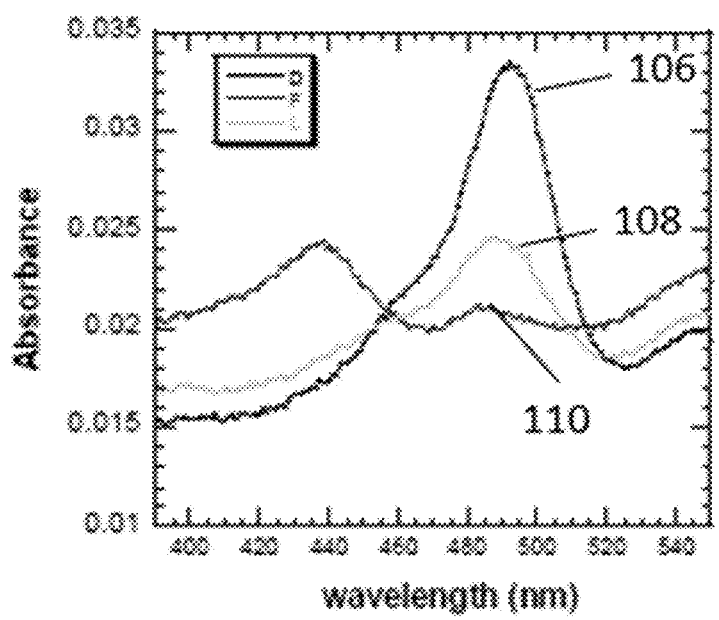
FIG. 6A shows effect of pH on the absorbance spectra of fluorescein-neomycin.
Figure 6B:
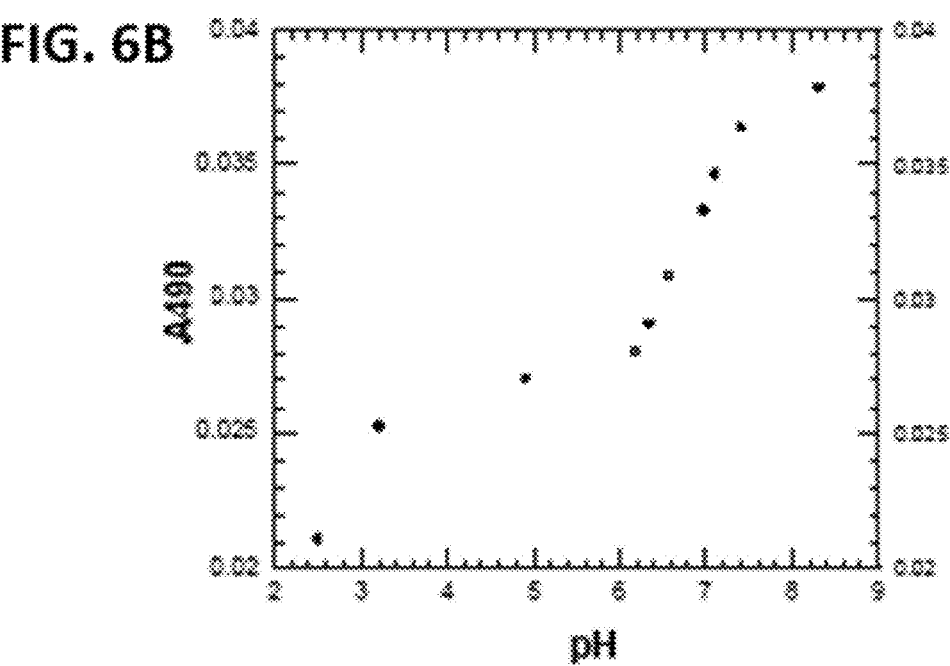
FIG. 6B shows absorbance at 490 nm of fluorescein-neomycin as function of pH.

Example 3 The pH Sensitivity of the Probe and Binding Site Electrostatic Potential The mechanism for change in fluorescence of F-Neo upon binding to A-site rRNA oligonucleotide (SEQ ID No. 1) using UV absorption spectroscopy was investigated. Effect of pH on the absorbance spectra of 3.0 mM fluorescein-neomycin in 20 mM MOPSO, 0.4 mM EDTA, 50 mM NaCl at the indicated pH values were studied. FIG. 6A shows the absorbance spectra of 3.0 mM fluorescein-neomycin at pH 7.10 (106), pH 5.95 (108) and pH 2.5 (110). FIG. 6B shows the absorbance at 490 nm of fluorescein-neomycin as function of pH.

Figure 7A:
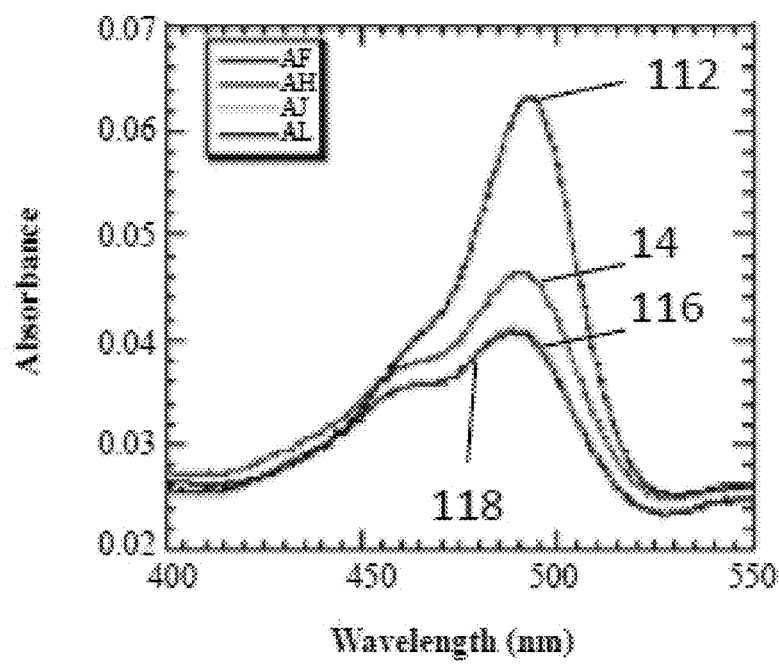
FIG. 7A shows the effect of A-site rRNA oligonucleotide (SEQ ID NO. 1) on the absorbance spectra of fluorescein-neomycin at pH 7.1.
Figure 7B:
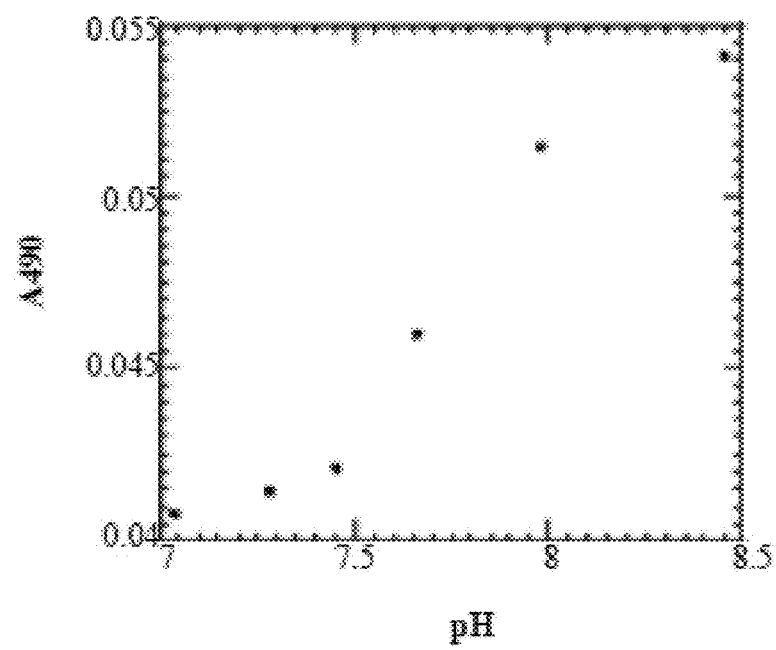
FIG. 7B shows the absorbance at 490 nm of fluorescein-neomycin:A-site complex as function of pH.

The effect of A-site rRNA oligonucleotide (SEQ ID No. 1) on the absorbance spectra of fluorescein-neomycin at pH 7.1 was recorded in FIG. 7. The absorbance spectra of 3.0 mM fluorescein-neomycin in 20 mM MOPSO, 0.4 mM EDTA, 50 mM NaCl at pH 7.1 with the addition of 0 mM (112), 1.1 mM (114), 2.2 mM (116) or 3.3 mM (118) of A-site oligonucleotide (SEQ ID NO. 1), respectively is shown in FIG. 7A. Absorbance at 490 nm of fluorescein-neomycin:A-site complex as function of pH is show in FIG. 7B, with 3.0 mM fluorescein-neomycin complexed with 3.3 mM A-site oligonucleotide (SEQ ID No. 1) in 20 mM MOPSO, 0.4 mM EDTA, 50 mM NaCl at the indicated pH values.

Figure 8A:
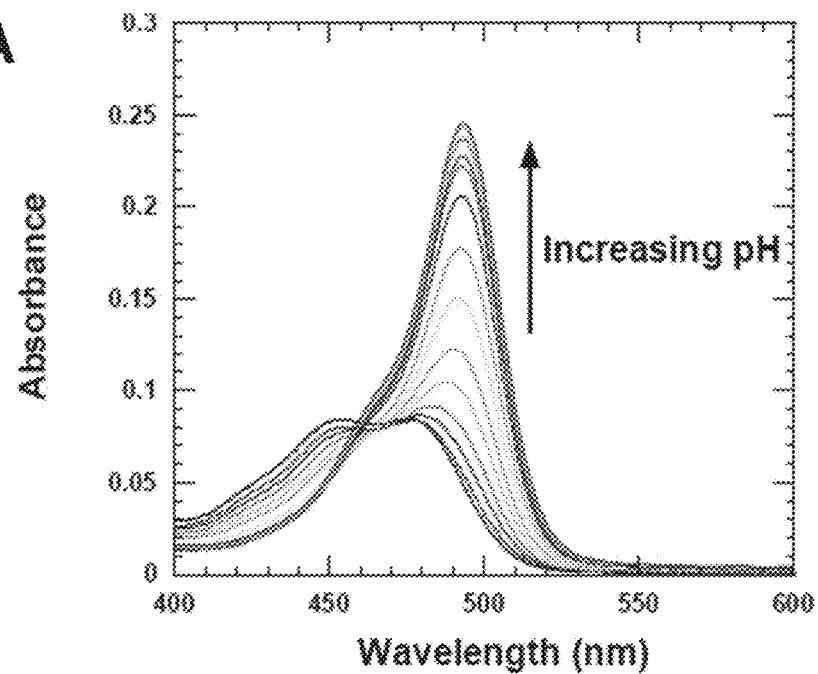
FIG. 8A shows absorbance spectra of fluorescein-neomycin with increasing pH showing the transition between mono-anion and di-anion species.
Figure 8B:
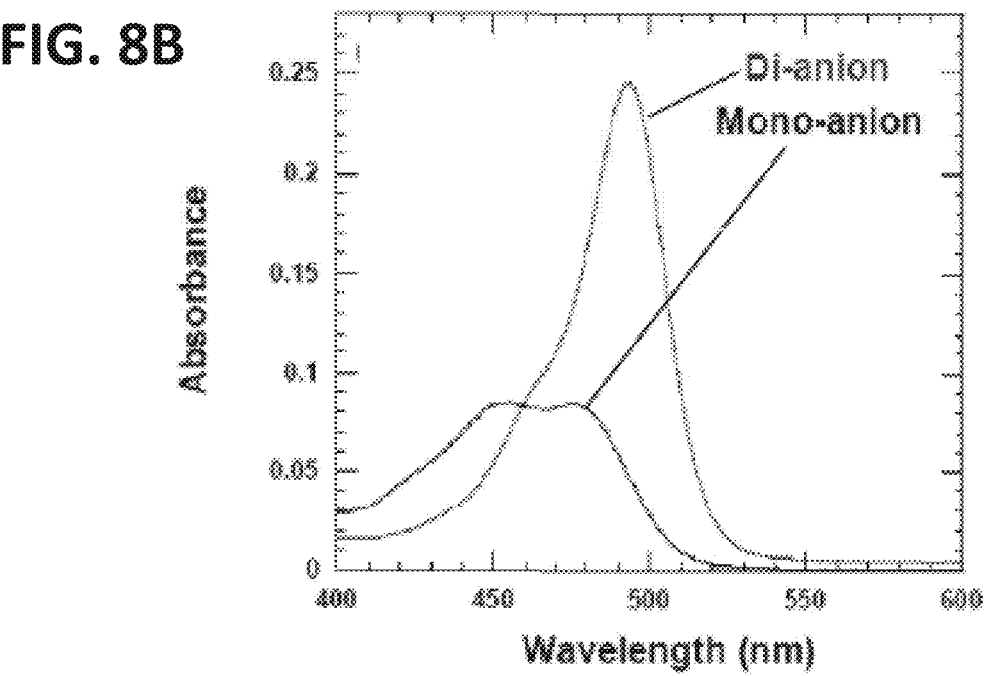
FIG. 8B shows the total change in absorbance spectra between the mono-anion and di-anion species of fluorescein neomycin.
Figure 8C:
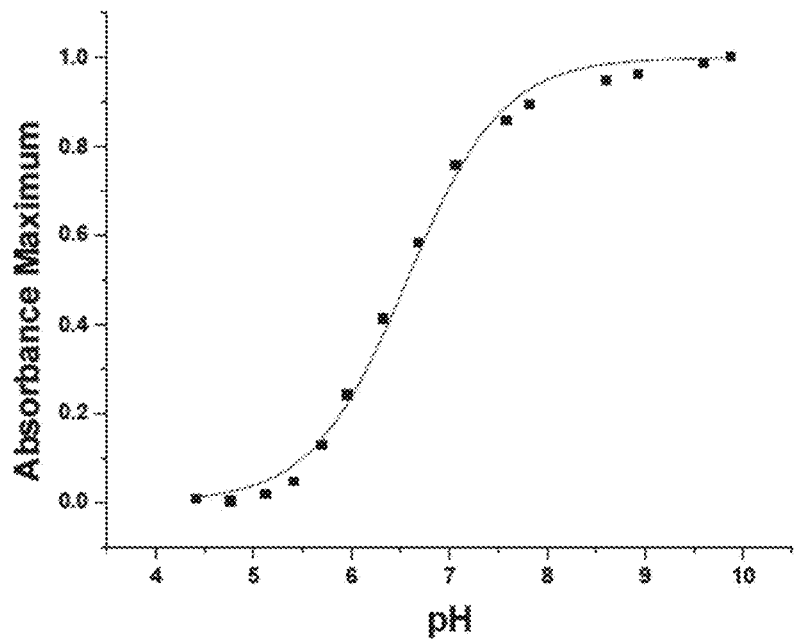
FIG. 8C shows the absorbance maximum plotted as a function of pH with the resulting inflection point representing the fluorescein phenolic pKa.

With increasing pH, fluorescein-neomycin undergoes a transition between mono-anion and di-anion species. Fluorescein-neomycin concentration was 10 µM in 100 mM NaCl, 10 mM SC, 0.5 mM EDTA. As indicated by its absorbance spectra in FIG. 8A, the F-neo transitions from a mono-anion to a di-anion with increasing pH. FIG. 8B compares the absorbance spectra between the mono-anion and di-anion species of fluorescein neomycin. FIG. 8C shows absorbance maximum plotted as a function of pH with the resulting inflection point representing the fluorescein phenolic pKa. The absorbance peak of about 490 nm in FIGS. 8A and 8B is consistent with the phenolate species of fluorescein. The pKa for the equilibrium of the phenol and phenolate forms of F-neo (42a) was measured by evaluating the absorbance spectrum as a function of pH and shown to be 6.84. This is very similar to the pka of 6.7 for reported for free fluorescein (martin and lindqvist, 1975) indicating the neomycin moiety does not alter this pKa appreciably. When monitoring the absorption spectrum in the presence of the A-site RNA (SEQ ID No. 1), a reduction in $A_{490}$ consistent with the change in pKa was observed. This $A_{490}$ reduction is consistent with a shift in equilibrium towards the protonated non-fluorescent form of fluorescein-neomycin upon binding to A-site. This titration curve suggests that the binding of A-site stabilizes the non-fluorescent protonated form of fluorescein-neomycin, due to an upward shift of the pKa of approximately one pH unit. This shift in pKa causes a change in the fluorescence intensity of F-neo (42a). The titration of F-neo (42a) with A-site oligonucleotide at pH 7.1 resulted in a decrease in the fluorescence observed at 490 nm, consistent with a shift for the highly fluorescent phenolate form to the non-fluorescent phenol form of the dye.

The following equilibrium can be used to explain the probe function:

$$FHNeo + Base = F(-)Neo + BH^+ \qquad \text{Eq. (2)}$$

where FHNeo represents the protonated form of F-neo (42a). Upon binding to A-site RNA, F(-)Neo is destabilized by the negative potential of the RNA backbone, shifting the equilibrium towards FHNeo. Thus the binding of F-neo (42a) to RNA raises the pKa, making F-neo (42a) a weaker acid.

Since it has been shown that a shift in phenolic pKa is directly proportional to the electrostatic potential ($\Psi$) at the position occupied by the fluorescein moiety (Friedrich, K., et al., (1988) *Eur. J Biochem.* 173, 227-231.) it can be concluded that the shift in pKa between free Fluorescein-neomycin and Fluorescein-neomycin bound to DNA's major groove reveals the electrostatic potential of the major groove, neomycin's binding site. The local electrostatic potential ($\Psi$) in the major groove is given by the following Equation 3.

$$\Psi = -[R \cdot T \cdot \ln 10/(N_A \cdot e)]\Delta pKa \qquad \text{Eq. (3)}$$

Where $\Delta pKa$ is the difference between the free Fluorescein-neomycin and the Fluorescein-neomycin in the presence of the electrostatic environment, R is the universal gas constant, T is the absolute temperature in kelvin, $N_A$ is the Avogadro constant, and e is the elementary charge. R=8.312 J mol−1K−1, T=298.2K, $N_A$=6.023×10²³ and e=1.602×10⁻¹⁹; $\Psi$ is expressed in mV. Thus a shift of +1 in the value of the pKa implies an electrostatic potential of −58.2 mV. The pH-dependent absorbance spectra of F-neo (42a)/A-site oligonucleotide complexes indicated that RNA binding causes a shift apparent pKa of F-neo (42a) to 7.7. Based on this Δpka of 0.86, the electrostatic potential of the microenvironment for the fluorescein moiety in the complex is determined to be −50.9 mV.

Figure 9:
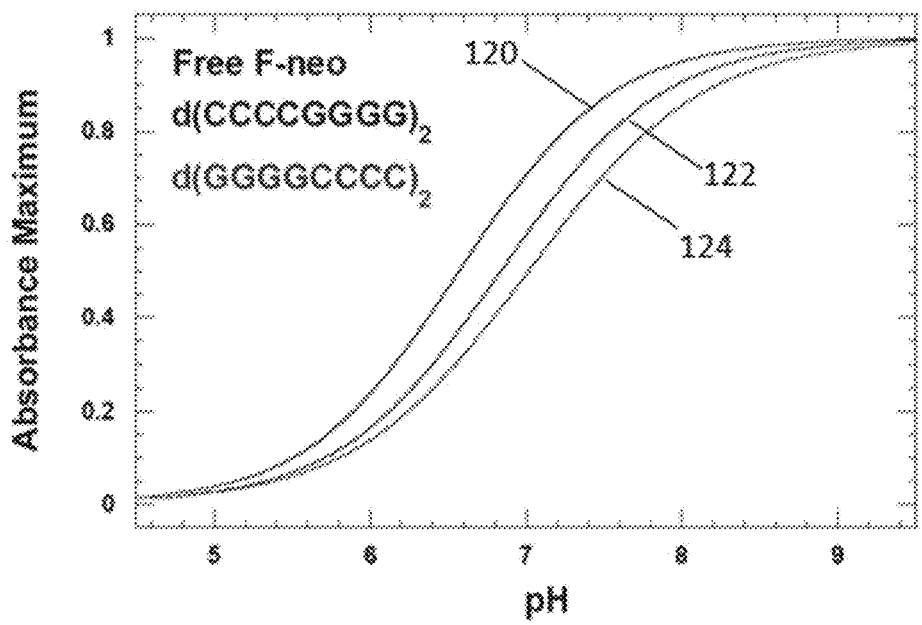
FIG. 9 is a plot showing the shift in absorbance maximum plotted as a function of pH for fluorescein-neomycin with one molar equivalent d(CCCCGGGG)$_2$, and d(GGGGC-CCC)$_2$ compared to free fluorescein-neomycin resulting in the shift in pKa.

Determination of the pKa was done using chemometric analysis of the absorption profiles at various pH values of the covalently attached fluorescein moiety (Kubista, M., et al., (1993) *Anal. Chem.* 65, 994-998, Kubista, M., et al., (1995) *Anal. Chim. Acta.* 302, 121-125.2, 3). The pH dependent absorption profile of free fluorescein-neomycin was first analyzed to determine its pKa. This was then repeated with one molar equivalent of d(GGGGCCCC)₂ and d(CCCCGGGG)₂ and the effect of these nucleic acids resulted in a pKa shift of the fluorescein-neomycin as recorded in FIG. 9. The electrostatic potential (P) calculated from the shift in pKa, and the ITC derived binding constant (K). Electrostatic potential experiments performed in 100 mM NaCl, 10 mM SC, 0.5 mM EDTA at 25° C. ITC experiments performed in 50 mM KCl, 10 mM SC, 0.5 mM EDTA (pH 6.0) at 25° C. As shown in FIG. 9, the shift in absorbance maximum plotted as a function of pH for fluorescein-neomycin with one molar equivalent d(CCCCGGGG)₂ (122), and d(GGGGCCCC)₂ (124) compared to free fluorescein-neomycin (120) resulting in the shift in pKa. Fluorescein-neomycin concentration was 10 μM. Table 1 represents the pKa values determined from the inflection point of the pH dependent absorbance scans of free fluorescein-neomycin, fluorescein-neomycin with one molar equivalent d(CCCCGGGG)₂ and d(GGGGCCCC)₂. The electrostatic potential (Y) calculated from the shift in pKa, and the ITC derived binding constant (K).

TABLE 1

| Oligonucleotide | pKa | ΔpKa | Ψ (mV) | K (M⁻¹) × 10⁵ |
|---|---|---|---|---|
| Free Fluorescein-neomycin | 6.57 | — | — | — |
| d(CCCCGGGG)₂ | 6.83 | 0.26 | −15.13 | 7.97 ± 10.9 |
| d(GGGGCCCC)₂ | 7.01 | 0.44 | −25.61 | 66.3 ± 9.7 |

With the change in pKa the electrostatic potential of the neomycin binding site was calculated using equation (2). The shift in phenolic pKa of fluorescein-neomycin in the presence of d(GGGGCCCC)₂ was considerably greater than the shift seen in the presence of d(CCCCGGGG)₂. Using the shifts in pKa the electrostatic potentials of each respective binding site was determined. The electrostatic potential of the neomycin binding site of d(GGGGCCCC)₂ was calculated to be −25.61 mV and d(CCCCGGGG)₂ was calculated to be −15.13 mV. The substantial difference in electrostatic potential between the two inverted duplexes d(GGGGCCCC)₂ and d(CCCCGGGG)₂ reflects a difference in electrostatic complementarity between the DNA duplexes and neomycin.

Electrostatic potential is a vital force driving the intermolecular association and molecular properties of small molecules (Weiner, P. K., et al., (1982) *PNAS.* 79, 3754-37584), actions of drug molecules, and analogs (Weinstein, H., et al., (1975) *Mol. Pharmacol.* 11, 671-6895), and enzyme catalysis (Warshel, A., (1981)*Acc. Chem. Res.* 14, 284-2906). Fluorescein has been exploited as a DNA probe to monitor hybrid formation in solution (Murakami, A., et al. (1991) *Nucl. Acids Res.* 19, 4097-41027), and with covalent attachment the electrostatic potential around the nucleic acid (Sjoback, R., et al., (1998) *Biopolymers.* 46, 445-4538). Here it was shown that a fluorescein-neomycin conjugate can be used to determine the electrostatic potential of DNA's major groove, the aminosugar binding site. The binding site specific electrostatic potentials of two inverted DNA duplexes were compared with the ITC-derived binding constants. The comparison between electrostatic potential and ITC-derived binding constants illustrated the influence of electrostatic potential on the affinity of neomycin. CD experiments performed show the difference in DNA conformations between d(GGGGCCCC)₂ and d(CCCCGGGG)₂. Drug-DNA recognition is dependent on the structural electrostatic complementarity (Arya, D. P. (2005) The Case for Neomycin, in *Topics in Current Chemistry: DNA Binders* (J.

B. Chaires, and M. J. Waring, Eds.) pp 149-178, Springer Verlag: Heidelburg, 9). The differences in CD spectra provide evidence showing how the difference in electrostatic potential of the major groove binding site is affected by conformational differences.

Figure 10:
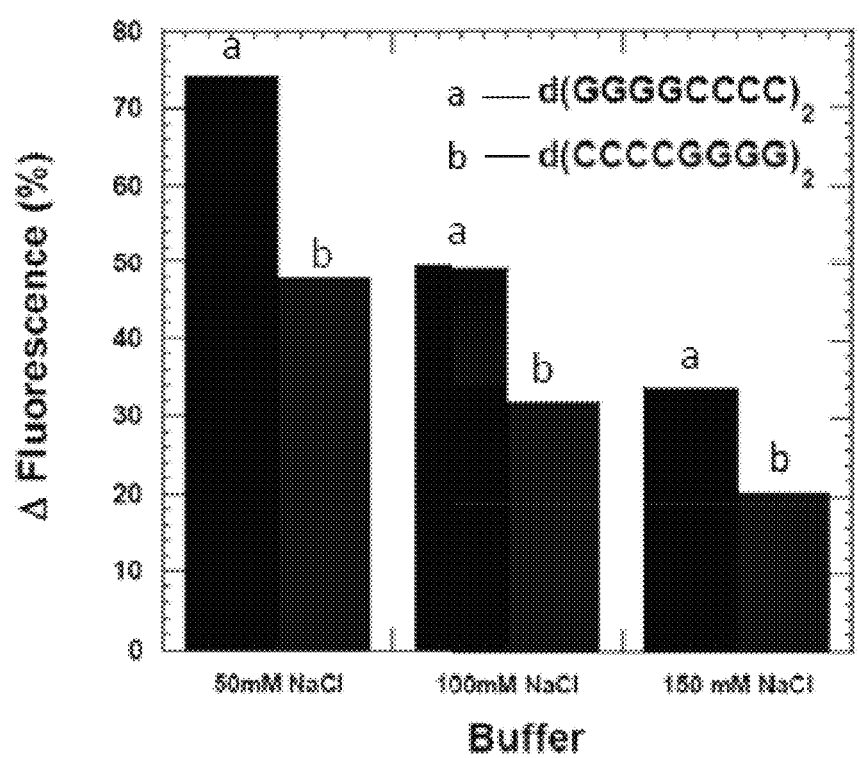
FIG. 10 is a plot representing the change in fluorescence (%) of fluorescein-neomycin with 1 equivalent d(GGGGC-CCC)$_2$ and d(CCCCGGGG)$_2$ in 3 different buffer salt concentrations.

Example 4 Use of F-Neo as a High Throughput Screening Probe to Identify High Affinity Major Groove Binding Sequences It has been shown that the fluorescence of a fluorescein-neomycin is quenched when bound to a nucleic acid target. In continued efforts to expand the applications of the fluorescein-neomycin conjugate, a fluorescence quenching study was performed to determine if the quenching of fluorescein-neomycin in the presence of DNA is representative of the neomycin affinity. Previous studies using the duplexes d(GGGGCCCC)$_2$ and d(CCCCGGGG)$_2$ have shown the binding is lower for d(CCCCGGGG)$_2$. This has been shown from the ITC derived binding constants, FID studies, and electrostatic potential studies. With these results the fluorescein-neomycin quenching for d(GGGGCCCC)$_2$ and d(CCCCGGGG)$_2$ is shown here, and also salt dependent studies here have shown neomycin binding decreases with increasing buffer salt concentration. For this reason the fluorescence quenching of fluorescein-neomycin with d(GGGGCCCC)$_2$ and d(CCCCGGGG)$_2$ was performed at three different buffer salt concentrations. If the fluorescein-neomycin quenching is directly related to the affinity for neomycin then d(GGGGCCCC)$_2$ would quench the fluorescence better than d(CCCCGGGG)$_2$ and the fluorescein-neomycin quenching for both duplexes would decrease with increasing buffer salt concentrations, as seen In Table 2. As the salt concentration is increased from 50 to 150 mM NaCl, AF values for both the DNA sequences drop significantly (from 73% to 33% and from 47% to 20%). Results from this study show here that the fluorescein-neomycin quenching can be applied to screening the 256 GC rich hairpins to identify which sequence neomycin has the highest affinity. Table 2 represents the change in fluorescence (%) values of fluorescein-neomycin with $1r_{dr}$ d(GGGGCCCC)$_2$ and d(CCCCGGGG)$_2$ in 3 different buffer salt concentrations and the ratio between the change in fluorescence (%) values of F-neo with d(CCCCGGGG)$_2$ compared to d(GGGGCCC)$_2$. Fluorescein-neomycin=1 µM, Buffer=10 mM SC, 0.5 mM EDTA, and either 50 mM NaCl, 100 mM NaCl, or 150 mM NaCl (pH=6.8). Experiment was performed in triplicate and the results were also polted in FIG. 10 showing the change in fluorescence (%) of fluorescein-neomycin with 1 equivalent d(GGGGCCCC)2 and d(CCCCGGGG)2 in 3 different buffer salt concentrations.

TABLE 2

| Buffer Salt Concentration | ΔF (%) with $1r_{dr}$ d(GGGGCCCC)$_2$ | ΔF (%) with $1r_{dr}$ d(CCCCGGGG)$_2$ | Ratio of ΔF (%) with d(CCCCGGGG)$_2$/ d(GGGGCCCC)$_2$ |
|---|---|---|---|
| 50 mM NaCl | 73.97 ± 5.78 | 47.75 ± 5.60 | 0.65 |
| 100 mM NaCl | 49.28 ± 1.12 | 32.18 ± 0.42 | 0.65 |
| 150 mM NaCl | 33.88 ± 3.33 | 20.36 ± 2.76 | 0.60 |

The results from the fluorescein-neomycin quenching experiment show the quenching of fluorescein-neomycin is related to the affinity of the DNA duplex for neomycin. In addition the effect of buffer salt concentration continues to show the fluorescein-neomycin quenching is correlated with the binding of fluorescein-neomycin which represents the binding for neomycin. Also the difference between the quenching of fluorescein-neomycin with d(GGGGCCCC)$_2$ and d(CCCCGGGG)$_2$ shows the same ratio of change in the different salt concentrations showing the binding of both d(GGGGCCCC)$_2$ and d(CCCCGGGG)$_2$ are both equally affected by the salt concentration of the buffer. This method of fluorescein-neomycin quenching can therefore be used for screening nucleic acid sequences of varying affinities.

Example 5 High Throughput Sequence Specificity Screening with a Thiazole Orange-Neomycin Conjugate Neomycin-thiazole orange was made with 2 different linker lengths TO-neo 1 (36b) and TO-neo2 (36a) and the chemical structures shown below.

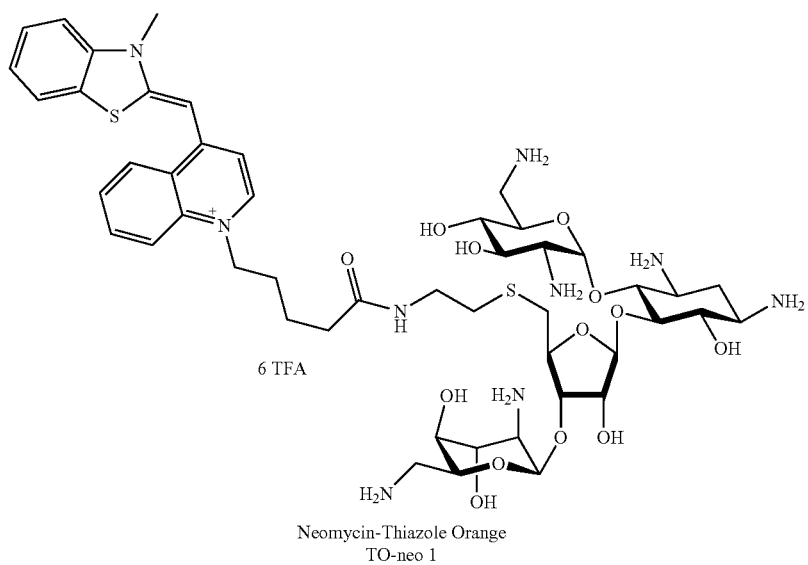

Neomycin-Thiazole Orange
TO-neo 1

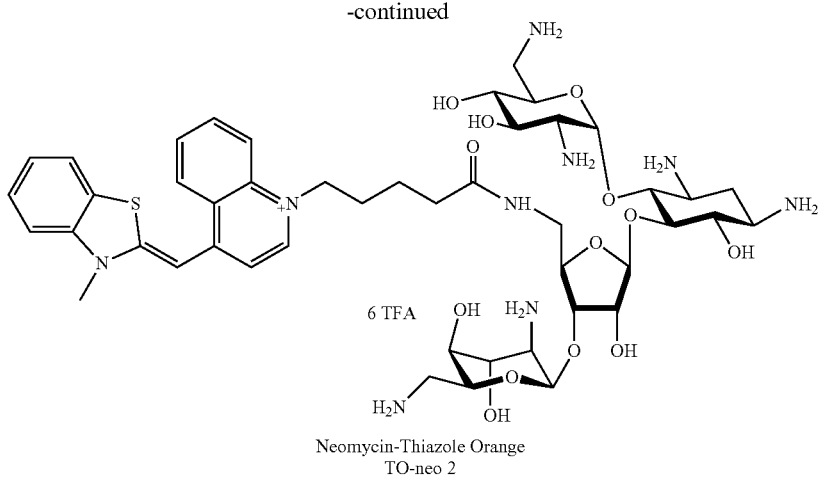

Neomycin-Thiazole Orange
TO-neo 2

Figure 11A:
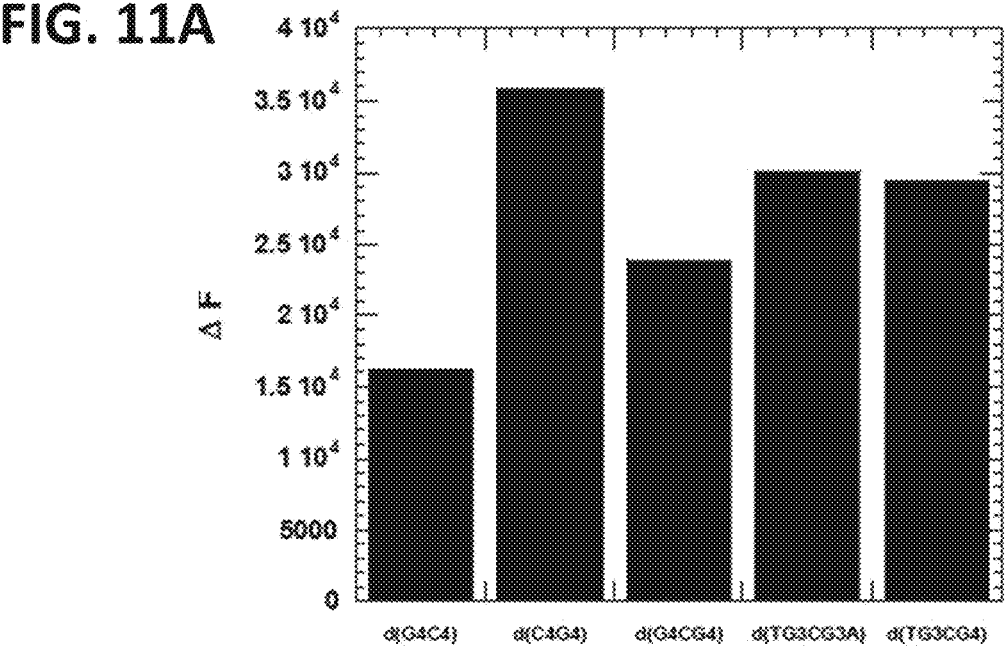
FIG. 11A is a plot showing the change in fluorescence of d(GGGGCCCC)$_2$, d(CCCCGGGG)$_2$, d(GGGGCGGGG)$_2$, d(TGGGCGGGA)$_2$, and d(TGGGCGGGG)$_2$ after addition of 1r$_{dd}$ neomycin-thiazole orange.
Figure 11B:
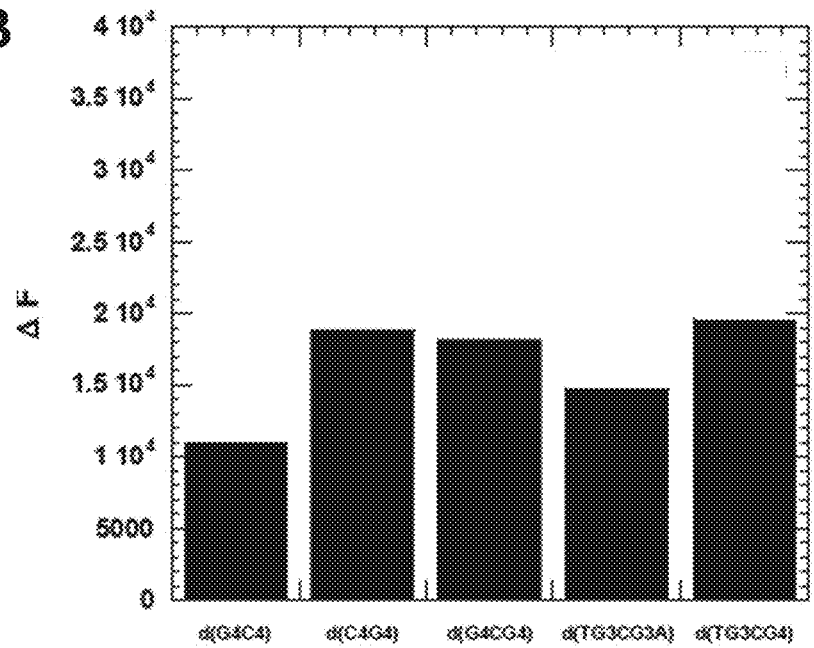
FIG. 11B is a plot showing the change in fluorescence of d(GGGGCCCC)$_2$, d(CCCCGGGG)$_2$, d(GGGGCGGGG)$_2$, d(TGGGCGGGA)$_2$, and d(TGGGCGGGG)$_2$ after addition of 1r$_{dd}$ thiazole orange control.

The change in fluorescence of d(GGGGCCCC)$_2$, d(CCCCGGGG)$_2$, d(GGGGCGGGG)$_2$, d(TGGGCGGGA)$_2$, and d(TGGGCGGGG)$_2$ in 50 mM NaCl, 10 mM SC, 0.5 mM EDTA (pH 6.0) after addition of 1r$_{dd}$ neomycin-thiazole orange and thiazole orange control were recorded in FIGS. 11A and 11B, respectively. With the addition of one molar equivalent of five various DNA sequences the fluorescence increase varies based on the affinity of neomycin-thiazole orange for the DNA duplex. This is indicated by the largest fluorescence increase. When a control experiment was performed with thiazole orange alone the results differed. This is to be expected since thiazole orange has some sequence specificity, although the pattern between the duplexes was different for the neomycin-thiazole orange. This indicates not only does the fluorescence increase correlated with the binding of neomycin-thiazole orange but also the sequence specificity for neomycin-thiazole orange is different than thiazole orange alone.

To gain a better understanding of the sequence specificity of neomycin conjugate 36a and 36b, a screening assay was performed with 256 GC rich hairpin duplexes. After showing neomycin-thiazole orange binding can be determined using five different DNA duplexes, the high throughput applications were demonstrated using 256 DNA hairpins with varying GC content. The assay using 256 DNA duplexes allows for determining the highest affinity sequence without the added variables of a pre-bound fluorescent marker such as ethidium bromide. In addition the magnitude of fluorescence enhancement of neomycin-thiazole orange allows for the assay to easily be performed on a 96 well plate reader.

The results from the 256 DNA hairpins assay show the highly sequence dependent affinity of neomycin-thiazole orange. In addition the assay shows how the neomycin-thiazole orange affinity for a particular duplex in a large library can be identified from a simple screening assay. Since this assay eliminates the need for a pre-bound fluorescent marker the assay is a simple 2 step process. First the baseline fluorescence of neomycin-thiazole orange is recorded, then DNA is added and the fluorescence is again recorded, and the assay is complete giving enough information for identifying the highest affinity sequences for further study. Addition of unlabeled drug to the DNA:TO-Neo2 complex displaces the TO-Neo from DNA leading to a decrease in fluorescence. The assay can therefore screen for target specificity as well as screen for drug binding to a specific target.

Example 6 The High Throughput Screening (HTS) of Mutations in Sequences of RNA

Disclosed is an HTS showing the difference in the binding affinity of fluorescene-neomycin (F-neo (42a)) to various synthetic RNA sequence 27 bases long designed to mimic the ribosomal A-site using a 96 well plate format and a fluorescent plate reader. Differences in binding are determined by the differential quenching of F-neo (42a) upon binding to the RNA.

The affinity of F-neo (42a) shows small but measurable differences for mutated RNA sequences. In order to demonstrate the ability to detect these differences similar ribosomal A-site mimics of E. coli ribosomal A-site (GGCGUCACACCUUCGGGUGAAGUCGCC) (SEQ ID No. 1), human (GGCGUCGCUACUUCGGUAAAAGUCGCC) (SEQ ID NO. 2), mitochondria (GGCGUCACCCUUCGGGACAAGUCGCC) (SEQ ID NO. 3), and a mutant mitochondria (GGCGUCACCCCUUCGGGGCAAGUCGCC) (SEQ ID NO. 4) ribosomal A-sites (highlighted in bold are bases that each sequence differs from E. coli sequence). Following the SOP's established for F-neo (42a) binding to E. coli A-site, each sequence was added at 0.1 µM RNA to 0.1 µM F-neo (42a) using 100 reads/well using a Tecan Genios Pro plate reader in a 96 well Greiner black plate. The emission was measured at wavelength 535 nm, using an excitation wavelength of 485 nm. All experiments were performed in 10 mM hepes (7.0), 50 mM NaCl, and 0.4 mM EDTA. Ten wells were averaged for each sequence and measurable differences were observed in the quenching of F-neo (42a), with fluorescence for E. coli of 7963 (±221), human of 9503 (±208), mitochondria of 11987 (±445), and mutant mitochondria of 8515 (±230).

The results of the A-site screening demonstrated the ability of the assay to detect small mutations in RNA sequences is shown in FIG. 12. The application of the assay can be extended to screen and to detect drug binding to mutants in other important RNAs such as siRNA, mRNA, miRNA, as well as others, and the scope of the assay is not limited to the sequences chosen here.

Example 7 Major Groove Binding—High Throughput Screening of GC DNA Binding Drugs The HTS by the displacement of a fluorescene-neomycin (F-neo (42a)) bound from a synthetic DNA sequence eight bases long designed to conform to A-form DNA by the synthetic molecule neomycin-anthraquinone (67) using a 96 well plate format and a fluorescent plate reader is disclosed.

bases long designed to conform to A-form DNA by the synthetic molecule neomycin-anthraquinone 67 using a 96 well plate format and a fluorescent plate reader was disclosed herein.

The high throughput screening (HTS) has been designed to determine the binding of drugs to the target sequence $d(G_4C_4)$. The target is predicted to exist predominately in the

67

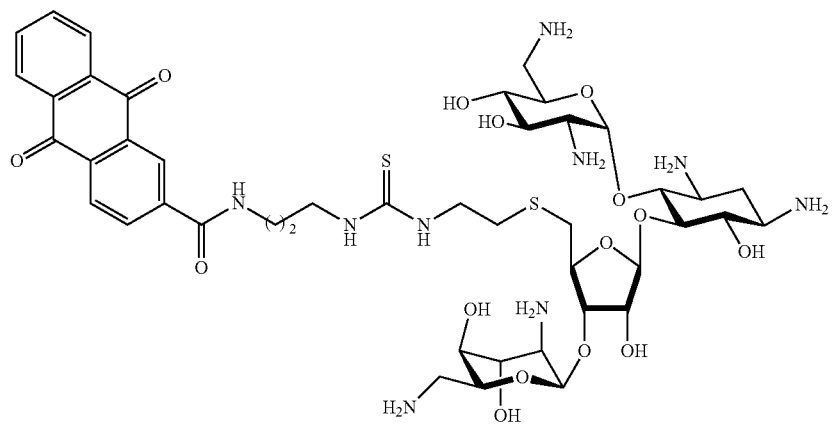

The high throughput screening (HTS) has been designed to determine the binding of drugs to the target sequence $d(G_4C_4)$. The target is predicted to exist predominately in the A-form conformation of DNA. This HTS involves the displacement of a fluorescene-neomycin (F-neo (42a)) by DNA binding molecules in a 96 well plate format using a fluorescent plate reader. Initial studies of this system have demonstrated that the binding of F-neo to A-form DNA results in the quenching of the fluorophore, and the displacement of F-neo (42a) by a competitive binding molecule is measured by an increase in fluorescence. The quality of the assay was determined by the calculation of a Z'-factor using equation 1 for the displacement of F-neo (42a) from the DNA by neomycin-anthraquinone 67. The final assay results were obtained using the average ($\mu_n$) and standard deviation ($\sigma_n$) from 36 wells of 0.1 µM F-neo (42a)/DNA $d(G_4C_4)$ as the negative control and from the average ($\mu_p$) and standard deviation ($\sigma_p$) 36 wells of 0.1 µM F-neo (42a)/DNA $d(G_4C_4)$ mixed with 0.3 µM neomycin-anthraquinone 67 as the positive control. The experiment resulted in Z'-factor of 0.84. The results indicate that the assay is suitable for the detection of drugs that bind to the DNA $d(G_4C_4)$ by the displacement of the F-neo (42a) probe in a high through-put format.

Example 8 Specific GC Rich DNA Binding

The HTS by the displacement of a thiazole-neomycin (TO-neo (36a)) bound from a synthetic DNA sequence eight bases long designed to conform to A-form DNA by the synthetic molecule neomycin-anthraquinone 67 using a 96 well plate format and a fluorescent plate reader. Initial studies of this system have demonstrated that the binding of TO-neo (36a) to GC DNA results in flourescence, and the displacement of TO-neo (36a) by a competitive binding molecule causes a loss of fluorescence. The quality of the assay was determined by the calculation of a Z'-factor using equation 1 for the displacement of TO-neo (36a) from the DNA by a neomycin-anthraquinone 67 conjugate. The final assay results were obtained using the average ($\mu_n$) and standard deviation ($\sigma_n$) from 24 wells of 1.0 µM TO-neo (36a)/DNA $d(G_4C_4)$ as the negative control and from the average ($\mu_p$) and standard deviation ($\sigma_p$) 24 wells of 1.0 µM F-neo (42a)/DNA $d(G_4C_4)$ mixed with 3.0 µM neomycin-anthraquinone 67 as the positive control. The experiment resulted in Z'-factor of 0.83. Our results indicate that the assay is suitable for the detection drugs that bind to the DNA $d(G_4C_4)$ by the displacement of the TO-neo (36a) probe in a high through-put format.

Example 9 High Throughput Screening of AT Rich DNA Binding Drugs

The HTS by the displacement of a fluorescene-neomycin dimer (F-neodimer 79) bound from a synthetic DNA hairpin $d(A_{12}A_5T_{12})$ designed to conform to B-form DNA by the synthetic molecule compound 60 using a 96 well plate format and a fluorescent plate reader is disclosed.

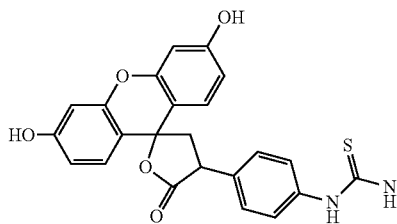
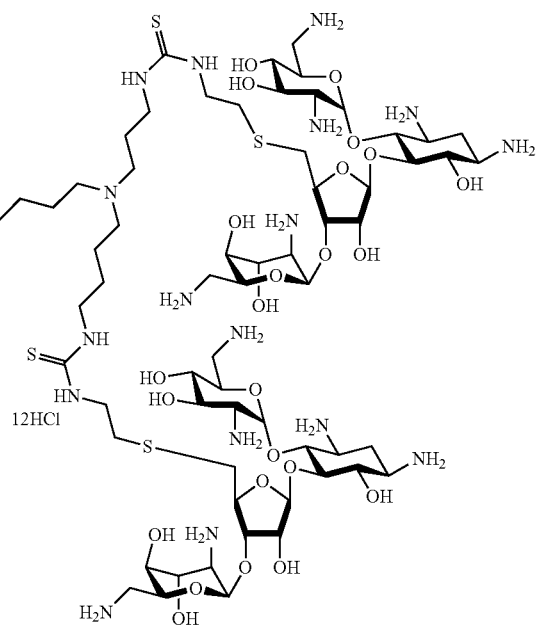

79

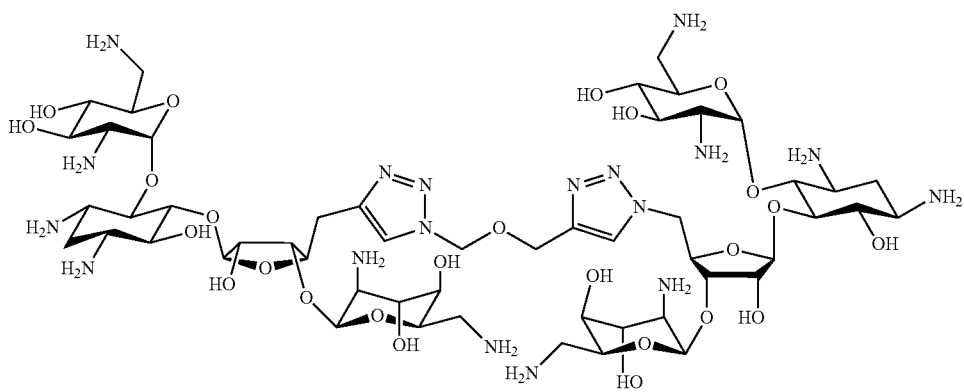

DPA 51

The high throughput screening (HTS) has been designed to determine the binding of drugs to AT rich sequence d($A_{12}A_5T_{12}$). The target is predicted to exist predominately in the B-form conformation of DNA. This HTS involves the displacement of an F-neodimer 79 by DNA binding molecules in a 96 well plate format using a fluorescent plate reader. Initial studies of this system have demonstrated that the binding of F-neodimer 79 to B-form DNA results in the quenching of the fluorophore, and the displacement of 79 by a competitive binding molecule is measured by an increase in fluorescence. The quality of the assay was determined by the calculation of a Z'-factor using equation 1 for the displacement of F-neodimer 79 from the DNA by compound 60. The final assay results were obtained using the average ($\mu_n$) and standard deviation ($\sigma_n$) from 36 wells of 0.5 µM F-neodimer 79/d($A_{12}A_5T_{12}$) as the negative control and from the average ($\mu_p$) and standard deviation ($\sigma_p$) 36 wells of 0.5 µM 79/d($A_{12}A_5T_{12}$) mixed with 1.5 µM compound DPA 51 (synthesis reported in Kumar, et. al Biochemistry, 2011) as the positive control. The experiment resulted in Z'-factor of 0.54. Our results indicate that the assay is suitable for the detection of drugs that bind to a B-form DNA d($A_{12}A_5T_{12}$) by the displacement of the F-neodimer 79 probe in a high through-put format.

Example 10 Development of Probes for Detection of Conformational Difference Nucleic Acid Disclosed is the use of fluorescent aminosugar probes such as F-neo (42a) to probe a variety of nucleic acid targets. Competition dialysis was used as a nucleic acid screening technique to illustrate the binding of F-neo (42a) to different nucleic acid structures.

Figure 13A:
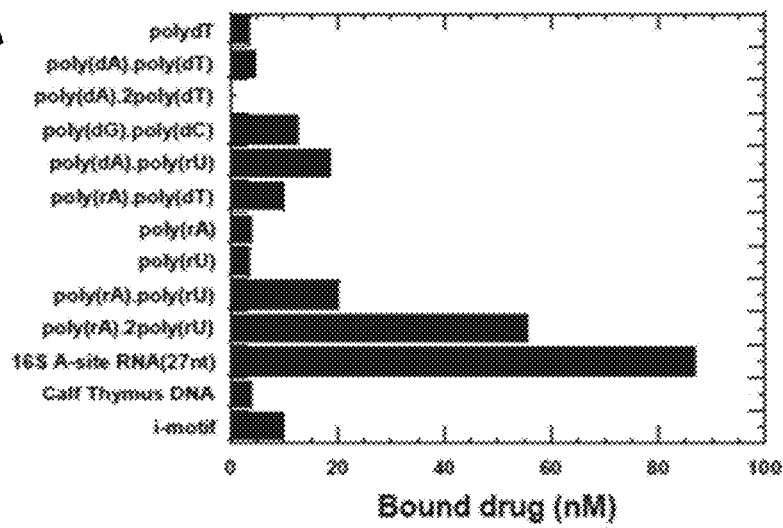
FIG. 13A shows a competition dialysis of various nucleic acids using the F-neo (42a) probe at 100 mM Na+.
Figure 13C:
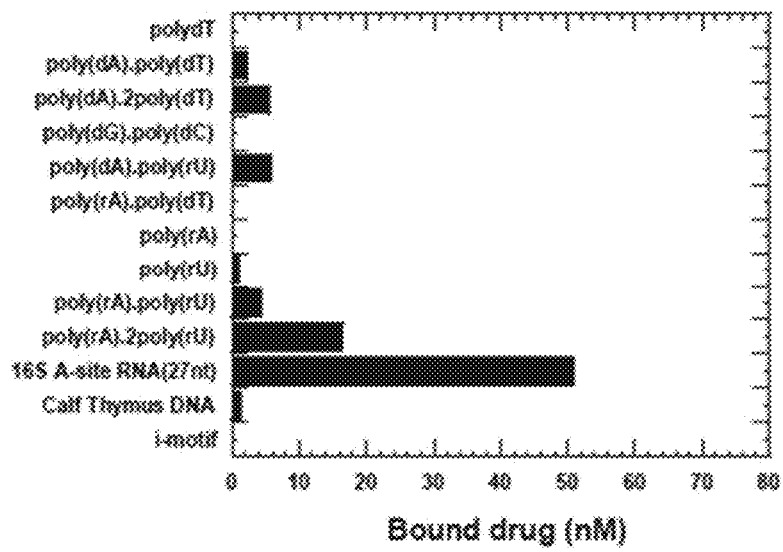
FIG. 13C shows a competition dialysis of various nucleic acids using the F-neo (42a) probe at 150 mM Na+.
Figure 13E:
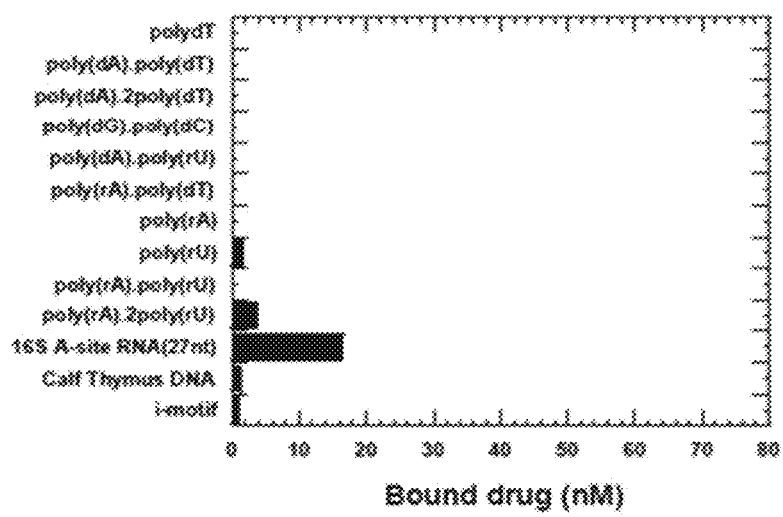
FIG. 13E shows a competition dialysis of various nucleic acids using the F-neo (42a) probe at 200 mM Na+.
Figure 13B:
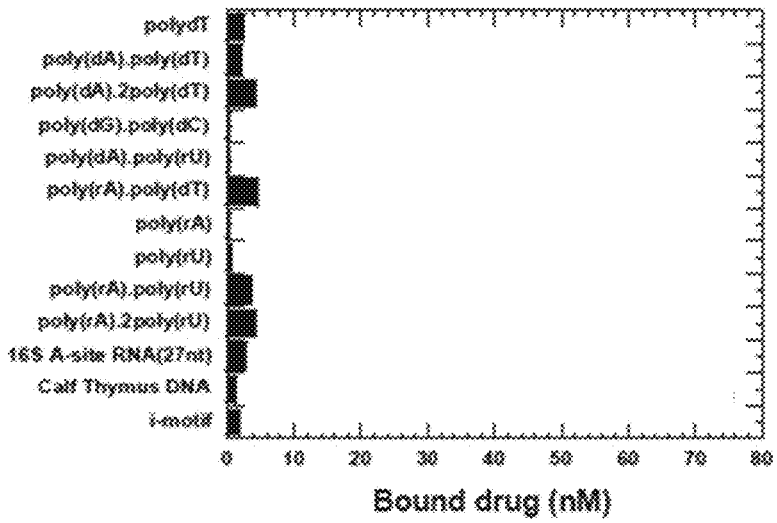
FIG. 13B shows a competition dialysis of various nucleic acids using fluorescein at 100 mM Na+.
Figure 13D:
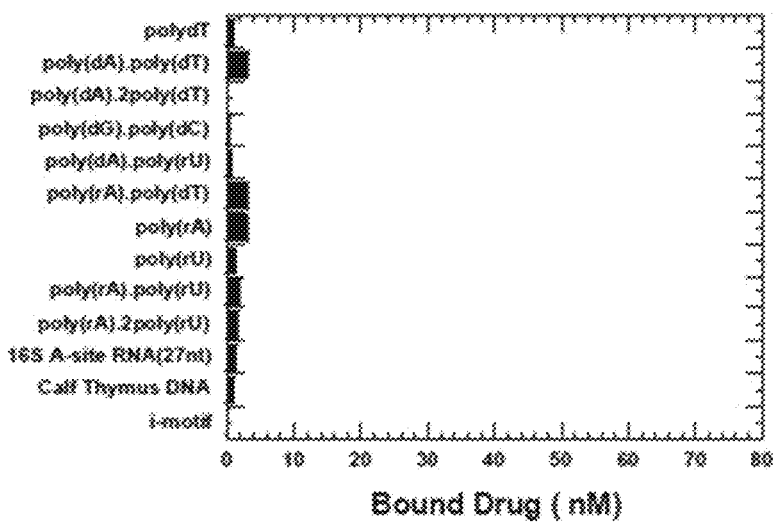
FIG. 13D shows a competition dialysis of various nucleic acids using fluorescein at 150 mM Na+.
Figure 13F:
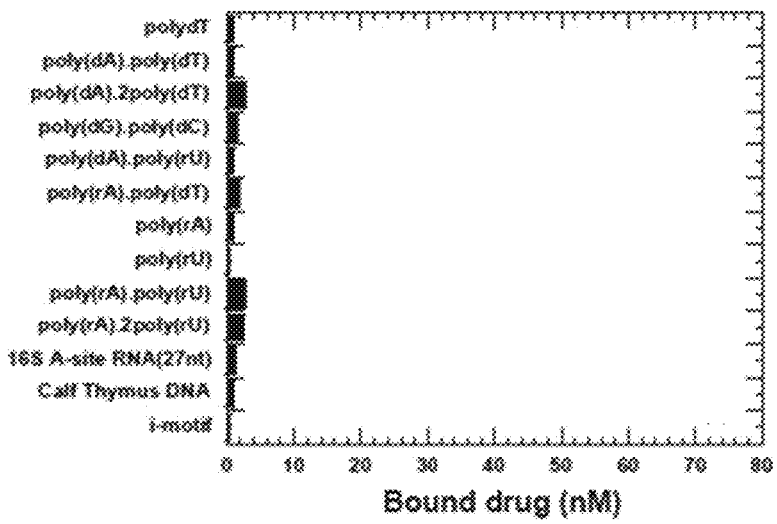
FIG. 13F shows a competition dialysis of various nucleic acids using fluorescein at 200 mM Na+.

Competition dialysis studies using a fluorescein-neomycin conjugate (F-neo (42a)). As a control, binding of fluorescein to nucleic acids was investigated in the competition dialysis assay and showed negligible binding. Comparative binding of F-neo (42a) to 13 different nucleic acid structures was examined which included single strand nucleic acids [poly(dT), poly(A), poly(U)], duplexes [poly(dA).poly(dT), poly(rA).poly(dT), poly(rA).poly(rU), poly(dA).poly(rU), poly(dG).poly(dC), calf thymus], triplexes [poly(dA).2poly(dT), poly(rA).2poly(rU)], i-motif (polydC) and 16S A-site rRNA (SEQ ID No. 1). The amount of F-neo (42a) bound to each nucleic acid is shown as a bar graph in FIG. 13. Because all nucleic acids are dialyzed simultaneously in the same ligand solution, the amount of bound F-neo (42a) is directly proportional to its affinity for each nucleic acid. FIG. 13a,c, e shows competition dialysis results of fluorescein-neomycin with various nucleic acids at (a) 100 mM Na+ (c), 150 mM Na+ (e) 200 mM Na+. FIG. 13*b,d,f* shows competition dialysis results of fluorescein with various nucleic acids at (b) 100 mM Na+ (d) 150 mM Na+ (f) 200 mM Na+. 200 μL of different nucleic acids (7.5 μM per monomeric unit of each polymer) was dialyzed for 72 h with 400 mL 100 nM ligand in 6 mM $Na_2HPO4$, 2 mM NaH2PO4, 1 mM $Na_2EDTA$, pH 7.0 and various Na+ concentrations as indicated.

Figure 15:
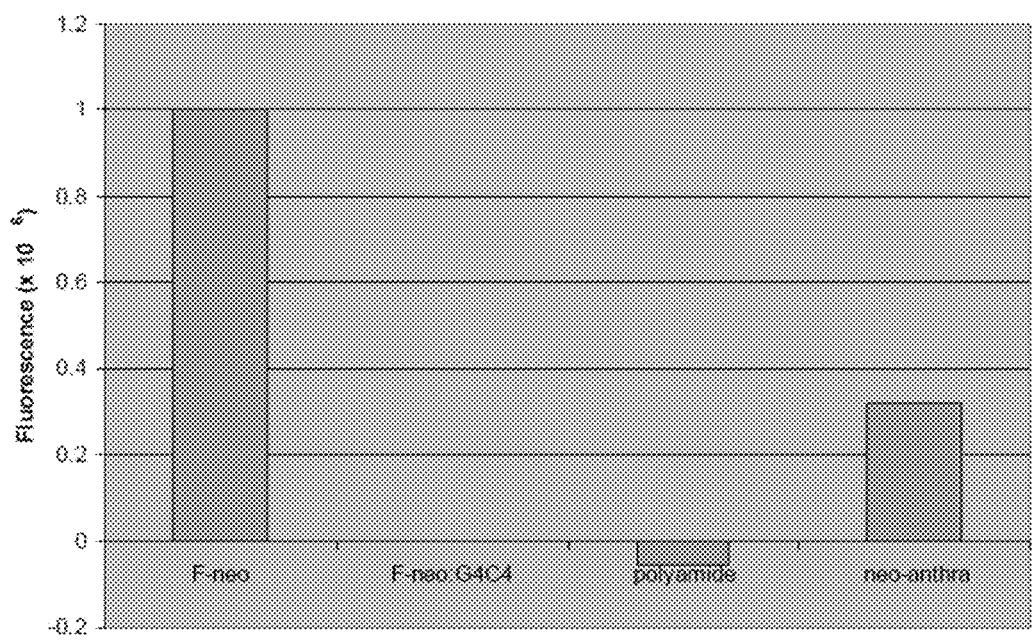
FIG. 15 shows the relative displacement of F-neo (42a) from DNA with a minor groove binder versus a major groove binder.

F-neo (42a) prefers to bind to 16S A-site rRNA yielding a bound ligand concentration of 85 nM in 100 mM $Na^+$, 50 nM in 150 mM $Na^+$, and 15 nM in 200 mM $Na^+$ is shown in FIG. 15. Binding to the RNA triplex poly(rA).2poly(rU) is comparable to A-site rRNA under low salt conditions, with 60 nM, 20 nM, and 5 nM bound F-neo (42a) in 100, 150, and 200 mM $Na^+$ respectively. F-neo (42a) also shows significant binding to RNA duplex poly(rA).poly(rU), DNA triplex poly(dA).2poly(dT), and hybrid duplex poly(dA).poly(rU) with approximately 10-20 nM bound drug under these salt conditions. However, F-neo (42a) exhibits moderate to very weak binding with the DNA duplex poly(dA).poly(dT), hybrid duplex poly(rA).poly(dT), calf thymus DNA, i-motif DNA, and all single-stranded nucleic acids studied here.

The binding of F-neo (42a) to nucleic acids is affected by the salt concentration. As $Na^+$ concentration increases from 100 to 200 mM, the amount of bound neomycin decreases approximately 4-5 times for each nucleic acid structure. Additionally, the counterintuitive and surprising absence of F-neo (42a) binding to poly(dA).2poly(dT) under 100 mM $Na^+$ can be explained by the non-formation of the DNA triplex under this salt concentration at ambient temperatures (~22° C.). As salt concentration is raised to 150 mM $Na^+$, triplex formation is favored and ligand binding is observed.

Competition dialysis reveals that F-neo (42a) binds the natural target 16S A-site rRNA and also shows comparable binding to RNA triplex. Analysis of the nucleic acid structures that are favored by neomycin suggests that they all display features characteristic of A-form conformation. The hybrid duplex, especially poly(dA).poly(rU), exhibits intermediate conformation between the A and B forms with a higher propensity for A-form. The low bound drug observed for poly(rA).poly(dT) can be attributed to the fact that this hybrid can exist in the B-form. In addition, GC-rich sequences are well known to adopt A-like conformation in aqueous solution. Highly ordered nucleic acids structures such as G-quadruplex and triplex also adopt a conformation exhibiting some A-form features as indicated by a strong band in the vicinity of either 260 nm or 205 nm in their CD spectrum. More importantly, the size of their major grooves lies intermediate between the widths and depths of an A-form major groove, and a B-form major groove.

This example demonstrates the ability of F-neo (42a) to discriminate different nucleic acids based on their propensity toward the A-form conformation. The F-neodimer (79) for example can be used to discriminate different nucleic acids based on their propensity toward the B-form conformation. Since DNA conformations vary from A to B forms, any DNA sequence can now be targeted by aminoglycoside (monomer/dimer) based probes disclosed herein.

Example 11 Detection of Major Groove Specific Substrates

Disclosed are fluorescent probes that bind specifically to the major groove of DNA. The probes bind specifically to the major groove are only competitively displaced by molecules that also bind in the major groove, showing little displacement of the probe by molecules that bind in the minor groove. These probes are ideally suited to screen for other drugs and proteins that bind DNA in the major groove.

A limited number of natural products have been known to interact in the major groove; however the major contributor to the DNA binding of these compounds has been the intercalating moiety or alkylation of the nucleophilic sites on DNA. More recent emergence of carbohydrate scaffolds such as neomycin and neomycin-neomycin dimer as reversible major groove binding molecules has presented new pharmacophores for DNA binding drugs (Hamilton & Arya, 2012). Fluorescent probes have been designed and synthesized using the aminoglycoside scaffolds that bind specifically in the major groove. These probes can be used as tools to screen for other molecules that interact specifically with the major groove of DNA or RNA. In order to demonstrate the ability of these probes to discriminate from major and minor groove binding molecules we present the results of a displacement assay using the fluorescent probe of thiazole orange conjugated to neomycin (TO-neo (36a)) bound to the DNA sequence $d(G_4C_4)_2$ with a minor groove binding compound 59 (Dervan, 2001).

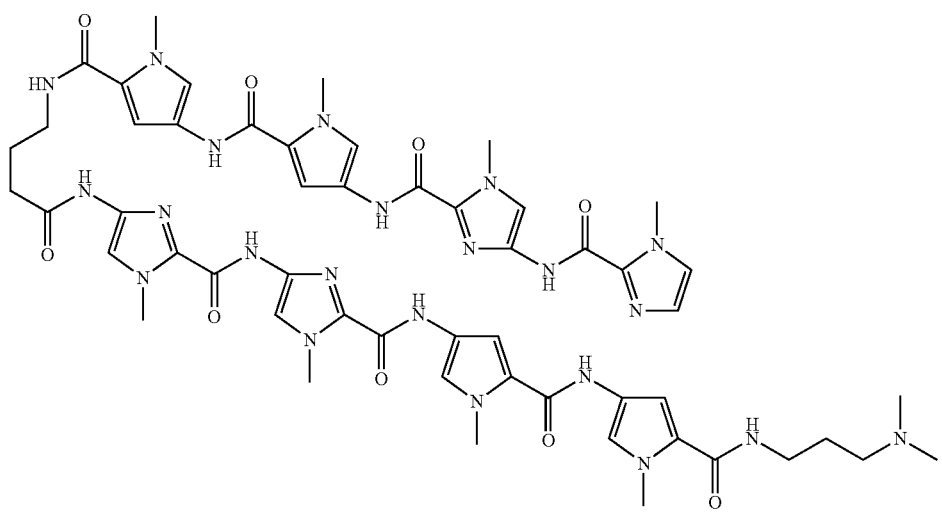

59

Figure 14:
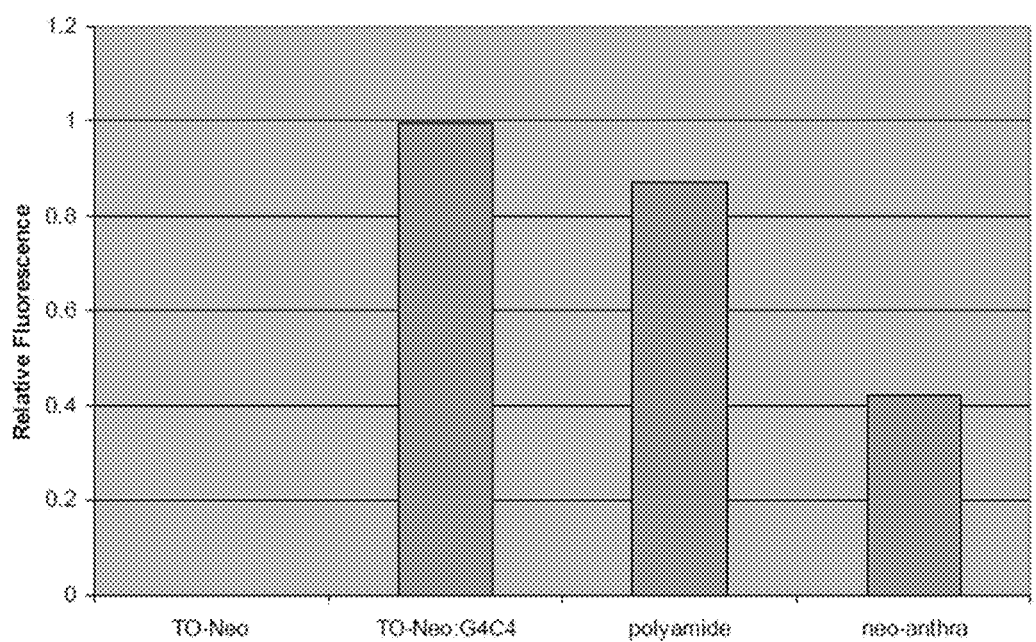
FIG. 14 shows the relative displacement of TO-neo (36a) from DNA with a minor groove binder versus a major groove binder.

FIG. 14 shows that the fluorescence of TO-neo (36a) increases upon binding to DNA. The fluorescence of the probe decrease approximately 60% with the addition of the neomycin-anthraquinone 67, a synthetic molecule predicted to bind in the major groove. However, with the addition of the minor groove binding compound 59, the change in fluorescence is less than 10%. The change in the fluorescence observed upon the addition of the compound 59 is approximately the same as that observed in the DMSO control.

Additionally, FIG. 15 shows results of a displacement assay using the fluorescent probe of fluorescein conjugated to neomycin (F-neo (42a)) bound to the DNA sequence d($G_4C_4$)$_2$ with the minor groove binding compound 59, demonstrate that the F-neo (42a) probe is not displaced by a molecule that binds in the minor groove. Upon binding to the DNA the fluorescence of F-neo (42a) is quenched. With the addition of one molar equivalent of neomycin-anthraquinone 67, we observe a significant increase in the fluorescence. This increase is not observed with the addition of the minor groove binding compound 59, in which the change in the fluorescence observed is approximately the same as that of the DMSO control.

Example 12 Quadruplex DNA Assays

Disclosed are fluorescent probes that bind to quadruplex DNA. The probes that bind are competitively displaced by molecules that bind to quadruplex DNA. These probes are ideally suited to screen for other drugs and proteins that bind to quadruplex DNA. We provide here the detailed experiment the HTS by the displacement of a thiazole orange-neomycin (TO-neo, Scheme 5) (36a) bound to a synthetic DNA d($G_4T_4G_4$)$_2$ (SEQ ID No. 5), which forms a DNA-quadruplex, by the synthetic molecule neomycin anthraquinone 67 (using a 96 well plate format and a fluorescent plate reader.

Over the last two decades, the ability of guanine rich nucleic acids to form four stranded structures and inhibit the functions of telomerase have generated immense interest in their biological functions (Zahler, Williamson, Cech, & Prescott, 1991). Since the structural elucidations of tetramolecular, bimolecular and unimolecular quadruplexes in early 90's, significant attention has been paid to develop small molecules that selectively recognize G-quadruplex nucleic acids with high specificity and affinity (Monchaud et al., 2008). A number of small molecules, most of which have extended planar aromatic ring systems, have been reported to bind to G-quadruplexes, with the majority having micromolar affinities (Pagano, Mattia, & Giancola, 2009). Most of these ligands primarily recognize G-quadruplexes through terminal stacking interactions between the i-ring systems of the ligand and the planar tetrad formed by a cyclic array of four guanosines. Groove recognition, however, also presents an enticing approach for selective recognition of quadruplex structures (Stephen, 2012). Studies have shown that the binding of aminoglycosides to DNA-quadruplexes suggest that quadruplex grooves are the binding domains of these ligands (Ranjan, Andreasen, Kumar, Hyde-Volpe, & Arya, 2010).

Neomycin binds to a dimeric form of a parallel quadruplex formed by the Tetrahymena telomere with nanomolar affinity. This binding is the highest affinity reported for a completely non-planar molecule binding to a quadruplex. Disclosed are probes using fluorescent molecules conjugated to neomycin as a tool for screening other high affinity and potential drug candidates that bind to quadruplex DNA.

Figure 16:
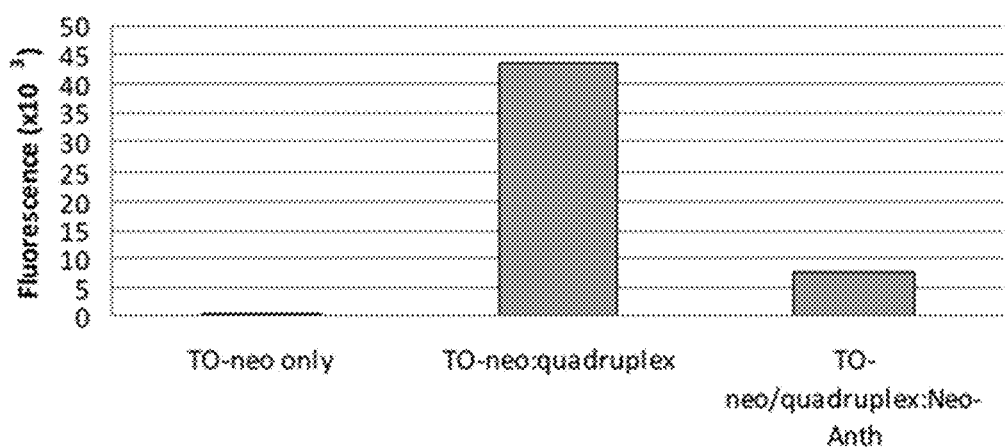
FIG. 16 shows the displacement of TO-neo (36a) from quadruplex DNA by neomycin-anthraquinone (67).

The high throughput screening (HTS) has been designed to determine the binding of drugs to the quadrulplex DNA d($G_4T_4G_4$)$_2$. This HTS involves the displacement of TO-neo (36a) by quadruplex binding molecules in a 96 well plate format using a fluorescent plate reader. Initial studies of this system have demonstrated that the binding of thiazole orange (TO) results in flourescence of the fluorophore, and the displacement of TO by a competitive binding molecule results in the loss of fluorescence. The current work shows the same is true of the conjugated TO-neo (36a) molecule. The quality of the assay was determined by the calculation of a Z'-factor using equation 1 for the displacement TO-neo (36a) from the quadruplex DNA by neomycin-anthraquinone 67. The final assay results show in FIG. 16 were obtained using the average ($\mu_n$) and standard deviation ($\sigma_n$) from 24 wells of 1.0 μM F-neo (42a)/DNA d($G_4T_4G_4$)$_2$ as the negative control and from the average ($\mu_p$) and standard deviation ($\sigma_p$) 24 wells of 1.0 μM F-neo (42a)/DNA d($G_4T_4G_4$)$_2$ mixed with 1.0 μM neomycin-anthraquinone 67 as the positive control. The experiment resulted in Z'-factor of 0.78. These results indicate that the assay is suitable for the detection of drugs that bind to the DNA quadruplexes by the displacement of the TO-neo (36a) probe in a high through-put format. The TO-neo (36a) probes can be extended to other aminoglycoside scaffolding, other fluorescent molecules, as well as other DNA that form quadruplexes.

Example 13 Synthesis and Characterizations

Synthesis of Neomycin-Thiazole Orange Conjugates

The Thiazole orange was synthesized using a procedure reported in the literature (Yang, P. et al. (2009). In our case, we changed the linker length to a short alkyl chain (5 carbon) than a longer chain (10 carbon) reported before (scheme 10). Thus a carboxyl group present in this thiazole orange derivative can be used towards coupling reactions.

An example of coupling of aminosugar (neomycin) with thiazole orange carboxylic acid is given in scheme 11. Hexa-N-Boc deoxy-neomycin-5"-amine 3 or 6 was reacted with thiazole orange-COOH conjugate in the presence of a coupling reagent (EDC). This leads to the formation of the Boc protected neomycin-thiazole orange conjugate which can be isolated after purification with column chromatography. The Boc protecting groups in the conjugate deprotected using trifluoroacetic acid to afford neomycin-thiazole orange conjugate as their TFA salt.

Scheme 10. Derivatization of thiazole orange for linkage to neomycin amine.

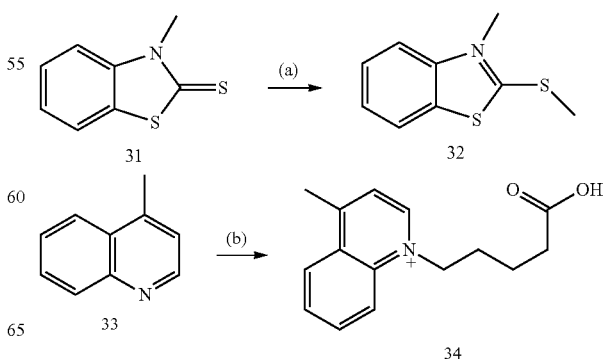

77 -continued
78 -continued
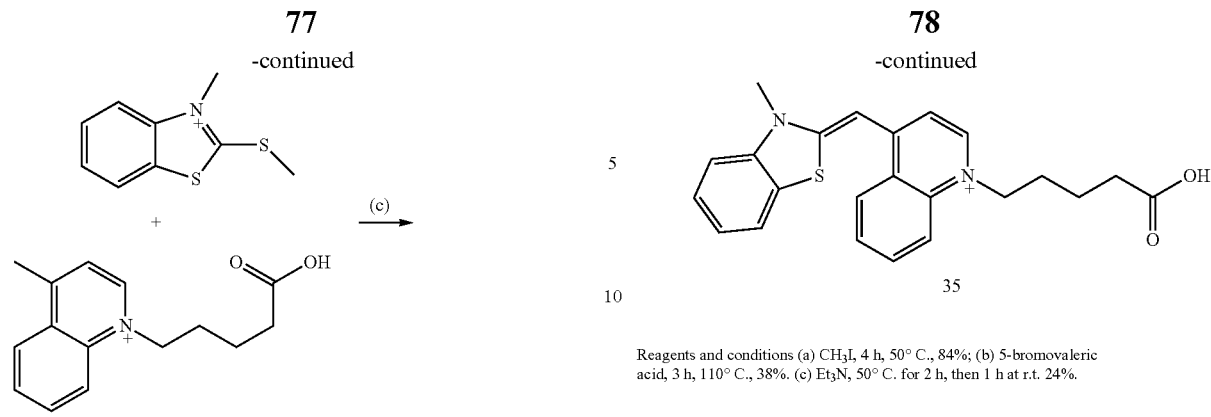
Reagents and conditions (a) CH₃I, 4 h, 50° C., 84%; (b) 5-bromovaleric acid, 3 h, 110° C., 38%. (c) Et₃N, 50° C. for 2 h, then 1 h at r.t. 24%.
Scheme 11. Synthesis of Neomycin-thiazole Orange conjugate.
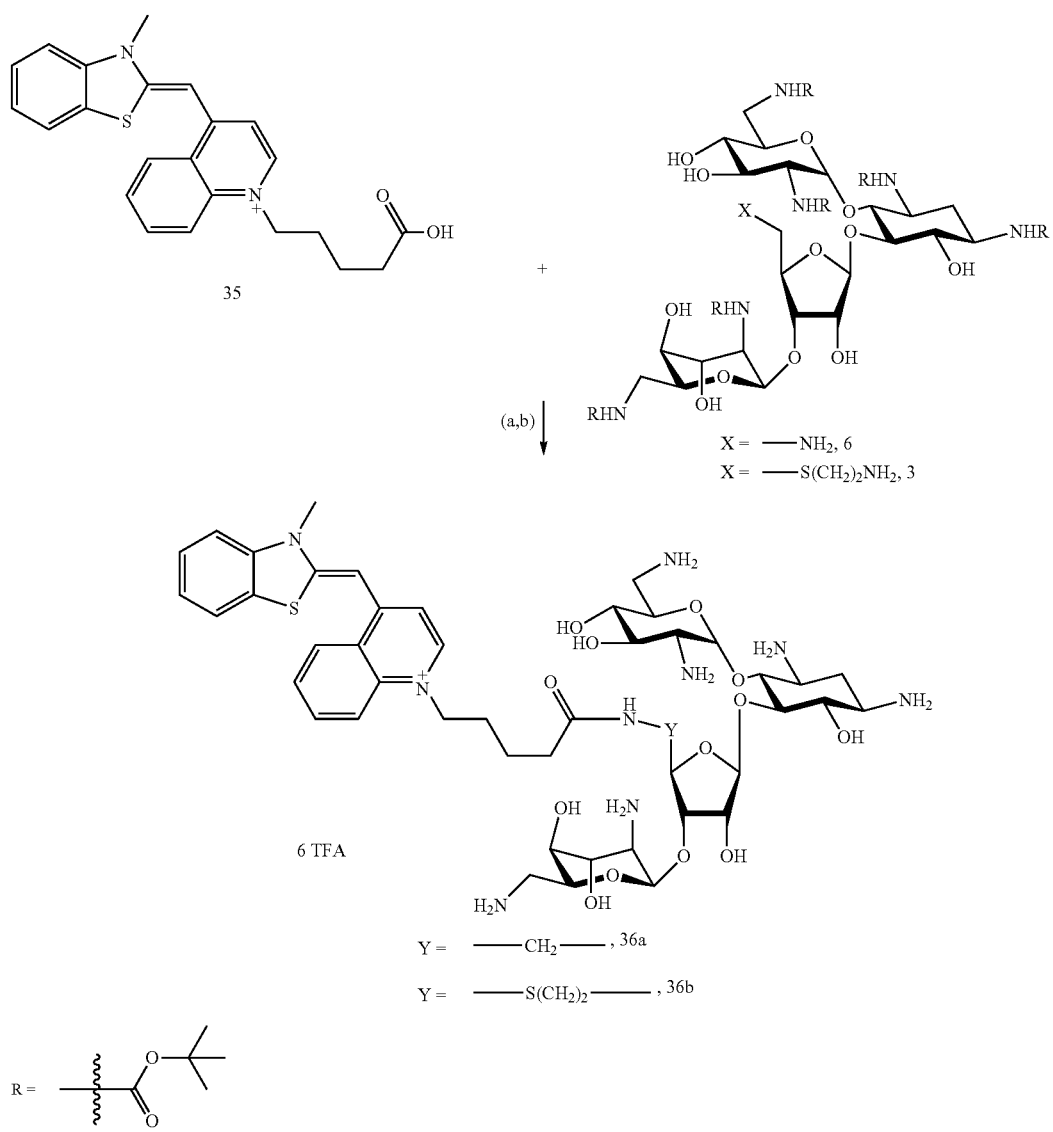
Reagents and Conditions: (a) DMF, TBTU, DIPEA, r.t. 65% (for 6) and 82% (for 7); (b) TFA, DCM, 3 h, r.t., 75% (for 6) and 80% for 7).

Synthesis of Neomycin-TO Conjugate (36a, Linker 1)

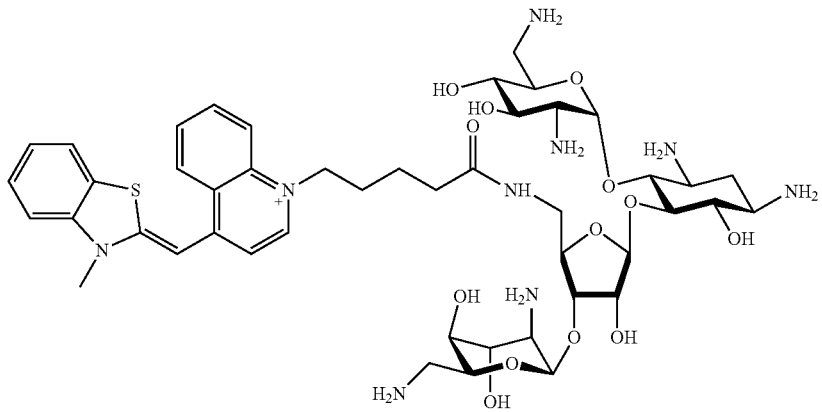

Synthesis of 3-methyl-2-(methylthio)benzo[d]thiazol-3-ium (32)

To a dry 100 mL round bottom flask was added 3-methylbenzothiazole-2-thione (2.0 g, 11.0 mmol) and iodomethane (3.2 g, 23.0 mmol, 2.0 equival). The reaction mixture was heated at 50° C. for 4 h under the atmosphere of argon. The reaction mixture turned into white precipitate. The reaction mixture was cooled back to room temperature. The obtained solid was suspended in MeOH (100.0 mL). Diethyl ether was (75.0 mL) was added to induce precipitation. The precipitate was collected via vacuum filtration and the solid obtained was washed with diethyl ether (3×10.0 mL). It was then dried under vacuum to give the desired product as white solid (3.0 g, 84%): $^1$H NMR (500 MHz, DMSO) δ 3.13 (s, 3H, SCH$_3$), 4.11 (s, 3H, NCH$_3$), 7.70-7.77 (m, 1H, Ar), 7.82-7.88 (m, 1H, Ar), 8.20 (d, J=8.42 Hz, 1H, Ar), 8.41 (d, J=8.06 Hz, 1H, Ar).

Synthesis of 1-(4-carboxybutyl)-4-methylquinolinium (34)

To a dry round bottom flask was added 4-methylquinoline (2.0 g, 14 mmol) and 5-bromovaleric acid (2.8 g, 15.0 mmol, 1.1 equival). and The contents were heated at 110° C. for 3 h under argon atmosphere. The resulting residue was dissolved in MeOH (20.0 mL) and the product was precipitated by addition of diethyl ether (40.0 mL). The precipitate was collected via vacuum filtration and washed with diethyl ether (3×10.0 mL). The obtained solid was dried under vacuum to give the desired compound as pink solid (2.2 g, 38%): $^1$H NMR (500 MHz, DMSO-d$_6$) δ 1.62 (p, J=7.0 Hz, 2H, CH$_2$), 1.90 (p, J=7.3 Hz, 2H, CH$_2$), 2.29 (t, J=6.9 Hz, 2H, CH$_2$), 3.00 (s, 3H, CH$_3$), 4.63 (t, J=6.9 Hz, 2H, NCH$_2$), 8.04-8.10 (m, 2H, Ar), 8.22-8.30 (m, 1H, Ar), 8.51-8.63 (m, 2H, Ar), 9.41 (d, J=6.23 Hz, 1H, Ar).

Synthesis of (Z)-1-(4-carboxybutyl)-4-((3-methylbenzo[d]thiazol-2(3H)-ylidene)methyl)quinolinium (35)

To a dry round bottom flask were added compound 34 (1.0 g, 2.4 mmol) and compound 32 (0.8 g, 2.4 mmol) then dry EtOH (24.0 mL). The resulting mixture was added with dry Et$_3$N (0.7 mL, 5.2 mmol, 2.2 eq) which resulted in an immediate deep red coloration of the reaction mixture. The reaction mixture was heated at 55° C. for 2 h and then at room temperature for 1 h under an argon atmosphere. The mixture was allowed to cool back to room temperature. Precipitation was induced by addition of diethyl ether (50.0 mL). The crude solid was suspended in acetone (70.0 mL)/diethyl ether (100.0 mL) for 1 h and then the precipitated solid was collected via vacuum filtration. The product was then washed with diethyl ether (3×20.0 mL). The mixture was dried under reduced pressure to give the desired product as a red solid (250 mg, 24%): $^1$H NMR (300 MHz, DMSO-d$_6$) δ 1.62 (p, J=7.0 Hz, 2H, CH$_2$), 1.90 (p, J=7.3 Hz, 2H, CH$_2$), 2.29 (t, J=6.9 Hz, 2H, CH$_2$), 4.03 (s, 3H, CH$_3$), 4.64 (t, J=6.9 Hz, 2H, NCH$_2$), 6.97 (s, 1H, CH), 7.38-7.49 (m, 2H, Ar), 7.62 (t, J=6.9 Hz, 1H, Ar), 7.70-7.90 (m, 2H, Ar), 7.97-8.03 (m, 1H, Ar), 8.06 (d, J=7.5 Hz, 1H, Ar), 8.17 (d, J=6.9 Hz, 1H, Ar), 8.67 (d, J=7.2 Hz, 1H, Ar), 8.81 (d, J=8.4 Hz, 1H, Ar), 8.85-9.15 (br, 1H, COOH); UV (H$_2$O) $\lambda_{max}$=503 nm. $\varepsilon_{503}$=8833.8 M$^{-1}$ cm$^{-1}$.

Synthesis of 36a

To a solution of Hexa-N-Boc deoxy-neomycin-5"-amine (30.0 mg, 24.0 µmol) in dry DMF (3.0 mL), TBTU (30.8 mg, 96.0 µmol, 4.0 equival.) was added, followed by the addition of DIPEA (24.8 mg, 0.2 mmol, 8.0 equival.) and (Z)-1-(4-carboxybutyl)-4-((3-methylbenzo[d]thiazol-2(3H)-ylidene)methyl)quinolinium 35 (14.0 mg, 32.0 µmol). The reaction mixture was stirred at room temperature under argon. The progress of the reaction was monitored by TLC. A new deep red colored spot was appeared on TLC which was ninhydin active. The volatiles were dried under reduced pressure. The crude mixture was purified using column chromatography on a silica gel column using dichloromethane-methanol as eluent [0 to 15% EtOH in DCM (v/v)], The desired product was obtained as deep red solid (25.4 mg, 65%): R$_f$=0.42 [10% MeOH in dichloromethane (v/v)]; $^1$H NMR (500 MHz, CD$_3$COCD$_3$) δ 8.78-8.90 (m, 1H, Ar), 8.18 (d, J=8.51 Hz, 1H, Ar), 8.00-8.12 (m, 2H), 7.85-7.98 (m, 3H, Ar), 7.76-7.84 (m, 4H, Ar), 7.68 (s, 1H, Ar), 7.01 (m, 2H), 6.54 (d, J=6.57 Hz, 1H, NH), 6.40 (br, s, 1H, NH), 6.25 (d, J=8.12 Hz, 1H, NH), 5.98-6.20 (m, 2H, NH), 5.04-5.20 (m, 1H), 4.90-5.02 (m, 2H), 4.60-4.90 (m, 4H), 4.40-4.60 (m, 6H), 3.98-4.30 (m, 12H), 3.70-3.92 (m, 4H), 3.55-3.70 (m, 4H), 3.30-3.55 (m, 4H), 3.20-3.34 (m, 2H), 1.80-1.86 (m, 1H), 1.60-1.78 (m, 1H), 1.30-1.60 (m, 54H, 6×Boc protons); MS (MALDI-TOF) m/z calcd. for C$_{76}$H$_{116}$N$_9$O$_{25}$ (M$^+$) 1586.84. found 1586.30 [M]$_+$; UV (DCM) $\lambda_{max}$=508 nm.

To this solution of N-Boc neomycin thiazole orange conjugate (8.0 mg, 5.0 µmol) in DCM (1.0 mL), TFA (0.1 mL) was added and the reaction mixture was stirred at room temperature for 3 h in dark. The progress of the reaction was monitored by TLC. Water (2 mL) was added to the reaction mixture and then it was washed with dichloromethane (3×3 mL). The aqueous layer was lyophilized to give the desired product (36a) as a dark red solid (4.6 mg, 75%): MS (MALDI-TOF) m/z calcd. for $C_{46}H_{68}N_9O_{13}S_2$ (M+H$_2$O$^+$), 1004.47. found 1004.28 [M]$^+$; UV (H$_2$O) $\lambda_{max}$=508 nm. $\varepsilon_{503}$=9960 M$^{-1}$ cm$^{-1}$.

Synthesis of Neomycin-TO Conjugate (36b, Linker 2)

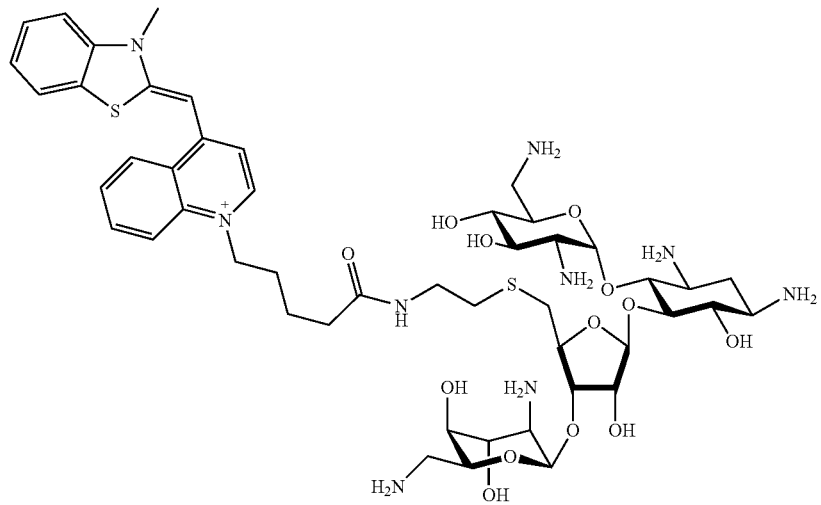

To a solution Hexa-N-Boc deoxy-neomycin-5"-amine (15.3 mg, 12.0 mol) in dry DMF (3.0 mL), TBTU (15.4 mg, 48.0 µmol, 4.0 mol equival.) was added, followed by the addition of DIPEA (12.4 mg, 96.0 µmol, 8.0 mol equiv) and 35 (7.0 mg, 24.0 µmol). The reaction mixture was stirred at room temperature under argon which resulted in new deep red colored spot on TLC plate that was also ninhydin active. The volatiles were evaporated under reduced pressure. The crude product was purified using column chromatography on silica gel using dichloromethane-ethanol (0 to 15% EtOH in DCM) as eluent. The desired product was obtained as deep red solid (17 mg, 82%): R$_f$=0.38 [10% MeOH in DCM (v/v)]; $^1$H NMR (500 MHz, CD$_3$COCD$_3$) δ 8.85-8.94 (d, J=7.09 Hz, 1H, Ar), 8.70-8.77 (d, J=8.51 Hz, 1H, Ar), 8.56-8.66 (br, s, 1H), 8.24 (d, J=8.52 Hz, 1H, Ar), 8.11 (d, J=7.57 Hz, 1H, Ar), 8.05 (t, J=7.41 Hz, 1H, Ar), 7.71-7.81 (m, 2H, Ar), 7.61-7.68 (m, 2H, Ar), 7.55 (m, J=6.46 Hz, 1H, Ar), 7.01 (m, 2H), 6.45-6.55 (br, s, 1H, NH), 6.37 (d, J=8.83 Hz, 1H, NH), 6.30 (d, J=8.20 Hz, 1H, NH), 6.22 (d, J=9.62 Hz, 1H, NH), 5.86-5.94 (br, s, 1H), 5.11 (d, J=5.68 Hz, 1H), 5.06 (br, s, 1H), 5.03 (br, s, 1H), 4.74-4.84 (m, 2H), 4.26-4.32 (m, 1H), 4.18-4.23 (m, 1H), 4.09-4.18 (m, 4H), 4.01-4.08 (m, 2H), 3.97 (t, J=9.46 Hz, 1H), 3.76-3.91 (m, 4H), 3.47-3.72 (m, 12H), 3.27-3.45 (m, 4H), 3.16-3.44 (m, 2H), 3.05-3.14 (m, 4H), 2.57-2.66 (m, 2H), 2.31-2.50 (m, 3H), 1.93 (p, J=2.21 Hz, 1H), 1.83 (p, J=6.94 Hz, 1H), 1.36-1.61 (m, 54H, 6×Boc protons); MS (MALDI-TOF) m/z calcd. for $C_{78}H_{120}N_9O_{25}S_2$ 1646.78 found 1646.67 [M]$^+$. . . UV (DCM) $\lambda_{max}$=508 nm.

To a solution of N-Boc neomycin-thiazole orange (8.2 mg, 5.0 µmol) in DCM (1.0 mL), TFA (0.1 mL) was added and the reaction mixture was stirred at room temperature for 3 h in dark. The progress of the reaction was monitored by TLC. Water (2.0 mL) was added to the reaction mixture. It was then washed with dichloromethane (3×3.0 mL). The aqueous layer was lyophilized to give the desired compound 36b as dark red solid (4.9 mg, 80%): $^1$H NMR (500 MHz, D$_2$O) δ 9.22 (d, J=5.99 Hz, 1H), 8.44 (d, J=8.99 Hz, 1H), 8.37 (d, J=8.51 Hz, 1H), 8.21 (d, J=8.04 Hz, 1H), 8.11 (d, J=8.67 Hz, 1H), 8.03 (d, J=8.20 Hz, 1H), 7.96 (t, J=8.04 Hz, 1H), 7.81-7.88 (m, 3H), 7.06-7.16 (m, 1H), 6.99 (t, J=6.78 Hz, 1H), 6.82 (d, J=5.84 Hz, 1H), 6.60-6.69 (m, 1H), 5.92-6.03 (m, 1H), 5.29-5.35 (m, 1H), 5.14-5.23 (m, 1H), 5.01 (t, J=7.14 Hz, 2H), 4.93 (t, J=7.26 Hz, 1H), 4.26-4.41 (m, 2H), 4.18-4.26 (m, 2H), 4.01-4.15 (m, 2H), 3.90-3.99 (m, 1H), 3.78-3.90 (m, 2H), 3.67-3.76 (m, 2H), 3.57-3.67 (m, 2H), 3.33-3.42 (m, 4H), 3.20-3.30 (m, 3H), 3.10-3.19 (m, 2H), 2.99-3.09 (m, 2H), 2.91-2.98 (m, 2H), 2.32-2.38 (m, 1H), 2.57-2.67 (m, 1H), 2.33-2.43 (m, 1H, H$_{l2eq}$), 2.15-2.29 (m, 2H), 1.96-2.01 (m, 1H), 8.04 (d, J=12.77 Hz, 1H, H$_{l2ax}$), 1.58-1.74 (m, 1H); MS (MALDI-TOF) m/z calcd. for $C_{48}H_{72}N_9O_{13}S_2$ 1064.47 found 1064.85[M+H$_2$O]$^+$; UV (H$_2$O) $\lambda_{max}$=508 nm. $\varepsilon_{503}$=13835 M$^{-1}$ cm$^{-1}$.

Synthesis of Neomycin Fluorescein Conjugates

Fluorescein-neomycin conjugates 42a-b were prepared by coupling an activated fluorescein ester 41a with neomycin amine 3 (Scheme 12a) or coupling of neomycin amine 3 with fluorescein isothiocyanate 41b (scheme 12b). The resulting Boc protected neomycin-fluorescein conjugate was purified using column chromatography on silica gel which was then followed by deprotection of Boc groups using trifluoroacetic acid to afford the desired compounds 42a-b in good in good yields.

Scheme 12a. Synthesis of neomycin-fluorescein conjugate (linker 1).
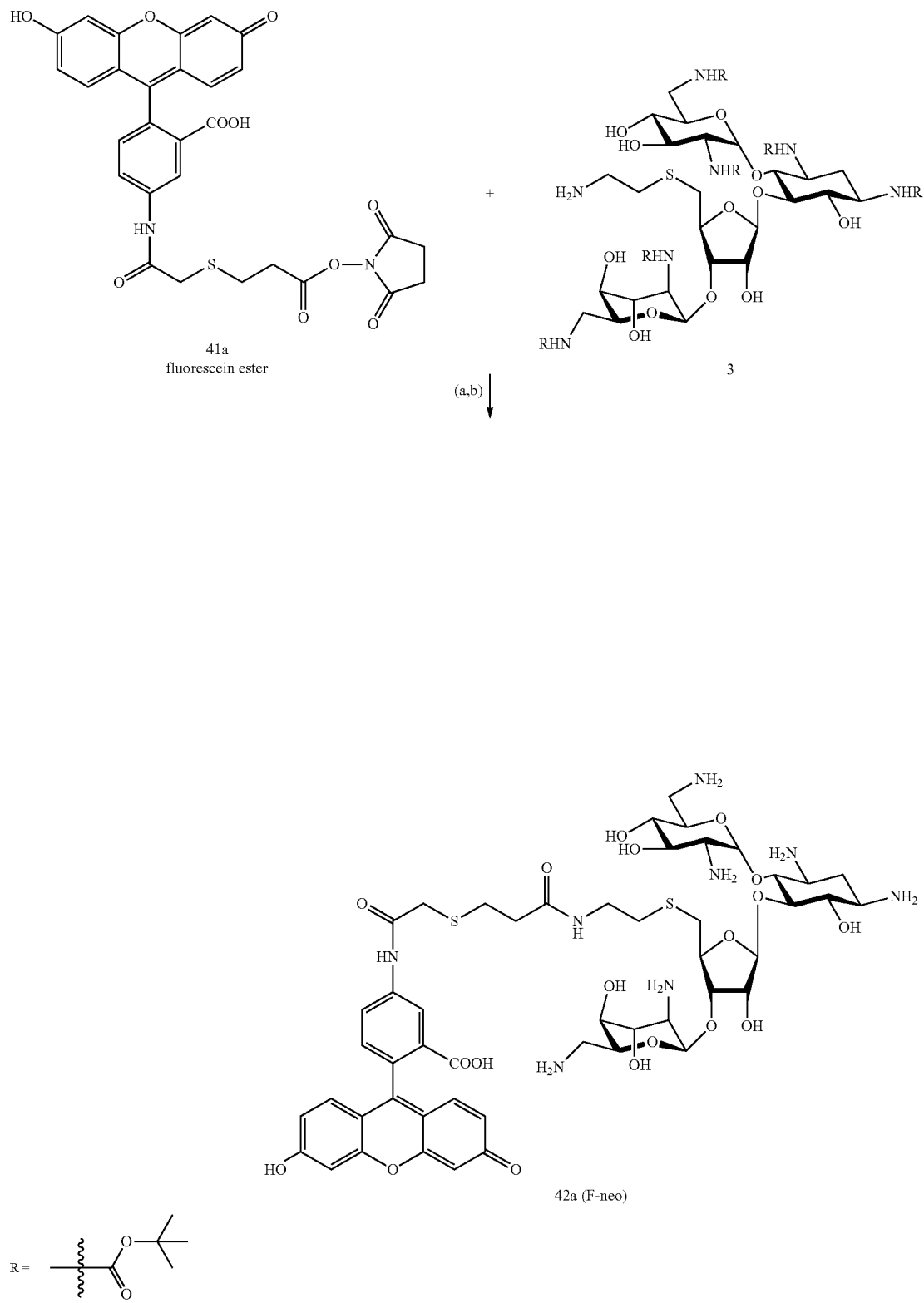
Reagents and conditions: (a) Dimethylformamide (DMF), 4-dimethyl amino pyridine (DMAP), rt
(b) TFA, dichloromethane (DCM), rt, 45% for steps a and b.

Scheme 12b. Synthesis of neomycin-fluorescein conjugate (linker 2).
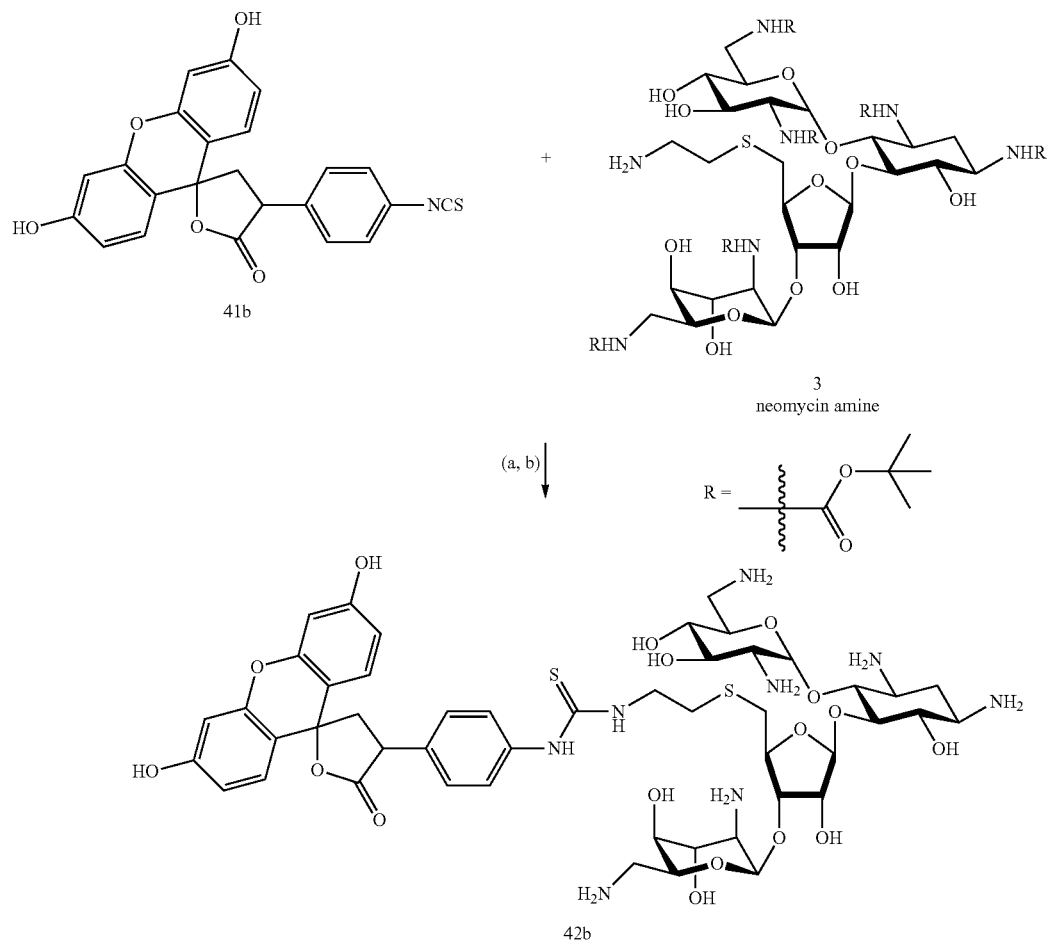
Reagents and conditions. (a) Dimethylformamide (DMF), 4-dimethyl amino pyridine (DMAP) rt
(b) TFA, dichloromethane (DCM), rt, 76% for two steps.
Synthesis of Neomycin-Fluorescein Conjugate (42a, Linker 1)
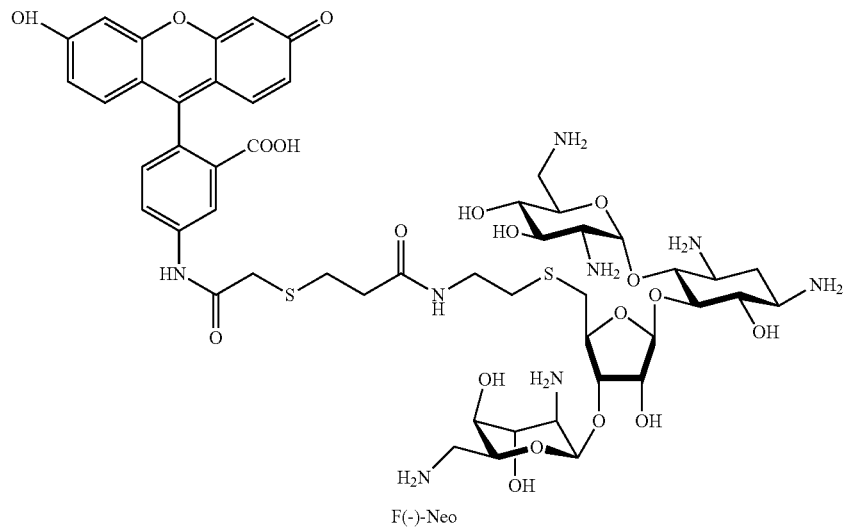
F(-)-Neo To a DMF solution (1 mL) of fluorescein succinimidyl ester 41a (5 mg, 0.0086 mmol) and 4-dimethyl-aminopyridine (catalytic amount) was added Boc protected neomycin amine 3 (10 mg, 0.0078 mmol) and stirred overnight at room temperature. The reaction mixture was concentrated under vacuum. Flash chromatography of the residue (8% (v/v) $CH_3OH$ in $CH_2Cl_2$) yielded the Boc protected conjugate as a yellow solid (10 mg): $R_f$ 0.21 (10% (v/v) $CH_3OH$ in $CH_2Cl_2$). The product was then dissolved in $CH_2Cl_2$ (3 mL) and trifluoroacetic acid (0.5 mL) was added to it. The mixture was stirred at room temperature for 3 h. After removing the solvents under vacuum, the residue was dissolved in $H_2O$ (2 mL) and extracted with dichloromethane (3×2 mL). The aqueous layer was concentrated under vacuum to yield the desired product (7 mg, 45% for two steps): UV-Vis ($H_2O$); λ=232, 455, 478 nm; ε (478 nm)=13, 260 $M^{-1}$ $cm^{-1}$; $^1H$ NMR (500 MHz, $D_2O$) J=9.3 Hz, 2H), 7.33-7.32 (d, J=8.20 Hz, 1H), 7.23 (s, br, 1H), 7.07-7.05 (d, J=9.36 Hz, 1H), 6.74-6.73 (d, J=6.73 Hz, 1H), 5.96-5.94 (m, 1H) (ring I-1'), 5.32-5.29 (br, 2H) (contains ring III-1"), 5.19 (s, br, 1H)(ring IV-1'''), 4.33-4.17 (m, 4H)(contains ring III-2''', ring IV-3"), 4.01-3.97 (t, J=9.67 Hz, 1H), 3.93-3.89 (t, J=10.3 Hz, 1H), 3.83-3.78 (m, 2H), 3.71 (s, br, 1H), 3.61-3.57 (t, J=9.89 Hz, 1H), 3.49-3.11 (m, 16H)(contains ring IV-2''', ring II 1', ring II-3'), 3.07-2.99 (m, 3H), 2.87-2.84 (m, 2H), 2.73-2.61 (m, 2H), 2.55-2.53 (t, J=6.52 Hz, 2H), 2.39-2.37 (br, 1H)(ring II, 2 eq), 1.83-1.76 (m, 1H)(ring II-2$_{ax}$). MS (MALDI-TOF) calcd m/z for $C_{50}H_{68}N_8O_{19}S_2$, 1167.26. found 1171.86 $[M+Na]^+$.

Synthesis of Neomycin-Fluorescein Conjugate
(42b, Linker 2)

To a solution of Boc-protected neomycin amine 3 (15 mg, 0.012 mmol) in dry pyridine (5 mL), fluorescein isothiocyanate 41b (5.4 mg, 0.013 mmol) was added with a catalytic amount of 4-dimethylaminopyridine (DMAP). The flask was purged with argon and covered in aluminum foil. The reaction was allowed to stir for 18 h and was monitored via TLC, which indicated formation of the product. Pyridine was dried under reduced pressure. The crude reaction mixture was purified by column chromatography using gradients of dichloromethane-methanol as eluent to afford the desired conjugate as an orange solid. $R_f$=0.29 (90:10 DCM:MeOH v/v); IR ($cm^{-1}$) 3358 (N–H), 2973, 2927 (C—H), 1691 (C=O), 1518 (aromatic C—H); $^1H$ NMR (500 MHz, $CD_3COCD_3$): δ 8.71 (s, 1H), 8.19 (s, 2H), 8.03 (d, J=2.09 Hz, 1H), 7.19 (d, J=1.88 Hz, 2H), 6.82-6.64 (m, 8H), 6.33-6.04 (m, 4H), 5.17-5.12 (m, 1H), 5.04 (s, 1H), 4.37 (s, 1H), 4.34-4.26 (m, 3H), 3.74-3.32 (m, 9H), 2.84 (s, 16H), 1.48-1.31 (m, 54H) MS (MALDI-TOF) m/z calcd for $C_{76}H_{110}N_8O_{29}S_2$ 1663.85. found 1685.76 $[M+Na]^+$. The Boc-protected conjugate (13 mg, 0.008 mmol) was dissolved in dichloromethane (2.5 mL) followed by addition of trifluoroacetic acid (0.4 mL). The mixture was covered with aluminum foil and stirred for 12 hours at room temperature. Water (2.0 mL) was added to the solution followed by washes with dichloromethane (3×1 mL). The aqueous layer was lyophilized to give the desired product as yellowish solid (quant).

Synthesis of Neomycin-Methidium Conjugate (52)

Neomycin methidium conjugate was prepared via formation of an amide bond. Commercially available methidium carboxylic acid 51 was coupled with Boc protected neomycin amine 3 using DCC/DMAP as coupling agent which led to the formation of the Boc protected neomycin-methidium conjugate that can be purified using column chromatography on a silica gel. The Boc protecting groups were then deprotected using trifluoroacetic acid to afford the desired conjugate 52 as their trifluoroacetate salt (scheme 13).

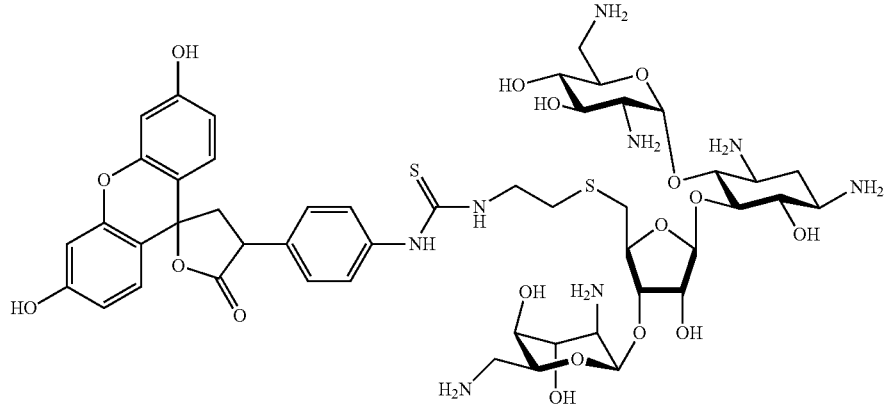

Scheme 13. Synthesis of neomycin-methidium conjugate.

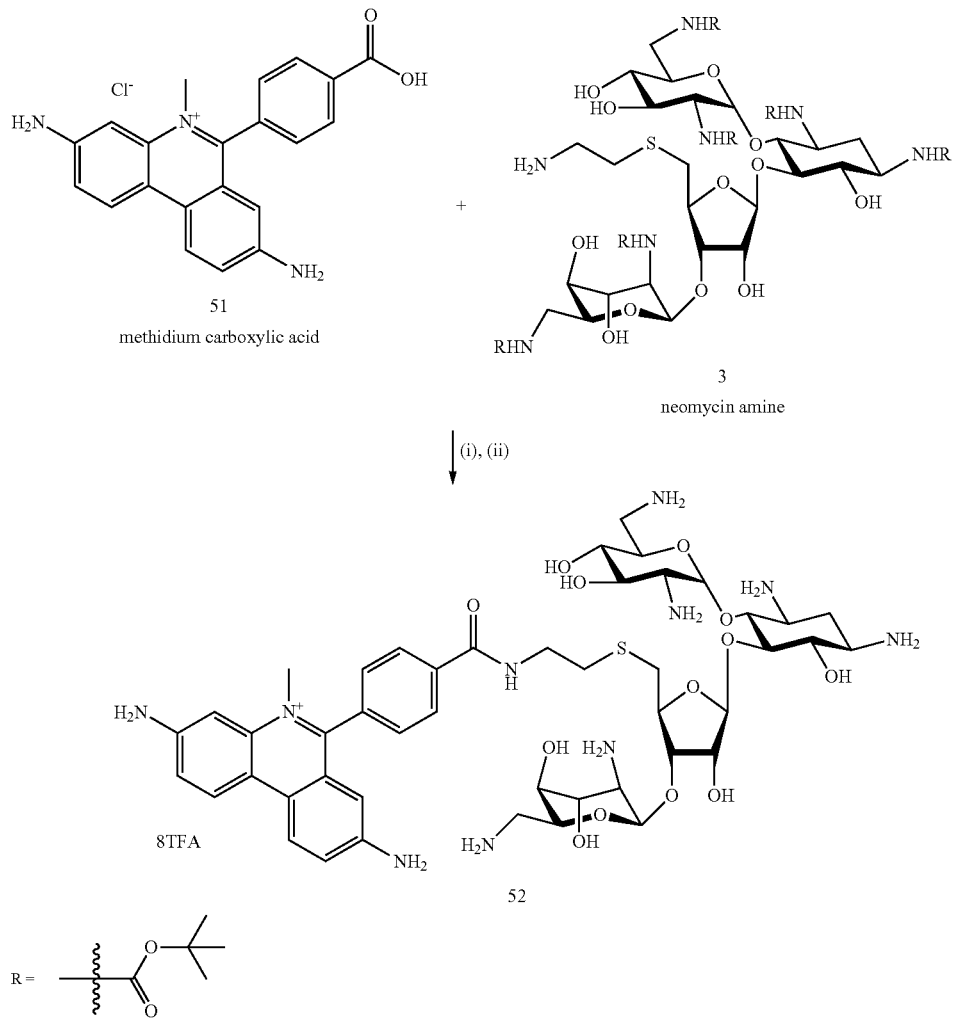

Reagents and conditions: (i) Boc neomycin amine, 6-(4-carboxyphenyl)-3,8-diamino-5-methylphen-anthridinium chloride, DCC, DMAP, DMF, 28 h, 80%; (ii) TFA/CH$_2$Cl$_2$, 1,2-ethanedithiol, 5 h, 90%.

Synthesis Procedure and Characterization of Neomycin-Methidium Conjugate (52)

To a solution of 6-(4-carboxyphenyl)-3,8-diamino-5-methylphenanthridinium chloride (8.6 mg, 0.023 mmol) in dry DMF (3.0 mL), dicyclohexylcarbodiimide (4.8 mg, 0.23 mmol) and dimethylaminopyridine (1 mg, 0.01 mmol) were added. The solution was allowed to stir under positive N$_2$ gas for 3 h. A solution of Boc-neomycin amine 3 (30 mg, 0.023 mmol) in dry DMF (3.0 mL) was added via cannula. The reaction was allowed to stir at room temperature under positive N$_2$ for 28 h. The volatiles were removed in vacuo. The dry solid was washed with CH$_2$Cl$_2$. The resulting solid was dried in vacuo. Flash chromatography (0%-25% MeOH:CH$_2$:Cl$_2$) afforded Boc protected 52 (30.8 mg, 80%) as a purple solid: R$_f$ 0.2 in 85:15 CH$_2$Cl$_2$:MeOH); UV max (95% CH$_3$OH) 286, 510 nm; IR (CHCl$_3$) 3405 (C—OH), 1600 (amide C=O) cm$^{-1}$; $^1$H NMR (500 MHz, methanol-d$_4$, 25° C.) δ) 5 (500 MHz, J=9.1 Hz), 8.56 (d, 1H, J=9.1 Hz, H10), 7.90 (d, 2H, J=8.7, H18, H20), 7.65 (d, 2H, J=8.8, H17, H21), 7.56 (dd, 1H, J=9.1, H4), 7.35-7.39 (m, 3H, H2, H7, H9), 5.41 (br, 1H), 4.92 (s, 1H), 4.34 (br, 2H), 4.04 (s, 1H), 4.00-3.98 (m, 1H), 3.89-3.80 (m, 1H), 3.76-3.71 (m, 1H), 3.61-3.69 (m, 2H), 3.55-3.52 (m, 1H), 3.51 (d, 2H), 3.47 (br, 1H), 3.4-3.2 (m, 1H), 3.19 (m, 1H), 2.93-2.91 (m, 4H), 2.85-2.83 (m, 4H), 2.81 (d, 2H), 2.79-2.70 (m, 2H), 1.96-1.86 (m, 1H), 1.71 (br, 1H), 1.36-1.48 (m, 54H); $^{13}$C NMR (125 MHz, methanol-d$_4$, 25° C.) δ) 5 (125 MHz, methanol-d3H, H2, H7, H9), 5.41 (br, 1H), 4.92 (s, 1H), 4.34 (br, 2H), 4.04 (s, 1H), 4.00-3.98 (m, 1H), 3.89-3.80 (m, 1H), 3.76-3.71 (m, 1H), 3.61-3.69 (m, 2H), 3.55-3.52 (m, 1H), 3.51 (d, 2H), 3.47 (br, 1H), 3.4-3.2 (m, 1H), 3.1, 43.3, 43.2, 41.7, 41.6, 33.3, 27.3; MALDI-TOF m/z (rel. intensity) calculated for C$_{51}$H$_{76}$N$_{10}$O$_{15}$SCl [M+H]$^+$1600.09 found 1600.01.

To a solution of Boc protected 52 (30.8 mg, 0.018 mmol) in 3 mL dichloromethane was added trifluoroacetic acid (3 mL). 1,2-ethanedithiol (100μ-ethanedithiol (100 0 in 3 mL dichloromethane was added trifluoroacetic acid (3 mL). 14.04 (s, 1H), 4.00-3.98 (m, 1H), 3.89-3.80 (m, 1H), 3.76-3.71 (m, 1H), 3.61-3.69 (m, 2H), 3.55-3.52 (m, 1H), 3.51 (d, 2H), 3.47 (br, 1H), 3.4-3.2 (m, 1H), 3.1, 43.3, 43. ratory HPLC using a reverse phase column, (0%-100% H₂O: MeCN 0.1% TFA, 15 min). The compound eluted at 20.93 min. Fractions containing the compound were lyophilized affording 52 (28.0 mg, 90%) as a maroon solid: UV max (95% H₂O) 288, 514 nm; IR (KBr) 3410 (C—OH), 1605 (amide C=O) cm⁻¹; ¹H NMR (500 MHz, D₂O, 25° C.) δ 25 (500 MHz, J=9.6 Hz, H1), 8.69 (d, 1H, J=9.6 Hz, H10), 7.86 (d, 2H, J=8.7, H18, H20), 7.66 (d, 2H, J=8.8, H17, H21), 7.52 (dd, 1H, J=9.6, H4), 7.35-7.39 (m, 3H, H2, H7, H9), 5.37 (br, 1H), 5.09 (s, 1H), 4.53 (br, 2H), 4.23 (s, 1H), 4.01-3.88 (m, 1H), 3.79-3.71 (m, 1H), 3.75-3.68 (m, 1H), 3.61-3.59 (m, 2H), 3.59-3.53 (m, 1H), 3.52 (d, 2H), 3.47 (br, 1H), 3.29-3.21 (m, 1H), 3.17-3.03 (m, 1H), 2.91-2.89 (m, 4H), 2.89-2.85 (m, 4H), 2.85 (d, 2H), 2.79 (m, 2H), 1.93 (m, 1H), 1.89 (br, 1H); ¹³C NMR (125 MHz, D₂O, 25° C.) δ 25 (125 MHz, D7.39 (m, 3H, H2, H7, H9), 5.37 (br, 1H), 5.09 (s, 1H), 4.53 (br, 2H), 4.23 (s, 1H), 4.01-3.88 (m, 1H), 3.79-3.71 (m, 1H), 3.75-3.68 (m, 1H), 3.61-3.59 (m, 2H), 3.59-3.53 (m, 1H), 3.52 (d, 2H), 3.47 (br, 1H), 3.29-3.21 (m, 1H), 3.17-3.03 (m8.7, 42.3, 40.5, 40.4, 29.3; MALDI m/z (rel intensity) calculated for C₄₆H₆₇N₁₀O₁₃SCl [M+H]⁺ 1000.07 found [M+Na]⁺ 1000.14.

Synthesis of Neomycin-Pyrene Conjugate (60)

Neomycin-pyrene conjugate was synthesized via the formation of an amide bond. Boc protected neomycin amine 3 was reacted with commercially available pyrene succinimidyl ester 59. Displacement of the succinimidyl ester group leads to the formation of the amide bond (scheme 14) and thus a Boc protected neomycin-pyrene conjugate can be prepared after purification using column chromatography. The Boc protected compound can be deprotected using trifluroacetic acid to give the desired conjugate 60 as a trifluoroacetate salt.

Scheme 14. Synthesis of neomycin pyrene conjugate via amide coupling. Reagent and conditions: (a)(i) Dry pyridine, DMAP, overnight r.t.,66%; (ii) TFA, DCM, 12 h, r.t., 82%.

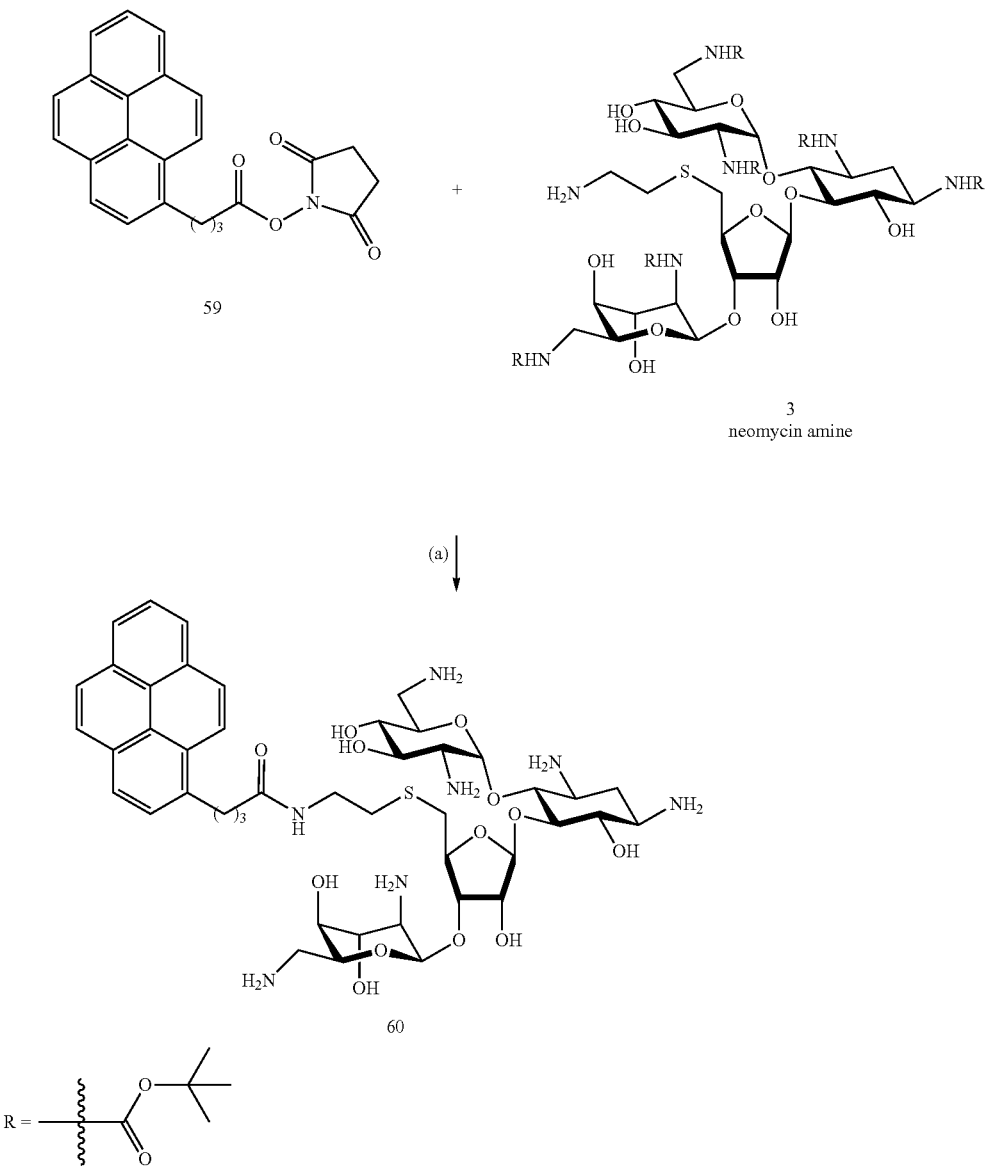

Synthesis of Neomycin Pyrene Conjugate (60)

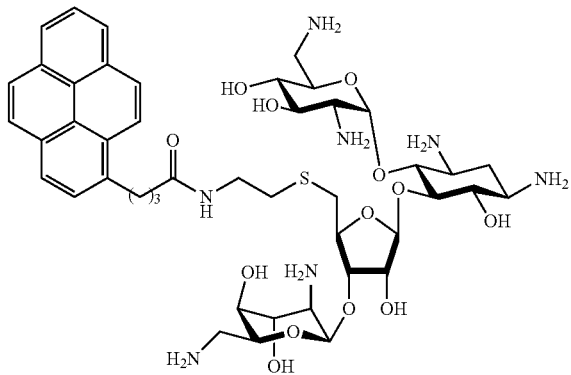

To a solution of Boc-protected neomycin amine (15 mg, 0.013 mmol) in dry pyridine (10 mL), a solution of pyrene succinimide ester (20 mg, 0.051 mmol) was added with a catalytic amount of 4-dimethylaminopyridine (DMAP). The flask was purged with argon and covered in aluminum foil. The reaction was allowed to stir for 18 h at room temperature and the progress of the reaction was monitored via TLC, which indicated formation of the product. Pyridine was dried under reduced pressure. The crude reaction mixture was purified by column chromatography using gradients of dichloromethane-methanol as eluent to afford Boc protected 60 as a white solid (13 mg, 66%): $^1$H NMR (300 MHz, CD$_3$COCD$_3$) δ 8.47 (d, J=9.82 Hz, 1H), 8.33-8.24 (m, 3H), 8.22 (d, J=2.13 Hz, 1H), 8.17-7.97 (m, 4H), 6.56-6.05 (m, 3H), 5.15 (m, 1H), 5.04 (s, 1H), 4.26 (d, J=4.38 Hz, 2H), 4.16 (s, 1H), 3.98-3.74 (m, 3H), 3.70-3.34 (m, 9H), 3.30-2.58 (m, 9H), 2.43 (t, J=7.18 Hz, 1H), 2.29-2.20 (m, 2H), 1.65-0.95 (m, 41H).

The Boc-protected 60 (13 mg, 0.008 mmol) was dissolved in dichloromethane (2.5 mL) followed by addition of trifluoroacetic acid (0.4 mL). The mixture was covered with aluminum foil and stirred for 12 h at room temperature. Water (2.0 mL) was added to the solution followed by washes with dichloromethane (3×1 mL). The aqueous layer was lyophilized to give the desired product 60 as yellowish solid (6.75 mg, 82%): NMR (300 MHz, CD$_3$COCD$_3$) δ 8.13-8.03 (m, 3H), 8.01-7.86 (m, 5H), 7.34 (d, J=8.16 Hz, 1H), 5.82 (d, J=4.08 Hz, 1H), 5.21 (d, J=3.71 Hz, 1H), 4.16-3.67 (m, 10H), 2.63 (s, 2H), 3.23-2.74 (m, 12H), 2.53-2.21 (m, 7H), 2.08 (d, J=5.56 Hz, 1H), 2.06-1.95 (m, 3H), 1.76 (d, J=12.98 Hz, 1H); MS (MALDI-TOF) m/z cacld. for C$_{45}$H$_{65}$N$_7$O$_{13}$S 944.10. found 966.90 [M+Na]$^+$; UV (water): λ$_{max1}$ (nm)=239, λ$_{max2}$ (nm)=274, λ$_{max2}$ (nm)=342.

Synthesis of Neomycin Dimer Thiazole Orange Conjugate (63)

For the synthesis of neomycin dimer-thiazole orange conjugate 63, first a linker 61 was constructed that had a pendant amine group for coupling to thiazole orange carboxylic acid which leads to the formation of 62. The Boc protecting groups in 62 can then be deprotected using trifluoroacetic acid and subsequently coupled with Boc protected neomycin isothiocyanate 4, to form Boc protected neomycin dimer-thiazole orange conjugate 63. The Boc groups can then be deprotected to give the desired neomycin dimer-thiazole orange conjugate as trifluoroacetate salt (scheme 15).

Scheme 15. Reagent and conditions. (a) TBTU, DIPEA, DMF, r.t.; (b) TFA/DCM, r.t., 3 h., 20% overall yeild for steps a and b.

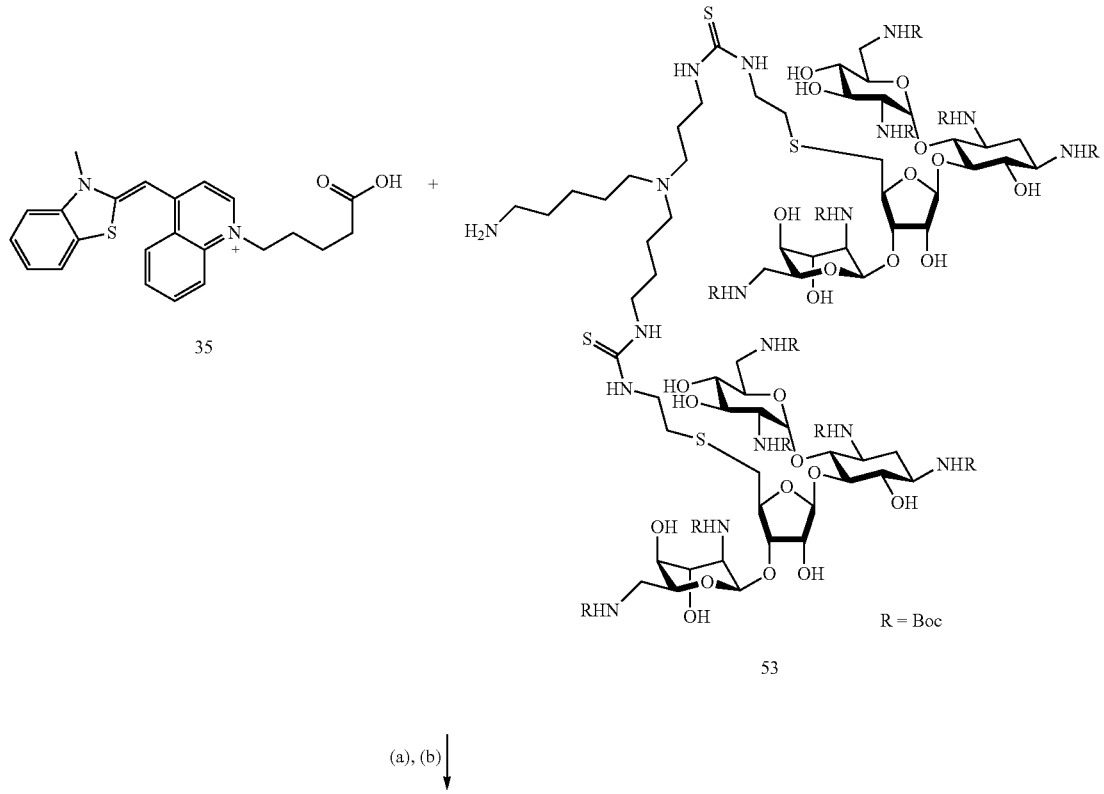

-continued

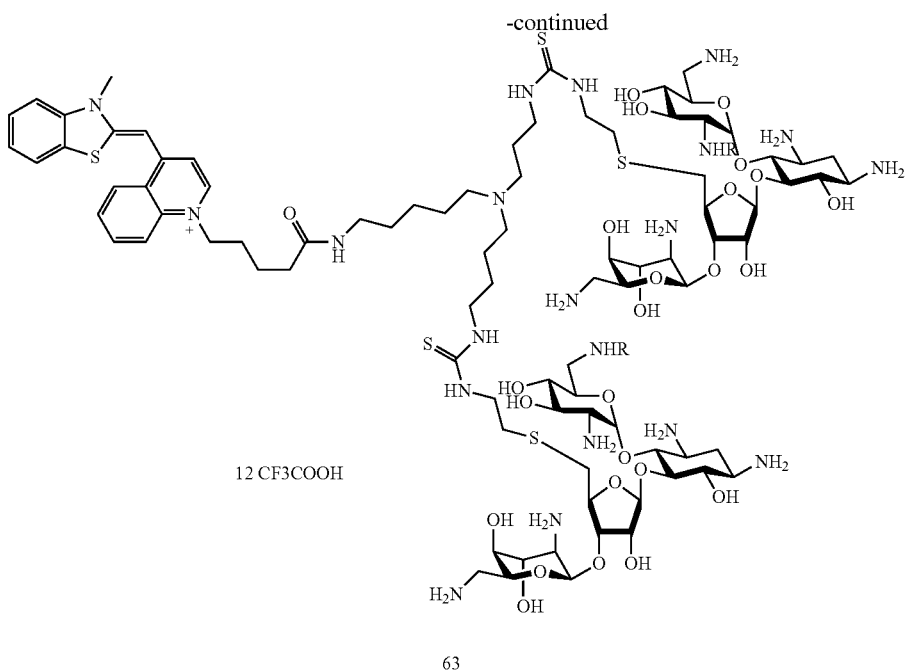

12 CF3COOH

63

Synthesis and Characterization of Thiazole Orange-Neomycin Dimer (63)

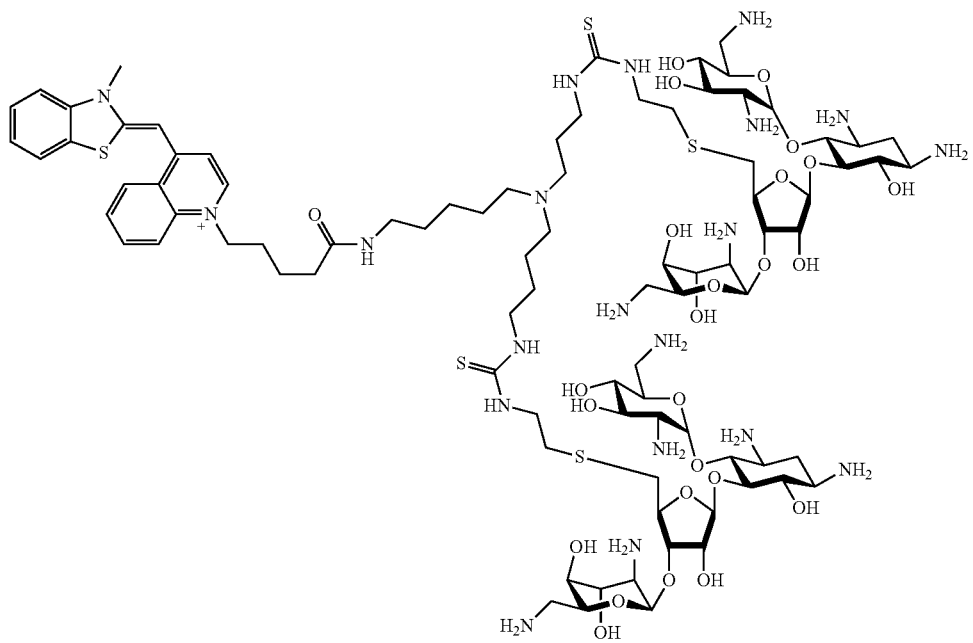

To a solution of neomycin dimer amine (53) (14.6 mg, 6.0 µmol) in dry DMF (2.0 mL), in dry DMF (3.0 mL), TBTU (7.9 mg, 24.0 µmol, 4.0 mol equival.) was added, followed by the addition of DIPEA (6.2 mg, 48.0 µmol, 8.0 mol equival.) and thiazole orange-COOH (35) (3.5 mg, 12.0 µmol). The reaction started in the atmosphere of argon at r.t. with constant stirring. The progress of the reaction was monitored by TLC. The reaction ran overnight in inert atmosphere in dark. The volatiles were removed on roto-vap. Column chromatography (0 to 25% EtOH in DCM) results in an orange solid (8.6 mg). [$R_f$ 0.24, 13% MeOH in DCM (v/v)].

The reaction mixture was then dissolved in DCM (1.0 mL) followed by addition of TFA (0.1 mL). The mixture was stirred at room temperature under darkness for 3 h during which the progress of the reaction was monitored by TLC. Water (2.0 m T) was added to the reaction mixture and then washed with DCM (3×3.0 mL). The water layer was lypholyzed that results in a dark red coloured compound 63 (6.05 mg, 20% overall yield for the two steps). $^1$H NMR (500 MHz, $D_2O$) δ 9.23 (m, 1H), 8.44 (d, J=8.84 Hz, 1H), 8.39 (d, J=8.36 Hz, 1H), 8.21-8.24 (m, 1H), 8.11-8.14 (m, 1H), 8.02 (d, J=8.20 Hz, 1H), 7.98 (t, J=8.04 Hz, 1H), 7.82-7.89 (m, 3H), 7.63-7.72 (m, 2H), 7.40-7.52 (m, 4H), 5.91-6.04 (m, 2H), 5.29-5.35 (m, 2H), 5.15-5.22 (m, 2H), 5.02 (t, J=7.24 Hz, 2H), 4.29-4.40 (m, 4H), 4.18-4.26 (m, 4H), 4.05-4.17 (m, 4H), 3.80-3.96 (m, 6H), 3.55-3.73 (m, 4H), 3.20-3.55 (m, 20H), 2.95-3.20 (m, 4H), 2.55-2.78 (m, 2H), 2.35-2.45 (m, 2H, $H_{I2eq}$), 2.18-2.30 (m, 2H), 1.97-2.13 (m, 2H), 1.87 (d, J=12.84 Hz, 2H, $H_{I2ax}$), 1.60-1.75 (m, 2H); MS MALDI-TOF calcd. for $C_{87}H_{149}N_{20}O_{25}S_5$ (M$^+$), 2035.56, obsd: 2036.122. UV (H$_2$O) $\lambda_{max}$=508 nm. $\varepsilon_{503}$=13835 M$^{-1}$ cm$^{-1}$.

Synthesis of Neomycin-Naphthalenediimide Conjugate (65)

A monoamine terminated naphthalene diimide can be prepared in few synthetic steps as described earlier. The amine terminated naphthalenediimide 64 can be reacted with Boc protected neomycin isothiocyanate 4 to form a thiourea linked Boc neomycin-naphthalene diimide conjugate (scheme 16) after purification using column chromatography. The Boc groups can then be deprotected using trifluoroacetic acid to give the desired conjugate 65 as trifluoroacetate salt.

Scheme 16. Synthesis of neomycin napthalenediimide conjugate via thiourea coupling. Reagent and conditions: (a)(i) Dry pyridine, DMAP, overnight, r.t., 86%; (ii) TFA, DCM, 3 h, r.t., 90%.

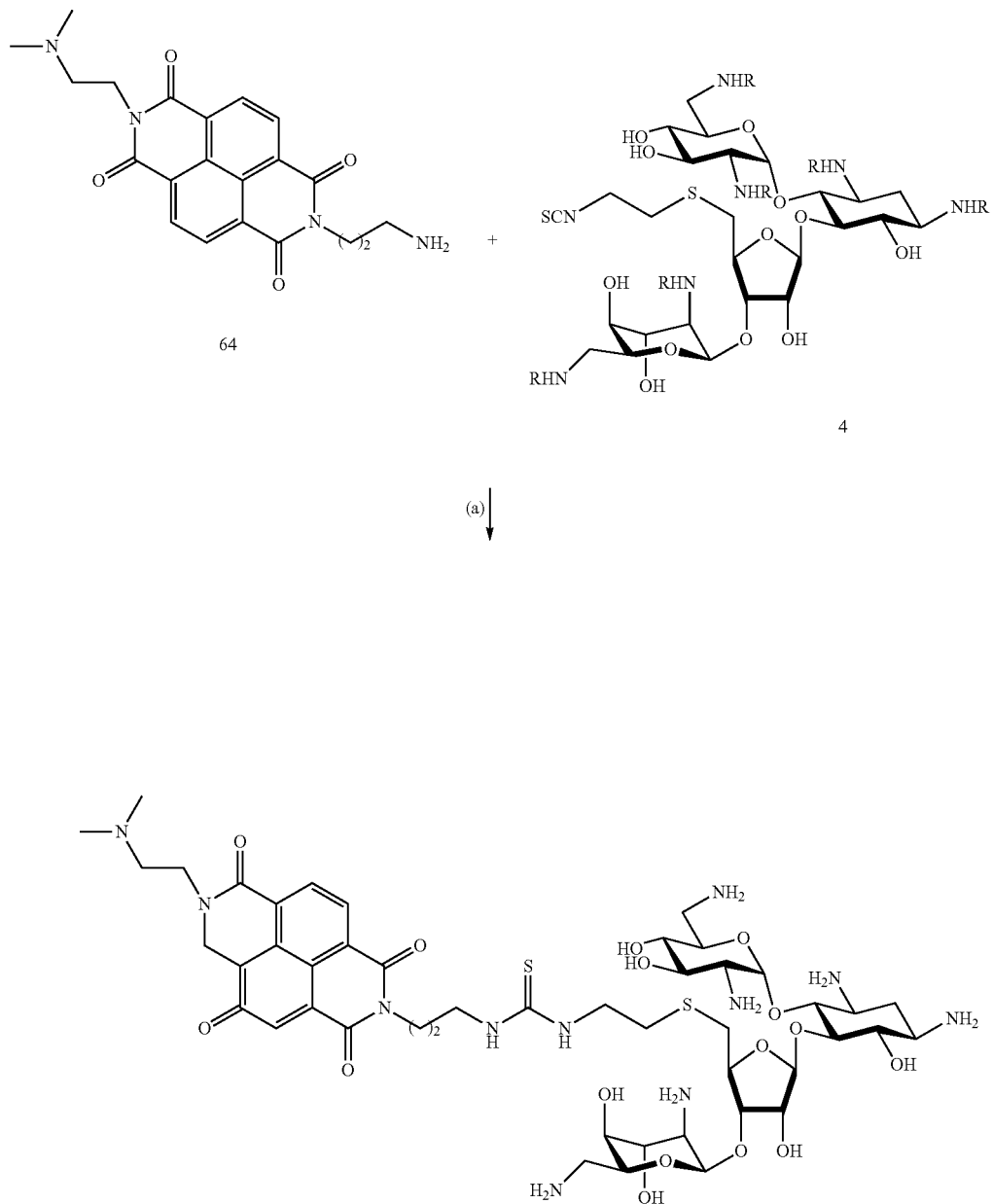

-continued

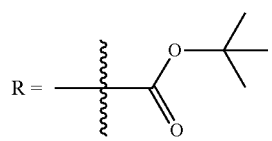

Synthesis of Neomycin-Napthalenediimide Conjugate (65)

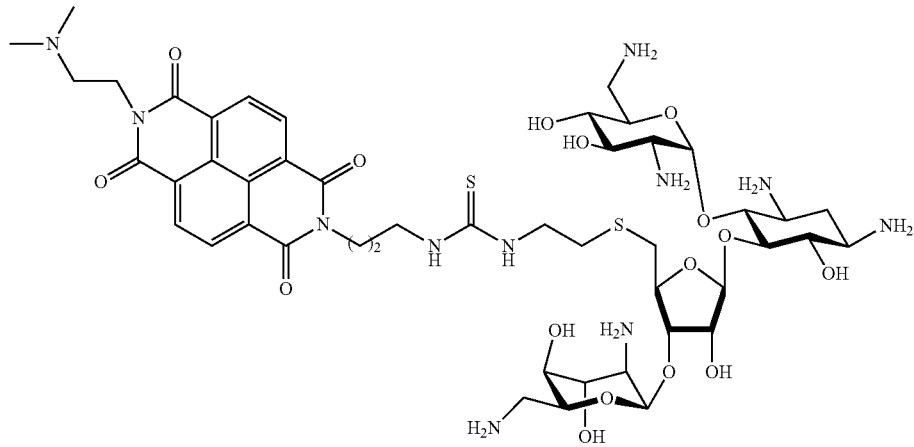

Preparation of Boc Protected Neomycin-Napthalenediimide Conjugate

To an anhydrous pyridine solution (2 mL) of Boc protected neomycin isothiocynate 4 (18 mg, 0.014 mmol) were added amine terminated napthalenediimide 64 (7.6 mg, 0.015 mmol) and DMAP (catalytic amount). After the mixture had been stirred under $N_2$ at room temperature overnight, the organic solvent was removed under vacuum. Flash chromatography of the residue (6% MeOH in $CH_2Cl_2$) yielded the desired product 65 as a white solid (15 mg, 86%): $R_f$=0.33 (silica gel, 6% MeOH in $CH_2Cl_2$); $^1$H NMR (CD$_3$OD) δ 8.74-8.77 (m, 4H), 5.40 (br, 1H), 5.37 (m, 1H), 5.11 (m, 1H), 4.90 (m, 1H), 4.23 (m, 1H), 4.09 (m, 2H), 3.82 (m, 4H), 3.76 (m, 2H), 3.67 (m, 2H), 3.44-3.56 (m, 6H), 3.00-3.30 (m, 9H), 2.84-2.86 (m, 4H), 2.70-2.78 (m, 6H), 2.69 (m, 4H), 2.35 (m, 6H), 2.03 (m, 2H), 1.94 (m, 1H), 1.40 (m, 54H); MS (MALDI-TOF) m/z calcd for $C_{77}H_{119}N_{11}O_{28}S_2Na$, 1610.96. found 1611.56.

Preparation of Neomycin Napthalenediimide Conjugate (65)

In a 10 mL round-bottom flask, Boc protected neomycin napthalenediimide conjugate (15 mg, 0.090 mmol) was dissolved in a 1:1 TFA/$CH_2Cl_2$ mixture (2 mL) and the solution stirred at room temperature for 3 h. The solvent was removed under vacuum, and the residue was dissolved in deionized water (20 mL). The aqueous layer was washed with ether (3×20 mL). Aqueous layer was lyophilized which yielded 3 as a yellow solid (9 mg, 90%): $^1$H NMR (CD$_3$OD) δ 8.74-8.77 (m, 4H), 5.40 (br, 1H), 5.37 (m, 1H), 5.11 (m, 1H), 4.90 (m, 1H), 4.90 (q, 2H) 4.23 (m, 2H), 4.09 (m, 2H), 3.82 (m, 6H), 3.76 (m, 6H), 3.67 (m, 2H), 3.44-3.56 (m, 6H), 3.00-3.30 (m, 12H), 2.84-2.86 (m, 6H), 2.70-2.78 (m, 8H), 2.69 (m, 4H), 2.45 (m, 2H), 2.03 (m, 2H), 1.94 (m, 1H), 1.45 (m, 2H).

Synthesis of Neomycin-Anthraquinone Conjugate (67)

To prepare neomycin anthraquinone conjugate, anthraquinone isothiocyanate 66 was reacted with neomycin amine 3 in the presence of DMAP catalyst. This leads to the formation of the Boc protected neomycin-anthraquinone conjugate which can be isolated pure after purification using column chromatography (scheme 17). The Boc protected conjugate can be deprotected using trifluoroacetic acid to give the desired conjugate 67 as trifluoroacetate salt

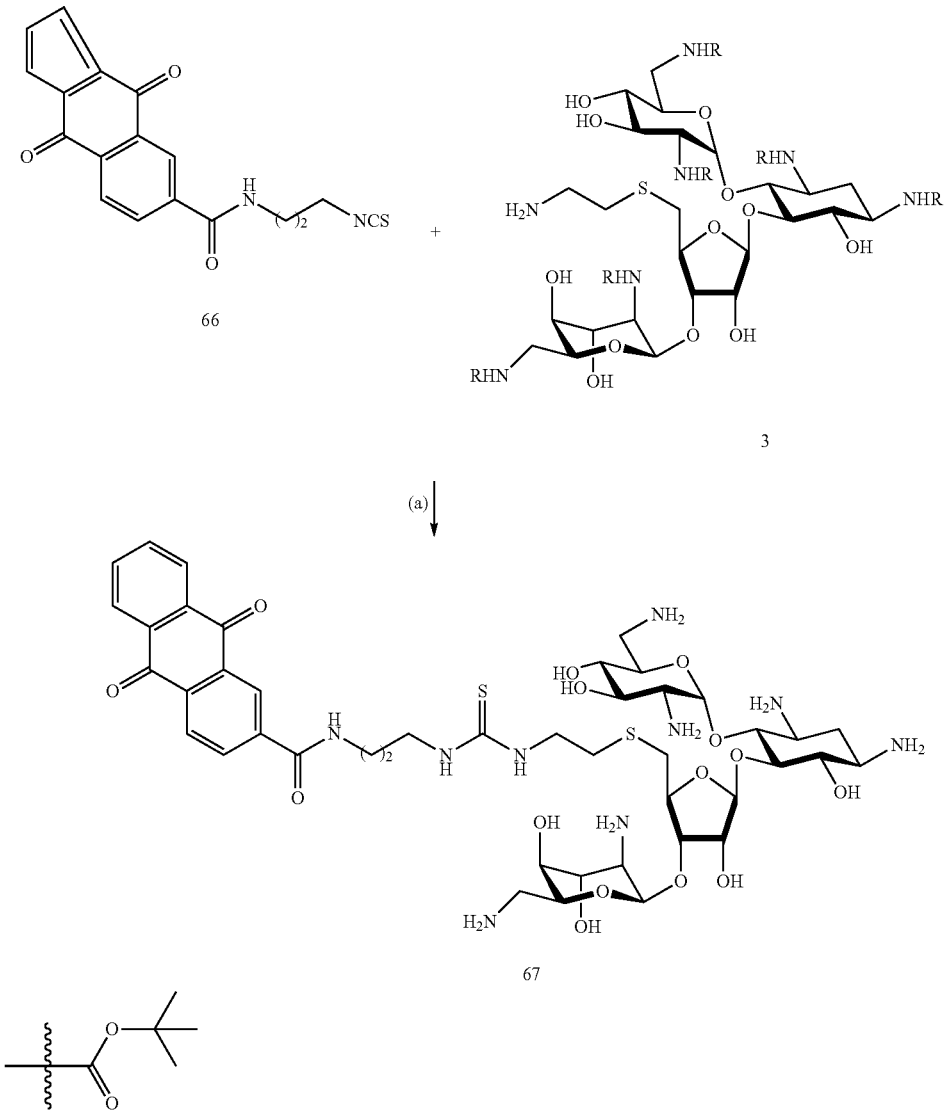
Preparation of Neomycin-Anthraquinone Conjugate (67)
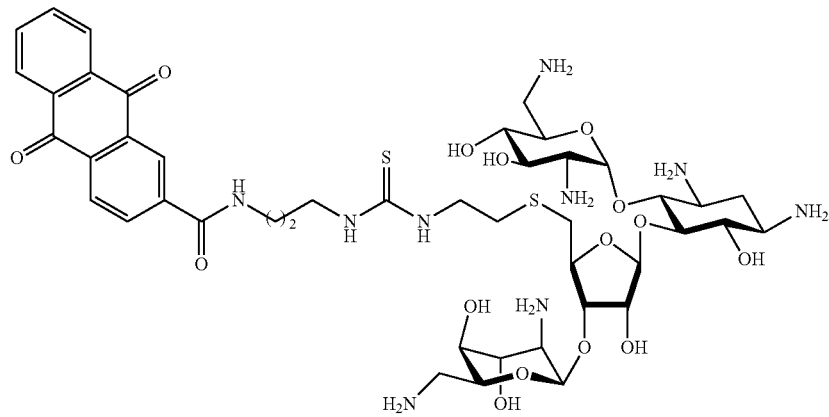

a. Preparation of Boc Protected Neomycin-Anthraquinone Conjugate

To an anhydrous pyridine solution (5 mL) of compound 12 (10.7 mg, 0.008 mmol) were added compound 6 (9.3 mg, 0.027 mmol) and DMAP (catalytic amount). After the mixture had been stirred at room temperature overnight, the organic solvent was removed under vacuum. Flash chromatography of the residue (5% MeOH in $CH_2Cl_2$) yielded the desired product as a white solid (7.1 mg, 86%): $R_f$=0.60 (silica gel, 10% MeOH in $CH_2Cl_2$); $^1$H NMR ($CD_3OD$) δ 8.60 (s, 1H), 8.20-8.40 (br, 1H), 5.37 (m, 1H), 5.11 (m, 1H), 4.90 (m, 1H), 4.23 (m, 1H), 4.09 (m, 2H), 3.82 (m, 4H), 3.76 (m, 2H), 3.67 (m, 2H), 3.44-3.56 (m, 6H), 3.00-3.30 (m, 9H), 2.84-2.86 (m, 4H), 2.70-2.78 (m, 6H), 2.69 (m, 4H), 2.35 (m, 6H), 2.03 (m, 2H), 1.94 (m, 1H), 1.40 (m, 54H); MS (MALDI-TOF) m/z calcd for $C_{74}H_{113}N_9O_{27}S_2Na$, 1646.86. found 1647.19.

b. Deprotection of Boc Protected Neomycin-Anthraquinone Conjugate

In a 10 mL round-bottom flask, Boc protected neomycin-anthraquinone conjugate (7.1 mg, 0.090 mmol) was dissolved in a 1:1 $TFA/CH_2Cl_2$ mixture (2 mL) and the reaction mixture was stirred at room temperature for 3 h. The solvent was removed under vacuum, and the residue was dissolved in deionized water (20 mL). The aqueous layer was washed with ether (3×20 mL). Aqueous layer was lyophilized which yielded the desired compound 67 as a yellow solid (9 mg, 90%): $^1$H NMR ($CD_3OD$) δ 8.60 (s, 1H), 8.20-8.40 (m, 4H), 7.8-7.84 (m, 2H), 5.40 (br, 1H), 5.37 (m, 1H), 5.11 (m, 1H), 4.90 (m, 1H), 4.50 (m, 2H), 4.23 (m, 1H), 4.09 (m, 2H), 3.82 (m, 4H), 3.76 (m, 2H), 3.67 (m, 2H), 3.44-3.56 (m, 8H), 3.00-3.30 (m, 10H), 2.84-2.86 (m, 4H), 2.70-2.78 (m, 6H), 2.69 (m, 4H), 2.35 (m, 6H), 2.03 (m, 2H), 1.94 (m, 1H); MS (MALDI-TOF) m/z calcd for $C_{44}H_{65}N_9O_{15}S_2Na$, 1047.2. found 1046.9.

Synthesis of Kanamycin-Pyrene Conjugate (69)

Kanamycin-pyrene can be synthesized by reaction of kanamycin amine 68 with pyrene succinimidyl ester 59 (scheme 18). This leads to the formation of Boc protected kanamycin-pyrene conjugate which can be deprotected in the presence of trifluoroacetic acid to give the desired conjugate 69.

Scheme 18. Regeant and conditions. (a) Pyridine, DMAP, 14 h, rt, 88%.

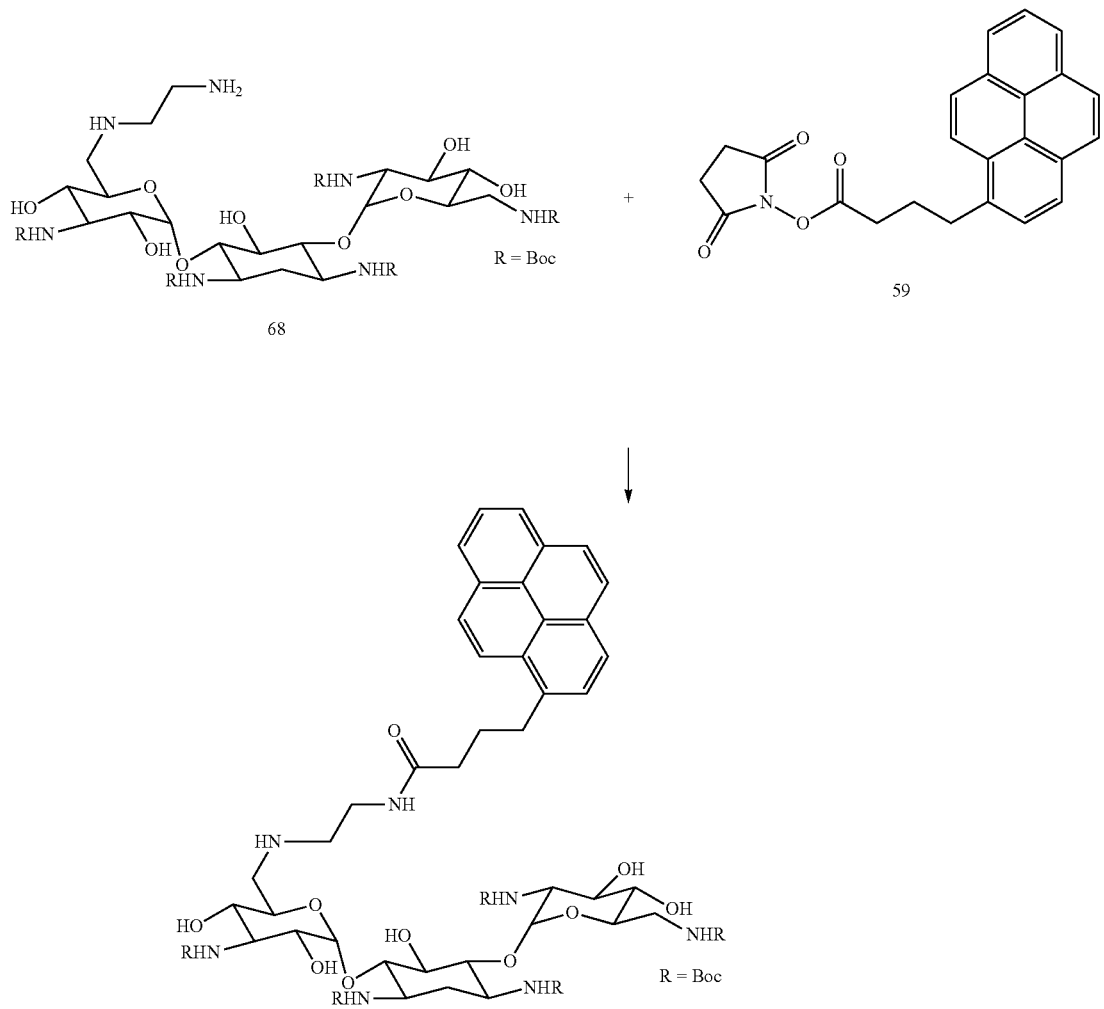

Preparation of Boc Protected Kanamycin-Pyrene (69)

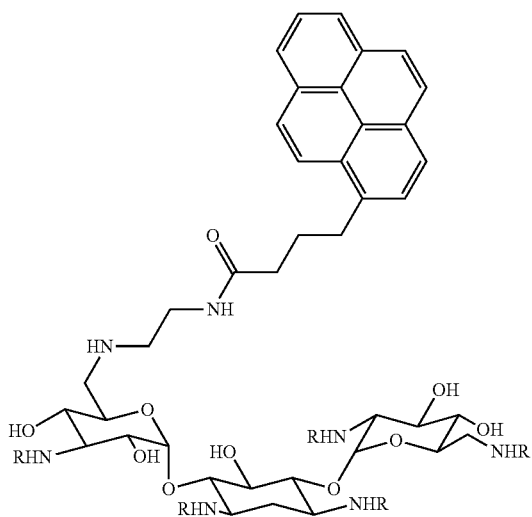

R=Boc

To a solution of Boc protected kanamycin amine (30 mg, 0.03 mmol) in pyridine, DMAP (catalytic) was added followed by addition of pyrene succinimidyl ester (1.25 mg, 0.64 mmol). The mixture was stirred at room temperature for 14 h. Volatiles were removed under reduced pressure. The crude mixture was purified on a silica gel column using ethyl acetate-methanol as eluent to afford the desired conjugate (Yield=88%). $R_f$=0.66 (ethyl acetate-methanol 86:14 v/v).

Synthesis of an Amino Functionalized Neomycin Dimer (53)

A tridentate linker 76 was designed and synthesized for the preparation of dimer conjugates. Compound 76 was prepared according to procedure reported in literature in which the primary amines of spermidine were selectively protected using tert-butyl phenyl carbonate (Phanstiel, Price, Wang, Juusola, Kline, & Shah, 2000). In the next step, the secondary amine was reacted with 5-bromovaleronitrile through nucleophilic substitution reaction in the presence of a base to introduce nitrile functionality (Phanstiel, Price, Wang, Juusola, Kline, & Shah, 2000). As shown in scheme 19, the TFA salt of 76 was then reacted with Hexa-N-Boc deoxy-neomycin-5"-isothiocyanate in a stoichiometry ratio of 2:1 to form nitrile functionalized neomycin dimer. The neomycin dimer with a nitrile was then reduced and converted into an amine functionalized neomycin dimer 53 (scheme 20), which can be coupled to fluorescent dyes.

Scheme 19. Reagents and conditions: a-b: (a) dry pyridine, triethylamine, r.t., 12 h, 79%.

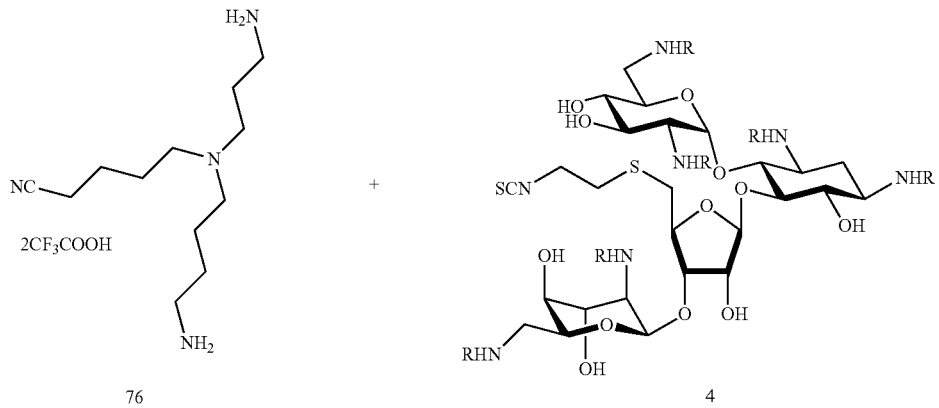

(a)

-continued
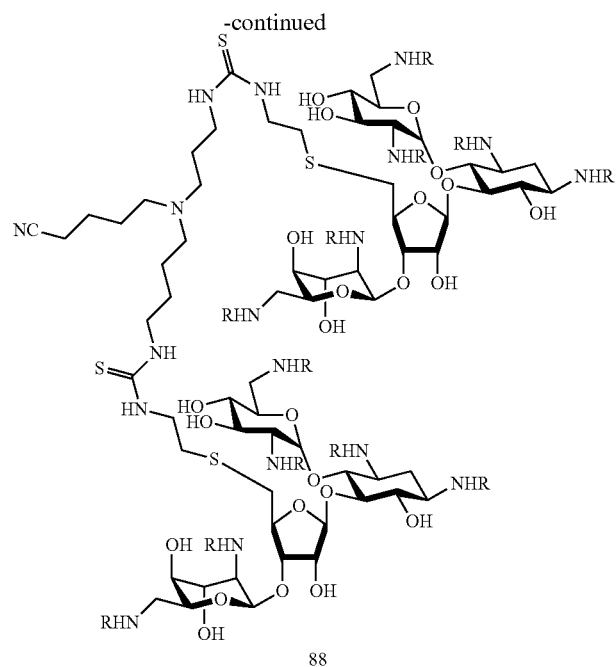
88
Scheme 20. Reagents and conditions: (a) EtOH, raney nickel, NH₃ gas, NH₄OH, H₂ gas, 12 h, r.t., 60%.
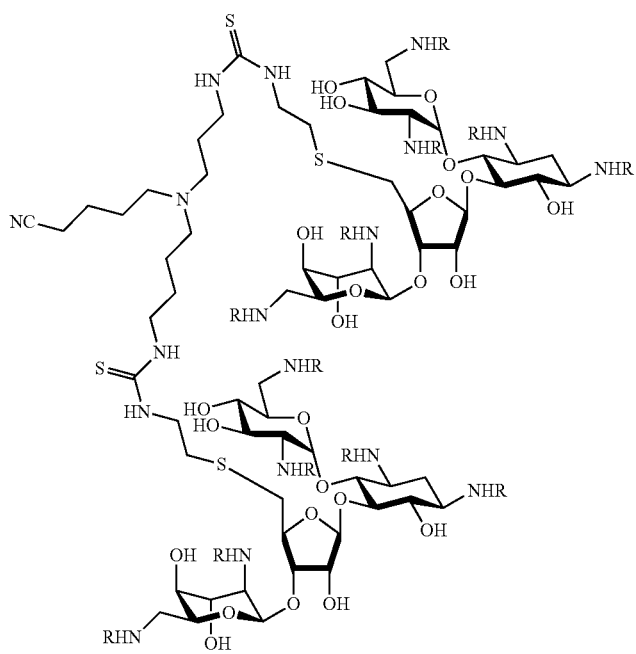
88
(a) ↓

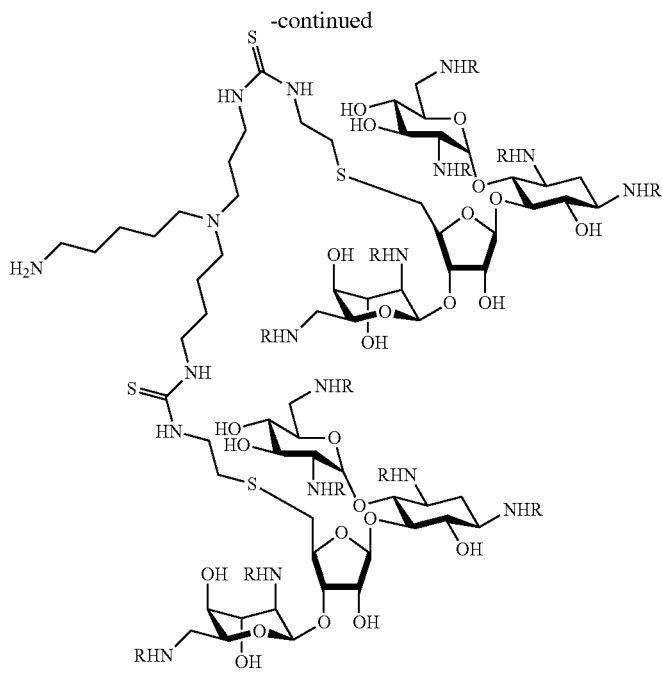

53

Reagents and conditions: (a) EtOH, raney nickel, NH₃ gas, NH₄OH, H₂ gas, 12 h, r.t., 60%.

Synthesis of Nitrile Functionalized Boc Protected Neomycin Dimer (88)

To a solution of 5-((4-aminobutyl)(3-aminopropyl)amino)pentanenitrile trifluoroacetic acid (6.8 mg, 16.0 µmol) in dry pyridine (2.0 mL), triethylamine (7.0 mg, 70.0 µmol) was added and the reaction mixture stirred for 15 min. followed by addition of Hexa-N-Boc deoxy-neomycin-5′′-isothiocyanate (4) (45.0 mg, 34.0 µmol) and the reaction started in the atmosphere of argon. The reaction was run overnight and the progress of the reaction was monitored by TLC. The reaction mixture was then dried and column chromatography (0 to 15% EtOH in DCM) results in an off white solid 88 (36.4 mg, 79%). [$R_f$ 0.31, 10% MeOH in DCM (v/v)]; IR (KBr, cm$^{-1}$) 3388 (broad), 2977, 2150, 1667, 1519, 1366, 1251; $^1$H NMR (500 MHz, CD$_3$COCD$_3$): δ 6.45-6.58 (m, 4H, NH$_{6IV}$), 6.35-6.41 (d, J=9.45 Hz, 2H, NH), 6.28-6.35 (d, J=5.04 Hz, 2H, NH), 6.07-6.27 (m, 8H, NH$_{1I}$, NH$_{3I}$, NH$_{2IV}$, and NH$_{2II}$), 5.90-6.04 (br, s, 4H), 5.14-5.32 (m, 8H), 4.81-4.91 (m, 4H), 4.63 (p, J=6.78 Hz, 4H), 4.53-4.59 (m, 4H), 4.43 (br, s, 2H), 4.16-4.33 (m, 8H), 4.06 (s, 4H), 3.90-3.96 (m, 4H), 3.73-3.90 (m, 14H), 3.53-3.73 (m, 20H), 3.41-3.54 (m, 10H), 3.10-3.35 (m, 18H), 3.01-3.10 (m, 4H), 2.54 (t, J=7.10 Hz, 4H), 2.20 (t, J=2.21 Hz, 2H), 1.94 (t, J=2.21 Hz, 2H), 1.75-1.83 (m, 4H), 1.66-1.75 (m, 4H), 1.56-1.61 (m, 2H), 1.27-1.55 (m, 114H, H$_{2Ieq}$, 6×boc, linker protons); MS MALDI-TOF calcd. for C$_{124}$H$_{220}$N$_{18}$O$_{48}$S$_4$ (M+Na$^+$), 2881.43, obsd: 2881.10.

Synthesis of Amino Functionalized Boc Protected Neomycin Dimer (53)

To a solution of 88 (25.0 mg, 90.0 µmol) in dry ethanol (10.0 mL), raney's nickel (20.0 mg, 50% slurry) and NH$_4$OH (50.0 µL) was added. The reaction mixture stirred at 0° C. for 5 min. following which ammonia gas was passed through the solution for 15 min. at 0° C. The solution was then allowed to come to r.t. and the flask was partially evacuated. The reaction mixture was stirring in the atm. of H2 gas overnight and the progress of the reaction was monitored by TLC. The reaction mixture was filtered and the solvents were evaporated. Column chromatography [0 to 20% EtOH in DCM, (v/v)] results in greenish powder (15 mg, 60%). [$R_f$ 0.41, 15% MeOH in DCM (v/v)]; IR (KBr, cm$^{-1}$) 3330-3450 (broad), 2967, 2959, 2855, 1696, 1526; $^1$H NMR (500 MHz, CD$_3$COCD$_3$) δ 7.14 (s, 1H), 6.68 (m, 1H), 5.86-6.33 (m, NH$_{6IV}$, NH$_{6II}$, NH$_{1I}$, NH$_{3I}$, NH$_{2IV}$, and NH$_{2II}$), 5.09-5.39 (m, 8H), 4.98-5.08 (m, 4H), 4.75-4.96 (br, s, 2H), 4.42-4.67 (m, 4H), 4.53-4.59 (m, 4H), 4.43 (br, s, 2H), 4.13-4.39 (m, 10H), 3.98-4.13 (m, 8H), 3.73-3.93 (m, 16H), 3.53-3.73 (m, 22H), 3.40-3.53 (m, 10H), 3.01-3.38 (m, 18H), 2.68-2.98 (m, 6H), 2.51-2.64 (m, 4H), 1.83-1.91 (m, 2H), 1.76-1.83 (m, 4H), 1.69-1.75 (m, 4H), 1.16-1.67 (m, 114H, H$_{2Ieq}$, 6×boc, linker protons); MS MALDI-TOF calcd. for C$_{124}$H$_{224}$N$_{18}$O$_{48}$S$_4$ (M+Na$^+$), 2885.43, obsd: 2886.07.

Synthesis of Neomycin Dimer-Anthraquinone Conjugate (70)

To prepare neomycin dimer anthraquinone conjugate 70, anthraquinone isothiocyanate 37 was reacted with neomycin dimer amine 53 in the presence of DMAP catalyst. This leads to the formation of the Boc protected neomycin dimer-anthraquinone conjugate which can be isolated pure after purification using column chromatography (scheme 21). The Boc protected conjugate can be deprotected using trifluoroacetic acid to give the desired conjugate 70 as trifluoroacetate salt.

Scheme 21. Reagents and conditions: a-b: (a) Dry pyridine, DMAP, 12 h., r.t., 77%; (b) DCM, CF₃COOH, r.t. 2 h, 90%.
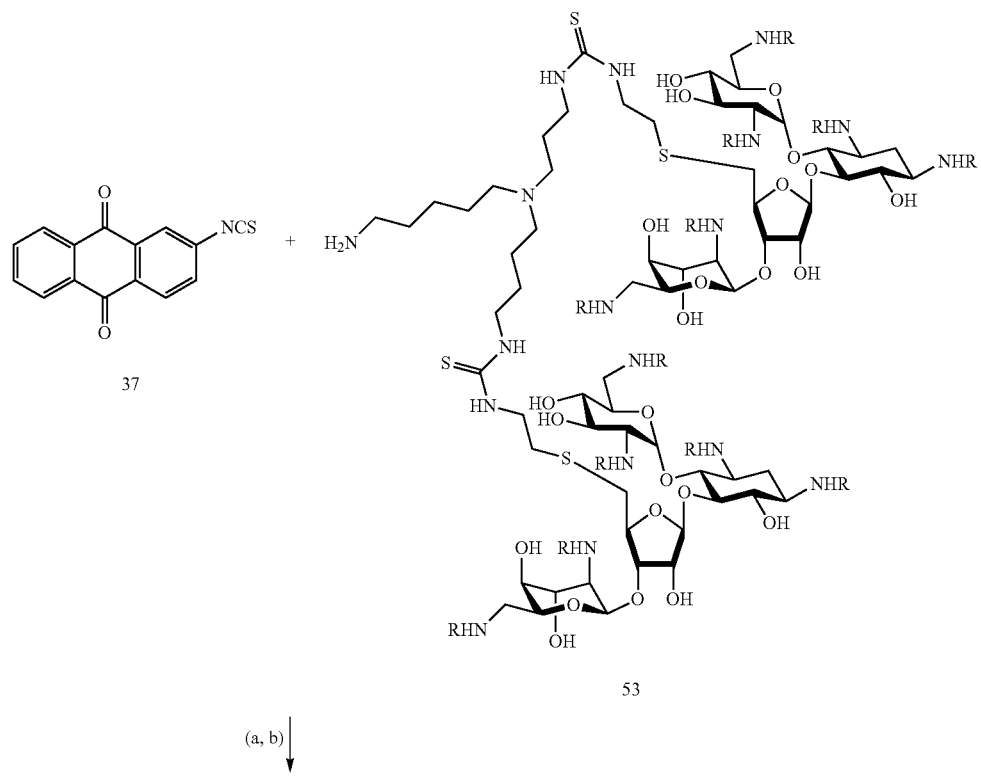
37 + 53
(a, b) ↓
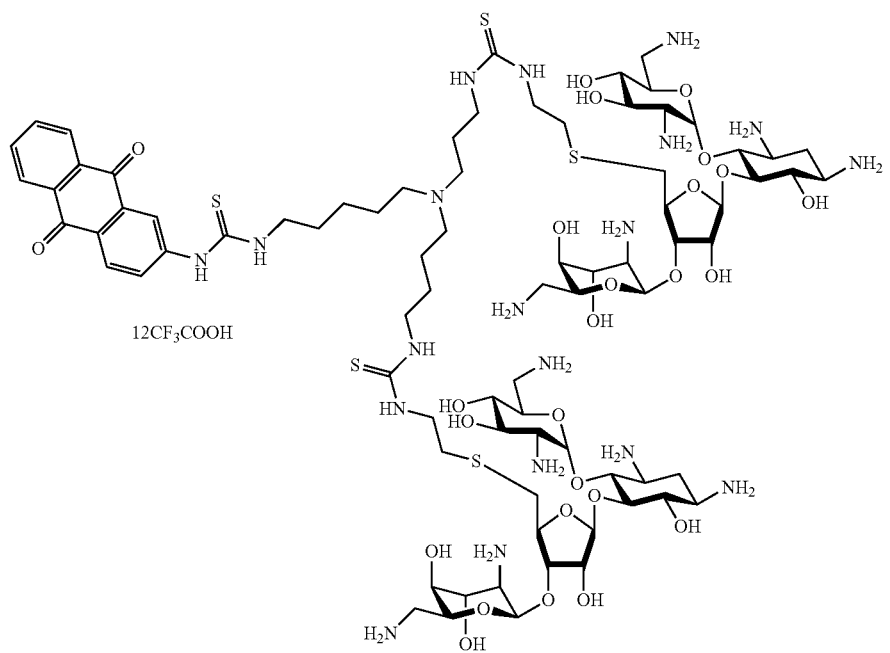
70

Synthesis and Characterization of Neomycin Dimer Anthraquinone (70)

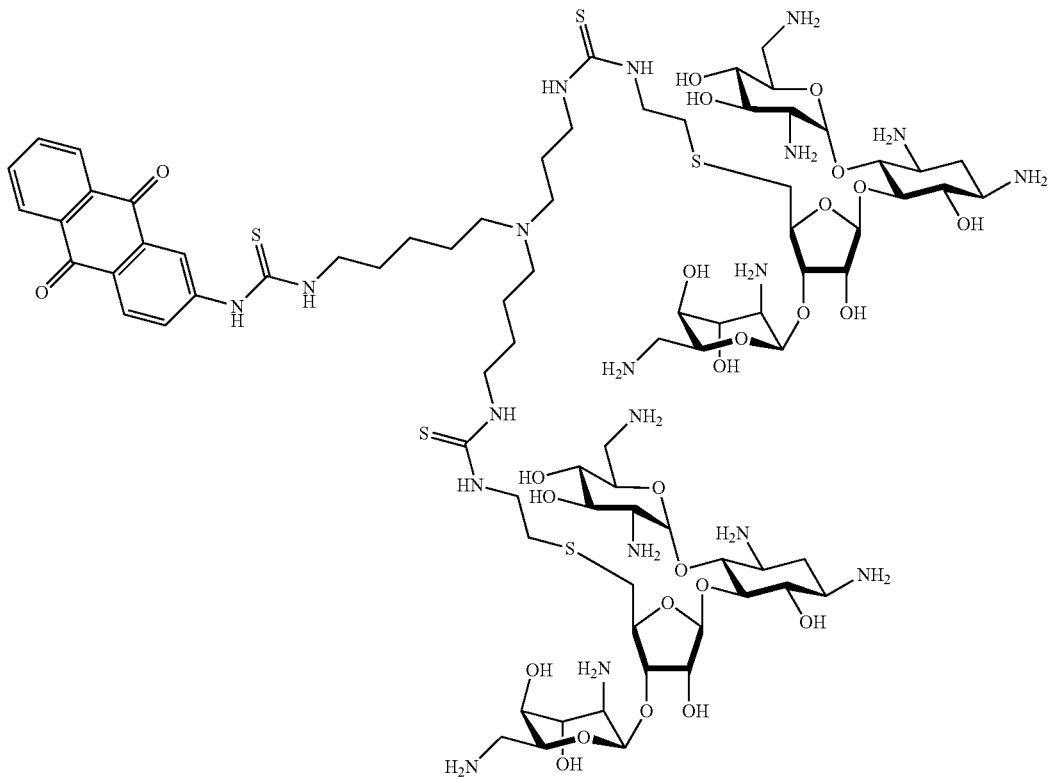

To a solution of N-Boc neomycin dimer amine 53 (22.0 mg, 9.0 mol) in dry pyridine (2.0 mL), anthraquinone isothiocynate 37 (2.8 mg, 10.0 mol) was added which was followed by addition of triethylamine (2.0 mg, 20.0 μmol). The reaction mixture was stirred at room temperature overnight under argon. The progress of the reaction was monitored by TLC. The solvents were evaporated under reduced pressure. The crude product was purified using column chromatography on silica gel using dichloromethane-methanol as eluent (0 to 10% MeOH in DCM (v/v)). The desired product was obtained as faint orange colored solid (22.1 mg, 77%): $R_f$=0.48 (10% EtOH in DCM (v/v)); IR (KBr, cm$^{-1}$) 3300-3500 (br), 2920, 2103 (br, —C=S), 1711, 1609; $^1$H NMR (500 MHz, CD$_3$COCD$_3$) d 8.20-8.35 (m, 4H aromatic hydrogens from anthraquinone), 7.90-8.01 (m, 4H, aromatic hydrogens from anthraquinone), 6.38-6.45 (t, J=6.15 Hz, 2H, NH$_{6IV}$), 6.18-6.30 (4H, NH$_{II}$, NH$_{6II}$), 6.05-6.15 (m, 4H, NH$_{2IV}$, NH$_{3I}$), 5.90-6.02 (br, s, 2H, NH$_{2II}$), 5.25-5.30 (m, 2H), 5.20-5.24 (m, 2H), 5.10-5.18 (m, 4H), 4.96-5.08 (m, 6H), 4.77-4.85 (m, 2H), 4.56-4.64 (m, 2H), 4.44-4.52 (m, 2H), 4.34-4.42 (m, 2H), 4.15-4.33 (m, 10H), 4.01-4.09 (m, 2H), 3.88-3.99 (m, 4H), 3.71-3.87 (m, 8H), 3.40-3.70 (m, 22H), 3.20-3.31 (m, 6H), 2.96-3.06 (m, 4H), 1.68-1.76 (m, 2H), 1.25-1.58 (m, 112H, 12×Boc, linker protons); MS (MALDI-TOF) m/z calcd. for C$_{140}$H$_{233}$N$_{19}$O$_{50}$S$_5$, 3142.77. found 3166.18 [M+Na]$^+$; UV (DCM) $\lambda_{max}$=254 nm. The Boc protected 70 was taken up in DCM-TFA solution (2.2 mL, 1:0.1 v/v) and stirred at room temperature under darkness for 2 h. Progress of reaction was checked by TLC. To this, deionized water (2.0 mL) was added and the mixture was washed with DCM (2×3 mL). The aqueous layer was lyophillized to afford the desired compound as slightly greenish white solid (22.3 mg, 90%); $^1$H NMR (500 MHz, D$_2$O) δ) MR (500 MHz, Droom temperature under darkness for 2 h. Progress of reaction was checked by TLC. To this, deionized water (2.0 mL) was added and the mixture was washed with DCM (2×3 m·82 (m, 2H, aromatic hydrogens from anthraquinone), 7.63-7.71 (m, 1H, aromatic hydrogens from anthraquinone), 5.91 (br, s, 2H), 5.24 (s, 2H), 5.08 (s, 2H), 4.18-4.30 (m, 8H), 4.10-4.18 (m, 4H), 4.05 (m, 2H), 3.85-4.01 (m, 2H), 3.74-3.84 (m, 4H), 3.60-3.73 (m, 4H), 3.15-3.61 (m, 18H), 2.90-3.17 (m, 4H), 2.60-2.89 (m, 4H), 2.31-2.41 (m, 2H, H$_{2Iax.}$), 1.78-1.91 (m, 2H, H$_{2Ieq.}$), 1.02-1.30 (m, 4H); MS (MALDI-TOF) m/z calcd. for C$_{80}$H$_{137}$N$_{19}$O$_{26}$S$_5$ 1941.38. found 1960.18 [M+H$_2$O]$^+$; UV (H$_2$O): $\lambda_{max}$=342 nm, $\varepsilon_{342}$=99018 M$^{-1}$ cm$^{-1}$.

Synthesis of Neomycin Dimer-Pyrene Conjugate (87)

Neomycin dimer-pyrene conjugate was synthesized via formation of an amide bond. Boc protected neomycin dimer amine 53 was reacted with pyrene succinimidyl ester 38, leading to the formation of the amide bond (scheme 22) and thus a Boc protected dimer-pyrene conjugate can be isolated after purification using column chromatography. The Boc protected compound can be deprotected using trifluroacetic acid to give the desired conjugate 87 as a trifluoroacetate salt.

Scheme 22. Synthesis of Neomycin dimer Pyrene conjugate. Reagents and conditions: a-b: (a) Dry pyridine, DMAP, 12 h, r.t., 94%; (b) DCM, CF$_3$COOH, r.t., 3 h, 95%.
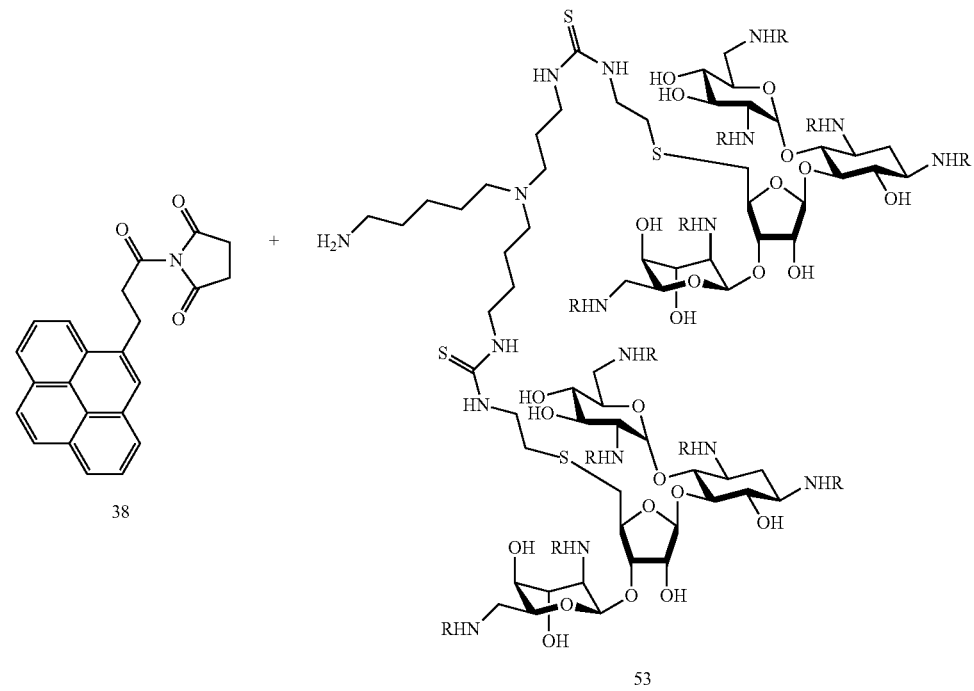
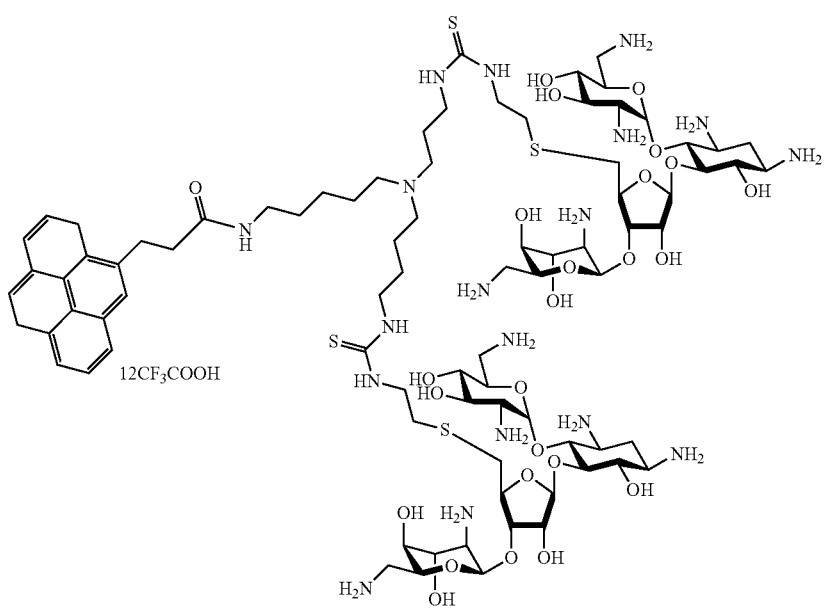

Synthesis and Characterization of Neomycin Dimer-Pyrene Conjugate (87)

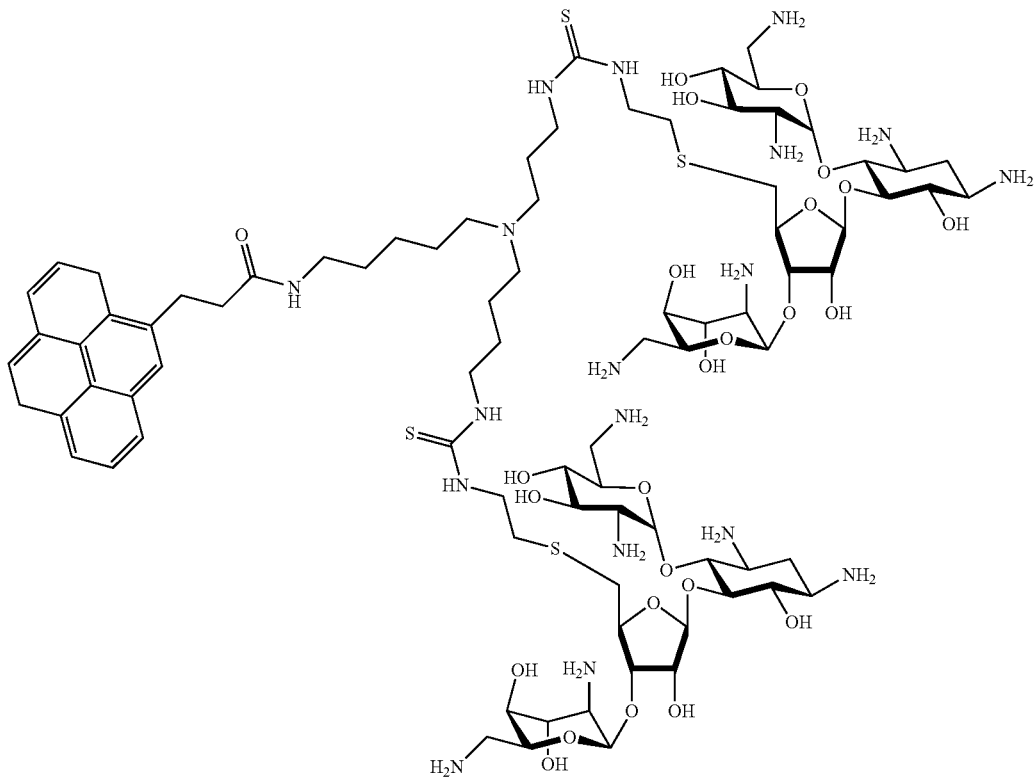

To a solution of N-Boc dimer amine 53 (22.0 mg, 9.0 µmol) in dry pyridine (2.0 mL), pyrene succinimide ester 38 (3.6 mg, 10.0 µmol) was added followed by addition of triethylamine (2.0 mg, 20.0 µmol). The reaction mixture was stirred at room temperature overnight under the atmosphere of argon. The progress of the reaction was monitored by TLC. The solvents were evaporated under reduced pressure. The crude product was purified using column chromatography on silica gel using dichloromethane-methanol as eluent [0 to 10% MeOH in DCM (v/v)]. The desired product was obtained as off white solid (26.1 mg, 94%): $R_f$=0.42 (10% EtOH in DCM (v/v)]; IR (KBr, cm$^{-1}$) 3300-3500 (br), 2975, 2918, 2105 (br, —C=S), 1705, 1619; $^1$H NMR (500 MHz, CD$_3$COCD$_3$) δ CDR (500 MHz, CD2975, 2918, v)]; wed by addition of triethylamine (2.0 mg, 20.0 µmol). The reaction mixture was stirred at r6.40-6.51 (m, 2H, NH$_{6IV}$), 6.30-6.36 (2H, NH$_{1I}$ or NH$_{6II}$), 6.20-6.27 (m, 2H, NH$_{II}$ or NH$_{6II}$), 6.05-6.20 (m, 4H, NH$_{2IV}$, NH$_{3I}$), 5.82-5.97 (br, s, 2H, NH$_{2II}$), 5.10-5.23 (m, 4H), 4.95-5.05 (m, 4H), 4.76-4.82 (m, 2H), 4.35-4.65 (m, 34H), 4.12-4.31 (m, 10H), 3.99-4.10 (m, 2H), 3.88-3.96 (m, 2H), 3.75-3.88 (m, 6H), 3.38-3.70 (m, 26H), 3.05-3.30 (m, 8H), 2.75-2.85 (m, 4H), 2.38-2.48 (m, 4H), 2.14-2.24 (m, 4H), 1.65-1.75 (m, 2H), 1.10-1.65 (m, 112H, 12×Boc, linker proton); MS (MALDI-TOF) m/z calcd. for C$_{143}$H$_{238}$N$_{18}$O$_{49}$S$_4$ (M+Na$^+$), 3144.76. found 3145.213; UV (DCM): λ$_{max}$=345 nm. The Boc protected compound was taken up in DCM-TFA solution (2.2 mL, 1:0.1 v/v) and stirred at room temperature under darkness for 2 h. Progress of reaction was checked by TLC. To this, deionized water (2.0 mL) was added and the mixture was washed with DCM (2×3 mL). The aqueous layer was lyophillized to afford the desired compound 87 as slightly greenish white solid (25.61 mg, 95%); $^1$H NMR (500 MHz, D$_2$O) δ 8.62-8.70 (m, 1H, aromatic hydrogens from Pyrene), 8.10-8.20 (m, 4H, aromatic hydrogens from Pyrene), 7.80-8.01 (m, 4H, aromatic hydrogens from Pyrene), 7.73-7.82 (m, 2H, aromatic hydrogens from Pyrene), 7.63-7.71 (m, 1H, aromatic hydrogens from Pyrene), 5.19-5.23 (m, 4H), 4.05-4.15 (m, 4H), 3.85-4.04 (m, 4H), 3.65-3.84 (m, 8H), 3.48-3.61 (m, 4H), 3.12-3.45 (m, 22H), 2.95-3.12 (m, 6H), 2.76-2.94 (m, 2H), 2.26-2.50 (m, 8H, H$_{2Iax.}$), 1.69-1.81 (m, 2H, H$_{2Ieq.}$), 1.02-1.30 (m, 4H); MS (MALDI-TOF) m/z for C$_{83}$H$_{142}$N$_{18}$O$_{25}$S$_4$ [M+H$_2$O]$^+$, calcd 1938.40. found 1938.91; UV (H$_2$O): λ$_{max}$=342 nm, ε$_{342}$=99018 M$^{-1}$ cm$^{-1}$.

Synthesis of Neomycin Dimer-Naphthalenediimide Conjugate (88)

A monoamine functionalized naphthalene diimide 64 can be prepared in few synthetic steps as described earlier. The isothiocyanate terminated naphthalenediimide 39 was reacted with Boc protected spermidine amine 61 to form a thiourea linked naphthalene diimide conjugate 88a (scheme 23) after purification using column chromatography. The Boc groups were deprotected using trifluoroacetic acid and the amine reacted with neomycin isothiocyanate 4 to give the desired conjugate 88 as trifluoroacetate salt.

Scheme 23. Reagents and conditions: (a-b): (a) Dry pyridine, DMAP, overnight, r.t., 22%; (b) TFA, DCM, 4 h, r.t., quant. (c) dry pyridine, 4, rt. Overnight, 55%; (d) DCM, TFA, rt, 2 h, 91%.
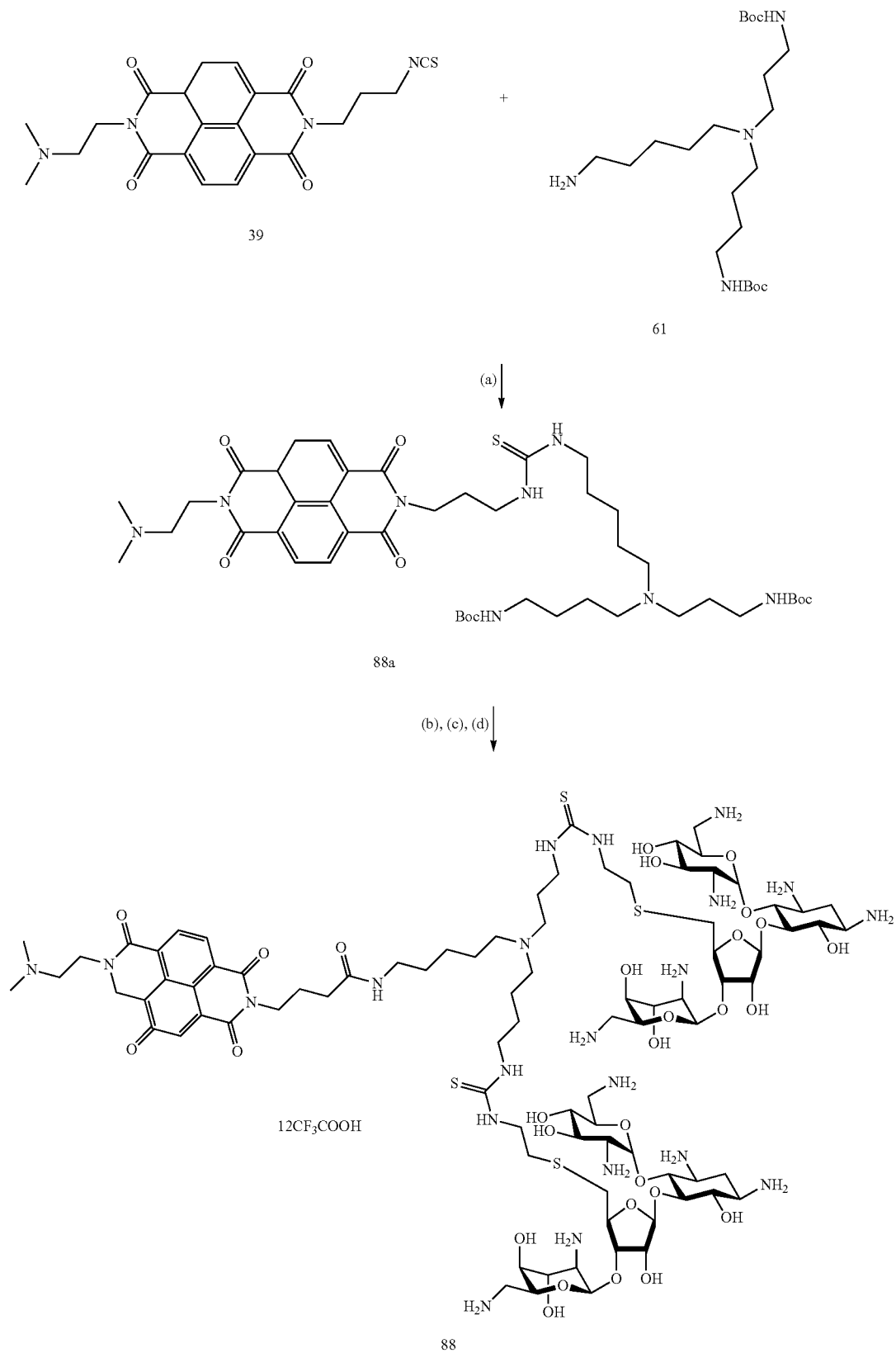

Neomycin Dimer Naphthalenediimide (88)

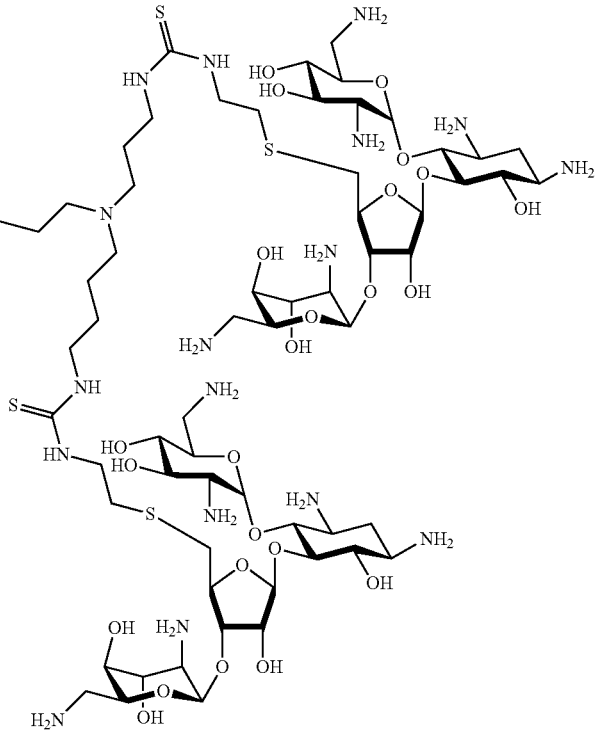

Synthesis of Spermidine N-Boc Naphthalenediimide (88a)

To a solution of Boc protected spermidine amine (61) (15.0 mg, 0.04 mmol) in pyridine (3.0 mL) a catalytic amount of DMAP, and Naphthalenediimide isothiocyanate (39) (34.1 mg, 0.10 mmol) were added, followed by stirring at room temperature overnight. Volatiles were evaporated under reduced pressure and the crude product was purified by column chromatography on silica gel using DCM-MeOH (0-15% MeOH in DCM) as eluent to afford desired compound 88a as off white solid (6.4 mg, 22%); $R_f$=0.32 [10% EtOH in DCM (v/v)]; $^1$H NMR (500 MHz, CD$_3$COCD$_3$) δ 8.78 (m, 4H), 4.22-4.38 (m, 2H), 3.50-3.70 (m, 3H), 3.21-3.38 (m, 2H), 3.08-3.21 (m, 2H), 2.29-2.38 (m, 2H).

Synthesis of Neomycin Dimer Naphthalenediimide Conjugate (88)

The Boc protected napthalenediimide derivative 88a from the previous step was taken up in DCM-TFA (2.0 mL, 1:1 v/v) and stirred at room temperature for 4 h. Volatiles were removed under reduced pressure and the residue was taken up in pyridine (3.0 mL). After five minutes of stirring, Boc protected neomycin isothiocyanate (4) (27.9 mg, 0.02 mmol) was added and the reaction mixture was stirred at room temperature overnight. Volatiles were evaporated and the crude product was purified by column chromatography using DCM-MeOH (0-15% MeOH in DCM) as eluent to afford desired compound Boc protected 88 as off white solid (13 mg, 55%); [$R_f$ 0.31, 10% EtOH in DCM (v/v)]; IR (KBr, cm$^{-1}$) 3350-3500 (br), 2972, 2109 (br, —C=S), 1701, 1625; $^1$H NMR (500 MHz, CD$_3$COCD$_3$) δ 8.70-8.90 (m, 4H, aromatic hydrogens from naphthalenediimine), 6.40-6.50 (m, 2H, NH$_{6IV}$), 6.05-6.30 (8H, NH$_{1I}$, NH$_{6II}$, NH$_{1I}$, NH$_{6II}$), 5.90-6.05 (br, s, 2H, NH$_{2II}$), 5.12-5.24 (m, 4H), 4.95-5.10 (m, 4H), 4.45 (br, s, 2H), 4.15-4.30 (m, 24H), 3.98-4.06 (m, 4H), 3.87-3.93 (m, 4H), 3.40-3.86 (m, 36H), 3.21-3.35 (m, 8H), 2.70-2.80 (m, 4H), 1.80-1.85 (m, 4H), 1.10-1.65 (m, 112H, 12×Boc, linker protons); MS (MALDI-TOF) m/z calcd. for C$_{143}$H$_{234}$N$_{21}$O$_{50}$S$_5$ (M+Na$^+$), 3322.93. found 3323.41; UV (Acetone): λ$_{max}$=378 nm.

The Boc protected compound from above step was taken up in DCM-TFA solution (2.2 mL, 1:0.1 v/v) and stirred at room temperature under darkness for 2 h. Progress of reaction was checked by TLC. To this, deionized water (2.0 mL) was added and the mixture was washed with DCM (2×3 mL). The aqueous layer was lyophillized to afford the desired compound as slightly greenish white solid (12.84 mg, 91%); $^1$H NMR (500 MHz, D$_2$O) δ 8.63-8.69 (m, 4H, aromatic hydrogens from Naphthalenediimide), 6.05-6.10 (m, 2H), 5.32-5.38 (m, 2H), 5.20-5.24 (br, s, 2H), 4.49 (t, J=5.36 Hz, 2H), 4.35-4.45 (m, 2H), 4.26-4.32 (m, 2H), 4.21-4.26 (m, 4H), 4.09-4.21 (m, 10H), 3.99 (t, J=10.25 Hz, 2H), 3.90 (t, J=9.14 Hz, 2H), 3.32-3.38 (m, 2H), 3.71-3.76 (m, 2H), 3.67 (t, J=10.24 Hz, 2H), 3.43-3.55 (m, 10H), 3.23-3.43 (m, 16H), 3.04-3.16 (m, 4H), 2.67-2.84 (m, 4H,), 2.33-2.41 (m, 2H, H$_{2Ieq}$), 1.91-2.06 (m, 6H, H$_{2Iax}$, linker protons from spermidine). MS MALDI-TOF m/z for C$_{86}$H$_{148}$N$_{22}$O$_{28}$S$_5$ [M+H$_2$O]$^+$, calcd 2116.57. found 2117.213; UV (H$_2$O): λ$_{max}$=383 nm, ε$_{383}$=16811 M$^{-1}$ cm$^{-1}$.

Synthesis of Neomycin-Dimer Fluorescein Conjugate (79)

The amino fictionalized neomycin dimer 53 was reacted with fluorescein-isothiocyanate 41b to synthesize Boc protected neomycin-dimer-fluorescein conjugate (Scheme 24). The amino groups were deprotected using trifluoroacetic acid to give the desired neomycin-dimer fluorescein conjugate 79 as their trifluoroacetate salt.

Scheme 24. Reagent and conditions. (a) dry DMF, triethylamine, 12 h, r.t., 68%; (b) Dioxane, 4 M HCl in dioxane, 15 min, 90%.
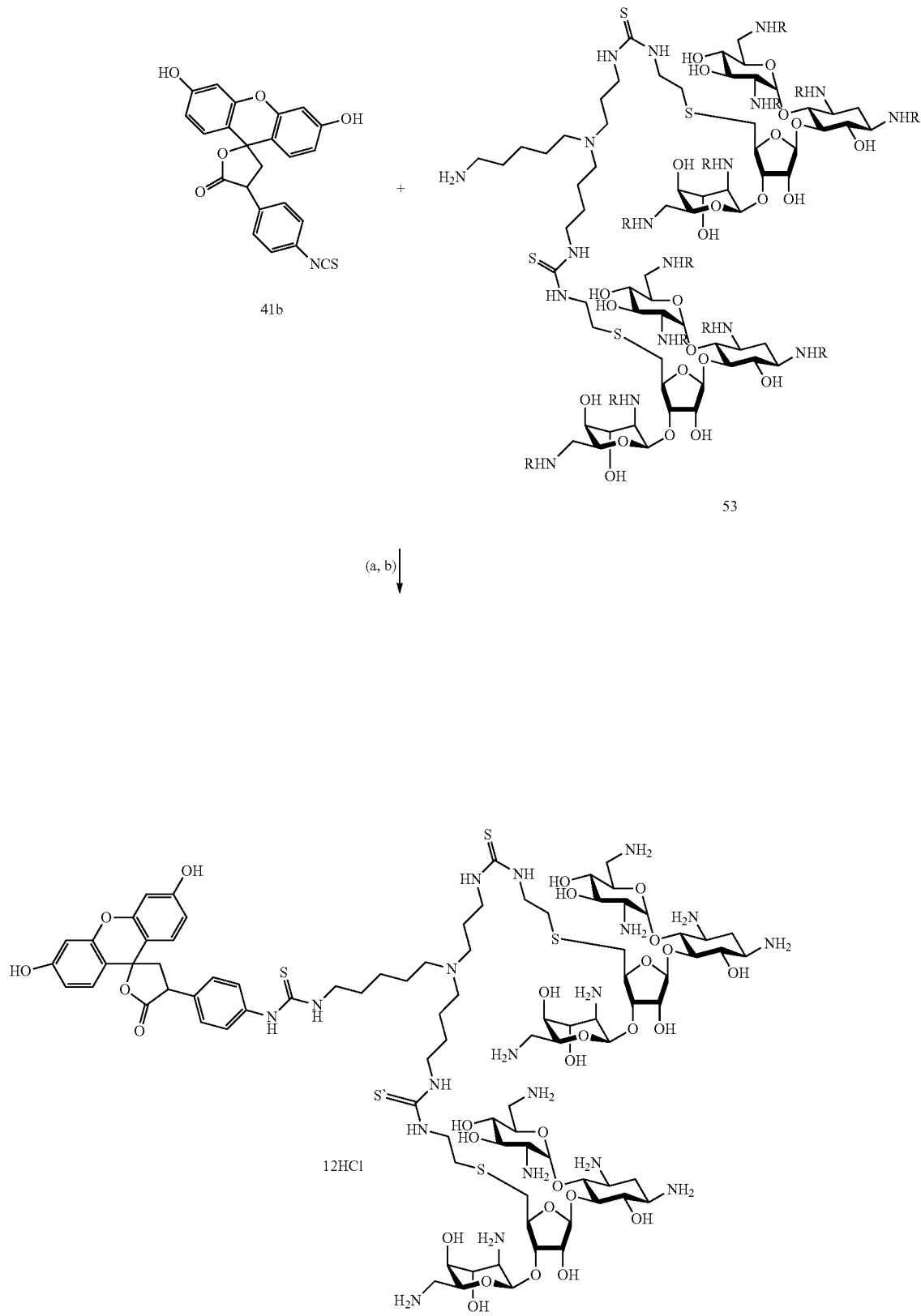

Synthesis of Neomycin Dimer-Fluorescein Conjugate (79)

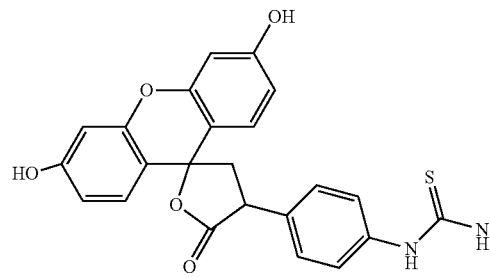
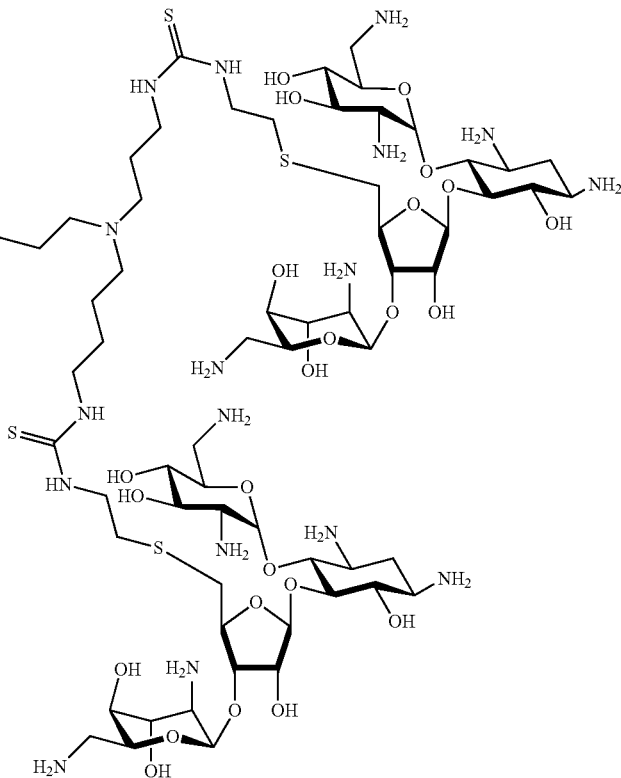

To a solution of neomycin dimer amine 53 (22.0 mg, 9.0 µmol) in dry DMF (2.0 mL), fluorescein isothiocyanate 41b (4.0 mg, 10.0 µmol) was added followed by addition of triethylamine (2.0 mg, 20.0 mµmol). The reaction mixture was stirred at room temperature under argon atmospheres. The stirring was continued overnight and the progress of the reaction was monitored by TLC. The solvents were evaporated under reduced pressure. The crude product was purified using column chromatography on silica gel using dichloromethane-methanol as eluent (0 to 20% MeOH in DCM (v/v)). The desired compound was obtained as orange solid (16.5 mg, 68%): $R_f$=0.41 [12% MeOH in DCM (v/v)]; $^1$H NMR (500 MHz, CD$_3$COCD$_3$) δ 9.20 (br, s, 1H), 7.73-7.80 (m, 4H), 7.64-7.70 (m, 2H), 7.10-7.20 (m, 2H), 6.63-6.78 (m, 7H), 6.40-6.50 (m, 2H, NH$_{6IV}$), 6.20-6.28 (m, 4H, NH$_{6II}$, NH$_{1I}$), 5.90-6.14 (m, 8H, NH$_{3I}$, NH$_{2IV}$, and NH$_{2II}$), 5.27 (m, 2H), 5.21 (m, 2H), 5.01-5.08 (m, 4H), 4.75 (m, 2H), 4.40-4.70 (m, 16H), 4.20-4.30 (m, 16H), 4.05 (m, 4H), 3.75-3.98 (m, 16H), 3.40-3.70 (m, 20H), 3.20-3.35 (m, 8H), 2.95-3.07 (m, 6H), 1.83-1.88 (p, 2H), 1.65-1.78 (m, 8H, linker protons from spermidine), 1.30-1.58 (m, 110H, H$_{2Ieq}$, 6xBoc).

To a solution of N-Boc neomycin dimer-fluorescein (15.0 mg, 50.0 µmol) in dioxane (2.0 mL), 4 N HCl in dioxane (1.0 mL) was added and the reaction mixture stirred for 15 min. A yellow precipitate was formed after stirring the reaction mixture for 20 min. The reaction mixture was washed with diethyl ether/hexane [3×2.0 mL, 1:1 (v/v)]. The precipitate was dissolved in water and then it was lyophilized to give the desired product as an orange solid (11.3 mg, 90%): $^1$H NMR (500 MHz, CD$_3$COCD$_3$) δ 8.61-8.67 (m, 1H), 8.10-8.20 (m, 1H), 7.72 (m, 1H), 7.23-7.32 (m, 3H), 7.10-7.20 (m, 3H), 7.02-7.10 (m, 1H), 5.30-5.50 (m, 2H), 5.10-5.30 (m, 2H), 4.30-4.50 (m, 4H), 4.20-4.30 (m, 4H), 4.10-4.20 (m, 6H), 3.75-4.04 (m, 10H), 3.60-3.80 (m, 12H), 3.25-3.60 (m, 24H), 3.02-3.20 (m, 10H), 2.70-2.98 (m, 4H), 2.35-2.50 (m, 2H, H$_{I2eq}$), 1.80-1.98 (m, 2H, H$_{I2ax}$), 1.50-1.60 (m, 2H), 1.10-1.40 (m, 6H); MS (MALDI-TOF) m/z calcd. For C$_{87}$H$_{143}$N$_{19}$O$_{29}$S$_5$(M+H$_2$O$^+$) 2077.89. found 2095.13 [M+H$_2$O]$^+$.

Synthesis of Neomycin-Boc Dimer with Azide Functionalization (86)

Neomycin dimers were synthesized by coupling a bisazide derivative with an alkyne terminated neomycin derivative. In the first step, a derivatized bisazido linker was synthesized in a two-step reaction (scheme 25). Bis(2-chloroethyl)amine was reacted with excess sodium azide at elevated temperature and converted into bis(2-azidoethyl) amine. The bis(2-azidooethyl)amine was then reacted with 6-bromo hexanoyl chloride under basic conditions to form a bisazide 83 that a bromo ended appendage from the middle of linker in high yields.

Scheme 25. Synthesis of N, N-bis (2-azidoethyl)-6-bromohexanamide. Reagents and conditions: a-c: (a) NaN$_3$, 48 h, 90° C., 90%; (b) 6-bromo hexanoyl chloride, NaOH, DCM, 1 h, 0°C., 86%.

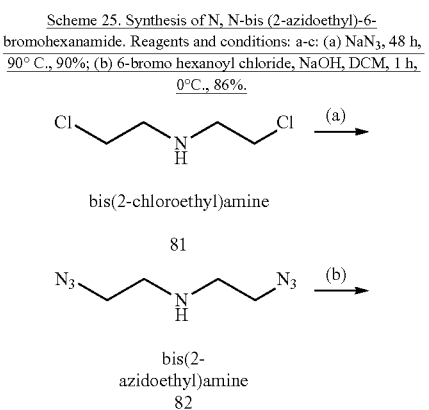

-continued

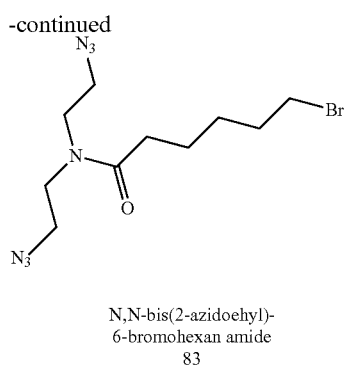

N,N-bis(2-azidoehyl)-
6-bromohexan amide
83

Neomycin dimer with a bromo functionalized dimer 85 was synthesized by reacting Hexa-N-Boc deoxy-neomycin-5"-alkyne 84 (2 mole equival.) with N,N-bis(2-azidoethyl)-6-bromohexanamide (1 mole equival.) using click chemistry (scheme 26). The bromide functionality on the neomycin dimer was substituted to an azido group via reaction with sodium azide. The azido ended neomycin dimer 84 can be reduced to the amine or directly coupled to fluorescent alkynes used to synthesize fluorescent neomycin dimer conjugates for the high throughput probing of nucleic acid binding.

Scheme 26. Synthesis of neomycin-Boc dimer with azide end. Reagents and conditions: a-b: (a) N, N-bis(2-azidoethyl)-6-bromohexanamide, CuSO₄, H₂O/EtOH, sodium ascorbate, r.t., 48 h, 80%. (b) NaN₃ DMF, 100° C., 14 h, 95%.

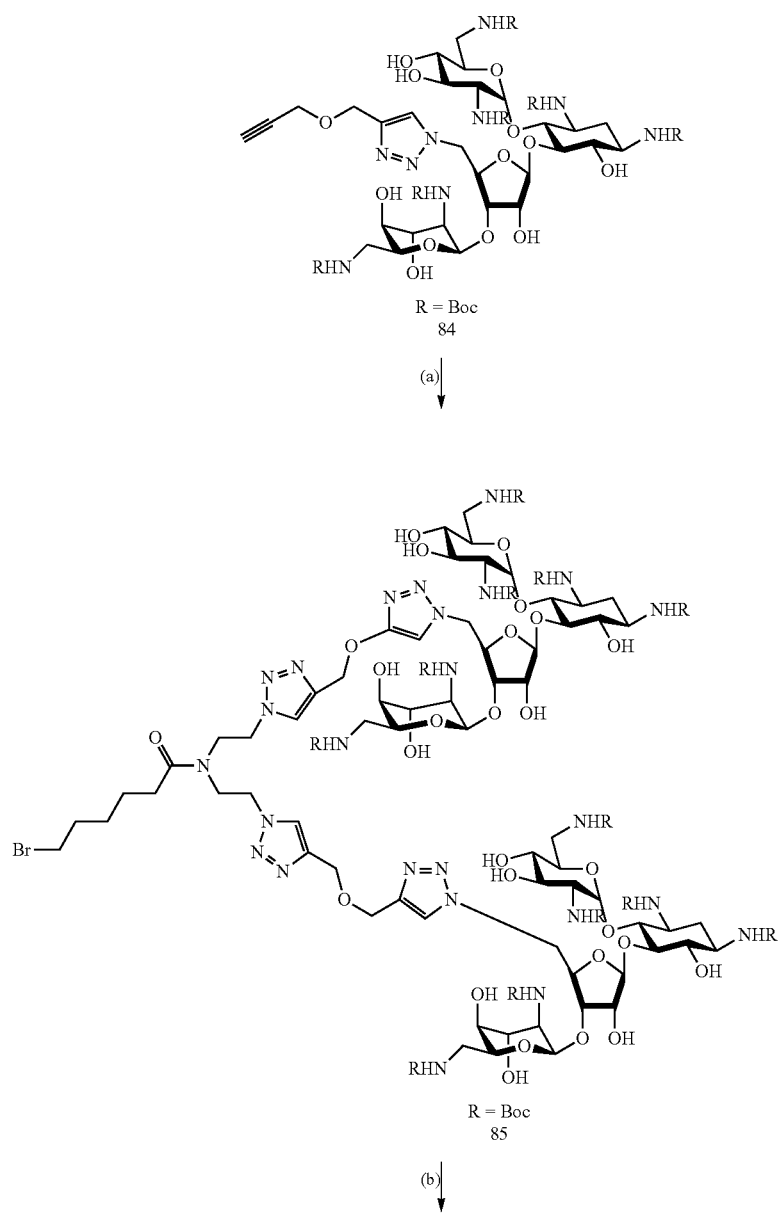

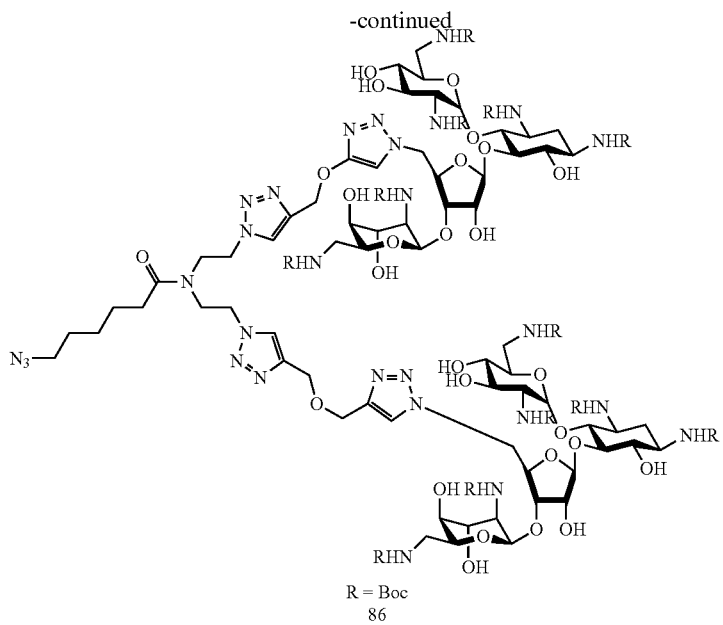

R = Boc
86

Synthesis of an Azido Functionalized Dimer for Conjugation to Fluorophores Via Click Chemistry

Synthesis of Bis(2-Azidoethyl)Amine (82)

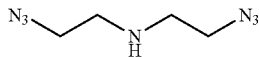

To a solution of bis(chloroethyl) amine hydrochloride (1.4 gm, 1.0 mmol) in water (10.0 mL), sodium azide (3.2 gm, 5.0 mmol) was added and the reaction mixture was stirred at 100° C. for 48 h. The reaction mixture was allowed to come to room temperature. It was followed by addition of 3M NaOH until the pH of the solution was 10. The reaction mixture was extracted with diethyl ether (3×20.0 mL). The organic layer was dried over $Na_2SO_4$. Removal of volatiles gave the desired compound as greenish colored oil (1.4 g, 90%): $R_f$=0.30 [15% $CH_3OH$ in $CH_2Cl2$ v/v)]; IR (neat, cm$^{-1}$) 3411 (broad), 2976, 2104 (—$N_3$), 1618, 1541; $^1$H NMR (500 MHz, CDCl$_3$) δ 3.35 (t, J=6.62 Hz, 4H, $N_3$—$\underline{CH_2}$—$CH_2$—N—), 2.85 (t, J=6.52 Hz, 4H, $N_3$—$CH_2$—$\underline{CH_2}$—N—); $^{13}$C NMR (500 MHz, CDCl$_3$): δ 51.27 ($N_3$—$\underline{CH_2}$—$CH_2$—N—), 48.04 ($N_3$—$CH_2$—$\underline{CH_2}$—N—).

Synthesis of N,N-Bis(2-Azidoethyl)-6-Bromohexanamide (83)

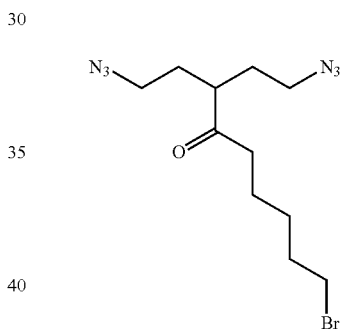

To a solution of bis (azido diethyl) amine (0.5 gm, 0.3 mmol) in dichloromethane (2.0 mL), an aqueous solution of 3M NaOH (2.6 mL) was added and the reaction mixture stirred at 0° C. for 15 min followed by addition of a solution of 6-bromohexanoyl chloride (1.3 gm, 0.6 mmol in 1.0 mL dichloromethane) dropwise. The reaction mixture was stirred for 1 h at 0° C. The organic layer was washed with 3N HCl (3×3.0 mL), dried over $Na_2SO_4$ and evaporation of solvent results in greenish oil (0.9 gm, 86%): $R_f$=0.5 [50% ethylacetate in hexane (v/v)]; IR (neat, cm$^{-1}$) 3340 (broad), 2914, 2104 (broad, $N_3$), 1701, 1465; $^1$H NMR (500 MHz, CDCl$_3$) δ 3.42-3.50 (m, 6H), 3.37-3.41 (m, 2H), 3.34 (t, J=6.62 Hz, 2H), 2.30 (t, J=7.41 Hz, 2H), 1.80 (p, J=6.93 Hz, 2H), 1.59 (p, J=7.72 Hz, 2H), 1.40 (p, J=7.41 Hz, 2H); $^{13}$C NMR (500 MHz, CDCl$_3$) δ 173.26, 49.91, 49.45, 48.11, 46.21, 33.72, 32.79, 32.52, 27.79, 24.11.

Synthesis of Neomycin Clickable Dimer Br-End (85)

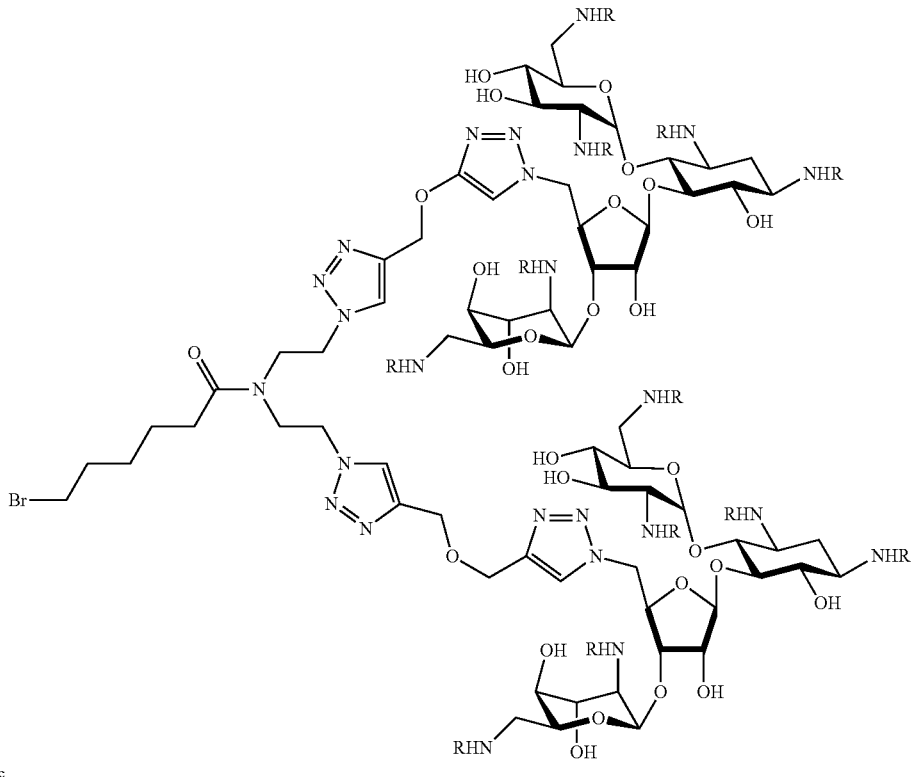

R=Boc

To a solution of Hexa-N-Boc deoxy-neomycin-5"-propargyl ether (43.0 mg, 14.0 µmol) in EtOH (2.0 mL), CuSO$_4$ (0.5 mg, 3.5 µmol, in 0.2 mL water), and sodium ascorbate (1.4 mg, 7.0 µmol, in 0.2 mL water) was added and the reaction mixture was stirred at room temperature for 15 min. N, N-bis(2-azidoethyl)-6-bromohexanamide (2.3 mg, 7.0 µmol) in EtOH (0.2 mL) was added dropwise and the reaction mixture was stirred vigorously at room temperature. The progress of the reaction was monitored by TLC. The crude product was purified on a silica gel column using dichloromethane-ethanol as eluent which yielded the desired product as yellowish solid (36.2 mg, 80%): R$_f$=0.38 [0 to 10% EtOH in DCM (v/v)]; $^1$H NMR (500 MHz, CD$_3$COCD$_3$): δ 8.21-8.34 (m, 2H, triazole), 8.04-8.15 (m, 2H, triazole), 6.52-6.67 (br, s, 2H, NH$_{6IV}$), 6.30-6.41 (br, s, 2H), 5.96-6.26 (m, 10H, NH$_{6II}$, NH$_{1I}$, NH$_{3I}$, NH$_{2IV}$, and NH$_{2II}$), 5.20-5.31 (m, 4H), 5.03-5.08 (m, 2H), 4.89-5.02 (m, 4H), 4.85 (d, J=8.35 Hz, 2H), 4.67-4.81 (m, 18H), 4.50-4.57 (br, s, 2H), 4.23-4.41 (m, 12H), 4.05 (s, 4H), 3.78-3.96 (m, 10H), 3.53-3.74 (m, 20H), 3.38-3.55 (m, 10H), 3.14-3.36 (m, 8H), 1.82 (p, J=6.94 Hz, 2H), 1.33-1.65 (m, 114H, H$_{2Ieq}$, 6×Boc, linker protons); MS (MALDI-TOF) m/z calcd. for C$_{128}$H$_{216}$BrN$_{25}$O$_{51}$ (M+H$_2$O$^+$), 3016.40. found 3016.40.

Synthesis of Neomycin Clickable Dimer Azide End (86)

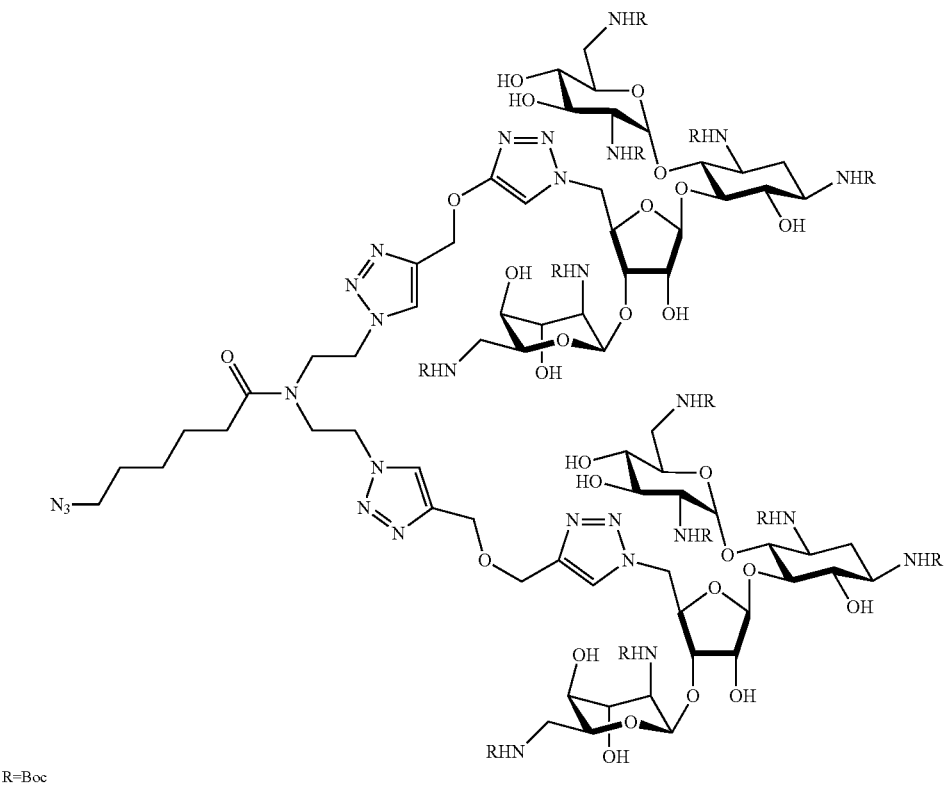

R=Boc

To a solution of 85 (100.0 mg, 3.3 µmol) in DMF (2.0 mL), NaN$_3$ (100.0 mg 1.5 mmol) was added and the reaction mixture was stirred at 100° C. for 14 h. The volatiles were removed under reduced pressure. The reaction mixture was dissolved in ethyl acetate (5.0 m) and then it was washed with water (3×5.0 m). The organic layer was dried over Na$_2$SO$_4$. Removal of volatiles under reduced pressure results in a brownish solid (93.8 mg, 95%). The product mixture was used in next step without further purification: IR (neat, cm$^{-1}$) 3300-3500 (broad), 2110 (—N$_3$), 1610-1650, 1505; $^1$H NMR (500 MHz, CD$_3$COCD$_3$) δ 8.20-8.31 (m, 2H, triazole), 8.06-8.16 (n, 2H, triazole), 6.55-6.69 (br, s, 2H, NH$_{6IV}$), 6.28-6.42 (br, s, 2H), 5.95-6.27 (m, 10H, NH$_{6II}$, NH$_{1I}$, NH$_{3I}$, NH$_{2IV}$, and NH$_{2II}$), 5.20-5.31 (m, 4H), 5.07-5.11 (m, 2H), 4.85-5.04 (m, 6H), 4.55-4.83 (m, 20H), 4.20-4.50 (m, 12H), 4.05 (s, 4H), 3.80-3.95 (m, 10H), 3.53-3.77 (m, 20H), 3.35-3.53 (m, 10H), 3.15-3.37 (m, 8H), 1.33-1.65 (m, 116H, H$_{2Ieq}$, 6×Boc, linker protons); MS (MALDI-TOF) m/z calcd. for C$_{128}$H$_{216}$N$_{28}$O$_{51}$ (M+H$_2$O$^+$), 2979.50. found 2980.10.

Synthesis of Alkyne Functionalized Neomycin (89)

A short alkyne free of triazole ring can also be prepared by reaction of Boc protected neomycin amine 6 with propargyl chloroformate (Scheme 27). This leads to the formation of a carbamate bond. The alkyne can then be used towards click chemistry reactions.

Scheme 27. (a) propargyl chloroformate, DCM, 0° C., 6 h., 72%

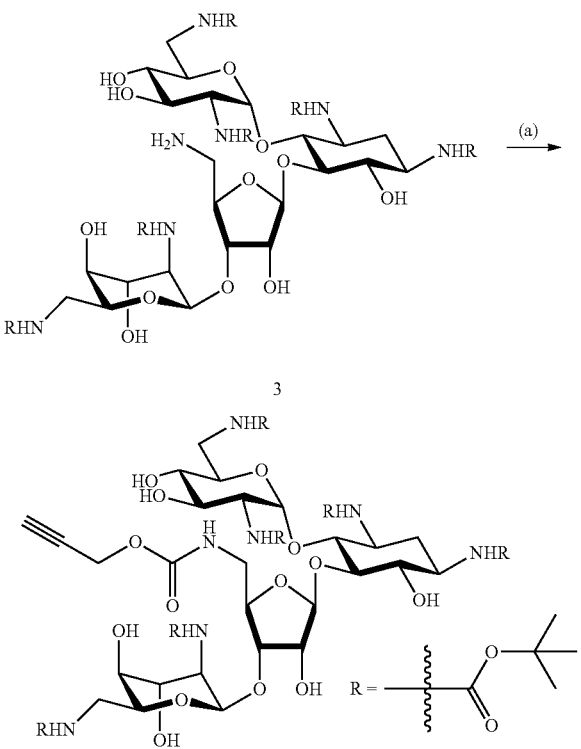

Synthesis of Hexa-N-Boc deoxy-neomycin-5"-propargyl alkyne (7)

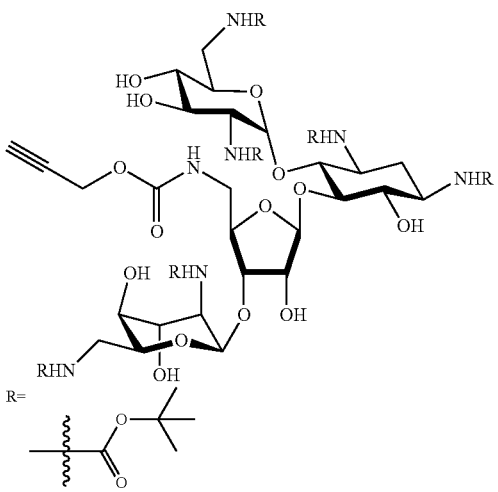

To a solution of Hexa-N-Boc deoxy-neomycin-5"-amine (60.00 mg, 0.05 mmol) in dry DCM (10.0 mL), triethylamine (10.0 mg, 0.1 mmol) was added followed by propargyl chloroformate (13.7 mg, 0.1 mmol) at −78° C. under the atmosphere of argon. The reaction mixture was stirred for 6 h and the progress of the reaction was monitored using TLC. The disappearance of starting material suggested completion of reaction. The reaction mixture was washed with water (10 mL) and the organic layer was dried over $Na_2SO_4$. The crude reaction mixture was purified using column chromatography on a silica gel column using dichloromethane-ethanol as eluent (0 to 10% EtOH in DCM). The desired product was obtained as white solid (46.0 mg, 72%): $R_f$=0.48 in 10% EtOH in dichloromethane (v/v)]; IR (KBr, $cm^{-1}$) 3300-3400 (br), 2960, 2910, 2112 (br, alkyne), 1712, 1608, 1450; $^1H$ NMR (500 MHz, $CD_3COCD_3$) δ 7.01 (s, 1H), 6.62 (s, 1H), 6.20-6.30 (m, 2H, $NH_{6IV}$ and $NH_{1I}$ or $NH_{6II}$), 6.12 (m, 1H, $NH_{1I}$ or $NH_{6II}$), 6.01-6.08 (m, 2H, $NH_{3I}$, $NH_{2IV}$), 5.92 (s, 1H, $NH_{2II}$), 5.10-5.20 (m, 3H), 4.92 (s, 3H), 4.30-4.40 (m, 2H), 4.10-4.25 (m, 4H), 4.01-4.09 (m, 4H), 3.95 (t, J=6.02 Hz, 2H), 3.70-3.87 (m, 6H), 3.35-3.70 (m, 18H), 3.30-3.40 (s, 4H), 2.97 (s, 1H), 1.20-1.65 (m, 56H, $H_{2Iax}$, 6×Boc); MS (MALDI-TOF) m/z calcd. for $C_{57}H_{97}N_7O_{26}$ $[M+Na^+]$, 1296.41, obsd: 1317.29 $[M+H_2O+2H]^+$.

REFERENCES

Andersen, E. S., S. A. Contera, et al. (2004). "Role of the trans-activation response element in dimerization of HIV-1 RNA." J Biol Chem 279(21): 22243-9.

Arya, D. P. (2005). Aminoglycoside-Nucleic Acid Interactions: The case for Neomycin. Topics in Current Chemistry: DNA Binders. J. B. Chaires and M. J. Waring. Heidelburg, Springer Verlag. 253: 149-178.

Arya, D. P., Coffee, R. L., Jr., Willis, B. and Abramovitch, A. I. (2001) Aminoglycoside-Nucleic Acid Interactions: Remarkable Stabilization of DNA and RNA Triple Helices by Neomycin. J. Am. Chem. Soc. 123(23), 5385-5395.

Arya, D. P. (2011) New approaches toward recognition of nucleic Acid triple helices. Acc. Chem. Res. 44, 134-146.

Arya, D. P., Micovic, L., Charles, I., Coffee, R. L., Jr., Willis, B. and Xue, L. (2003) Neomycin Binding to DNA Triplex Watson-Hoogsteen (W-H) Groove: A Model. J. Am. Chem. Soc. 125, 3733-3744.

Arya, D. P. and R. L. Coffee Jr. (2000). "DNA Triple Helix Stabilization by Aminoglycoside Antibiotics." Bioorganic and Medicinal Chemistry Letters 10(17): 1897-1899.

Arya, D. P. and R. L. Coffee, Jr. (2000). "DNA triple helix stabilization by aminoglycoside antibiotics." Bioorganic and Medicinal Chemistry Letters 10(17): 1897-9.

Arya, D. P., R. L. Coffee, Jr., et al. (2001). "Neomycin-Induced Hybrid Triplex Formation." Journal of the American Chemical Society 123(44): 11093-11094.

Arya, D. P., R. L. Coffee, Jr., et al. (2001). "Aminoglycoside-Nucleic Acid Interactions: Remarkable Stabilization of DNA and RNA Triple Helices by Neomycin." Journal of the American Chemical Society 123(23): 5385-5395.

Arya, D. P., R. L. Coffee, et al. (2004). "From triplex to B-form duplex stabilization: reversal of target selectivity by aminoglycoside dimers." Bioorganic & Medicinal Chemistry Letters 14(18): 4643-4646.

Arya, D. P., L. Micovic, et al. (2003). "Neomycin Binding to DNA Triplex Watson-Hoogsteen (W-H) Groove: A Model." Journal of the American Chemical Society 125: 3733-3744.

Arya, D. P. and B. Willis (2003). "Reaching into the major groove of B-DNA; Synthesis and nucleic acid binding of a neomycin-Hoechst 33258 conjugate." Journal of the American Chemical Society 125(41): 12398-12399.

Arya, D. P., L. Xue, et al. (2003). "Combining the Best in Triplex Recognition: Synthesis and Nucleic Acid Binding of a BQQ-Neomycin Conjugate." Journal of the American Chemical Society 125(27): 8070-8071.

Arya, D. P., L. Xue, et al. (2003). "Aminoglycoside (neomycin) preference is for A-form nucleic acids, not just RNA: results from a competition dialysis study." J Am Chem Soc 125(34): 10148-9.

9. Arya, D. P. (2005) The Case for Neomycin, in Topics in Current Chemistry: DNA Binders (J. B. Chaires, and M. J. Waring, Eds.) pp 149-178, Springer Verlag: Heidelburg.

Bailly, C., P. Colson, et al. (1993). "The different binding modes of Hoechst 33258 to DNA studied by electric linear dichroism." Nucleic Acids Res 21(16): 3705-9.

Bailly, C., P. Colson, et al. (1996). "The binding mode of drugs to the TAR RNA of HIV-1 studied by electric linear dichroism." Nucleic Acids Res 24(8): 1460-4.

Barbieri, C. M. and Pilch, D. S. (2006) Complete thermodynamic characterization of the multiple protonation equilibria of the aminoglycoside antibiotic paromomycin: A calorimetric and natural abundance N-15 NMR study. Biophys. J. 90, 1338-1349.

Blanchard, S. C., Fourmy, D., Eason, R. G. and Puglisi, J. D. (1998) rRNA Chemical Groups Required for Aminoglycoside Binding. Biochemistry (N. Y.) 37, 7716-7724.

Bannwarth, S. and A. Gatignol (2005). "HIV-1 TAR RNA: the target of molecular interactions between the virus and its host." Curr HIV Res 3(1): 61-71.

Berkhout, B. (1992). "Structural features in TAR RNA of human and simian immunodeficiency viruses: a phylogenetic analysis." Nucleic Acids Res 20(1): 27-31.

Charles, I., Xue, L., & Arya, D. P. 2002. Synthesis of aminoglycoside-DNA conjugates. Bioorganic & medicinal chemistry letters, 12(9): 1259-1262.

Cho, J. and R. R. Rando (2000). "Specific binding of Hoechst 33258 to site 1 thymidylate synthase mRNA." Nucleic Acids Res 28(10): 2158-63.

Cordingley, M. G., R. L. LaFemina, et al. (1990). "Sequence-specific interaction of Tat protein and Tat peptides with the transactivation-responsive sequence element of human immunodeficiency virus type 1 in vitro." Proc Natl Acad Sci USA 87(22): 8985-9.

Dassonneville, L., F. Hamy, et al. (1997). "Binding of Hoechst 33258 to the TAR RNA of HIV-1. Recognition of a pyrimidine bulge-dependent structure." Nucleic Acids Res 25(22): 4487-92.

Dingwall, C., I. Ernberg, et al. (1990). "HIV-1 tat protein stimulates transcription by binding to a U-rich bulge in the stem of the TAR RNA structure." Embo J 9(12): 4145-53.

Eftink, M. R. (1997). "Fluorescence methods for studying equilibrium macromolecule-ligand interactions." Methods Enzymol 278: 221-57.

François, B., Russell, R. J. M., Murray, J. B., Aboul-ela, F., Masquida, B., Vicens, Q. and Westhof, E. Crystal structures of complexes between aminoglycosides and decoding A site oligonucleotides: role of the number of rings and positive charges in the specific binding leading to miscoding. *Nucleic Acids Research* 33, 5677-5690.

Faber, C., H. Sticht, et al. (2000). "Structural rearrangements of HIV-1 Tat-responsive RNA upon binding of neomycin B." J Biol Chem 275(27): 20660-6.

Frankel, A. D. (1992). "Activation of HIV transcription by Tat." Curr Opin Genet Dev 2(2): 293-8.

Friedrich, K., and Woolley, P. (1988) Electrostatic Potential of Macromolecules Measured by pKa Shift of a Fluorophore 1. the 3' Terminus of 16S RNA. Eur. J. Biochem. 173, 227-231.

Froeyen, M. and P. Herdewijn (2002). "RNA as a target for drug design, the example of Tat-TAR interaction." Curr Top Med Chem 2(10): 1123-45.

Grzesiek, S. and A. Bax (1993). "Measurement of amide proton exchange rates and NOEs with water in 13C/15N-enriched calcineurin B." J Biomol NMR 3(6): 627-38.

Hamasaki, K. and R. R. Rando (1998). "A high-throughput fluorescence screen to monitor the specific binding of antagonists to RNA targets." Anal Biochem 261(2): 183-90.

Hamma, T. and P. S. Miller (2003). "Interactions of hairpin oligo-2'-O-methylribonucleotides containing methylphosphonate linkages with HIV TAR RNA." Antisense Nucleic Acid Drug Dev 13(1): 19-30.

Hamma, T., A. Saleh, et al. (2003). "Inhibition of HIV tat-TAR interactions by an antisense oligo-2'-O-methylribonucleoside methylphosphonate." Bioorg Med Chem Lett 13(11): 1845-8.

Haq, I., J. E. Ladbury, et al. (1997). "Specific binding of hoechst 33258 to the d(CGCAAATTTGCG)2 duplex: calorimetric and spectroscopic studies." J Mol Biol 271(2): 244-57.

Herbert, A., K. Lowenhaupt, et al. (1995). "Double-stranded RNA adenosine deaminase binds Z-DNA in vitro." Nucleic Acids Symp Ser 33: 16-9.

Hermann, T. and Westhof, E. (1998) Aminoglycoside binding to the hammerhead ribozyme: a general model for the interaction of cationic antibiotics with RNA. *J. Mol. Biol.* 276, 903-912.

Hermann, T. (2000). "Strategies for the Design of Drugs Targeting RNA and RNA-Protein Complexes." Angew Chem Int Ed Engl 39(11): 1890-1904.

Hermann, T. and D. J. Patel (2000). "RNA bulges as architectural and recognition motifs." Structure 8(3): R47-54.

Hermann, T. and E. Westhof (1998). "RNA as a drug target: chemical, modelling, and evolutionary tools." Curr Opin Biotechnol 9(1): 66-73.

H. Xi, E. Davis, N. Ranjan, L. Xue, D. Hyde-Volpe, D. P. Arya, Thermodynamics of nucleic Acid "shape readout" by an aminosugar, Biochemistry. 50 (2011) 9088-9113.

Jin, E., V. Katritch, et al. (2000). "Aminoglycoside binding in the major groove of duplex RNA: the thermodynamic and electrostatic forces that govern recognition." J Mol Biol 298(1): 95-110.

Kaul, M., Barbieri, C. M., Kerrigan, J. E. and Pilch, D. S. (2003) Coupling of drug protonation to the specific binding of aminoglycosides to the A site of 16S rRNA: elucidation of the number of drug amino groups involved and their identities. *J. Mol. Biol.* 326, 1373-1387.

Kaul, M. and Pilch, D. S. (2002) Thermodynamics of aminoglycoside-rRNA recognition: the binding of neomycin-class aminoglycosides to the A Site of 16S rRNA. *Biochemistry* 41, 7695-7706.

Krebs, A., V. Ludwig, et al. (2003). "Targeting the HIV trans-activation responsive region—approaches towards RNA-binding drugs." Chembiochem 4(10): 972-8.

Kubista, M., Sjoback, R., and Albinsson, B. (1993) Determination of Equilibrium Constants by Chemometric Analysis of Spectroscopic Data. Anal. Chem. 65, 994-998.

Kubista, M., Sjoback, R., and Nygren, J. (1995) Quantitative Spectral Analysis of Multicomponent Equilibria. Anal. Chim. Acta. 302, 121-125.

Kolb, H. C., Finn, M. G., & Sharpless, K. B. 2001. Click chemistry: Diverse chemical function from a few good reactions. Angewandte Chemie International Edition, 40(11): 2004-2021.

Kumar, S. 2011. Targeting DNA and RNA using dimeric aminoglycosides (Ph.D ed). Clemson, S.C.: Clemson University.

Kumar, S., Kellish, P., Robinson, W. E., Wang, D., Appella, D. H., and Arya, D. P. (2012) Click Dimers to Target HIV TAR RNA Conformation. *Biochemistry.* 51, 2331-2347.

Lapidot, A., V. Vijayabaskar, et al. (2004). "Structure-activity relationships of aminoglycoside-arginine conjugates that bind HIV-1 RNAs as determined by fluorescence and NMR spectroscopy." FEBS Lett 577(3): 415-21.

Leng, F., W. Priebe, et al. (1998). "Ultratight DNA Binding of a New Bisintercalating Anthracycline Antibiotic." Biochemistry 37(7): 1743-1753.

Loontiens, F. G., L. W. McLaughlin, et al. (1991). "Binding of Hoechst 33258 and 4',6'-diamidino-2-phenylindole to self-complementary decadeoxynucleotides with modified exocyclic base substituents." Biochemistry 30(1): 182-9.

Loontiens, F. G., P. Regenfuss, et al. (1990). "Binding characteristics of Hoechst 33258 with calf thymus DNA, poly[d(A-T)], and d(CCGGAATTCCGG): multiple stoichiometries and determination of tight binding with a wide spectrum of site affinities." Biochemistry 29(38): 9029-39.

Loret, E. P., P. Georgel, et al. (1992). "Circular dichroism and molecular modeling yield a structure for the complex of human immunodeficiency virus type 1 trans-activation response RNA and the binding region of Tat, the trans-acting transcriptional activator." Proc Natl Acad Sci USA 89(20): 9734-8.

Luedtke, N. W. and Y. Tor (2003). "Fluorescence-based methods for evaluating the RNA affinity and specificity of HIV-1 Rev-RRE inhibitors." Biopolymers 70(1): 103-19.

Lynch, S. R. and Puglisi, J. D. (2001a) Structural Origins of Aminoglycoside Specificity for Prokaryotic Ribosomes. *J. Mol. Biol.* 306, 1037-1058.

Lynch, S. R. and Puglisi, J. D. (2001b) Structure of a Eukaryotic Decoding Region A-site RNA. *J. Mol. Biol.* 306, 1023-1035.

Marciniak, R. A., B. J. Calnan, et al. (1990). "HIV-1 Tat protein trans-activates transcription in vitro." Cell 63(4): 791-802.

Matsumoto, C., K. Hamasaki, et al. (2000). "A high-throughput screening utilizing intramolecular fluorescence resonance energy transfer for the discovery of the molecules that bind HIV-1 TAR RNA specifically." Bioorg Med Chem Lett 10(16): 1857-61.

Mei, H.-Y. (1995). "Inhibition of an HIV-1 Tat-derived peptide binding to TAR RNA by aminoglycoside antibiotics." Bioorganic and Medicinal Chemistry Letters 5(22): 2755-2760.

Moazed, D. and H. F. Noller (1987). "Interaction of antibiotics with functional sites in 16S ribosomal RNA." Nature 327(6121): 389-94.

Murakami, A., Nakaura, M., Nakatsuji, Y., Nagahara, S., Tran-Cong, Q., and Makino, K. (1991) Fluorescent-Labelled Oligonucleotide Probes: Detection of Hybrid Formation in Solution by Fluorescence Polarization Spectroscopy. Nucl. Acids Res. 19, 4097-4102.

Phanstiel, Price, H. L., Wang, L., Juusola, J., Kline, M., & Shah, S. M. 2000. The effect of polyamine homologation on the transport and cytotoxicity properties of polyamineâˆ'(DNA-intercalator) conjugates. The Journal of organic chemistry, 65(18): 5590-5599.

Pilch, D. S., M. A. Kirolos, et al. (1995). "Berenil Binding to Higher Ordered Nucleic Acid Structures: Complexation with a DNA and RNA Triple Helix." Biochemistry 34(49): 16107-16124.

Pilch, D. S., M. A. Kirolos, et al. (1995). "Berenil [1,3-bis (4'-amidinophenyl)triazene] Binding to DNA Duplexes and to a RNA Duplex: Evidence for Both Intercalative and Minor Groove Binding Properties." Biochemistry 34(31): 9962-76.

Piotto, M., V. Saudek, et al. (1992). "Gradient-tailored excitation for single-quantum NMR spectroscopy of aqueous solutions." J Biomol NMR 2(6): 661-5.

Rajur, S. B., J. Robles, et al. (1997). "Hoechst 33258 Tethered by a Hexa(ethyleneglycol) Linker to the 5'-Termini of Oligodeoxynucleotide 15-Mers: Duplex Stabilization and Fluorescence Properties." J. Org. Chem. 62(3): 523-529.

Rando, R. R., & Wang, Y. 1996. *Methods and kits for RNA binding compounds, for RNA isolation, for detg. serum aminoglycoside antibiotics, for detecting bacteria or viruses, and for increasing aminoglycoside antibiotic-RNA binding interaction potency* President and Fellows of Harvard College, USA.

Ren, J. and J. B. Chaires (2000). "Preferential Binding of 3,3'-Diethyloxadicarbocyanine to Triplex DNA." J Am Chem Soc 122(2): 424-425.

Ren, J. and J. B. Chaires (2001). Rapid Screening of Structurally Selective Ligand Binding to Nucleic Acids. Methods in Enzymology. New York, Academic Press. 340: 99-108.

Rich, A. (1993). "DNA comes in many forms." Gene 135(1-2): 99-109.

Riguet, E. and C. Bailly (2004). "A Route for Preparing New Neamine Derivatives Targeting HIV-1 TAR RNA." Tetrahedron 60: 8053-8064.

Riguet, E., J. Desire, et al. (2005). "Neamine dimers targeting the HIV-1 TAR RNA." Bioorg Med Chem Lett 15(21): 4651-5.

Riguet, E., S. Tripathi, et al. (2004). "A peptide nucleic acid-neamine conjugate that targets and cleaves HIV-1 TAR RNA inhibits viral replication." J Med Chem 47(20): 4806-9.

Rostovtsev, V. V., Green, L. G., Fokin, V. V., & Sharpless, K. B. 2002. A stepwise huisgen cycloaddition process: Copper(I)-catalyzed regioselective ligation of azides and terminal alkynes. Angew Chem Int Edit Angew Chem Int Edit, 41(14): 2596.

Roy, S., U. Delling, et al. (1990). "A bulge structure in HIV-1 TAR RNA is required for Tat binding and Tat-mediated trans-activation." Genes Dev 4(8): 1365-73.

Sehlstedt, U., P. Aich, et al. (1998). "Interactions of the Antiviral Quinoxaline Derivative 9-OH-B220 {2,3-dimethyl-6-(dimethylaminoethyl)-9-hydroxy-6H-indolo-[2, 3-b]quinoxaline} with Duplex and Triplex Forms of Synthetic DNA and RNA." J. Mol. Biol. 278(1): 31-56.

Sjoback, R., Nygren, J., and Kubista, M. (1998) Characterization of Fluorescein-Oligonucleotide Conjugates and Measurement of Local Electrostatic Potential. Biopolymers. 46, 445-453.

Vicens, Q. and E. Westhof (2003). "RNA as a drug target: the case of aminoglycosides." Chembiochem 4(10): 1018-23.

Vicens, Q. and Westhof, E. (2001) Crystal Structure of Paromomycin Docked into the Eubacterial Ribosomal Decoding A Site. Structure 9, 647-658.

Wang, S., P. W. Huber, et al. (1998). "Binding of neomycin to the TAR element of HIV-1 RNA induces dissociation of Tat protein by an allosteric mechanism." Biochemistry 37(16): 5549-57.

Wang, Y., K. Hamasaki, et al. (1997). "Specificity of aminoglycoside binding to RNA constructs derived from the 16S rRNA decoding region and the HIV-RRE activator region." Biochemistry 36(4): 768-79.

Wang, H. 1998. Design and synthesis of RNA binding aminoglycoside antibiotics (Ph.D ed). California, San Diego: University of California, San Diego.

Warshel, A. (1981) Electrostatic Basis of Structure-Function Correlation in Proteins. Acc. Chem. Res. 14, 284-290.

Weiner, P. K., Langridge, R., Blaney, J. M., Schaefer, R., and Kollman, P. A. (1982) Electrostatic Potential Molecular Surfaces. PNAS. 79, 3754-3758.

Weinstein, H., Maayani, S., Srebrenik, S., Cohn, S., and Sokolvosky, M. (1975) A Theoretical and Experimental Study of the Semirigid Cholinergic Agonist 3-Acetoxyquinuclidine. Mol. Pharmacol. 11, 671-689.

Wei, A. P., D. K. Blumenthal, et al. (1994). "Antibody-mediated fluorescence enhancement based on shifting the intramolecular dimer↔monomer equilibrium of fluorescent dyes." Anal Chem 66(9): 1500-6.

Willis, A., III and D. P. Arya (2006). An Expanding View of Aminoglycoside-Nucleic Acid Recognition. Advances in Carbohydrate Chemistry and Biochemistry. D. Horton, Elsevier. 60: 251-302.

Willis, A., III and D. P. Arya (2006). "Major Groove Recognition of DNA by Carbohydrates." Current Organic Chemistry 10(6): 663-673.

Willis, B. and D. P. Arya (2006). "Recognition of B-DNA by Neomycin-Hoechst 33258 Conjugates." Biochemistry 45(34): 10217-10232.

Xavier, K. A., P. S. Eder, et al. (2000). "RNA as a drug target: methods for biophysical characterization and screening." Trends Biotechnol 18(8): 349-56.

Xu, Y. Z. and E. T. Kool (1997). "A Novel 5'-iodonucleoside Allows Efficient Nonenzymatic Ligation of Single-stranded and Duplex DNAs." Tetrahedron Letters 38(32): 5595-5598.

Xu, Z. T., D. S. Pilch, et al. (1997). "Modulation of nucleic acid structure by ligand binding: Induction of a DNA center dot RNA center dot DNA hybrid triplex by DAPI intercalation." Bioorganic and Medicinal Chemistry 5(6): 1137-1147.

Yajima, S., H. Shionoya, et al. (2006). "Neamine derivatives having a nucleobase with a lysine or an arginine as a linker, their synthesis and evaluation as potential inhibitors for HIV TAR-Tat." Bioorg Med Chem 14(8): 2799-809.

Yang, P.; De Cian, A.; Teulade-Fichou, M.; Mergny, J.; Monchaud, D. Engineering Bisquinolinium/Thiazole Orange Conjugates for Fluorescent Sensing of G-Quadruplex DNA, 2009, 48, 2188-2191.

Zaman, G. J., P. J. Michiels, et al. (2003). "Targeting RNA: new opportunities to address drugless targets." Drug Discov Today 8(7): 297-306.

Xi, H., Kumar, S., Dosen-Micovic, L. and Arya, D. P. (2010) Calorimetric and spectroscopic studies of aminoglycoside binding to AT-rich DNA triple helices. *Biochimie* 92, 514-529.

We claim:

1. A nucleic acid probe comprising thiazole orange, a linker moiety having a first end and a second end, and a nucleic acid binding moiety, wherein the thiazole orange is covalently attached to the first end of the linker moiety and the second end of the linker moiety is covalently attached to the nucleic acid binding moiety, wherein the nucleic acid binding moiety comprises an aminoglycoside moiety comprising unbound primary, secondary, and/or guanidino amino group(s) available for nucleic acid binding, and wherein the linker moiety is covalently attached to the nucleic acid binding moiety through a hydroxyl group of the aminoglycoside moiety.

2. The probe of claim 1, wherein the aminoglycoside moiety is amikacin, apramycin, arbekacin, bambermycins, butirosin, dibekacin, dihydrostreptomycin, fortimicin, geneticin, gentamicin, isepamicin, kanamycin, lividomycin, micronomicin, neamine, neomycin, netilmicin, paromomycin, ribostamycin, sisomicin, spectinomycin, streptomycin, streptonicozid, tobramycin, trospectomycin, viomycin, an analog thereof, a derivative thereof, a homo dimer thereof, a heterodimer thereof or pharmaceutically acceptable salt thereof.

3. The probe of claim 1, wherein the aminoglycoside moiety is neomycin, a homo dimer thereof, or a hetero dimer thereof.

4. The probe of claim 1, wherein the nucleic acid binding moiety further comprises a secondary binding moiety linked to the aminoglycoside moiety.

5. The probe of claim 4, wherein the secondary binding moiety is a minor groove binder.

6. The probe of claim 4, wherein the secondary binding moiety is Hoechst 33258, Hoechst 33342, Hoechst 34580, distamycin A, netropsin, 4',6-diamidino-2-phenylindole (DAPI), 4,4'(1-Triazene-1,3-diyl)bis(benzenecarboximidamide), lexitropsin, 4-[(3-Methyl-6-(benzothiazol-2-yl)-2,3-dihydro-(benzo-1,3-thiazole)-2-methylidene)]-1-methyl-pyridinium iodide (BEBO), or BOXTO (4-[6-(benzoxazole-2-yl-(3-methyl-)-2,3-dihydro-(benzo-1,3-thiazole)-2-methylidene)]-1-methyl-quinolinium chloride).

7. The probe of claim 1, wherein the linker moiety is one of

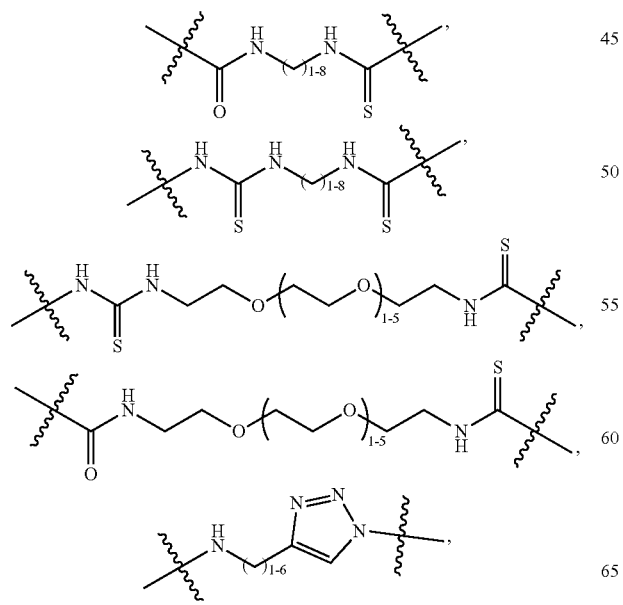

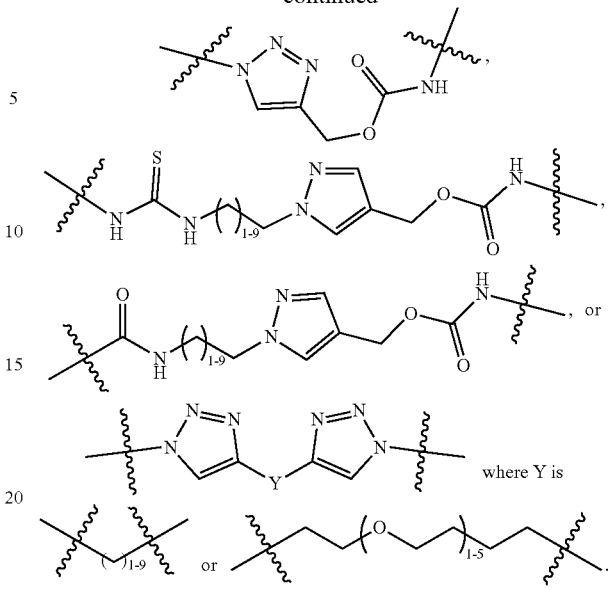

8. The probe of claim 1, wherein the linker moiety is

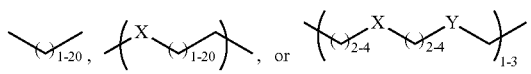

where X is O, S, or NH, and Y is O, S, or NH.

9. The probe of claim 1, wherein the linker moiety is $-(L_1)_v-$, wherein v is independently 1-20, and wherein each $(L_1)$ is independently O, N, S, $C_1$-$C_8$ alkyl, $C_2$-$C_8$ alkenyl, $C_2$-$C_8$ alkoxy, aryl, heteroaryl, heterocyclyl,

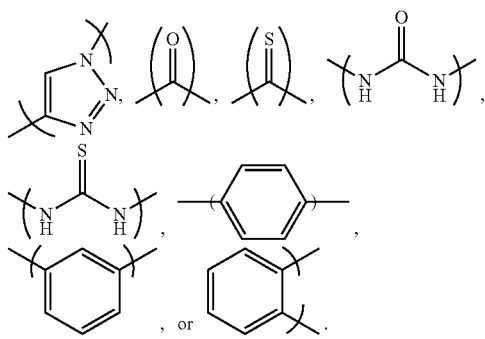

10. The probe of claim 1, wherein the linker moiety is O, N, S, $C_1$-$C_8$ alkyl, $C_2$-$C_8$ alkenyl, $C_2$-$C_8$ alkoxy,

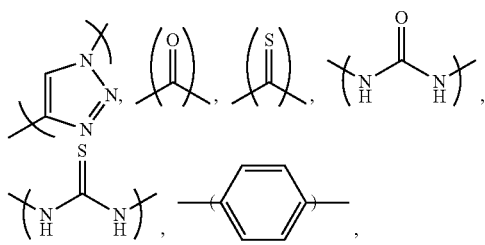

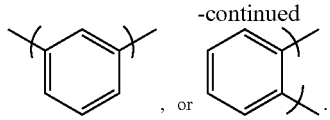, or 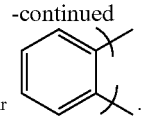.

11. The probe of claim 1, wherein a fluorescence of the probe changes upon binding of the probe to a nucleic acid.

12. The probe of claim 1, wherein the nucleic acid binding moiety binds to RNA, A-DNA, B-DNA, double stranded DNA, triple stranded DNA, or quadruplex DNA.

13. The probe of claim 12, wherein the nucleic acid binding moiety binds to a major groove of the DNA.

14. The probe of claim 2, wherein the neomycin is neomycin B or neomycin C.

15. The probe of claim 2, wherein the gentamicin is gentamicin A, gentamicin C1, gentamicin C1a, or gentamicin C2.

16. The probe of claim 2, wherein the kanamycin is kanamycin A, kanamycin B, or kanamycin C.

17. The probe of claim 12, wherein the nucleic acid binding moiety binds to a major groove of the double stranded DNA.

18. The probe of claim 12, wherein the double stranded DNA is A-DNA.

19. The probe of claim 12, wherein the double stranded DNA is B-DNA.

20. The probe of claim 1, wherein the linker moiety is covalently attached to the 5" OH position of the ribose ring of neomycin B.

* * * * *

SEQUENCE LISTING

```
<160> NUMBER OF SEQ ID NOS: 5

<210> SEQ ID NO 1
<211> LENGTH: 27
<212> TYPE: RNA
<213> ORGANISM: Artificial Sequence
<220> FEATURE:
<223> OTHER INFORMATION: rRNA A-site oligonucleotide

<400> SEQUENCE: 1
ggcgucacac cuucggguga agucgcc                                              27

<210> SEQ ID NO 2
<211> LENGTH: 27
<212> TYPE: RNA
<213> ORGANISM: Homo sapiens

<400> SEQUENCE: 2
ggcgucgcua cuucgguaaa agucgcc                                              27

<210> SEQ ID NO 3
<211> LENGTH: 27
<212> TYPE: RNA
<213> ORGANISM: Escherichia coli

<400> SEQUENCE: 3
ggcgucaccc cuucgggaca agucgcc                                              27

<210> SEQ ID NO 4
<211> LENGTH: 27
<212> TYPE: RNA
<213> ORGANISM: Artificial Sequence
<220> FEATURE:
<223> OTHER INFORMATION: Mutant Escherichia coli

<400> SEQUENCE: 4
ggcgucaccc cuucgggca agucgcc                                               27

<210> SEQ ID NO 5
<211> LENGTH: 12
<212> TYPE: DNA
<213> ORGANISM: Artificial Sequence
<220> FEATURE:
<223> OTHER INFORMATION: d(G4T4G4)2

<400> SEQUENCE: 5
ggggttttgg gg                                                              12
```